US009062095B2

(12) United States Patent
Jahns et al.

(10) Patent No.: US 9,062,095 B2
(45) Date of Patent: Jun. 23, 2015

(54) MUTANT DOUBLE CYCLIZED RECEPTOR PEPTIDES INHIBITING $\beta_1$-ADRENOCEPTOR ANTIBODIES

(75) Inventors: Roland Jahns, Würzburg (DE); Valérie Jahns, Würzburg (DE); Martin J. Lohse, Würzburg (DE); Viacheslav Nikolaev, Würzburg (DE)

(73) Assignee: JULIUS-MAXIMILIANS-UNIVERSTITAT-WURZBURG, Wurzburg (DE)

( * ) Notice: Subject to any disclaimer, the term of this patent is extended or adjusted under 35 U.S.C. 154(b) by 821 days.

(21) Appl. No.: 12/733,347

(22) PCT Filed: Aug. 22, 2008

(86) PCT No.: PCT/EP2008/006932
§ 371 (c)(1),
(2), (4) Date: Feb. 23, 2010

(87) PCT Pub. No.: WO2009/027063
PCT Pub. Date: Mar. 5, 2009

(65) Prior Publication Data
US 2010/0209445 A1    Aug. 19, 2010

(30) Foreign Application Priority Data

Aug. 24, 2007   (EP) .................................... 07016637

(51) Int. Cl.
*C07K 7/00*         (2006.01)
*C07K 7/64*         (2006.01)
*G01N 33/68*        (2006.01)
*A61K 38/00*        (2006.01)

(52) U.S. Cl.
CPC . *C07K 7/64* (2013.01); *A61K 38/00* (2013.01); *G01N 33/6854* (2013.01)

(58) Field of Classification Search
USPC ......... 530/326, 324, 325, 403; 514/21.4, 16.4
See application file for complete search history.

(56) References Cited

U.S. PATENT DOCUMENTS

2003/0207330 A1*  11/2003  Wescott et al. ................. 435/7.1
2004/0001827 A1*   1/2004  Dennis ......................... 424/144.1
2008/0206264 A1*   8/2008  Anglister et al. .......... 424/184.1

FOREIGN PATENT DOCUMENTS

| EP | 1 270 030 A1 | 1/2003 |
| WO | WO 01/21660 A1 | 3/2001 |
| WO | WO 01/83693 A2 | 11/2001 |
| WO | WO 2006/103101 A2 | 10/2006 |

OTHER PUBLICATIONS

Buck et al., "The Dogfish Peptides Scyliorhinin I and Scyliorhinin II Bind With Differential Selectivity to Mammalian Tachykinin Receptors," European Journal or Pharmacology, 144, pp. 109-111 (1987).
Fridell et al., "A Cyclized Peptide for Studies of Human Parvovirus B19 Infection," Journal of Immunological Methods, 138, pp. 125-128 (1991).
Jahns et al., "A New Cyclic Receptor-Peptide Prevents Development of Heart Dilatation and Failure Induced by Antibodies Activating Cardiac Beta1-Adrenergic Receptors," Circulation, American Heart Association, vol. 112, No. 17, Suppl. S., p. U53 (2005).
American, Heart, Association: 2007. Dallas; Heart disease and stroke statistics—2007 update. Circulation 115: e69-e171.
Anderton 2001 Immunology 104: 367-376.
Baba 2004 Eur. Heart J. 25: 1108-1115 [0425] Boivin 2005 Eur. J. Heart Fail. 4, suppl. 1:24 (104).
Caforio 2002 Eur. J. Heart Fail. 4: 411-417 [0427] Chiale 2001 Circulation 103: 1765-1771.
Chien 2000 Oncol. 27: 9-17.
Christ 2001 J. Mol. Cell. Cardiol. 33: 1515-1525.
Christ 2006 J. Mol. Cell. Cardiol. 41: 716-723.
Elies 1996 J. Immunol. 157: 4203-4211.
Engelhardt 1999 Proc. Natl. Acad. Sci. USA 96: 7059-7064.
Eriksson 2003 Nat. Med. 9: 1484-1490.
Fabrizio 1994 Drugs Ther. 8: 89-94.
Felix 2000 J. Am. Coll. Cardiol. 35: 1590-1598.
Ferrari 1995 J. Exp. Med. 182: 59-65.
Freedman 2004 J. Clin. Invest. 113: 1379-1382.
Fu 1993 J. Clin. Invest. 91: 1964-1968.
Goser 2006 Circulation 114: 1693-1702.
Hershko 2005 Ann. N.Y. Acad. Sci. 1051: 635-646.
Hoebeke 1996 Int. J. Cardiol. 54: 103-111.
Iwata 2001a J. Am. Coll. Cardiol. 37: 418-424.
Iwata 2001b Circ. Res. 88: 578-586.
Jahns 1996 Eur. J. Pharmacol. 316: 111-121.
Jahns 1999a J. Am. Coll. Cardiol. 34: 1545-1551.
Jahns 1999b Circulation 99: 649-654.
Jahns 2000 J. Am. Coll. Cardiol. 36: 1280-1287.
Jahns 2004 J. Clin. Invest. 113: 1419-1429.
Jahns 2006 Trends Cardiovasc Med 16: 20-24.
Khoynezhad 2007 Eur. J. Heart Fail. 9: 120-123.
Kuhl 2005 Circulation 112: 1965-1970.
Li 2006 177: 8234-8240.
Limas 1992 Am. Heart J. 123: 967-970.
Limas 1996 Int. J. Cardiol. 54: 113-116.
Limas 1997 Circulation 95: 1979-1980.

(Continued)

*Primary Examiner* — David Lukton
(74) *Attorney, Agent, or Firm* — Faegre Baker Daniels LLP

(57) ABSTRACT

The present invention relates to novel β-AR homologous cyclopeptide-mutants comprising only two cysteine residues able to form an intramolecular linkage, to linear peptides that can form these cyclopeptide-mutants and to nucleic acid molecules encoding these cyclopeptide-mutants and linear peptides. Moreover, vectors and recombinant host cells comprising said nucleic acid molecule and a method for producing the disclosed cyclopeptide-mutants are provided. Further provided is a composition comprising the peptides, nucleic acid molecules, vectors or host cells of the invention. The present invention also relates to therapeutic and diagnostic means, methods and uses taking advantage of the peptides of the invention and to means, methods and uses for detecting anti-β-adrenergic receptor antibodies like anti-β-adrenergic receptor antibodies.

54 Claims, 41 Drawing Sheets

(56) References Cited

OTHER PUBLICATIONS

Limas 2004 Am. J. Cardiol. 93: 1189-1191.
Lohse 2003 Circ. Res. 93: 896-906.
Luppi 1998 Circulation 98: 777-785.
MacLellan 2003 Nat. Med. 9: 1455-1456.
Maekawa 2007 Circulation 115: 5-8.
Magnusson 1994 Circulation 89: 2760-2767.
Magnusson 1996 Int. J. Cardiol. 54: 137-141.
Mahrholdt 2006 Circulation 114: 1581-1590.
Matsui 1995 Autoimmunity 21: 85-88.
Matsui 2001 Autoimmunity 43: 217-220.
Mobini 2004 Autoimmunity Rev. 3: 277-284.
Morita 2005 J. Clin. Invest. 115: 518-526.
Neumann 1990 J. Am. Coll. Cardiol. 16: 839-846.
Nikolaev 2007 J. Am. Coll. Cardiol. 50: 423-431.
Okazaki 2003 Nat. Med. 9: 1477-1483.
Okazaki 2005 Trends Mol Med 11: 322-326.
Pohlner 1997 Am. J. Cardiol. 80: 1040-1045.
Richardson 1996 Circulation, 93, 841-842.
Richardson, Report of the 1995 World Health Organization/International Society and Federation of Cardiology Task Force on the Definition and Classification of Cardiomyopathies 1996 Circulation, 93, 841-842.
Rosamond et al. "Heart Disease and Stroke Statistics—2007 Update: A Report From the American Heart Associateion Statistics Committee and Stroke Statistics Subcommittee." Circulation 106, 2007: 115:e69-e171.
Rose et al. Defining Criteria for Autoimmune Diseases (Witebsky's postulates revisited) 1993 Immunol. Today 14: 426-430.
Schultheiss et al. Immununological Analysis of Auto-Antibodies Against the AdenineNucleotide Translocator in Dilated Cardiomyopathy 1985 J. Mol. Cell. Cardiol. 17: 603-617.
Schultheiss, "Antibody-Mediated Enhancement of Calcium Permeability in Cardiac Myocytes" 1988 J. Exp. Med. 168: 2102-2109.
Schulze et al., Disturbance of myocardial energy metabolism in experimental virus myocarditis by antibodies against the adenine nucleotide translocator 1999 Cardiovasc. Res. 44: 91-100.
Sewald 2002 Peptides: Chemistry and Biology, Willey-VCH.
Smulski et al "Structural basis of the cross-reaction between an antibody to the Trypanosoma cruzi ribosomal P2(3 protein and the human (31 adrenergic receptor" 2006 FASEB J. 20: 1396-1406.
Stork et al. "Stimulating autoantibodies directed against the cardiac β1-adrenergic receptor predict increased mortality in idiopathic cardiomyopathy" 2006 Am. Heart J. 152: 697-704.
Wallukat et al. "Anti-/31-Adrenoceptor Autoantibodies with Chronotropic Activity from the Serum of Patients with Dilated Cardiomyopathy: Mapping of Epitopes in the First and Second Extracellular Loops" 1995 J. Mol. Cell. Cardiol. 27: 397-406.
Wallukat, "Specific Removal of b1-Adrenergic Autoantibodies from Patients with Idiopathic Dilated Cardiomyopathy" 2002 N. Engl. J. Med. 347: 1806.
Boivin et al. A novel receptor-homologous cyclic peptide prevents beta1-adrenoceptor antibody-induced progressive cardiomyopathy 2005 Eur. J. Heart Fail. 4, suppl. 1: 24 (104).
Witebsky et al. "Chronic thyroiditis and autoimmunization" 1957 J. Am. Med. Assoc. 164: 1439-1447.
Woodiwiss et al. "Reduction in Myocardial Collagen Cross-Linking Parallels Left Ventricular Dilatation in Rat Models of Systolic Chamber Dysfunction;" 2001 Circulation 103: 155-160.
Wang et al. "Effects of anti-peptide antibodies against human M2 muscarinic receptors on cardiac function in rats in vivo" 1996 Blood Pressure 3: 25-27.

* cited by examiner

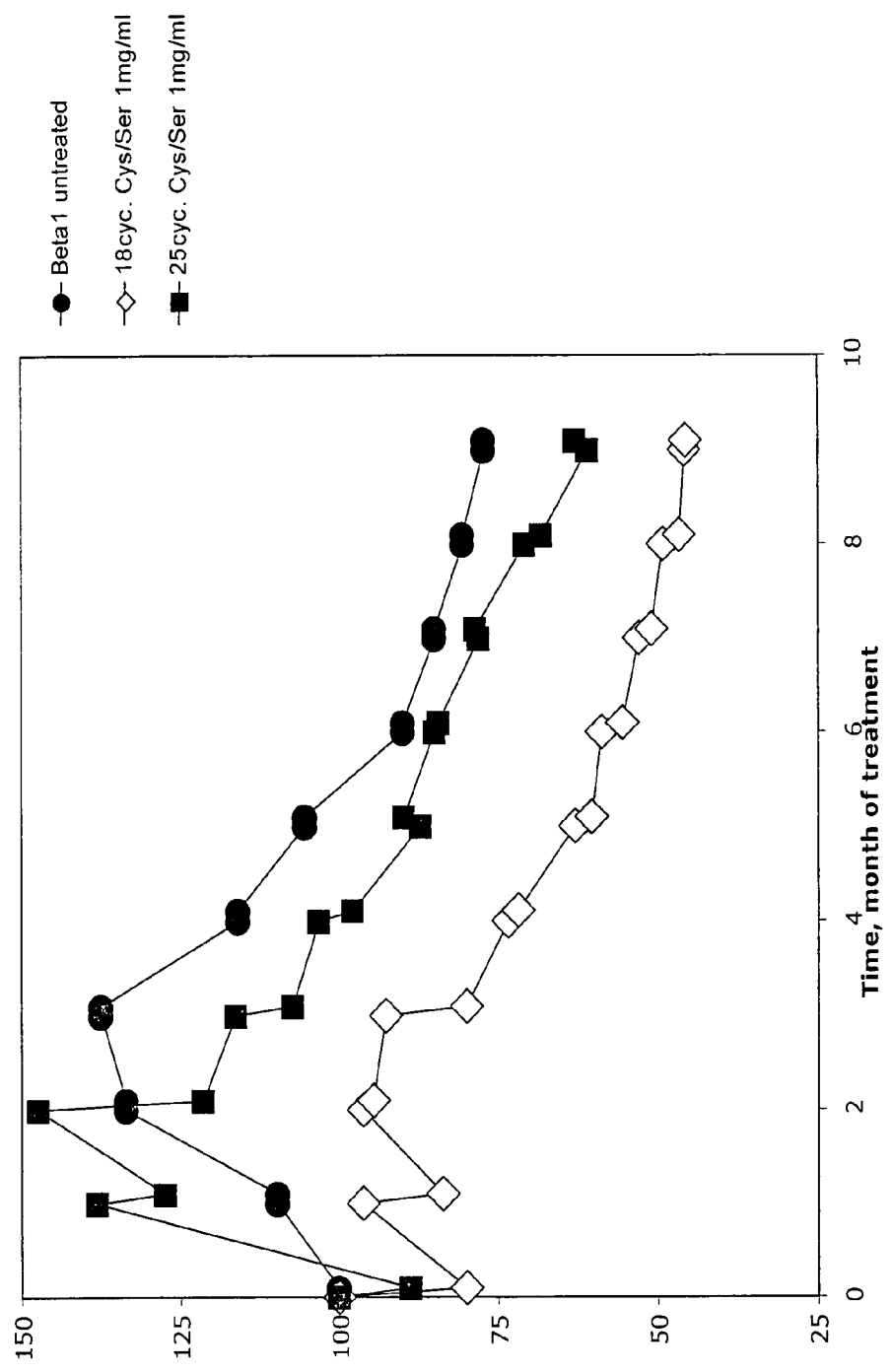
Figure 16.A

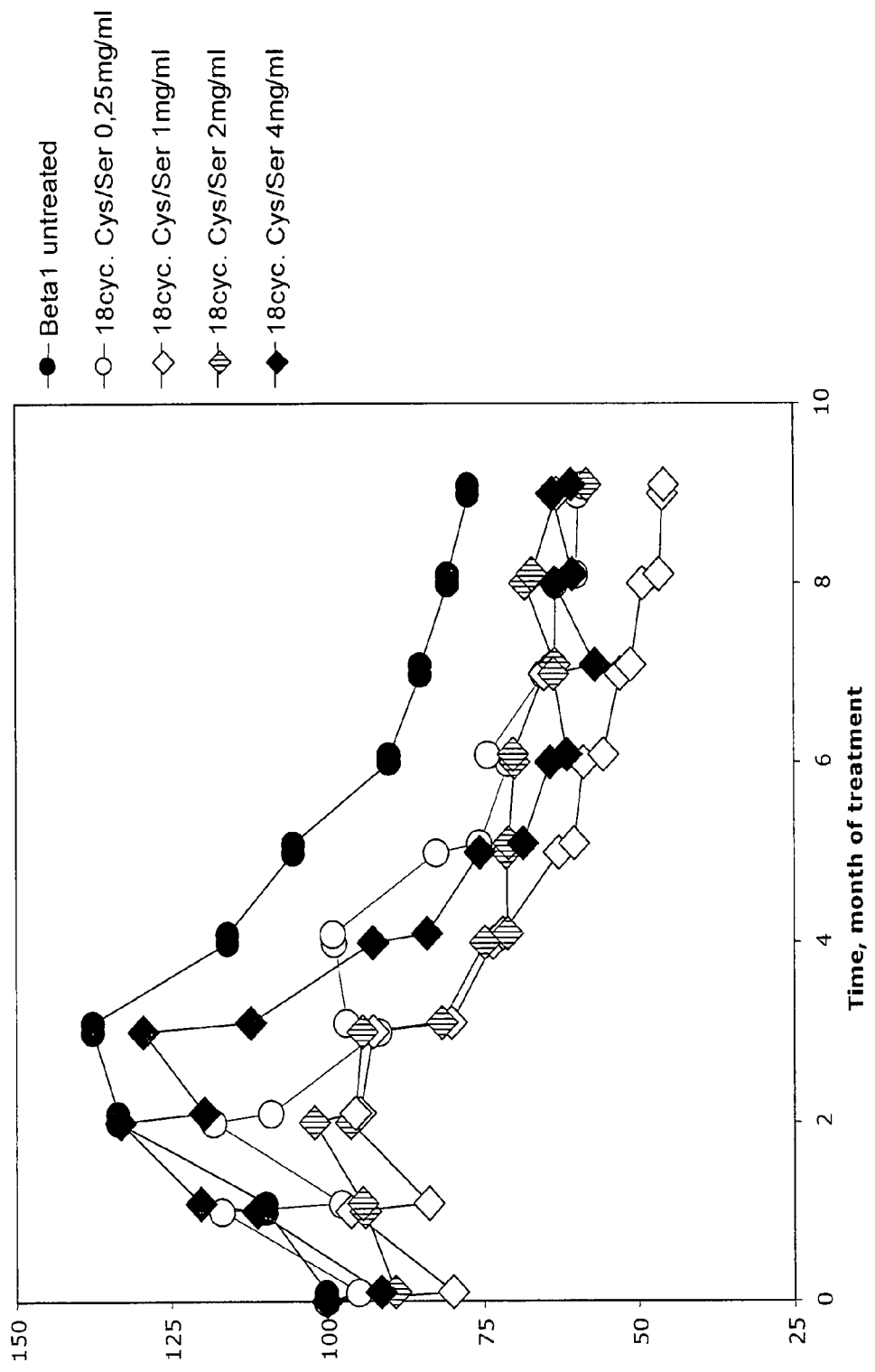
Figure 16.B

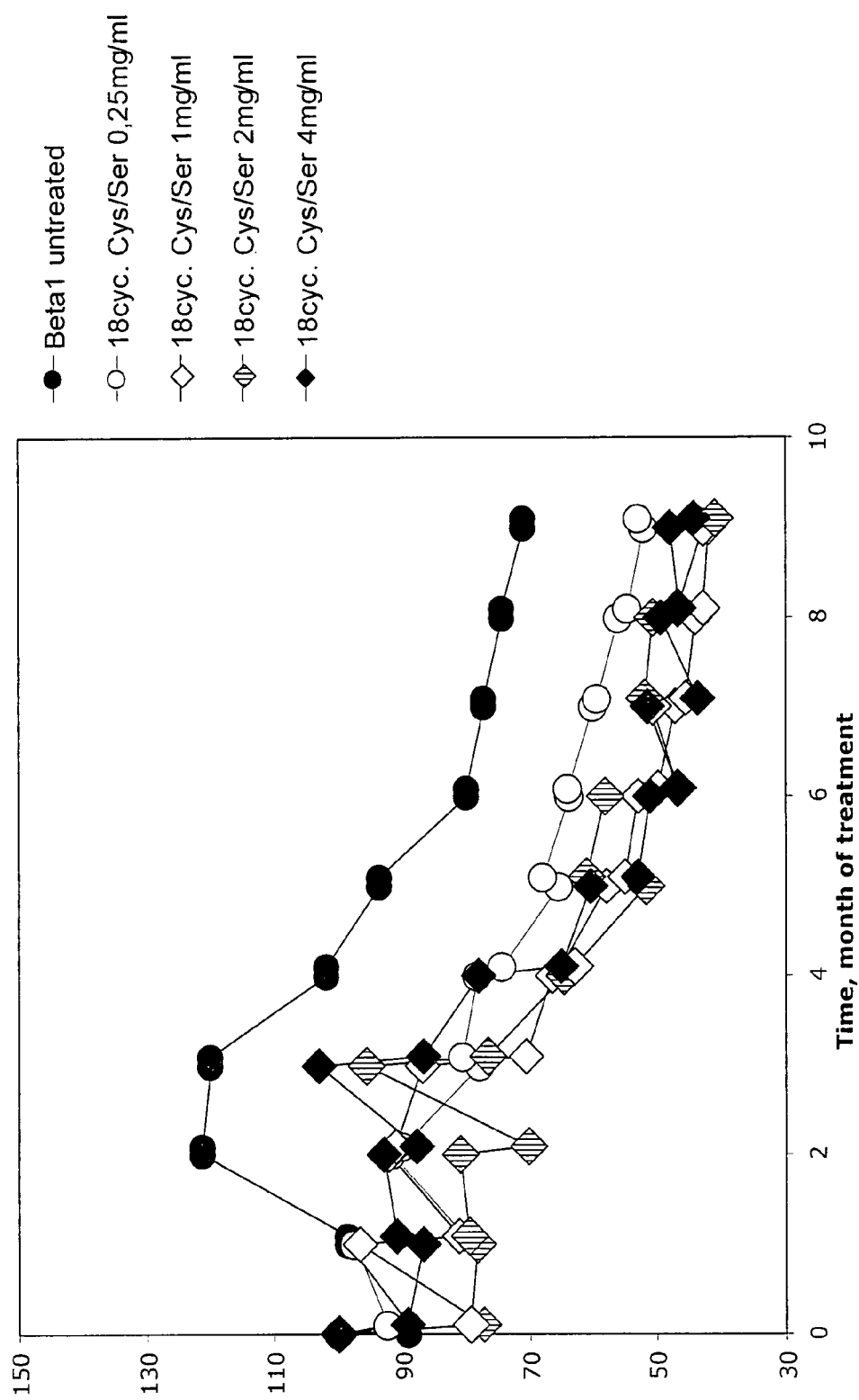
Figure 16.C

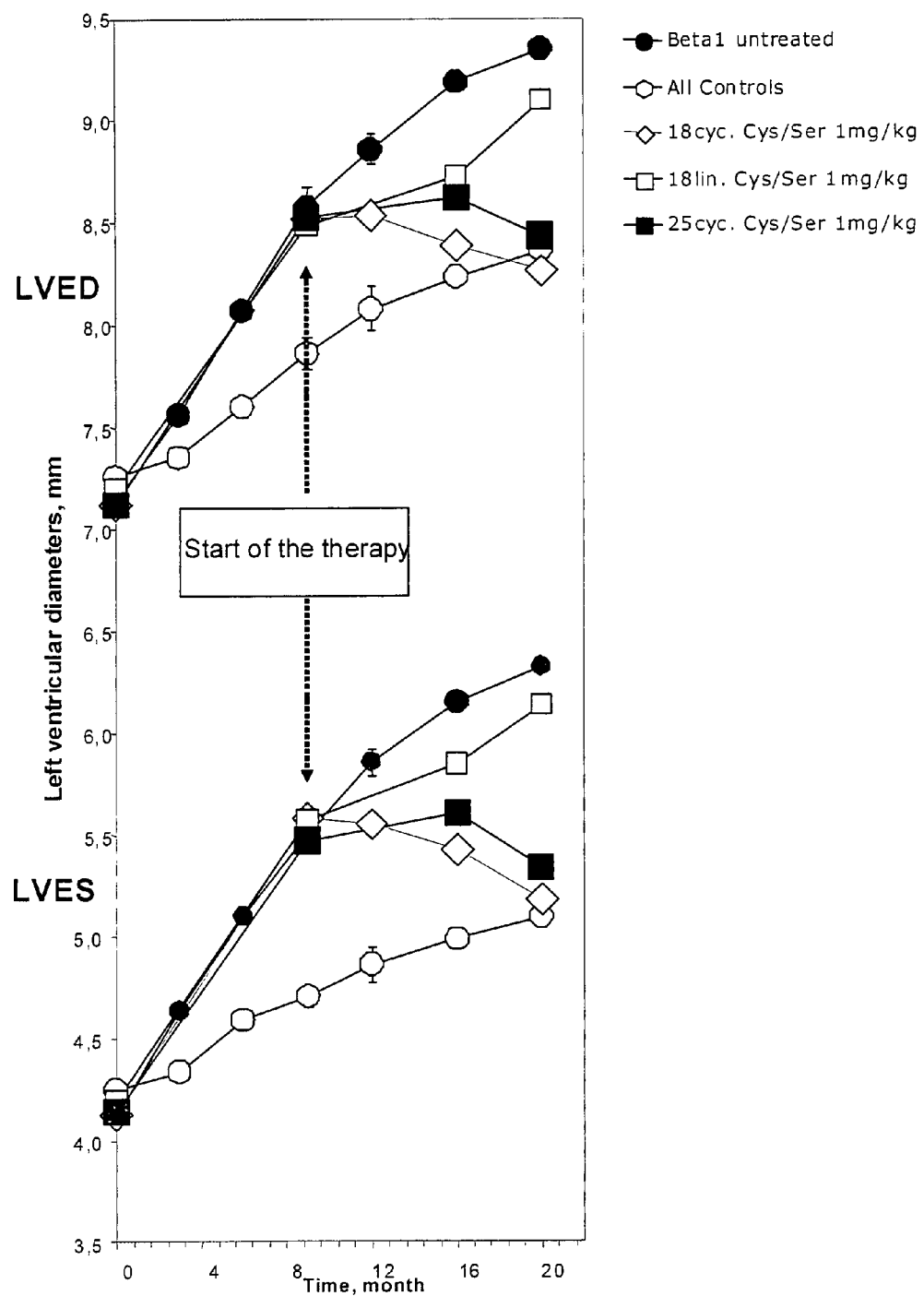
Figure 17. A

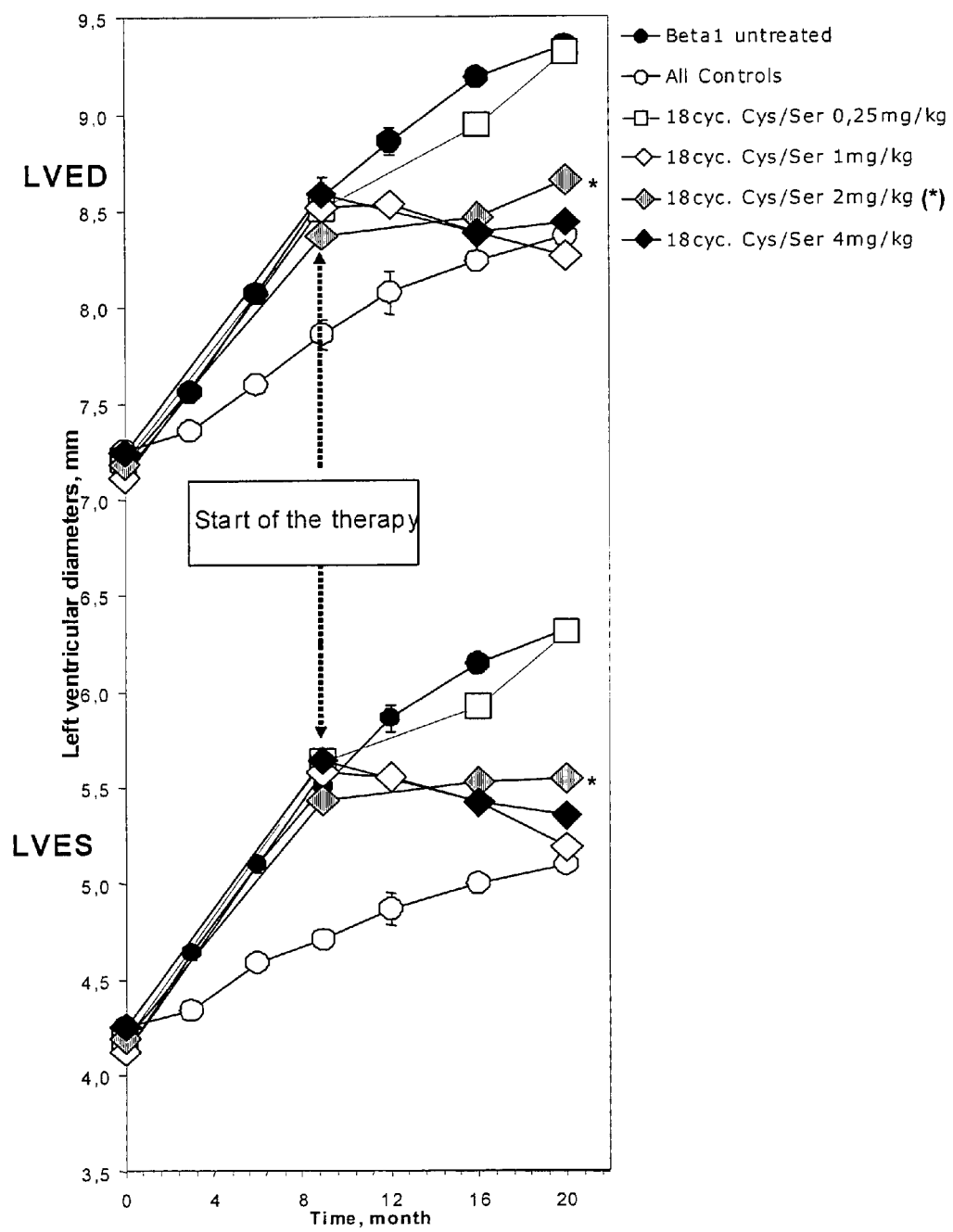
Figure 17. B

A

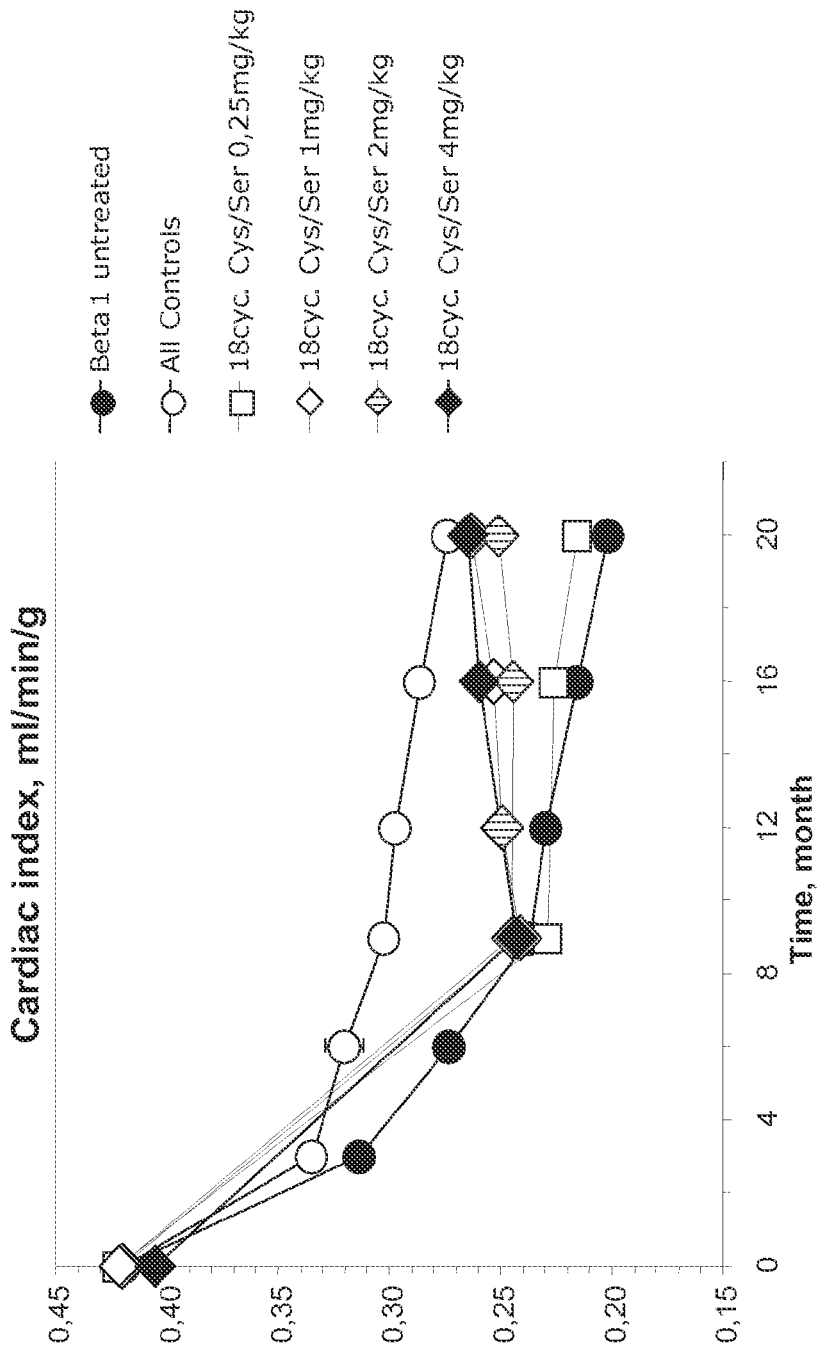

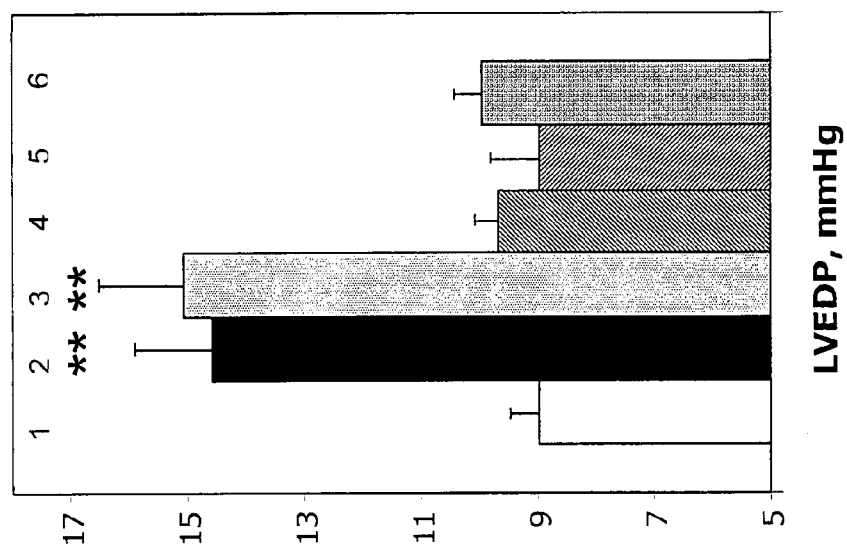
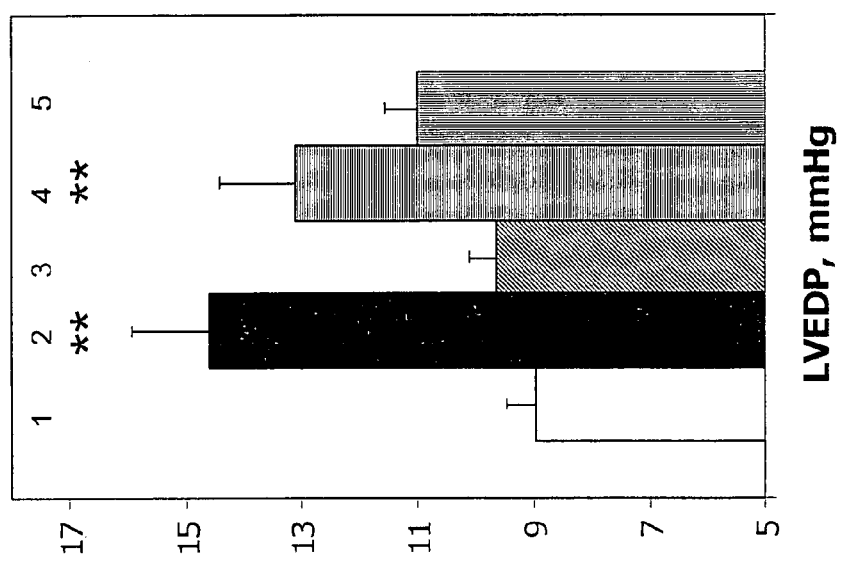
Figure 20C

Figure 27.
A
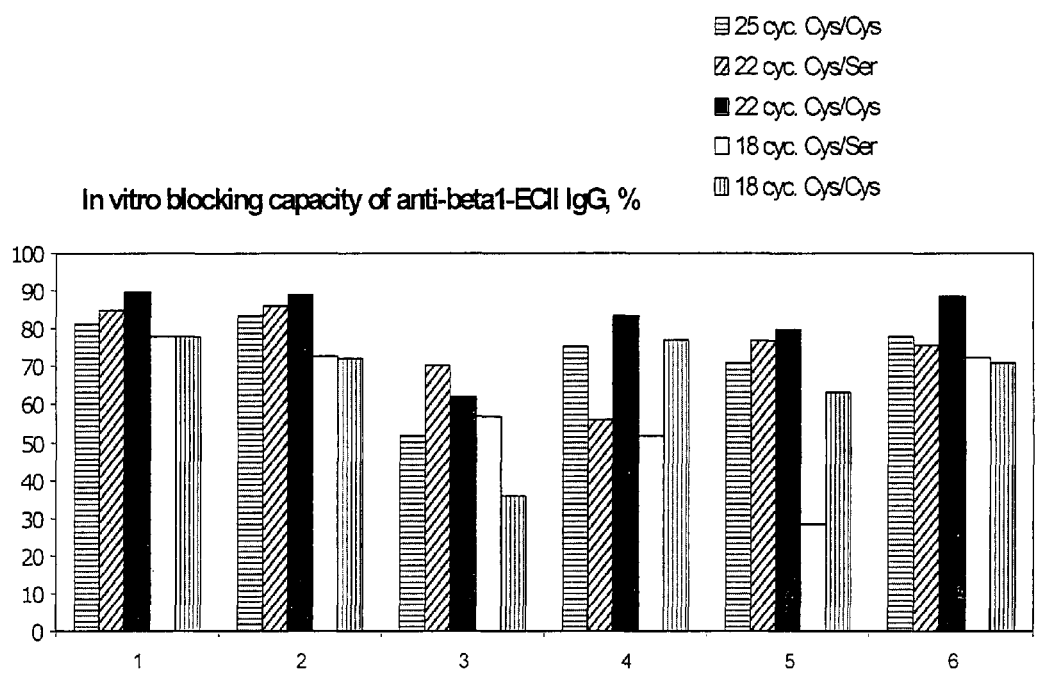
B
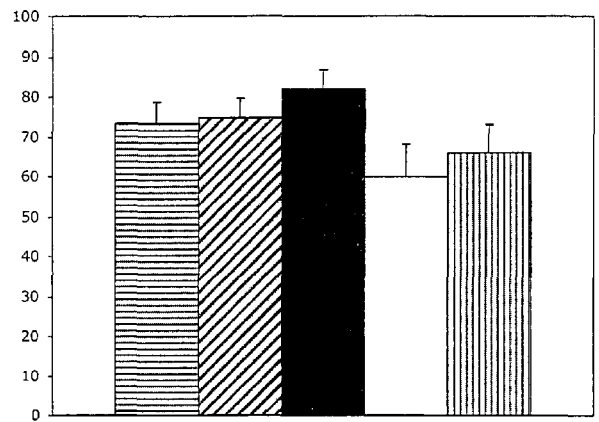

Figure 28.
A
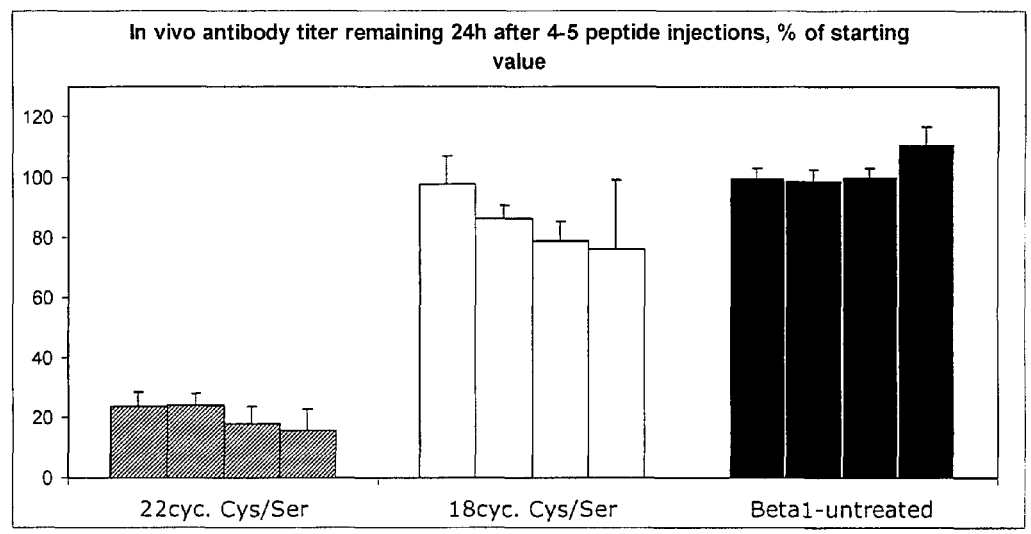
B
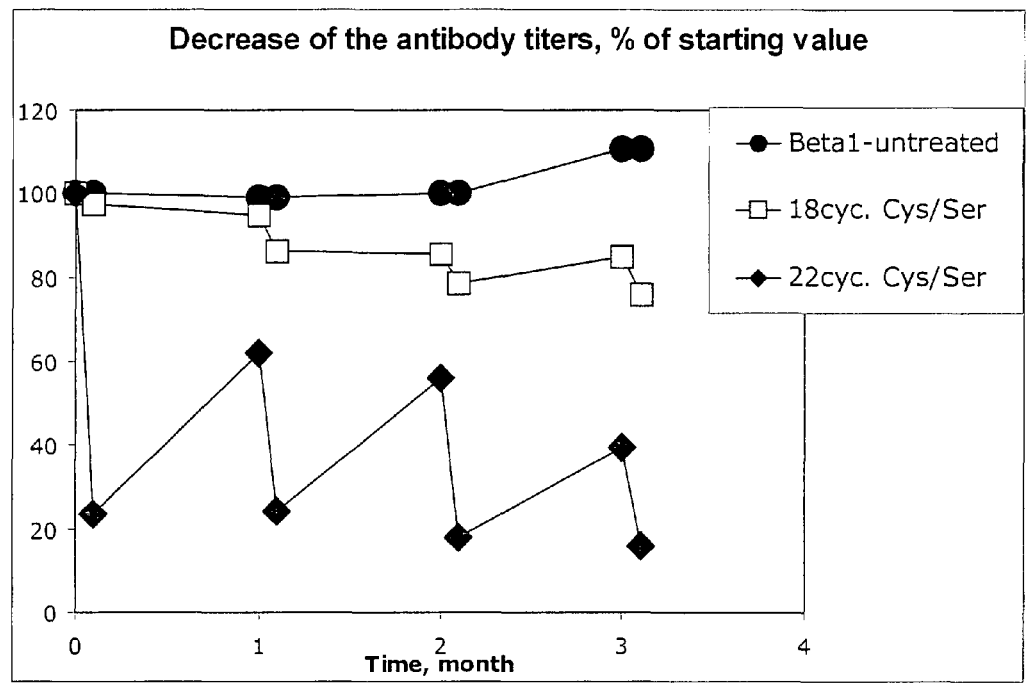

MUTANT DOUBLE CYCLIZED RECEPTOR PEPTIDES INHIBITING $\beta_1$-ADRENOCEPTOR ANTIBODIES

CROSS-REFERENCE TO RELATED APPLICATIONS

This application is the National Stage of International Application No. PCT/EP2008/006932, filed Aug. 22, 2008, which claims benefit to European Application No. 07016637.6 filed on Aug. 24, 2007. The contents of the applications cited above are incorporated by reference in their entirety.

FIELD OF THE INVENTION

The present invention relates to novel β-AR homologous cyclopeptide-mutants comprising only two cysteine residues able to form an intramolecular linkage, to linear peptides that can form these cyclopeptide-mutants and to nucleic acid molecules encoding these cyclopeptide-mutants and linear peptides. Moreover, vectors and recombinant host cells comprising said nucleic acid molecule and a method for producing the disclosed cyclopeptide-mutants are provided. Further provided is a composition comprising the peptides, nucleic acid molecules, vectors or host cells of the invention. The present invention also relates to therapeutic and diagnostic means, methods and uses taking advantage of the peptides of the invention and to means, methods and uses for detecting anti-β-adrenergic receptor antibodies like anti-$\beta_1$-adrenergic receptor antibodies.

BACKGROUND OF THE INVENTION

Progressive cardiac dilatation and pump failure of unknown etiology has been termed "idiopathic" dilated cardiomyopathy (DCM) (Richardson 1996 Circulation, 93, 841-842). DCM represents one of the main causes of severe heart failure with an annual incidence of up to 100 patients and a prevalence of 300-400 patients per million (AHA report 2007). Mutations in genes encoding myocyte structural proteins (Morita 2005) and several cardiotoxins, including alcohol, anthracyclines, and, more recently, therapeutically used monoclonal antibodies (e.g., trastuzumab) account for about one third of DCM cases (Chien 2000, Fabrizio and Regan 1994). The etiology of the remaining two thirds is still poorly understood, however.

At present the large majority of DCM is thought to arise from an initial (mostly viral) infection leading to acute myocarditis which upon activation of the immune system may progress to (chronic) autoimmune myocarditis resulting in cardiac dilatation and severe congestive heart failure; the latter progression occurs particularly, when associated (a) with the development of autoantibodies against distinct myocyte sarcolemmal or membrane proteins which are essential for cardiac function (Freedman 2004, Jahns 2006), or (b) with chronic inflammation of the myocardium and viral persistence (Kühl 2005). These recent findings are further strengthened by the fact, that patients with DCM often have alterations in both cellular and humoral immunity (Jahns 2006, Limas 1997, Luppi 1998, Mahrholdt 2006). Under such conditions an initial acute inflammatory reaction may proceed into a kind of low-grade inflammation (MacLellan 2003) facilitating the development of abnormal or misled immune responses to the primary infectious trigger (Freedman 2004, Kühl 2005, MacLellan and Lusis 2003, Maekawa 2007, Smulski 2006).

In the context of their humoral response a substantial number of DCM patients have been found to develop cross-reacting antibodies and/or autoantibodies to various cardiac antigens, including mitochondrial proteins (e.g., adenine nucleotide translocator, lipoamide and pyruvate dehydrogenase (Pohlner 1997, Schultheiss 1985, Schultheiss 1988, Schulze 1999)), sarcolemmal proteins (e.g., actin, laminin, myosin, troponin (Caforio 2002, Göser 2006, Li 2006, Neumann 1990, Okazaki 2003)), and membrane proteins (e.g., cell surface adrenergic or muscarinergic receptors (Christ. 2006, Fu 1993, Jahns 1999b, Magnusson 1994). From these, only a few selected antibodies appear to be able to cause myocardial tissue injury and to induce severe congestive heart failure by itself, however. In addition, the individual genetic predisposition (including the respective human leucocyte antigen (HLA)- and the major histocompatibility complex (MHC)-phenotype (Limas 1996)) may also significantly contribute to the susceptibility to self-directed immune reactions and the phenotypic expression of the disease (Limas 2004, MacLellan 2003).

Homologies between myocyte surface molecules such as membrane receptors and viral or bacterial proteins have been proposed as a mechanism for the elaboration of endogenous cardiac autoantibodies by antigen mimicry (Hoebeke 1996, Mobini 2004). Chagas' heart disease, a slowly evolving inflammatory cardiomyopathy, is one of the most prominent examples for this mechanism (Elies 1996, Smulski 2006). The disease originates from an infection with the protozoon *Trypanosoma cruzi*; molecular mimicry between the ribosomal P2β-protein of *T. cruzi* and the N-terminal half of the second extracellular loop of the $\beta_1$-adrenergic receptor ($\beta_1$-AR) results in generation of cross-reacting antibodies in about 30% of the Chagas' patients (Ferrari 1995). Because receptor-autoantibodies from patients with DCM preferentially recognize the C-terminal half of the same loop (Wallukat 1995), it was speculated that these antibodies might originate from molecular mimicry between the $\beta_1$-AR and a hitherto unidentified viral pathogen (Magnusson 1996). Another—probably more relevant—mechanism leading to the production of endogenous cardiac autoantibodies would be primary cardiac injury followed by (sudden or chronic) liberation of a "critical amount" of antigenic determinants from the myocyte membrane or cytoplasm, previously hidden to the immune system. Such injury most likely occurs upon acute infectious (myocarditis), toxic, or ischemic heart disease (myocardial infarction) resulting in myocyte apoptosis or necrosis (Caforio 2002, Rose 2001). Presentation of myocardial self-antigens to the immune system may then induce an autoimmune response, which in the worst case results in perpetuation of immune-mediated myocyte damage involving either cellular (e.g., T-cell), or humoral (e.g., B-cell) immune responses, or co-activation of both the innate and the adaptive immune system (Eriksson 2003, Rose 2001).

From a pathophysiological point of view, it seems reasonable to link the harmful (e.g., cardiomyopathy-inducing) potential of a heart-specific autoantibody to the accessibility and to the functional relevance of the corresponding target. Myocyte surface receptors are easily accessible to autoantibodies (Okazaki 2005). The two most promising candidates are the cardiac $\beta_1$-AR (representing the predominant adrenocepter subtype in the heart) and the M2-muscarinic acetylcholine receptor; against both receptors autoanti-bodies have been detected in DCM patients (Fu. 1993, Jahns 1999b, Matsui 1995). Whereas anti-muscarinic antibodies (exhibiting an agonist-like action on the cardiac M2 acetylcholine-receptor) have been mainly associated with negative chronotropic effects at the sinuatrial level (e.g., sinus node dysfunction, atrial fibrillation (Baba 2004, Wang. 1996)), agonistic anti-$\beta_1$-AR antibodies have been associated with both the occurrence of severe arrhythmia at the ventricular level (Christ 2001, Iwata 2001a), and the development of (maladaptive) left ventricular hypertrophy, finally switching to left ventricular enlargement and progressive heart failure (Iwata 2001b, Jahns 1999b, Khoynezhad 2007). Both autoantibodies appear to be directed against the second extracellular loop of the respective receptors. To generate an autoimmune response, myocyte membrane proteins (e.g., receptors) must be degraded to small oligopeptides able to form a complex with a MHC or HLA class II molecule of the host (Hoebeke 1996). In case of the human $\beta_1$-AR computer-based analysis for potential immunogenic amino-acid stretches has shown, that the only portion of the receptor molecule containing B- and T-cell epitopes and being accessible to antibodies was in fact the predicted second extracellular receptor loop ($\beta_1$-EC$_{II}$) (Hoebeke 1996). This might explain the successful use of second loop-peptides for the generation of $\beta_1$-specific receptor antibodies in different animal-models (Iwata 2001b, Jahns. 2000, Jahns 1996). Moreover, in the last decade several groups have independently demonstrated that second loop antibodies preferentially recognize intact native $\beta_1$-AR in various immunological assays (whole cell-ELISA, immunoprecipitation, immunofluorescence), indicating that they are "conformational" (Hoebeke 1996, Jahns 2006). Functional testing revealed that the same antibodies also affected receptor function, such as intracellular cAMP-production and/or cAMP-dependent protein kinase (PKA) activity, suggesting that they may act as allosteric regulators of $\beta_1$-AR activity (Jahns 2000, Jahns 2006). The structure of the $\beta_1$-AR was also analyzed by Warne (2008 Nature. DOI:10. 1038).

Following Witebsky's postulates (Witebsky 1957) indirect evidence for the autoimmune etiology of a disease requires identification of the trigger (e.g., the responsible self-antigen), and induction of a self antigen-directed immune response in an experimental animal, which then must develop a similar disease. Direct evidence, however, requires reproduction of the disease by transfer of homologous pathogenic antibodies or autoreactive T-cells from one to another animal of the same species (Rose 1993).

To analyze the pathogenetic potential of anti-$\beta_1$-AR antibodies, Jahns et al. has chosen an experimental in vivo approach, which met the Witebsky criteria for direct evidence of autoimmune diseases. DCM was induced by immunizing inbred rats against $\beta_1$-EC$_{II}$ (100% sequence homology between human and rat; indirect evidence); then the disease was reproduced in healthy animals by isogenic transfer of rat anti-$\beta_1$-AR "autoantibodies" (direct evidence) (Jahns 2004). The animals developed progressive left ventricular (LV)-dilatation and dysfunction, a relative decrease in LV wall-thickness, and selective downregulation of $\beta_1$-AR, a feature that is also seen in human DCM (Lohse 2003).

These results, together with an agonist-like short-term effect of the antibodies in vivo (Jahns 2004), suggest that both the induced and the transferred cardiomyopathic phenotypes can be attributed mainly to the mild but sustained receptor activation achieved by stimulatory anti-$\beta_1$-AR antibodies. This hypothesis is supported by the large body of data available on the cardiotoxic effects of excessive and/or long term $\beta_1$-AR activation seen after genetic or pharmacological manipulation (Engelhardt 1999, Woodiwiss 2001). Therefore, anti-$\beta_1$-AR induced dilated immune-cardiomyopathy (DiCM) can now be regarded as a pathogenetic disease entity of its own, together with other established receptor-directed autoimmune diseases such as myasthenia gravis or Graves' disease (Freedman 2004, Hershko 2005, Jahns 2004, Jahns 2006).

The clinical importance of cardiac autoantibodies is difficult to assess, since low titers of such antibodies can also be detected in the healthy population as a part of the natural immunologic repertoire (Rose 2001). However, regarding functionally active anti-$\beta_1$-AR antibodies previous data from Jahns et al. has demonstrated that their prevalence is almost negligible in healthy individuals (<1%) provided that a screening procedure based on cell-systems presenting the target (e.g., the $\beta_1$-AR) in its natural conformation is used (Jahns 1999b). By employing the latter screening method, occurrence of anti-$\beta_1$-AR autoantibodies could also be excluded in patients with chronic valvular or hypertensive heart disease (Jahns 1999a). In contrast, the prevalence of stimulating anti-$\beta_1$-AR was ~10% in ischemic (ICM) and ~30% in dilated cardiomyopathy (DCM) (Jahns 1999b), which was significantly higher than in healthy controls, but in the lower range of previous reports on DCM collectives (33% to 95% prevalence) (Limas 1992, Magnusson 1994, Wallukat 1995). It seems conceivable that differences in screening methods aiming to detect functionally active anti-$\beta_1$-AR autoantibodies most likely account for the wide range of prevalences reported in the past (Limas 1992). In fact, only a minor fraction of ELISA-defined human anti-$\beta$-AR autoantibodies was able to bind to cell surface located native $\beta$-AR. Only this fraction recognized (as determined by immunofluorescence) and activated (as determined by increases in cellular cAMP and/or PKA activity) human $\beta_1$-AR expressed in the membrane of intact eukaryotic cells (Jahns 2000, Jahns 1999b). Therefore, cell systems presenting the target in its natural conformation represent an essential tool in the screening for functionally relevant anti-$\beta$-AR autoantibodies (Nikolaev 2007).

Clinically, the presence of anti-$\beta_1$-AR autoantibodies in DCM has been shown to be associated with a more severely depressed cardiac function (Jahns 1999b), the occurrence of more severe ventricular arrhythmia (Chiale 2001), and a higher incidence of sudden cardiac death (Iwata 2001a). Recent data comparing antibody-positive with antibody-negative DCM patients over a follow-up period of more than 10 years not only confirmed a higher prevalence of ventricular arrhythmia in the presence of activating anti-$\beta_1$-AR, but also revealed that antibody-positivity predicted an almost three-fold increased cardiovascular mortality-risk (Stork 2006). Taken together, the available clinical data underscore the pathophysiological relevance of functionally active anti-$\beta_1$-AR antibodies in DCM.

One today generally accepted pharmacological strategy would be the use of beta-blocking agents in order to attenuate or even abolish the autoantibody-mediated stimulatory effects, at least if $\beta$-blockers can indeed prevent the antibody-induced activation of $\beta_1$-AR (Freedman 2004, Jahns 2000, Matsui 2001, Jahns 2006). New therapeutic approaches actually include elimination of stimulatory anti-$\beta_1$-AR by non-selective or selective immunoadsorption (Hershko 2005, Wallukat 2002), or direct targeting of the anti-$\beta_1$-EC$_{II}$ antibodies and/or the anti-$\beta_1$-EC$_{II}$ producing B-cells themselves (that is, induction of immune tolerance) (Anderton 2001). Non-selective immunoadsorption, however, because of an increased risk of infection after immunoglobulin depletion, requires the substitution of human IgG on the ground of safety (Felix 2000) with all possible side effects of substituted human proteins known in the art including severe anaphylactic reactions and death.

WO 01/21660 discloses certain peptides homologous to epitopes of the 1$^{st}$ and the 2$^{nd}$ loop of $\beta_1$-AR, and proposes to apply these peptides for medical intervention of dilatative cardiomyopathy (DCM). Even if WO 01/21660 mentions marginally that peptides may be modified in order to protect them against serum proteases, for example by cyclization, corresponding examples and embodiments are not given and any in vitro or in vivo effect of the proposed peptides on the course of DCM or on the course of receptor-antibody titers is not shown. Moreover, in WO 01/21660 intends to rely on the above mentioned non-selective immunoadsorption approaches bearing the correspondingly mentioned risks.

In contrast thereto, the newly developed $\beta_1$-EC$_{II}$-homologous cyclopeptides (e.g. $\beta_1$-EC$_{II}$-CPs) were employed six weeks after the active induction of stimulatory anti-$\beta_1$-EC$_{II}$ antibodies. $\beta_1$-EC$_{II}$-CPs are cyclopeptides containing 3 cysteine residues and hence, can form intramolecular bonds, whereby there is a potential option to form two intramolecular bonds (besides the cyclization between the N- and C-terminus), individually. $\beta_1$-EC$_{II}$-CP significantly reduced the amount of circulating anti-$\beta_1$-EC$_{II}$ antibodies and effectively prevented development of cardiac dilatation and dysfunction (Boivin 2005). The above-mentioned $\beta_1$-EC$_{II}$-CPs were also disclosed in WO 2006/103101.

BRIEF SUMMARY OF THE INVENTION

In view of the present art, the technical problem underlying the present invention is the provision of improved and easily obtainable means and methods for the medical intervention of diseases related to anti-$\beta$-AR antibodies, particular to anti-$\beta_1$-EC$_{II}$ antibodies.

The technical problem is solved by provision of the embodiments characterized in the claims.

Accordingly, in a first aspect, the present invention relates to $\beta$-AR homologous cyclopeptide-mutants (also termed herein as "cyclic peptides" or "cyclopeptides" and the like), particularly to $\beta_1$-AR homologous cyclopeptide-mutants, namely $\beta_1$-EC$_{II}$ homologous cyclopeptide-mutants. The structure of these cyclopeptide-mutants/cyclic peptides is characterized by being able to form only one individual intramolecular disulphide bond.

Particularly, in the first aspect, the present invention relates to a cyclic peptide of formula I:

$$\text{cyclo}(x\text{-}x_h\text{-Cys-}x\text{-}x^a\text{-}x^b\text{-}x^c\text{-}x\text{-Cys-}y\text{-}x_i\text{-}x), \quad (I)$$

wherein
a) x is an amino acid other than Cys;
b) h is any integer from 1 to 15;
c) i is any integer from 0 to 14;
d) one of $x^a$, $x^b$ and $x^c$ is Pro;
e) y is an amino acid other than Cys; and
f) the cyclic peptide consists of at least 16 and of at most 25 amino acids.

Particular preferred embodiments, as discussed below, are specific cyclic peptides as depicted in formulas VII, IX, IX', VI or VIII.

DETAILED DESCRIPTION OF THE INVENTION

The present invention solves the above identified technical problem since, as documented herein below and in the appended examples, it was surprisingly found that mutant cyclic peptides containing only two cysteines, which can form one single defined, individual intramolecular disulfide bond, are also able to inhibit anti-$\beta$-AR antibodies, and are useful in inhibiting stimulatory anti-$\beta_1$-AR antibodies.

It was furthermore surprisingly found in context of the present invention that the peptide-mutants with a cyclic structure (i.e. the cyclic peptides) as described and provided herein are superior to their linear counterparts in terms of both, the recognition or scavenging of conformational anti-$\beta$-AR antibodies and their antibody-neutralizing (i.e. pharmaceutical) potential. These findings were obtained by the exemplarily employment of ELISA competition assays and functional (cAMP) FRET-assays, respectively.

In addition, the inventive cyclic peptides comprising only two cysteines, which can form one single defined, individual intramolecular disulfide bond, can easily be obtained/manufactured, biochemically characterized and purified. This is particularly true when pure fractions of the same cyclopeptide isomers are required. In context of this invention, a mixture of cyclopeptide isomers, i.e. stereo-isomers, comprising cyclopeptide isomers with different intramolecular disulphide bonds is avoided. As documented herein below, because of this avoidance a specific and clean medical product (fulfilling GMP standards) comprising isomers all with the same intramolecular disulfide bond can be obtained.

It was a further, surprising finding in context of the present invention, and as illustrated in the appended examples, that the exact nature of the exchange of one of the cysteine residues with a serine residue markedly determined the antibody neutralizing potency of cyclic peptides derived from $\beta_1$-EC$_{II}$.

Particularly, a Cys→Ser exchange like that at position 18 of the herein exemplarily and preferably disclosed 25-meric cyclopeptide (formulas VII/IX), at position 17 of the herein exemplarily and preferably disclosed 22-meric cyclopeptide (formula IX') or at position 14 of the herein exemplarily and preferably disclosed 18-meric cyclopeptide (formulas VI/VIII), respectively, yields cyclic peptides (Cys-Ser cyclic peptides) with excellent antibody-neutralizing and pharmacological effects in vitro (FIGS. 4-11 and 27), whereas the Cys→Ser exchange at position 17, 16 or 13 of the herein exemplarily disclosed 25-meric, 22-meric or 18-meric cyclic peptide, respectively (Ser-Cys cyclic peptides), had, surprisingly, almost no inhibitory effect. This inhibitory effect could neither be detected regarding their properties as antibody-scavengers nor in terms of their capability of inhibiting functional antibody-effects; as neutralization of receptor-stimulation in vitro as shown in, for example, FIGS. 4-10).

It was a further finding in context of the present invention that an almost perfect steric imitation of the ECII-$\beta_1$-AR domain can be obtained by a second loop-homologous cyclized peptide comprising 22 amino acids, for example 21 amino-acids of the published original primary sequence of the human $\beta_1$-AR, i.e. amino-acids 200 (R) to 221 (T) (numbering according to Frielle et al. 1987, PNAS 84, pages 7920-7924), with an additional amino acid residue (for example glycine (G)) to close the synthetic cycle at position 222 to form a 22 AA cyclopeptide.

Without being bound by theory, the cardio-protective and immunomodulating activity of the cyclic peptides largely depends on their conformation. It was additionally found out in context of this invention that an introduction of the smallest naturally occurring amino-acid glycine at the (predicted) ring closure site (or at the position corresponding thereto) leads to an enhanced binding of anti-$\beta_1$-AR autoantibodies, i.e. apparently further enhances the similarity of the 22 AA cyclopeptide with the ECII-$\beta_1$-AR domain. Particularly, the appended examples, inter alia, indicate that the cyc22AA cyclopeptides have a significantly higher antibody-blocking efficiency in vivo than other ECU-imitating cyclopeptides larger (i.e., cyc25AA peptides) or smaller (i.e., cyc18AA peptides). Computer-aided modelling studies with said 22 AA cyclopeptide confirmed an excellent imitation of the predicted second extracellular loop structure with a calculated difference in size of only 4.5 Ångström (4.5 Å) at the base of the cyclopeptide (opposed to the assumed antibody-binding site), when compared with the predicted native second extracellular loop backward helix (see also appended FIG. 24). Moreover, it was demonstrated herein and in the appended examples that particularly said 22 AA cyclopeptide reduces the titer of anti-$\beta_1$-AR autoantibodies with an extraordinary high efficiency.

Since replacement of one of the three cysteines present in the cyclic 22 AA peptide allows for the introduction of a reinforced disulfide bridge (as a second "internal" cycle, generated by double cyclization) between the two remaining cysteines, the resultant cyclic 22 AA cyclopeptide also represents a biochemically unambiguously defined product (see also FIGS. 25 and 26).

It was also surprisingly found that a Gln↔D-Glu exchange at position 25 (25-meric cyclopeptide-mutants) or 18 (18-meric cyclopeptide-mutants) did not significantly influence the blocking capacity of the cyclopeptides, regardless of their length; i.e., 25 versus 18 amino-acids as shown in FIGS. 6,7 and 9).

The examples below also document that the cyclic peptides as disclosed herein show improved features, for example as compared to peptides comprising three Cys residues (for example the Cys/Cys cyclic peptides disclosed in WO 2006/103101). Examples of improved features of the cyclic peptides of this invention are an extremely good capacity for blocking anti-$\beta_1$-AR antibodies and their advanced producibility according to GMP standards.

In context of the present invention, the in vitro findings were generally confirmed in in vivo tests (FIGS. 12-16 and 28/29). Interestingly, the difference in the blocking efficiency of the $Cys_{18,17 \text{ or } 14} \rightarrow Ser_{18,17 \text{ or } 14}$ mutated cyclopeptides compared with that of the linear peptides was even more pronounced in vivo (FIGS. 5, 7, and 14-16). The established rat model of anti-beta1-adrenergic antibody-induced autoimmune-cardiomyopathy (Jahns, 2004) served to assess the efficacy of the generated beta1-ECII homologous cyclopeptide mutants in vivo. The in vivo data indicate, that the efficiency of the disclosed mutated cyclopeptides (e.g. 18AA Cys/Ser cyclopeptide) might equally depend on the administered dose (FIGS. 14-16).

In addition, the in vivo experiments demonstrated that the antibody-blocking capacity of mutant cyclopeptides is seemingly not affected by a reduction in the number of amino acids from a 25-meric to a 18-meric cyclopeptide; both in vitro and in vivo data demonstrate an excellent comparability of these two 2 cysteine-containing single disulfide bond 25AA Cys/Ser or 18AA Cys/Ser cyclopeptide mutants. It should be noted, however, that both 1.0 mg/kg 25AA-meric Cys/Ser as well as high dose (i.e., 4.0 mg/kg Bw) 18AA-meric Cys/Ser mutants led to an initial transient increase in antibody-titers, and thus postponed a significant reduction in receptor antibody titers to the third or fourth cyclopeptide-application (third or fourth month of therapy). This phenomenon did not occur with either 1.0 or 2.0 mg/kg Bw doses of 18AA Cys/Ser cyclopeptide mutants (FIG. 16B,C).

Animals to which particularly the 18meric or 25meric cyclic peptide as disclosed herein was administered showed no signs of abnormalities, and only the desired effect of the administered peptide, namely the blockage of anti-$\beta_1$-AR antibodies, was detected. Accordingly, the peptides as provided herein display no undesired side effects or toxicity at the applied dosage regimen. This was further demonstrated herein by showing that no toxicity on the kidney was exerted by the cyclic peptides of the invention (no mechanical obstruction of glomerular membranes was detected; FIG. 23). In addition, the routine laboratory parameters indicative of kidney function remained normal under 12 months of CP-application and did not differ from untreated control animals. (FIG. 22A, B).

The antibody-blocking capacity of mutated cyclopeptides of this invention is not affected by the length of the peptide, as long as the peptide is not shorter than 18 AA and not longer than 25 AA. This was exemplarily demonstrated by the reduction of the number of amino acids of the peptide from 25 to 18. Within the range of 18 to 25 amino acids, cyclic peptides having 22 amino acids are most effective in accordance with this invention and, accordingly, are a particular preferred embodiment. An example of such a particular preferred 22mer cyclic peptide is shown in formula IX'.

One advantage of the cyclopeptide mutants of the present invention is—by mutating one particular cysteine (preferably the Cys corresponding to Cys 216 of the amino acid sequence of $\beta_1$-AR) to a serine-residue and by reinforcing formation of the unique possible intramolecular S—S bridge through a second S—S specific cyclization procedure—that their conformational restraint is increased. In comparison to peptides known in the art, this increased restraint of the inventive peptides leads to a molecule that better mimics the epitope presented in the native conformation of the second $\beta_1$-$EC_{II}$ loop on the cell surface.

Beta blockers, such as bisoprolol, which are used in the art for the treatment of DCM and other diseases which are caused by stimulatory anti-$\beta_1$-AR antibodies, significantly reduce both heart rate and blood pressure. In contrast thereto, an in vivo-application of the mutant cyclopeptides of the present invention has no negative impact on lung function, heart rate or blood pressure (FIGS. 20 and 21). In addition, a number of important laboratory parameters to assess liver and kidney function were not influenced by the repeated cyclopeptide injections (FIGS. 22a/b and 23). Therefore, the cyclic peptides of the present invention are, inter alia, particularly suitable for the treatment of distinct patient groups which otherwise could not be treated by using a beta blocker, i.e. patients who, for example, already suffer from bradycardia or for whom the use of beta blockers is not possible because of contraindications (like those suffering from obstructive lung disease or hypotension).

As mentioned, a further advantage of the means and methods of the present invention, particularly over means and methods taking advantage of (cyclic)peptides derived from $\beta_1$-$EC_{II}$ still having 3 cysteines (as, for example disclosed in WO 2006/103101), is that the formation of mixtures of cyclopeptide isomers can be avoided.

The biochemical characterization of a mixture of different cyclopeptide isomers, formed during cyclization of peptides comprising three or more Cys residues, is laborious. Accordingly, the production of pure cyclic peptide fractions containing only one sort of a cyclopeptide isomer is time and cost intensive, when taking advantage of peptides comprising three or more Cys residues. This is particularly true, when the cyclic peptides are produced under GMP standards.

In contrast thereto, the cyclic peptides of the present invention can easily be characterized and produced as pure fractions of the same isomer. This leads to a high reproducibility. The particular advantage of the peptides of the present invention is that mixtures of isomers, which have to be separated and must be characterized in laborious testings, are avoided, and that at least one further production step (separation and/or biochemical characterization) is finally omitted (see also Sewald 2002).

The present invention is, inter alia, based on the experiments described in the appended examples.

In context of these examples, one of the cysteines either at position 17 or at position 18 of the $\beta_1$-EC$_{II}$ 25AA-cyclopeptide was replaced by a serine residue (Cys$_{17 \, or \, 18}$→Ser$_{17 \, or \, 18}$ mutation), so that only one individual, single intramolecular disulfide bond (S—S) can be formed (FIG. 1). Measures like this provides the potential to reduce side effects and to maintain or to increase the biological efficacity of the constructs of the present invention. The cyclic peptides of this invention can be obtained, in contrast to the peptides of the prior art which form mixtures of isomers, by simple, robust and highly reproducible manufacturing processes. These can be scaled up efficiently. Furthermore these processes avoids separation of isomers mixtures and are suitable for GMP standards. The appended examples provide for corresponding manufacturing/production methods.

In the appended examples, the cyclization of the inventive peptides was, inter alia, obtained by the introduction of a "DGlu" mutation, e.g. at the (ring) closure site of the cyclic peptide; Gln↔DGlu mutation as shown in FIG. 2.

Furthermore, the number of amino acids (AA) was reduced from 25AA to 22AA and further to 18AA in further sets of cyclopeptide-mutants of the present invention. This measure provides the potential to minimize the potential immunologic side effects of the constructs. The 18AA cyclopeptide-mutants contained a cysteine→serine exchange either at position 14 or at position 13 (18AA containing Cys$_{13}$-Ser$_{14}$ or Ser$_{13}$-Cys$_{14}$ mutant cyclopeptides, respectively), either combined with a (further) glutamine-exchange/D-glutamic acid, e.g. at the ring closure site of the cyclic peptide (Gln↔D-Glu mutation), or not (FIG. 2). The 22AA cyclopeptide-mutants contained a cysteine-serine exchange at position 17 (22AA containing Cys$_{16}$-Ser$_{17}$), optionally combined with the introduction of a Gly residue at position 22 (a possible ring closure site of the cyclic peptide; FIG. 24).

Taken together, the herein provided experimental in vitro data as well as the in vivo data clearly demonstrate that the antibody-blocking capacity of the disclosed mutant cyclopeptides is not affected by the reduction of the number of amino acids from a 25-meric to a 18-meric cyclopeptide when using a dose ranging from 0.25 to 5.0 mg/kg body weight (Bw) and in particular from 1.0 to 2.0 mg/kg Bw. In vitro and in vivo data demonstrate an excellent comparability of the two 2 cysteine-containing single disulfide bond 25AA Cys/Ser (formulas VII/IX) or 18AA Cys/Ser (formulas VI/VIII) cyclopeptide mutants at a dose of 1.0 mg/kg Bw; FIGS. 16 to 21. However, "intermediate" cyclic peptides of 19 to 24 AA exhibit an increased activity in accordane with this invention. Particularly, cyclic peptides of 22 AA exhibit an increased activity in accordane with this invention. A preferred example of such an "intermediate" cyclic peptide is a cyclic peptide comprising or consisting of the amino acid residues as shown in formula IX'.

Moreover, the exact nature of the exchange of one of the cysteine residues with a serine residue (i.e., Cys/Ser or Ser/Cys-mutation) markedly determined the potency of the disclosed cyclic peptides in vitro and also in vivo (FIGS. 6-10 and 14-16).

β-adrenergic receptors (β-AR), particularly $\beta_1$-adrenergic receptors ($\beta_1$-AR), are well known in the art. For example, the nucleotide and amino acid sequence (SEQ ID NO. 40) of the human $\beta_1$-AR (also known as adrenergic β-1-receptor (ADRB1)) can be obtained from databank entry NM_000684 or NP_000675. β-ARs are known to form two extracellular domains termed herein as $EC_I$ and $EC_{II}$ or $\beta_{(1)}$-$EC_I$ and $\beta_{(1)}$-$EC_{II}$. As mentioned above, the cyclic peptides of the present invention share sequence similarity with $\beta_1$-$EC_{II}$, particularly with the amino acid stretch DEARRCYNDPKC-CDFV (SEQ ID NO. 33) or RAESDEARRCYNDPKCCD-FVTNR (SEQ ID NO. 34) of the human $\beta_1$-AR (amino acid positions 204 to 219 or 200 to 222, respectively) or, particularly, with the amino acid stretch DEARRCYNDPK (SEQ ID NO. 45) or ESDEARRCYNDPK (SEQ ID NO. 46) of the human $\beta_1$-AR. The term "β-AR" as used herein preferably refers to a $\beta_1$-adrenergic receptor ($\beta_1$-AR), more preferably to the human $\beta_1$-AR as described above.

A cyclic peptide provided herein has as least one of the features selected from the group consisting of:

a) being capable of binding (auto-)antibodies against the $EC_{II}$ loop of $\beta_1$-adrenergic receptor ($\beta_1$-AR);

b) being capable of inhibiting the interaction between $\beta_1$-AR and (auto-)antibodies against the $EC_{II}$ loop of $\beta_1$-AR;

c) mimicking at least one epitope presented in the native conformation of the $EC_{II}$ loop of $\beta_1$-AR; and d) being capable of reducing an antibody-mediated activation of $\beta_1$-AR.

The structure of $\beta_1$-AR was, inter alia, analyzed by Warne (2008 Nature. DOI:10. 1038).

As mentioned above, the cyclic peptide of the present invention is defined by the general formula cyclo(x-$x_h$-Cys-x-$x^a$-$x^b$-$x^c$-x-Cys-y-$x_i$-x) (formula I). In this formula, "y" may be any amino acid residue but Cys, preferably "y" may be any amino acid residue except Pro and except Cys. Generally, "y" may be any amino acid, as long as this amino acid does not form an intramolecular linkage (e.g. a disulphide bond) with another amino acid of the cyclic peptide provided herein (e.g. with another Cys of the cyclic peptide provided herein). Preferably, "y" may be any amino acid similar to Cys (i.e. having a similar chemical structure and/or a similar behavior within a 3 dimensional peptide structure), with the exception that it does not form an intramolecular linkage (e.g. a disulphide bond) with another amino acid of the cyclic peptide provided herein (e.g. with another Cys of the cyclic peptide provided herein). More preferably, "y" may be any polar amino acid but Cys, like Thr or Ser. Most preferably, in the cyclic peptide provided herein, "y" is Ser or a Ser analogue. "Ser analogue" in this context means a residue, particularly an amino acid residue, having a structural character similar to that of Ser. "Ser analogue" refers to, for example, a(n) (amino acid) residue having a similar chemical structure like that of Ser and/or a similar behavior within a 3 dimensional peptide structure like that of Ser. As a further example, "y" may also be selenocysteine or an analogue thereof.

In general, the meaning of terms like "any amino acid (residue) but Cys" or "amino acid (residue) other than Cys" is clear to the skilled person. Particularly, as used throughout this invention, such terms refer to any amino acid, as long as this amino acid does not form an intramolecular linkage (e.g. a disulphide bond) with another amino acid of the cyclic peptide provided herein (e.g. with another Cys of the cyclic peptide provided herein).

As mentioned, one main feature of the cyclic peptides of this invention is that they comprise only two Cys able to form an intramolecular linkage. Such cyclic peptides can, for example, be obtained by substituting a third Cys of a peptide homologous to the $\beta_1$-$EC_{II}$ by a different amino acid. Thereby, the Cys to be substituted is the one corresponding to the $2^{nd}$ or, which is preferred, $3^{rd}$ Cys of the $\beta_1$-$EC_{II}$ which lie in direct proximity to each other (amino acid position 215 and 216 of human $\beta_1$-AR (see also NP_000675 and SEQ ID NO.

40). These two Cys residues, are referred to herein as "Cys-Cys", "Cys/Cys", "Cys$_{215}$-Cys$_{216}$" or "Cys$_{215}$/Cys$_{216}$" and the like).

The resulting mutant peptides or mutations as disclosed herein are accordingly termed as "Cys-Ser", "Cys/Ser", "Cys$_{13, 16\,or\,17}$-Ser$_{14, 17\,or\,18}$" or "Cys$_{13, 16\,or\,17}$/Ser$_{14, 17\,or\,18}$" mutant peptides or mutations or "Ser-Cys", "Ser/Cys", "Ser$_{13\,or\,17}$-Cys$_{14\,or\,18}$" or "Ser$_{13\,or\,17}$/Cys$_{14\,or\,18}$" mutant peptides or mutations, depending which of the Cys is replaced and how many amino acids the mutant peptide comprises.

Alternatively, the mutant peptides as disclosed herein are defined by referring to the particular amino acid exchanges at a certain position. Then, the mutant peptides/mutations are, for example, termed "Cys$_{14, 17\,or\,18}$→Ser$_{14, 17\,or\,18}$" mutant peptides/mutations or "Cys$_{13\,or\,17}$→Ser$_{13\,or\,17}$" mutant peptides/mutations, depending on whether the Cys corresponding to Cys$_{216}$ or the Cys corresponding to the Cys$_{215}$, respectively, of β$_1$-AR is replaced by a different amino acid. The indices "14, 17 or 18" or "13 or 17" relate to the position in the exemplified cyclic peptide of the invention, whereby position 1 corresponds to the first "x" as defined in formula I, i.e cyclo($\underline{x}$-x$_h$-Cys-x-x$^a$-x$^b$-x$^c$-x-Cys-y-x$_i$-x).

Accordingly, terms like "Cys$_{13}$-Ser$_{14}$" or "Cys$_{13}$/Ser$_{14}$" mutant peptides/mutations are used in the same sense as "Cys$_{14}$→Ser$_{14}$" mutant peptides/mutations and, in this particular example, refer to 18mer peptides disclosed herein. Terms like "Cys$_{16}$-Ser$_{17}$" or "Cys$_{16}$/Ser$_{17}$" mutant peptides/mutations are used in the same sense as "Cys$_{17}$→Ser$_{17}$" mutant peptides/mutations and, in this particular example, refer to 22mer peptides disclosed herein. Terms like "Cys$_{17}$-Ser$_{18}$" or "Cys$_{17}$/Ser$_{18}$" mutant peptides/mutations are used in the same sense as "Cys$_{18}$→Ser$_{18}$" mutant peptides/mutations and, in this particular example, refer to 25mer peptides disclosed herein.

Analogously, terms like "Ser$_{13}$-Cys$_{14}$" or "Ser$_{13}$/Cys$_{14}$" mutant peptides/mutations are used in the same sense as "Cys$_{13}$→Ser$_{13}$" mutant peptides/mutations and, in this particular example, refer to 18mer peptides disclosed herein, and terms like "Ser$_{17}$-Cys$_{18}$" or "Ser$_{17}$/Cys$_{18}$" mutant peptides/mutations are used in the same sense as "Cys$_{17}$→Ser$_{17}$" mutant peptides/mutations and, in this particular example, refer to 25mer peptides disclosed herein.

The exemplarily indices given above refer to the position of the indicated amino acid within the herein disclosed particular 18mer, 22 mer or 25mer peptide, respectively. In context of this invention, the starting point with respect to an indicated amino acid position given for a cyclic peptide disclosed herein is the N-terminal amino acid of the linearized backbone the cyclic peptide (like the first "x" in formula I, see above). The starting point with respect to an indicated amino acid position given for a linear peptide disclosed herein is its N-terminal amino acid.

The findings as provided herein and in the appended examples demonstrate an comparability of 25AA, 22 AA and 18AA cyclopeptides without any Cys mutation with the cyclic 25AA, 22AA or 18AA Cys$_{18, 17\,or\,14}$→Ser$_{18, 17\,or\,14}$ (Cys-Ser) mutants, but not with the cyclic 25AA or 18AA Cys$_{17\,or\,13}$→Ser$_{17\,or\,13}$ (Ser-Cys) mutants.

As also mentioned above, in the formulas of the cyclic peptide of the present invention, h can be any integer from 1 to 15, preferably from 5 to 9, and/or i can be any integer from 0 to 14, preferably from 1 to 14, more preferably from 0 to 6 and even more preferably from 1 to 6. Accordingly, h can be 1, 2, 3, 4, 5, 5, 6, 7, 8, 9, 10, 11, 12, 13, 14 or 15 and/or i can be 0, 1, 2, 3, 4, 5, 6, 7, 8, 9, 10, 11, 12, 13 or 14. Preferably, h is 5, 8 or 9 and/or i is 3, 4 or 6. More preferably, h is 8 and/or i is 4. In particularly preferred embodiments of this invention, x$_h$ stands for the particular amino acid stretches DEARR (SEQ ID NO. 35), AESDEARR (SEQ ID NO. 47) or RAESDEARR (SEQ ID NO. 36) and/or x$_i$ stands for the particular amino acid stretches DFV (SEQ ID NO. 37), DFVT (SEQ ID NO. 48) or DFVTNR (SEQ ID NO. 38). In more preferred particular embodiments of this invention, x$_h$ stands for the particular amino acid stretch AESDEARR (SEQ ID NO. 47) and/or x$_i$ stands for the particular amino acid stretch DFVT (SEQ ID NO. 48).

The cyclic peptide of the present invention (or the cyclic part thereof) may consist of at least 18 amino acids and of at most 25 amino acids. Accordingly, the cyclic peptide of the present invention may consist of 18, 19, 20, 21, 22, 23, 24 or 25 amino acids, whereby particularly 18 or 25 amino acids are preferred and particularly 22 amino acids are most preferred. In a less preferred embodiment, also smaller peptides, i.e. peptides comprising 16 or 17 amino acids are envisaged.

A particularly preferred cyclic peptide in context of this invention is one of (21+1=)22AA length, having a defined maximum and minimum size of the cyclic molecule dependent on the respective amino-acid composition, constituted by 21-amino-acids from the original primary sequence of the human beta1-adrenergic receptor (i.e., amino-acids 200 to 221; Frielle 1987, PNAS 84, 7920-7924) with an additional glycine as 22$^{nd}$ amino-acid at the assumed ring closure site (position 222).

Without being bound by theory, the number of amino acids and thus the length of the primary structure (i.e. the amino acid backbone) of cyclic peptides binding anti-β$_1$-AR antibodies is crucial for their biological effects and/or successful/effective manufacture.

A peptide-length equal or above 26 amino acids (primary structure) may be stimulating directly (that is, without the use of carrier proteins) immunocompetent T-cells and thus may provoke an undesired paradoxal increase of anti-β1-receptor antibody production through T-cell mediated B-cell stimulation.

A peptide-length below 16 amino acids (primary structure) leads to undesired crystallization during the production process and problems in dissolving the synthesized products in an aqueous solution, e.g. for purposes of i.v. or s.c. injections In a less preferred embodiment of this invention also cyclic peptides falling under the above given definitions a) to f) of formula I and consisting of only 16 amino acids or, even less preferred, consisting of only 17 amino acids are provided. A non-limiting example of such a less preferred cyclic peptide is the peptide cyclo(Ala-Arg-Arg-Cys-Tyr-Asn-Asp-Pro-Lys-Cys-Ser-Asp-Phe-Val-Tyr-Gln/DGlu) (formable by an amino acid backbone as depicted in SEQ ID NO. 39).

It is particularly preferred herein that the disclosed cyclic peptide contains only one Pro. Accordingly, it is particularly preferred that neither the y nor an x of the formulas depicted herein, except of exactly one of x$^a$, x$^b$ and x$^c$, is not Pro. Within the amino acid stretch x$^a$, x$^b$ and x$^c$ as depicted in formula I (or other formulas), it is preferred that x$^c$ is Pro.

It is particularly envisaged herein that an acidic amino acid, like Asp or Glu, precedes the Pro contained in the cyclic peptide of the invention. Accordingly, it is preferred that x$^b$ as depicted in formula I (or other formulas) is an acidic amino acid, like Asp or Glu. Particularly, when x$^c$ is Pro, x$^b$ may be an acidic amino acid, when x$^b$ is Pro, x$^a$ may be an acidic amino acid and when x$^a$ is Pro, the x of formula I (or other formulas) lying between x$^a$ and the first Cys may be an acidic amino acid.

More specifically, the cyclic peptide of the present invention may be defined by formula I' or I":

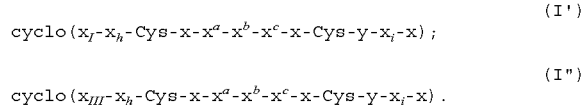

$$\text{cyclo}(x_I\text{-}x_h\text{-}Cys\text{-}x\text{-}x^a\text{-}x^b\text{-}x^c\text{-}x\text{-}Cys\text{-}y\text{-}x_i\text{-}x); \quad (\text{I}')$$

$$\text{cyclo}(x_{III}\text{-}x_h\text{-}Cys\text{-}x\text{-}x^a\text{-}x^b\text{-}x^c\text{-}x\text{-}Cys\text{-}y\text{-}x_i\text{-}x). \quad (\text{I}'')$$

Even more specifically, the cyclic peptide of the present invention may be defined by formula I''' or I'''':

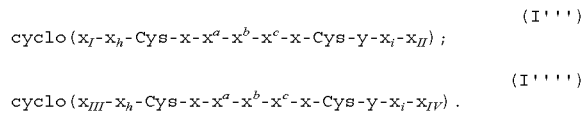

$$\text{cyclo}(x_I\text{-}x_h\text{-}Cys\text{-}x\text{-}x^a\text{-}x^b\text{-}x^c\text{-}x\text{-}Cys\text{-}y\text{-}x_i\text{-}x_{II}); \quad (\text{I}''')$$

$$\text{cyclo}(x_{III}\text{-}x_h\text{-}Cys\text{-}x\text{-}x^a\text{-}x^b\text{-}x^c\text{-}x\text{-}Cys\text{-}y\text{-}x_i\text{-}x_{IV}). \quad (\text{I}'''')$$

In general, $x_I$ and $x_{II}$ as depicted in formula I' and I''' (and in the other formulas depicted herein) may, as mentioned, any amino acid but Cys. However, particularly when the ring closure of the cyclic peptides of the invention occurs between $x_I$ and $x_{II}$, it is particularly envisaged that $x_I$ and $x_{II}$ are such amino acids able to form a peptide bond, or the like, with each other under conditions of a "head to tail" cyclization. "Head to tail" cyclizations are known in the art (e.g. Kates and Albericio: Solid phase synthesis, CRC-Press, 2000; Williams, Chemical Approaches to the Synthesis of Peptides, CRC-Press 1997; Benoiton: Chemistry of Peptide Synthesis. CRC-Press, 2005) and examples thereof are given in the experimental part. Possible examples of amino acids that may be $x_I$ are Gly, Val, Thr, Ser and, preferably, Ala. Possible examples of amino acids that may be $x_{II}$ are Glu and, preferably, Gln. Less preferred, $x_{II}$ may also be Asp or Asn. Most preferred, $x_I$ is Ala and $x_{II}$ is Gln or Glu (preferrably DGlu).

Accordingly, in the cyclic peptides of this invention $x_{II}$ as referred to in formula I' and I''' can be Gln or Glu, wherein Glu may also be DGlu (D-Glu; D-Glutamic acid). However, naturally amino acids are preferred herein. Therefore, it is more preferred that $x_{II}$ is Gln.

The skilled person is able chose amino acid residues appropriate to be $x_I$ and/or $x_I$, of formula I' and I''' in accordance with this invention on the basis of the teaching provided herein and his knowledge of the art (e.g. Williams, Chemical Approaches to the Synthesis of Peptides, CRC-Press 1997; Benoiton: Chemistry of Peptide Synthesis. CRC-Press, 2005).

$x_{III}$ and $x_{IV}$ as depicted in formula I'' and I'''' (and in the other formulas depicted herein) may, as mentioned, any amino acid but Cys. However, particularly when the ring closure of the cyclic peptides of the invention occurs between $x_{III}$ and $x_{IV}$, it is particularly envisaged that $x_{III}$ and $x_{IV}$ are such amino acids able to form a peptide bond, or the like, with each other under conditions of a "head to tail" cyclization. A possible example of an amino acid that may be $x_{III}$ is Arg. One possible, and most preferred, example of an amino acid that may be $x_{IV}$ is Gly or a Gly analogue. "Gly analogue" in this context means a residue, particularly an amino acid residue, having a structural character similar than that of Gly. Particularly, "Gly analogue" refers to, for example, a(n) (amino acid) residue having the same (or even a smaller) size than a Gly residue. It was surprisingly found in context of this invention that particularly a small (amino acid) residue like Gly at the "$X_{IV}$" position leads to an improved mimicking of the ECII of β1-AR by the corresponding cyclic peptides of the invention. The skilled person is able chose amino acid residues appropriate to be $x_{III}$ and/or $x_{IV}$ of formula I'' and I'''' in accordance with this invention on the basis of the teaching provided herein and his knowledge of the art (e.g. Williams, Chemical Approaches to the Synthesis of Peptides, CRC-Press 1997; Benoiton: Chemistry of Peptide Synthesis. CRC-Press, 2005).

It is further particularly preferred herein that the cyclic peptides of this invention lack Trp and/or His. Accordingly, it is particularly envisaged in context of the invention, that neither an x nor y as depicted in any of Formula I to I'''' is Trp or His. Furthermore, it is preferred that the provided cyclic peptides lack sites susceptible for hydrolysis or cleaving proteases, like, for example, serum proteases. The meanings of the terms "hydrolysis" and "(serum) proteases" are well known in the art.

A peptide as provided herein can also be described as a peptide consisting of or comprising an amino acid sequence homologous to SEQ ID NO. 33 (representing a wild type amino acid stretch comprising epitopes of $\beta_1$-$EC_{II}$), wherein (a) the amino acid corresponding to position 13 (or, less preferred, corresponding to position 12) of SEQ ID NO. 33 is not Cys and the amino acid corresponding to positions 6 and 12 (or, less preferred, corresponding to position 6 and 13) of SEQ ID NO. 33 is Cys, (b) wherein said amino acid sequence contains no further Cys able to form an intramolecular linkage within the peptide, i.e. within that part of the peptide being homologous to SEQ ID NO. 33, and wherein the peptide can function as a cyclic peptide in accordance with this invention, e.g. is able to block anti-β-AR antibodies, or wherein the peptide can form such a cyclic peptide. Optionally, the further provisions given herein with respect to the structure of the disclosed linear and/or cyclic peptides apply here, mutatis mutandis. The so defined peptide consists of a stretch of 16 amino acids being homologous to SEQ ID NO. 33 flanked at the N- and C-terminus by one or more amino acids, preferably naturally occurring amino acids, like the "$x_I$"/"$x_{III}$" at position 1 and the "$x_{II}$"/"$x_{IV}$" at the last position of formulas I' to I'''' given herein.

In context of the invention, and in particular in context of the (wild type) SEQ ID NO. 33, "homologous" means identical on amino acid level for at least 18.75%, at least 37.5%, at least 50%, at least 56.25%, at least 62.5%, at least 68.75%, at least 75%, at least 81.25%, at least 87.5% or 93.75%, wherein the higher values are preferred.

In general, the meaning of the term "amino acid" or "amino acid residue" is known in the art and is used herein accordingly. Thereby, it is of note that when an "amino acid" is a component of a peptide/protein the term "amino acid" is used herein in the same sense than "amino acid residue".

Particularly, an "amino acid" or "amino acid residue" as referred to herein is preferably envisaged to be a naturally occurring amino acid, more preferably a naturally occurring L-amino acid (except the above mentioned DGlu). However, albeit less preferred, an "amino acid" or "amino acid residue" in context of this invention may also be a non-naturally occurring (i.e. a synthetic) amino acid, like, for example, norleucine or β-alanine, or, particularly in case of "y" of the formulas depicted herein, selenocysteine or an analog thereof.

Also known in the art is the meaning of the terms "acidic amino acid(s)", "basic amino acid(s)", "aliphatic amino acid(s)" and "polar amino acid(s)" (for example, Stryer, Biochemie, Spectrum Akad. Verlag, 1991, Item I. 2.). These terms are correspondingly used throughout this invention. Thereby, the particular provisos given herein with respect to the cyclic peptides of the invention also apply.

Particularly, the term "acidic amino acid(s)" as used herein is intended to mean an amino acid selected from the group comprising Asp, Asn, Glu, and Gln, preferably Asp and Glu; the term "basic amino acid(s)" as used herein is intended to mean an amino acid selected from the group comprising Arg, Lys and His, preferably Arg and Lys; the term "aliphatic amino acid(s)" as used herein is intended to mean any amino acid selected from the group comprising Gly, Ala, Ser, Thr, Val, Leu, Ile, Asp, Asn, Glu, Gln, Arg, Lys, Cys and Met; and the term "polar amino acid(s)" as used herein is intended to mean any amino acid selected from the group comprising Cys, Met, Ser, Tyr, Gln, Asn and, less preferred, Trp.

In a more general embodiment of the first aspect of this invention, the cyclic peptide as provided herein may be a cyclic peptide of formula II, III or III':

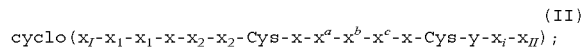

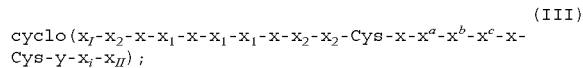

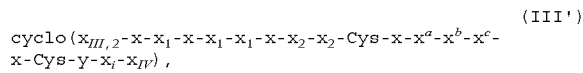

wherein
a) $x_1$ is individually and independently selected from the group consisting of acidic amino acids; and/or
b) $x_2$ is individually and independently selected from the group consisting of basic amino acids.

In a more specific embodiment of the first aspect of this invention, the cyclic peptide as provided herein may be a cyclic peptide of formula IV, V or V':

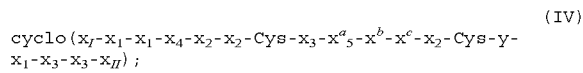

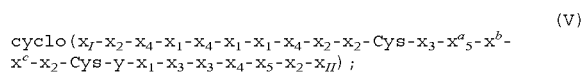

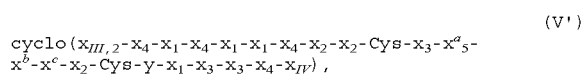

wherein
a) $x_1$ is individually and independently selected from the group consisting of acidic amino acids;
b) $x_2$ is individually and independently selected from the group consisting of basic amino acids;
c) $x_3$ is individually and independently selected from the group consisting of Leu, Ile, Val, Met, Trp, Tyr and Phe;
d) $x_4$ is individually and independently selected from the group consisting of Ser, Thr, Ala and Gly; and/or
e) $x_5$ is individually and independently selected from the group consisting of Gln and Asn.

In a further embodiment of the first aspect of this invention, the cyclic peptides comprise an amino acid stretch as defined by amino acid position 2-12 or 2-14 of formula II or IV, an amino acid stretch as defined by amino acid position 4-16 or 4-18 of formula III or V or an amino acid stretch as defined by amino acid position 3-15 or 3-17 of formula or III' or V': In a more general embodiment of the first aspect of this invention, the cyclic peptide as provided herein may be a cyclic peptide of formula II, III or III'

In a further particular embodiment of the first aspect of this invention, the cyclic peptide as provided herein may comprise the amino acid stretch
 aci-Glu-Ala-bas-bas-Cys-Tyr-neu-aci-neu-bas;
 aci-neu-aci-Glu-Ala-bas-bas-Cys-Tyr-neu-aci-neu-bas;
 aci-Glu-Ala-bas-bas-Cys-Tyr-neu-aci-neu-bas-Cys-Ser;
 or
 aci-neu-aci-Glu-Ala-bas-bas-Cys-Tyr-neu-aci-neu-bas-Cys-Ser,
wherein "ad" stands for acidic amino acid, "neu" stands for neutral amino acid and "bas" stands for basic amino acid. Each amino acid residue of the above two amino acid stretches may also be defined independently as the corresponding amino acid residue of any one of formulas I, II, III, III', IV, V, and V' as provided herein.

In a further particular embodiment of the first aspect of this invention, the cyclic peptide as provided herein may comprise the amino acid stretch (SEQ ID NO. 45)
Asp-Xxx$_1$-Xxx$_4$-Arg-Arg-Cys-Xxx$_3$-Asn-Asp-Pro-Lys
or (SEQ ID NO. 46)
Glu-Ser-Asp-Xxx$_1$-Xxx$_4$-Arg-Arg-Cys-Xxx$_3$-Asn-Asp-Pro-Lys, wherein Xxx$_1$ is defined as "x" or "x$_1$", Xxx$_3$ is defined as "x" or "x$_3$" and/or Xxx$_4$ is defined as "x" or "x$_4$" as mentioned in the above depicted formulas. For example, the above-mentioned amino acid stretch may be (SEQ ID NO. 45)
Asp-Glu-Ala-Arg-Arg-Cys-Tyr-Asn-Asp-Pro-Lys
or (SEQ ID NO. 46)
Glu-Ser-Asp-Glu-Ala-Arg-Arg-Cys-Tyr-Asn-Asp-Pro-Lys.

It is particularly envisaged herein that the cyclic peptides of this invention comprise one or more epitopes beared by $\beta_1$-EC$_{II}$, like, for example, epitopes beared by any of the above mentioned amino acid stretches (or by parts of the disclosed cyclic peptides comprising these amino acid stretches). In this context, the term "epitope" particularly refers to an amino acid stretch to which an (au SEQ ID NO. 42, 44, 9 to 12, 25 to 28, 49, 50, 53 and 54 due to the degeneracy of the genetic code.

Out of the cyclic peptides according to this invention, those cyclic peptides being Cys-Ser mutant peptides, i.e. having the Cys corresponding to the third Cys of the $\beta_1$-EC$_{II}$ (the Cys at position 216 of ($\beta_1$-AR) exchanged by Ser, are particularly preferred. The above given examples refer to such particularly preferred cyclic peptides. As demonstrated in the appended examples, such cyclic peptides are particularly useful in inhibiting or diagnosing anti-$\beta_1$-AR antibodies.

The particular structure of the above exemplified particularly preferred cyclic peptides is given by any one of the following formulas VI to IX':

cyclo(Arg-Ala-Glu-Ser-Asp-Glu-Ala-Arg-Arg-Cys-
Tyr-Asn-Asp-Pro-Lys-Cys-Ser-Asp-Phe-Val-Thr-Gly); (IX')

cyclo(Ala-Asp-Glu-Ala-Arg-Arg-Cys-Tyr-Asn-Asp-
Pro-Lys-Cys-Ser-Asp-Phe-Val-Gln); (VI)

cyclo(Ala-Arg-Ala-Glu-Ser-Asp-Glu-Ala-Arg-Arg-
Cys-Tyr-Asn-Asp-Pro-Lys-Cys-Ser-Asp-Phe-Val-Thr-
Asn-Arg-Gln); (VII)

cyclo(Ala-Asp-Glu-Ala-Arg-Arg-Cys-Tyr-Asn-Asp-
Pro-Lys-Cys-Ser-Asp-Phe-Val-DGlu); (VIII)
and cyclo(Ala-Arg-Ala-Glu-Ser-Asp-Glu-Ala-Arg-Arg-
Cys-Tyr-Asn-Asp-Pro-Lys-Cys-Ser-Asp-Phe-Val-Thr-
Asn-Arg-DGlu). (IX)

Non limiting examples of less preferred cyclic peptides according to this invention are cyclic peptides selected from the group consisting of:
a) cyclic peptides formable or formed by the amino acid sequence as depicted in any one of SEQ ID NO. 5 to 8 and 21 to 24;
b) cyclic peptides formable or formed by an amino acid sequence as encoded by a nucleotide sequence as depicted in any one of SEQ ID NO. 13 to 16 and 29 to 32; and
c) cyclic peptides formable or formed by an amino acid sequence as encoded by a nucleotide sequence which differs from the nucleotide sequence as depicted in any one of SEQ ID NO. 29 to 32 due to the degeneracy of the genetic code.

The particular structure of the above exemplified less preferred cyclic peptides is given by any one of the following formulas X to XIII:

cyclo(Ala-Asp-Glu-Ala-Arg-Arg-Cys-Tyr-Asn-Asp-
Pro-Lys-Ser-Cys-Asp-Phe-Val-Gln); (X)

cyclo(Ala-Arg-Ala-Glu-Ser-Asp-Glu-Ala-Arg-Arg-
Cys-Tyr-Asn-Asp-Pro-Lys-Ser-Cys-Asp-Phe-Val-Thr-
Asn-Arg-Gln); (XI)

cyclo(Ala-Asp-Glu-Ala-Arg-Arg-Cys-Tyr-Asn-Asp-
Pro-Lys-Ser-Cys-Asp-Phe-Val-DGlu); (XII)

cyclo(Ala-Arg-Ala-Glu-Ser-Asp-Glu-Ala-Arg-Arg-
Cys-Tyr-Asn-Asp-Pro-Lys-Ser-Cys-Asp-Phe-Val-Thr-
Asn-Arg-DGlu). (XIII)

The above peptides are less preferred embodiments of this invention since peptides as the "Cys-Ser" mutant peptides ("Cys-Ser" cyclic peptides) are, inter alia, in vivo more functional than the herein defines less preferred "Ser-Cys" mutant peptides ("Ser-Cys" cyclic peptides).

In this context it is of note that most preferred examples of the cyclic peptides according to this invention are particularly those cyclic peptides, the pharmacological and/or diagnostic function of which has been demonstrated in the appended examples (e.g. those characterized by any one of formula VI to IX').

It will be understood that for the various peptides of the present invention a certain flexibility and variability in the primary sequence, i.e. the amino acid sequence backbone, is possible as long as the overall secondary and tertiary structure of the respective peptides, which is defined by at least some fixed amino acid residues and by their spatial arrangement, is ensured (see, e.g., formula I, supra).

Based on the teaching provided herein, the skilled person is, one the one hand, readily in the position to find out corresponding variants of the peptides of the invention. One the other hand, the skilled person is able to test whether a given variant of peptides of the present invention still has the desired function, for example the ability to specifically bind to β-AR antibodies, and therefore has the potential for a corresponding medical intervention, like the therapeutic and diagnostic applications described and provided herein. Corresponding experimental guidance for such tests, i.e. respective assays, are exemplarily provided and described herein, particularly in the appended examples.

Accordingly, also provided herein are variants of the herein disclosed and described peptides, given that, first, these variants are still functionally active in accordance with this invention, i.e. functionally active as binding partners for anti-β-AR antibodies, particularly for anti-$\beta_1$-AR antibodies against the $\beta_1$-EC$_{II}$, more particularly functionally active as inhibitors of $\beta_1$-AR and even more preferably active in inhibiting the interaction between $\beta_1$-AR and anti-$\beta_1$-AR antibodies against the $\beta_1$-EC$_{II}$, more preferably auto-anti-$\beta_1$-AR antibodies against the $\beta_1$-EC$_{II}$; and, second, that these variants are not present in form of isomers mixtures or do not form isomers mixtures when cyclized in accordance with production method of this invention. These variants are envisaged to have only two certain Cys residues forming or being able to form only one individual intramolecular linkage (e.g. disulphide bond).

Within the variants of the peptides of the present invention it is, for example, envisaged that one or more amino acids of said peptides are replaced by other one or more naturally occurring or synthetic amino acids. In this context, it is preferred that this/these amino acid exchange(s) is/are (a) conservative amino acid exchange(s), i.e. that the replacement amino acid belongs to the same category of amino acids than the amino acid to be replaced. For example, an acidic amino acid may be replaced by another acidic amino acid, a basic amino acid may be replaced by another basic amino acid, an aliphatic amino acid may be replaced by another aliphatic amino acid, and/or a polar amino acid may be replaced by another polar amino acid.

Accordingly, particularly preferred and provided variants of the (cyclo) peptides of the present invention are variants wherein at least one of an acidic amino acid of is replaced by a different amino acid selected from the group consisting of acidic amino acids, at least one of the basic amino acids is replaced by a different amino acid selected from the group consisting of basic amino acids, at least one of a polar amino acid is replaced by a different amino acid selected from the group consisting of polar amino acids and/or at least one of an aliphatic amino acid is replaced by a different amino acid selected from the group consisting of aliphatic amino acids (given that the above mentioned-requirements are fulfilled).

It is particularly envisaged that the amino acid exchanges which lead to variants of the disclosed (cyclic) peptides are such, that the pattern of polarity and charge within the tertiary structure of the resulting variant still substantially mimics the three-dimensional structure of the corresponding $EC_{II}$ epitope(s) of $\beta_1$-AR.

With respect to the "Variants" of the (cyclo) peptides of the present invention the herein defined Cys may also be replaced by other amino acids, as long as the replacement still leads to an individual intramolecular linkage, like that of a disulphide bond, within the cyclopeptide, i.e. the avoidance of isomers mixtures formation during cyclization and/or a correct mimicry of the $EC_{II}$ of $\beta_1$-AR. Such amino acid may, inter alia, be a non-naturally occurring amino acid, like a non-naturally occurring amino acid having an —SH group able to form a disulphide bond. However, it is preferred herein that the Cys given in formula I, above, is indeed a naturally occurring amino acid, preferably Cys itself.

It will also be acknowledged by the ones skilled in the art that one or several of the amino acids forming the (cyclic) peptide of the present invention may be modified. In accordance therewith any amino acid as used herein may also represent its modified form. For example, an alanine residue as used herein may comprise a modified alanine residue. Such modifications may, among others, be a methylation or acylation or the like, whereby such modification or modified amino acid is preferably comprised by the present invention as long as the thus modified amino acid and more particularly the peptide containing said thus modified amino acid is still functionally active as defined herein, like functionally active as an inhibitor of anti-$\beta_1$-AR antibodies, preferably active in inhibiting the interaction between $\beta_1$-AR and antibodies, and more preferably auto-antibodies directed against $\beta_1$-AR. Respective assays for determining whether such a peptide, i.e. a peptide comprising one or several modified amino acids, fulfils this requirement, are known to the one skilled in the art and, among others, also described herein, particularly in the example part hereof.

The invention also provides derivatives of the disclosed (cyclic) peptides such as salts with physiologic organic and anorganic acids like HCl, $H_2SO_4$, $H_3PO_4$, malic acid, fumaric acid, citronic acid, tatratic acid, acetic acid.

As used herein, the sequences of the peptides disclosed are indicated from the N-terminus to the C-terminus, whereby the N-terminus is at the left side and the C-terminus is at the right side of the respective depicted amino acid sequence. When referring to cyclic peptides, the corresponding sequences are indicated from the side corresponding to the left side of formula I to the side corresponding to the right side of formula I.

A "cyclic peptide" or "cyclopeptide" and the like in accordance with the present invention is a peptide intramolecularly forming a molecular ring structure within its amino acid backbone/primary amino acid sequence by at least one, preferably by at least two, more preferably by exactly two intramolecular linkages having covalent character. The forming of this molecular ring structure is, in context of this invention, also termed "cyclization".

In one particularly preferred embodiment, the cyclic peptide of this invention has two intramolecular linkages having covalent character, wherein one of these linkages is an intramolecular linkage between the N- and C-terminal ends of a peptide being the amino acid backbone/primary amino acid sequence of the cyclic peptide disclosed and the other one is an intramolecular linkage between two non-terminal amino acids of this peptide. As mentioned, these two non terminal amino acids may be two Cys.

Generally, "cyclization" in accordance with this invention may occur by at least one linkage which is a covalent binding selected from the group consisting of S—S linkages, peptide bonds, carbon bonds such as C—C or C=C, ester bonds, ether bonds, azo bonds, C—S—C linkages, C—N—C linkages and C=N—C linkages. Particularly, the peptide bond as mentioned throughout this invention can be formed by the $NH_2$ group of an N-terminal amino acid and the COOH group of an C-terminal amino acid of a peptide forming the amino acid backbone/primary amino acid sequence of the cyclic peptide disclosed.

Preferably, an intramolecular linkage between the N- and C-terminal ends of a peptide forming the amino acid backbone/primary amino acid sequence of the cyclic peptide disclosed is a peptide bond and an intramolecular linkage between two non-terminal amino acids of this peptide is an S—S linkage (i.e. disulphide bond).

In context of this invention, an intramolecular S—S linkage within the cyclic peptide provided can be formed between two Cys residues within the amino acid backbone/primary amino acid sequence of said cyclic peptide.

Within the cyclic peptides of this invention, not only the above mentioned two particular intramolecular covalent linkage may be formed but also further intramolecular linkages may occur, with the proviso that the herein described functionality of the cyclic peptides is maintained and that the cyclic peptides can still easily be characterized biochemically, which, e.g., means that no isomers mixtures are formed during cyclization of the corresponding amino acid backbone/primary amino acid sequence.

For example, such further intramolecular linkages are additional bonds formed by a side chain of $NH_2$ groups and COOH groups of the constituent amino acids.

Terms like "amino acid backbone" or "primary amino acid sequence" as used throughout the present invention refer, on the one hand, to that structural component or part of a cyclic peptide which is formable or formed by its corresponding amino acid sequence. On the other hand, these terms refer to the linear peptides able to form the cyclic peptides of this invention by cyclization.

In one particular embodiment of the first aspect of this invention, a cyclic peptide is provided which is obtainable by the method for producing a cyclic peptide as provided herein. The definitions given herein-above also apply with respect to this particularly provided cyclic peptide of the present invention.

In one embodiment of the first aspect of this invention also such peptides are provided, the disclosed cyclic peptides are formable by or are formed by. Particularly these peptides are the linear peptides forming or being able to form the herein disclosed cyclic peptides, i.e. the amino acid backbone/primary amino acid sequence thereof.

In general, such a linear peptide can be any peptide, the covalent linkage of the N- and C-terminus of which results in a cyclic peptide as disclosed in accordance with the present invention. For example, such a linear peptide may be some kind of an intermediate compound in an procedure of producing the cyclic peptides of this invention, like the method for producing a cyclic peptide as disclosed herein.

In general, the N- and C-terminal end of a linear-peptide provided herein may be any amino acid pair lying in direct proximity to each other within the amino acid backbone of a cyclic peptide disclosed in context of this invention. In other words, cyclization (ring closure) of the cyclic peptide of this invention may generally occur between any of said amino acid pairs. The skilled person is readily in the position to find out such particular amino acid pairs which are effective/suitable to act as N- and C-terminal ends of a herein disclosed linear peptide, i.e. which are effective/suitable to act as an amino acid pair being involved in the ring closure/cyclization as defined in context of this invention.

In one preferred but non-limiting example, the cyclization (ring closure) of a linear peptide of this invention may occur between Ala and Gln or Glu, i.e. the N-terminal amino acid of this linear peptide would be Ala and the C-terminal amino acid would be Gln or Glu. Examples of such linear peptides able to form the cyclic peptide of the present invention are SEQ ID NO. 1 to 4 and, less preferred SEQ ID NO. 5 to 8.

In another preferred but non-limiting example, the cyclization (ring closure) of a linear peptide of this invention may occur between Lys and Pro, i.e. the N-terminal amino acid of this linear peptide would be Lys and the C-terminal amino acid would be Pro. Examples of such linear peptides able to form the cyclic peptide of the present invention are SEQ ID NO. 17 to 20 and, less preferred SEQ ID NO. 21 to 24.

In a more preferred but non-limiting example, particularly when a 22mer cyclic peptide is provided, the cyclization (ring closure) of a linear peptide of this invention may occur between Arg and Gly, i.e. the N-terminal amino acid of this linear peptide would be Arg and the C-terminal amino acid would be Gly. An examples of such a linear peptide able to form the cyclic peptide of the present invention is SEQ ID NO. 41.

In another more preferred but non-limiting example, particularly when a 22mer cyclic peptide is provided, the cyclization (ring closure) of a linear peptide of this invention may occur between Lys and Pro, i.e. the N-terminal amino acid of this linear peptide would be Lys and the C-terminal amino acid would be Pro. An examples of such a linear peptide able to form the cyclic peptide of the present invention is SEQ ID NO. 43.

Besides their amino acid backbone, the cyclic peptides of the invention may further comprise (e.g. have covalently bound) (a) further substituent(s), like labels, anchors (like proteinaceous membrane anchors), tags (like HIS tags) and the like. Appropriate substituents and methods for adding them to the cyclic peptided of this invention are known to those of ordinary skill in the art.

Examples of labels in this context include, inter alia, fluorochromes (like fluorescein, rhodamine, Texas Red, etc.), enzymes (like horse radish peroxidase, β-galactosidase, alkaline phosphatase), radioactive isotopes (like 32P, 33P, 35S, 125I or 123I, 135I, 124I, 11C, 15O), biotin, digoxygenin, colloidal metals, chemi- or bioluminescent compounds (like dioxetanes, luminol or acridiniums). One particularly envisaged label that may be bound to the peptide of this invention is a fluorochrome belonging to a FRET pair of fluorochromes, for example a GFP variant (e.g. GFP, eGFP, EYFP or ECFP).

A variety of techniques are available for labeling biomolecules, are well known to the person skilled in the art and are considered to be within the scope of the present invention and comprise, inter alia, covalent coupling of enzymes or biotinyl groups, phosphorylations, biotinylations, random priming, nick-translations, tailing (using terminal transferases). Such techniques are, e.g., described in Tijssen, "Practice and theory of enzyme immunoassays", Burden and von Knippenburg (Eds), Volume 15 (1985); "Basic methods in molecular biology", Davis L G, Dibmer M D, Battey Elsevier (1990); Mayer, (Eds) "Immunochemical methods in cell and molecular biology" Academic Press, London (1987); or in the series "Methods in Enzymology", Academic Press, Inc. Detection methods comprise, but are not limited to, autoradiography, fluorescence microscopy, direct and indirect enzymatic reactions, etc.

The substituent(s) can be bound (e.g. covalently) to the cyclic peptides of the invention directly or via linkers. The skilled person is readily in the position to find out appropriate linkers to be employed in this context.

In a further aspect, the present invention relates to a nucleic acid molecule comprising a nucleotide sequence encoding the amino acid backbone/primary amino acid sequence of a cyclic peptide as disclosed in context of this invention. The present invention also relates to a nucleic acid molecule comprising a nucleotide sequence encoding the linear peptides as provided and described herein.

For example, such nucleic acid molecule may comprise a nucleotide sequence as depicted in any one of SEQ ID NO. 42, 44, 9 to 12, 25 to 28, 49, 50, 53 and 54 or, less preferred, SEQ ID NO. 13 to 16 and 29 to 32 or a nucleotide sequence which differs therefrom due to the degeneracy of the genetic code.

The meanings of the terms "nucleic acid molecule(s)", "nucleic acid sequence(s)" and "nucleotide sequence(s)" and the like are well known in the art and are used accordingly in context of the present invention.

For example, when used thoughout this invention, these terms refer to all forms of naturally occurring or recombinantly generated types of nucleotide sequences and/or nucleic acid sequences/molecules as well as to chemically synthesized nucleotide sequences and/or nucleic acid sequences/molecules. These terms also encompass nucleic acid analogues and nucleic acid derivatives such as e.g. locked DNA, PNA, oligonucleotide thiophosphates and substituted ribo-oligonucleotides. Furthermore, these terms also refer to any molecule that comprises nucleotides or nucleotide analogues.

Preferably, the terms "nucleic acid molecule(s)", "nucleic acid sequence(s)" and "nucleotide sequence(s)" and the like refer to deoxyribonucleic acid (DNA) or ribonucleic acid (RNA). The "nucleic acid molecule(s)", "nucleic acid sequence(s)" and "nucleotide sequence(s)" may be made by synthetic chemical methodology known to one of ordinary skill in the art, or by the use of recombinant technology, or may be isolated from natural sources, or by a combination thereof. The DNA and RNA may optionally comprise unnatural nucleotides and may be single or double stranded. "Nucleic acid molecule(s)", "nucleic acid sequence(s)" and "nucleotide sequence(s)" also refer to sense and anti-sense DNA and RNA, that is, a nucleotide sequence which is complementary to a specific sequence of nucleotides in DNA and/or RNA.

Furthermore, the terms "nucleic acid molecule(s)", "nucleic acid sequence(s)" and "nucleotide sequence(s)" and the like may refer to DNA or RNA or hybrids thereof or any modification thereof that is known in the state of the art (see, e.g., U.S. Pat. No. 5,525,711, U.S. Pat. No. 4,711,955, U.S. Pat. No. 5,792,608 or EP 302175 for examples of modifications). These molecules of the invention may be single- or double-stranded, linear or circular, natural or synthetic, and without any size limitation. For instance, the "nucleic acid molecule(s)", "nucleic acid sequence(s)" and/or "nucleotide sequence(s)" may be genomic DNA, cDNA, mRNA, anti-sense RNA, ribozymal or a DNA encoding such RNAs or chimeroplasts (Cole-Strauss Science 1996 273(5280) 1386-9). They may be in the form of a plasmid or of viral DNA or RNA. "Nucleic acid molecule(s)", "nucleic acid sequence(s)" and "nucleotide sequence(s)" and the like may also refer to (an) oligonucleotide(s), wherein any of the state of the art modifications such as phosphothioates or peptide nucleic acids (PNA) are included.

The nucleic acid molecules as provided herein are particularly useful for producing a cyclic peptide of the invention, for example by the corresponding method disclosed herein.

In another aspect, the present invention also relates to a vector comprising the nucleic acid molecule as disclosed herein and described above.

Said vector may be a cloning vector or an expression vector, for example, a phage, plasmid, viral or retroviral vector. Retroviral vectors may be replication competent or replication defective. In the latter case, viral propagation generally will occur only in complementing host/cells. The herein provided nucleic acid molecule may be joined to a particular vector containing selectable markers for propagation in a host. Generally, a plasmid vector is introduced in a precipitate, such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

Preferably, the nucleic acid molecule of this invention is operatively linked to expression control sequences (e.g. within the herein disclosed vector) allowing expression in prokaryotic or eukaryotic cells or isolated fractions thereof. Expression of said polynucleotide comprises transcription of the nucleic acid molecule, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogen), pSPORT1 (GIBCO BRL). Preferably, said vector is an expression vector and/or a gene transfer vector. Expression vectors derived from viruses such as retroviruses, adenoviruses, vaccinia virus, adeno-associated virus, herpes viruses, or bovine papilloma virus, may be used for delivery of the polynucleotides or vector of the invention into a targeted cell population. Methods which are well known to those skilled in the art can be used to construct a vector in accordance with this invention; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells.

The term "isolated fractions thereof" refers to fractions of eukaryotic or prokaryotic cells or tissues which are capable of transcribing or transcribing and translating RNA from the vector of the invention. Said fractions comprise proteins which are required for transcription of RNA or transcription of RNA and translation of said RNA into a polypeptide. Said isolated fractions may be, e.g., nuclear and cytoplasmic fractions of eukaryotic cells such as of reticulocytes. Kits for transcribing and translating RNA which encompass the said isolated fractions of cells or tissues are commercially available, e.g., as TNT reticulolysate (Promega).

Again, like the nucleic acid molecules of the invention, also the vectors as provided and described herein are particularly useful for producing a cyclic peptide of the invention, for example by the corresponding method disclosed herein.

In a further aspect, the present invention relates to a recombinant host cell comprising the nucleic acid molecule and/or the vector as disclosed herein. In context of this aspect, the nucleic acid molecule and/or the vector as disclosed herein can, inter alia, be used for genetically engineering host cells, e.g., in order to express and isolate the amino acid backbone/primary amino acid sequence of the cyclic peptide disclosed herein, and hence, the linear peptide of this invention.

Said host cell may be a prokaryotic or eukaryotic cell; see supra. The nucleic acid molecule or vector which is present in the host cell may either be integrated into the genome of the host cell or it may be maintained extrachromosomally.

The host cell can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*, or those belonging to the group of hyphal fungi, for example several penicillia or aspergilla strains. The term "prokaryotic" is meant to include all bacteria which can be transformed or transfected with a nucleic acid molecule for the expression of an amino acid backbone/primary amino acid sequence of the cyclic peptide disclosed herein, and hence, the linear peptide of this invention. Prokaryotic hosts may include gram negative as well as gram positive bacteria such as, for example, *E. coli, S. typhimurium, Serratia marcescens* and *Bacillus subtilis*. A nucleic acid molecule coding for an amino acid backbone/primary amino acid sequence of the cyclic peptide disclosed herein, and hence, the linear peptide of this invention, can be used to transform or transfect a host using any of the techniques commonly known to those of ordinary skill in the art. Methods for preparing fused, operably linked genes and expressing them in bacteria or animal cells are well-known in the art (Sambrook, supra). The genetic constructs and methods described therein can be utilized for expression of the above mentioned amino acid backbone/primary amino acid sequence and linear peptide in, e.g., prokaryotic hosts.

In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The expressed peptides can then be isolated from the grown medium, cellular lysates, or cellular membrane fractions. The isolation and purification of the microbially or otherwise expressed peptides may be by any conventional means such as, for example, preparative chromatographic separations and immunological separations such as those involving the use of monoclonal or polyclonal antibodies (Ausubel, Current Protocols in Molecular Biology, Green Publishing Associates and Wiley Interscience, N.Y. (1994)).

Again, like the nucleic acid molecules and the vectors as provided and described herein, also the corresponding host cells are particularly useful for producing a cyclic peptide of the invention, for example by the corresponding method disclosed herein.

In yet another aspect, the present invention relates to a method for producing a cyclic peptide of the present invention, comprising the steps of a) (i) culturing the recombinant host cell of the present invention under conditions such that the amino acid backbone of the herein disclosed cyclic peptide (or the linear peptide of this invention) is expressed, and recovering said amino acid backbone (or said linear peptide of this invention); or
   (ii) chemically synthesizing the amino acid backbone of the herein disclosed cyclic peptide (or the linear peptide of this invention); and
b) cyclization of said amino acid backbone (or said linear peptide) to form the herein disclosed cyclic peptide.

The definitions given herein-above with respect to the term "cyclization" apply here, mutatis mutandis. In the particular context of the above method, the meaning of the term "cyclization" encompasses both, forming of the intramolecular bridge (disulphide bond) and the ring closure by covalently connecting the N- and C-termini of the backbones of the cyclic peptides to be produced. T The definitions given herein with respect to the cyclic peptide, its amino acid backbone or the corresponding linear peptide according to this invention, as well as with respect to the host cell provided herein, apply here, mutatis mutandis.

As already mentioned above with respect to the provided cyclic and linear peptides, in a preferred embodiment of this further aspect of the invention, the N-terminal amino acid of the amino acid backbone/linear peptide to be cyclized in order to produce a cyclic peptide of this invention is Ala, Arg or Lys and the corresponding C-terminal amino acid is Gln, Gly or Glu (also DGlu is possible) or Pro. However, as mentioned-above, also other N- and C-terminal amino acids are envisaged, i.e. also other cyclization (ring closure) sites can be employed in context of the disclosed method.

The person skilled in the art is readily able to put the herein disclosed method for producing a cyclic peptide into practice, based on his common general knowledge and the prior art like WO 2006/103101, which discloses a general methology how to synthesize peptides and, particularly cyclic peptides. Also, the teachings of the invention, for example in the appended experimental part (example 1), provides for enabling technical guidance.

In the non-limiting example 1 of the invention, the cyclopeptide mutants were first synthesized in form of their linear peptides/amino acid backbones (for example by applying a chemical synthesis approach, like the Fmoc/tert butyl strategy (as described in WO 2006/103101; Chen W. C. and White P. D.: Fmoc Solid Phase Peptide Synthesis, Oxford University Press 2003)), and were then cyclized covalently on the backbone by condensation of the C-terminal carboxyl group with the amino group of the N-terminal amino acid ("head to tail" cyclization; Kates S, and Albericio F.: Solid phase synthesis, CRC-Press, 2000).

Subsequently, a disulphide bond is established between those two cysteine residues of the linear peptides which are able to form a disulphide bond (e.g. between $Cys_7$ and $Cys_{13}$ of the 18mer peptide, between $Cys_{10}$ and $Cys_{16}$ of the 22mer peptide or between $Cys_{11}$ and $Cys_{17}$ of the 25mer peptide) by chemical interaction known in the art (e.g. Benoiton N. L.: Chemistry of Peptide Synthesis. CRC-Press, 2005).

In general, in context of the "cyclization" step of the above described method, the ring closure of the linear backbone of the cyclic peptides to be produced may be performed before or after the formation of the S—S bridge. In other words, the S—S bridge between the two Cys residues of the AA chain of the peptides may be the first step in the "cyclization" procedure of the described production process and the ring closure may be the second step, or vice versa. The skilled person is able to find out which of these particular approaches is appropriate for a given setup of the production preconditions.

As mentioned above, the linear peptides/amino acid backbones of the cyclic peptides to be produced can also be produced by recombinant engineering techniques. Such techniques are well known in the art (e.g. Sambrook, supra). As also mentioned above, by this kind of production of said linear peptides/amino acid backbones particular advantage can be taken of the herein disclosed and described nucleic acid molecules, vectors and/or host cells. The definitions correspondingly given above apply here, mutatis mutandis.

Several approaches of peptide synthesis particular synthesis approaches of cyclic peptides are known in the art. (e.g. Williams, Chemical Approaches to the Synthesis of Peptides, CRC-Press 1997; Benoiton: Chemistry of Peptide Synthesis. CRC-Press, 2005). The skilled person is readily in the position to apply the prior art knowledge to the particular requirements of the disclosed method for producing cyclic peptides, based of the herein provided teaching.

As already mentioned above, this invention also relates to a cyclic peptide obtainable or obtained by the above described method, but also to a corresponding linear peptide (amino acid backbone/primary sequence of the corresponding cyclic peptide) obtainable or obtained by the above described method as some kind of an intermediate product (particularly a product obtainable or obtained by step a) of the above described method).

In general, the cyclic peptide according to the present invention may, inter alia, be used in medical intervention approaches. Such approaches comprise the use as or in a diagnostic agent and for the manufacture of a medicament for the treatment of diseases or the use in or as a composition, preferably a pharmaceutical composition, a diagnostic composition or a diagnostic kit, preferably for the detection of anti-β-AR antibodies, more preferably for the detection of anti-$β_1$-AR antibodies.

As mentioned, the antibodies as defined or described herein are preferably autoantibodies.

Non-limiting uses and applications of the compounds, particularly the cyclic peptide according to the present invention are described herein, for example in the following.

The present invention also relates to a composition comprising a cyclic or a linear peptide, a nucleic acid molecule, a vector or a recombinant host cell as disclosed and provided in context of the present invention, and optionally a carrier.

In one particular embodiment of this aspect, said composition is a pharmaceutical composition and said carrier is a pharmaceutically acceptable carrier.

The composition of this invention, particularly pharmaceutical composition of this invention, is particularly useful when employed in the treatment, amelioration or prevention as described and defined herein. Accordingly, the pharmaceutical composition of this invention may be used for the treatment, amelioration or prevention of a disease where the activity of a β-AR is enhanced or for the treatment of a patient having antibodies against a β-AR. Moreover, the pharmaceutical composition of this invention may be used for inducing immune tolerance of a patient, particularly immune tolerance of a patient with respect to immunogenic stretches of the endogenous $β_1$-AR.

Apart from containing at least one cyclic peptide of the present invention, the (pharmaceutical) composition provided may either comprise two or a plurality (like at least 3 or at least 5) of cyclic peptides of the present invention.

Likewise, not only one, but also two or a plurality (like at least 3 or at least 5) of said cyclic peptides may be administered to a patient in need of medical intervention in accordance with the present invention. Thereby, the administration of said more than one of cyclic peptides may be simultaneously or successively.

Moreover, in on particular embodiment, the present invention relates to the pharmaceutical composition, the method or uses for medical intervention or the cyclic peptide or the pharmaceutical composition as disclosed herein, wherein said cyclic peptide is administered with or said pharmaceutical composition comprises at least one further pharmaceutically active agent.

Said at least one further pharmaceutically active agent may be a β receptor blocker, preferably a selective β-AR blocker, like, for example, a $β_1$-AR blocker selected from the group consisting of atenolol, metoprolol, nebivolol, bisoprolol and the like.

Without being bound by theory, this kind of particular combination provides for protection from antibody-induced, selective $β_1$-AR downregulation by the herein provided cyclic peptides, since $β_1$-AR is at the same time upregulated by betablockers, like bisoprolol or metoprolol, and ultimately results in a synergistic effect of the cyclic peptides and the additional β-blocker(s).

The carrier optionally comprised in the (pharmaceutical) composition of the invention or to be administered together with the (pharmaceutical) composition or the cyclic peptide of the invention may particularly be a pharmaceutically acceptable carrier, excipient or diluent.

Such carriers are well known in the art. The skilled person is readily in the position to find out such carriers which are particularly suitable to be employed in accordance with the present invention.

In the following, several non-limiting administration schemes and the use of correspondingly suitable pharmaceutically acceptable carrier are described.

For an administration of the pharmaceutical composition and/or the cyclic peptides in accordance with this invention via subcutaneous (s.c.) or intravenous (i.v.) injection, compounds of the invention may be formulated in aqueous solution, preferably in physiologically compatible buffers such as Hank's solution, Ringer's solution, or physiologically saline buffer. For transmucosal and transpulmonal administration, penetrants appropriate to the barrier to be permeated are used in the formulation. Such penetrants are generally known in the art.

The use of pharmaceutical acceptable carriers to formulate the compounds according to the present invention into dosages or pharmaceutical compositions suitable for systemic, i.e. intravenous/intraarterial, or subcutaneous administration is within the scope of the present invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for subcutaneous or oral administration. Such carriers enable the compounds according to the present invention to be formulated as tablets, pills, capsules, dragees, liquids, gels, syrups, slurries, suspensions and the like, for oral ingestion by a subject to be treated.

Compounds according to the present invention, or medicaments comprising them, intended to be administered intracorporally/intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered near the cell surface. Delivery systems involving liposomes are disclosed in U.S. Pat. No. 4,880,635 to Janoff et al. The publications and patents provide useful descriptions of techniques for liposome drug delivery.

Pharmaceutical compositions comprising a compound according to the present invention for parenteral and/or subcutaneous administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil or castor oil, or synthetic fatty acid esters, such as ethyl oleate or triglycerides, or liposomes. Aqueous injections suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions and to allow for a constantly slow release of the substance in the organism.

It is clear to the skilled person that, in accordance with the present invention, the disclosed pharmaceutical composition or cyclic peptide may be administered in a pharmaceutically/therapeutically effective dose, which means that a pharmaceutically/therapeutically effective amount of the compound administered is reached. Preferably, a pharmaceutically/therapeutically effective dose refers to that amount of the compound administered (active ingredient) that produces amelioration of symptoms or a prolongation of survival of a subject which can be determined by the one skilled in the art doing routine testing.

It is of note that the dosage regimen of the compounds to be administered in accordance with the present invention will be determined by the attending physician and clinical factors. As is well known in the medical arts, that dosages for any one patient depends upon many factors, including the patient's size, body surface area, age, the particular compound to be administered, sex, time and route of administration, general health, and other drugs being administered concurrently. A person skilled in the art is aware of and is able to test the relevant doses, the compounds to be medically applied in accordance with the present invention are to be administered in.

As shown herein, the effect of the cyclic peptides provided herein, namely the blockage of anti-$β_1$-AR antibodies, can be obtained in a dose dependent manner. Thereby, the efficiency of the Cys→Ser mutated cyclopeptides as disclosed herein depends on a threshold concentration (FIGS. 14, 15, and 16 B,C).

Accordingly, the disclosed pharmaceutical composition or cyclic peptide may particularly be administered in a manner that it is present in a concentration, i.e. reaches a threshold concentration, of at least 0.05 mg per kg body weight, preferably in a concentration of at least 0.1 mg per kg body weight, more preferably in a range of 0.1 mg per kg body weight (100 µg/kg) to 100 mg per kg body weight, more preferably in a range of 1 mg per kg body weight to 100 mg per kg body weight and most preferably in a range of 1 mg per kg body weight to 10 mg per kg body weight. Particularly, the effective dose of the disclosed pharmaceutical composition or cyclic peptide may be at about 1 mg per kg body weight. Also higher concentrations of the disclosed pharmaceutical composition or cyclic peptide are generally envisaged to be reached by correspondingly applied administration schemes. For example, such higher concentrations may be at least 2, 3, 4 or 5 mg per kg body weight. Concentrations of at least 1 mg per kg body weight or at least 2 mg per kg body weight are preferred.

One particularly preferred, non-limiting administration scheme to be applied in context of this invention is an s.c. or i.v. application every two or four weeks.

In this context, it is of note that in the rat model employed herein a dose of 1 to 4 mg/kg i.v. every other month were sufficient to obtain therapeutic levels of the compounds according to the present invention, with the respective dosage for humans preferably being about 0, 3-10 mg/kg i.v. or s.c, more preferably being about 1-10 mg/kg i.v. or s.c., even more preferably being about 1-5 mg/kg i.v. or s.c.

As demonstrated herein, the administration of the disclosed cyclic peptides may initially trigger a transient opposite immune response, in particular when applied in higher doses. Such transient immune responses in the long run are compensated by the antibody-inactivating activity of the administered cyclic peptides. This may lead to an decelerated effect of the administered cyclic peptides, i.e. a decelerated elimination of anti-$\beta_1$-AR antibodies and hence a decelerated reduction of (aberrant) $\beta_1$-AR activity.

The present invention also relates to a method for
a) the treatment, amelioration or prevention of a disease where the activity of a $\beta$-AR, preferably $\beta_1$-AR, is enhanced;
b) the treatment of a patient having antibodies against a $\beta$-AR, preferably against $\beta_1$-AR, or suffering from or being at risk to develop a disease as disclosed herein; or
c) inducing immune tolerance,
comprising the step of administering to a patient in need of such medical intervention a pharmaceutically active amount of a cyclic peptide and/or of a pharmaceutical composition as disclosed herein, and optionally a pharmaceutically acceptable carrier.

The present invention also relates to a cyclic peptide or a pharmaceutical composition as disclosed herein, and optionally a pharmaceutically acceptable carrier, for
a) the treatment, amelioration or prevention of a disease where the activity of a $\beta$-AR, preferably $\beta_1$-AR, is enhanced;
b) the treatment of a patient having antibodies against a $\beta$-AR, preferably against $\beta_1$-AR, or suffering from or being at risk to develop a disease as disclosed herein; or
c) inducing immune tolerance.

The diseases to be medically intervened (treated, ameliorated, prevented or diagnosed) in accordance with this invention or the diseases the patient as defined and described herein suffers from are preferably those, where the $\beta_1$-AR is activated in a non-physiological manner, more preferably is activated by antibodies, more preferably by auto-antibodies which are directed against the $\beta_1$-AR.

Exemplarily and preferably, the diseases to be medically intervened in accordance with this invention or the diseases the patient as defined and described herein suffers from comprise, however, are not limited thereto, the group of heart diseases.

Particularly, the heart diseases to be medically intervened in accordance with this invention or the heart diseases the patient as defined and described herein suffers from may comprise but are not limited to infectious and non-infectious heart disease, ischemic and non-ischemic heart disease, inflammatory heart disease and myocarditis, cardiac dilatation, idiopathic cardiomyopathy, (idiopathic) dilated cardiomyopathy (DCM), immune-cardiomyopathy, heart failure, and any cardiac arrhythmia including ventricular and/or supraventricular premature capture beats as well as any atrial arrhythmia including atrial fibrillation and/or atrial flutter.

In other words, the heart disease as referred to in the descriptions and definitions given herein with respect to the methods or the cyclic peptide or the pharmaceutical composition of the invention may be heart diseases selected from the group comprising infectious and non-infectious heart disease, ischemic and non-ischemic heart disease, inflammatory heart disease and myocarditis, cardiac dilatation, idiopathic cardio-myopathy, (idiopathic) dilated cardiomyopathy (DCM), immune-cardiomyopathy, heart failure, and any cardiac arrhythmia including ventricular and/or supraventricular premature capture beats as well as any atrial arrhythmia including atrial fibrillation and/or atrial flutter.

It is of note that the most preferred disease to be medically intervened (treated, ameliorated, prevented or diagnosed) in accordance with this invention or the most preferred disease the patient as defined and described herein suffers from is DCM, preferably idiopathic DCM.

A particular subgroup of the "patients" for the purpose of the present invention are those patients suffering from any of the diseases described herein, more particularly the group of heart diseases described herein and having at the same time antibodies directed against $\beta$-ARs, more preferably antibodies against the $\beta_1$-AR, whereby the antibodies are preferably auto-antibodies.

A disease to be medically intervened (treated, ameliorated, prevented or diagnosed) in accordance with this invention or a disease the patient as defined and described herein suffers from is intended to be induced by antibodies against a $\beta$-AR, preferably by antibodies against $\beta_1$-AR. Preferably, these antibodies are auto-antibodies.

The means and methods provided herein are particularly useful when provided in the prophylaxis/prevention of a disease as defined herein. This means that a patient may be treated with the cyclic peptide and/or pharmaceutical composition of the invention prior to the onset (of symptoms) of a disease as defined herein. For example, this preventive treatment may follow a preceding diagnostic application that, e.g., takes advantage of the diagnostic means and methods provided herein. Thereby, it is preferred that a preventive treatment taking advantage of the therapeutic means and methods of this invention is applied, when the risk to develop a disease as defined herein is diagnosed, e.g. when anti-$\beta$-AR (auto-) antibodies are detected.

In this context, a preferred "patient" is one bearing at risk to develop a disease as defined herein. Particularly, such a patient is one having anti-$\beta$-AR (auto-)antibodies, preferably anti-$\beta_1$-AR (auto-)antibodies, but not (yet) suffering from a disease as defined herein, or symptoms thereof.

The immune tolerance to be induced in context of this invention is envisaged to be particularly obtained by suppression of the production of antibodies against immunogenic stretches of the $\beta$-AR molecule, which, without being bound by theory, may be due to a blockade of the antigen-recognition sites of the antibody-producing early (mature) B-cells and memory B-cells.

It is within the present invention that the provided pharmaceutical composition or cyclic peptide is particularly useful for the treatment, prevention and/or amelioration of any of the diseases and patient groups or patients as defined herein including the detection of anti-β-AR antibodies in these patients by using the aforementioned compounds.

A "patient" for the purposes of the present invention, i.e. to whom a compound according to the present invention is to be administered or who suffers from the disease as defined and described herein or who is intended to be diagnosed in accordance with this invention, includes both humans and other animals and organisms. Thus the compounds and methods of this invention are applicable to or in connection with both human therapy and veterinary applications including diagnostic(s), diagnostic procedures and methods as well as staging procedures and methods. In the preferred embodiment the patient is a mammal, and in the most preferred embodiment the patient is human.

The mutant cyclic peptides according to the present invention may also be used for the preparation of a medicament for the treatment, prevention and/or amelioration of any of the diseases and patient groups/patients as defined herein. What is said herein for the pharmaceutical composition applies also to the medicament for the manufacture of which the peptides of the present invention may be used.

In a still further aspect, the present invention is related to a diagnostic agent comprising or being a cyclic peptide or a composition according to this invention, and optionally at least one further biologically active compound.

Preferably the herein disclosed diagnostic agent consists of or comprises a mutant peptide of the present invention, whereby the mutant peptide comprises a label. Such label may be selected from the group comprising radioactive labels and fluorescent labels. Respective labels are known to the ones skilled in the art. The definitions and descriptions of labels as given herein-above apply here, mutatis mutandis. Typically, the peptide is the part of the diagnostic agent conferring specific binding characteristics to the diagnostic agent, preferably binding to anti-$β_1$-AR antibodies, whereas the label confers the signalling characteristics to the diagnostic agent.

The diagnostic agent of this invention may comprise, apart from (a) labelled or unlabelled mutant peptide(s) of the present invention, a further biologically active compound. Such further biologically active compound may be a means to confer signalling characteristics to the diagnostic agent, particularly in case the mutant peptides of the present invention are unlabelled. For example, the further biologically active compound can be an antibody, preferably a monoclonal antibody, and more preferably a labelled antibody specifically binding to a mutant peptide of the present invention or to a complex consisting of a mutant peptide of the present invention and an anti-β-AR antibody, preferably an anti-$β_1$-AR antibody.

In a further aspect, the present invention relates to a method for diagnosing a disease as defined and described herein comprising the steps of
a) detecting antibodies against a β-AR (for example in a sample) using the cyclic peptide or the composition or the diagnostic agent of the present invention; and
b) diagnosing for said disease, when the titer of said antibodies is increased.

In a further aspect, the present invention is related to a method for diagnosing a patient which can be treated using the mutant peptides, pharmaceutical compositions and medicaments according to the present invention. In context of this particular method also a step of detecting antibodies against a β-AR (for example in a sample) using the compounds of the present invention and/or a step of considering whether the outcome of said detection step indicates a disease as defined herein, may be employed. As mentioned, a disease as defined herein or the risk to develop a disease as defined herein is indicated, when the titer of said anti-β-AR antibodies is increased.

In another aspect, the present invention relates to a cyclic peptide, a composition or a diagnostic agent as provided and described herein for diagnosing (for example in a sample) a disease as defined herein. Again, a disease as defined herein or the risk to develop a disease as defined herein is indicated by an increased titer of anti-β-AR antibodies.

In context of the present invention the term "increased titer of anti-β-AR antibodies" means that the titer of anti-β-AR antibodies (for example in a sample derived from a patient to be diagnosed in accordance with this invention) is higher than that of a healthy control patient, i.e. a patient not suffering from a disease as defined herein and/or a patient lacking anti-β-AR antibodies.

As mentioned, in healthy patients, anti-β-AR antibodies are usually hardly or not at all present or detectable. Accordingly, an "increased titer of anti-β-AR antibodies" in accordance with the present invention preferably refers to any occurrence of anti-β-AR antibodies, i.e. any occurrence of a detectable amount of anti-β-AR antibodies.

A suitable "sample" in accordance with the present invention includes, but is not limited to, (a) biological or medical sample(s), like, e.g. (a) sample(s) comprising cell(s) or tissue(s). For example, such (a) sample(s) may comprise(s) biological material of biopsies. The meaning of "biopsies" is known in the art. For instance, biopsies comprise cell(s) or tissue(s) taken, e.g. by the attending physician, from a patient/subject as described herein. Exemplarily, but not limiting, the biological or medical sample to be analysed in context of the present invention is or is derived from blood, plasma, white blood cells, urine, semen, sputum, cerebrospinal fluid, lymph or lymphatic tissues or cells, muscle cells, heart cells, cells from veins or arteries, nerve cells, cells from spinal cord, brain cells, liver cells, kidney cells, cells from the intestinal tract, cells from the testis, cells from the urogenital tract, colon cells, skin, bone, bone marrow, placenta, amniotic fluid, hair, hair and/or follicles, stem cells (embryonic, neuronal, and/or others) or primary or immortalized cell lines (lymphocytes, macrophages, or cell lines). Preferred "samples" in accordance with the present invention are those derived from blood or plasma. The biological or medical sample as defined herein may also be or be derived from biopsies, for example biopsies derived from heart tissue, veins or arteries.

In a further aspect, the present invention relates to a diagnostic kit, for example a diagnostic kit for the detection of antibodies against a β-AR, comprising the cyclic peptide, composition or diagnostic agent of the invention.

The kit in accordance with the present invention comprises at least one of the compounds as disclosed according to the invention, like, for example a cyclic or linear peptide of the present invention, a nucleic acid molecule, vector or host cell of the invention or a composition or diagnostic agent according to the present invention. In one particular embodiment the kit further comprises an instruction leaflet, and/or a buffer for use in the application of the kit, and/or at least one reaction vessel for carrying out the detection reaction for which the kit is or is to be used. In a further embodiment, at least one, some or all of the reagents used in connection with the application of said kit are present as portions useful in carrying out the reaction(s) for which the kit is to be used.

The cyclic peptides, diagnostic agents or kits of this invention may also be applied for the detection of $\beta_1$-AR. Accordingly, the cyclic peptides, diagnostic agents or kits of this invention may particularly be useful for identifying/detecting bound anti-$\beta_1$-AR antibodies on cell- and/or tissue surfaces. For example, the cyclic peptides, diagnostic agents or kits of this invention may be used for in imaging purposes, like single photone emission computed tomography (SPECT), MiBi, PET, magnetic resonance tomography (MRT) or other diagnostic imaging techniques employed in medicine. Due to the 131I-labelled CP-distribution pattern in vivo (FIG. 30), the cyclic peptides, diagnostic agents of this invention may, for example, be particularly useful as organ-specific tracers.

One particular approach for using the compounds according to the present invention as a diagnostic and in a diagnostic method, respectively, is a three-step screening procedure. For example, this method comprises performing an ELISA with the cyclic peptides according to the present invention as well as determining immunofluorescence and determining cAMP responses in cells expressing native human R-AR. It is to be acknowledged that each and any of the aforementioned steps can as such be preformed for the detection of said antibodies using the cyclic peptides according to the present invention. A large number of patients, for example heart failure patients, may thus be screened for functionally active anti-$\beta_1$-AR antibodies. In connection with such (but also with other herein disclosed) diagnostic methods, the definition of functionally active anti-$\beta_1$-AR antibodies is preferably based on their effects on receptor-mediated signalling, that is, their effects on cellular cAMP levels and on the activity of the cAMP-dependent protein kinase (PKA). Cyclic AMP is an universal second messenger of many G protein-coupled receptors including the $\beta$-AR family. It exerts its effects via PKA, cAMP-gated ion channels, phosphodiesterases, and exchange proteins directly activated by cAMP, known as Epac1 and 2. The prior art describes several fluorescence methods for measuring cAMP in intact cells which can all be used in connection with the diagnostic method of the present invention. Fluorescence resonance energy transfer (FRET) between green fluorescent protein (GFP) variants fused to the regulatory and catalytic subunits of PKA has been described to study the spatio-temporal dynamics of cAMP in neurons (Hempel C M, Vincent P, Adams S R, Tsien R Y, Selverston A I. Nature. 1996; 384:113-114) or cardiac myocytes. (Zaccolo M, Pozzan T., Science. 2002; 295:1711-1715).

More recently, single chain fluorescence indicators have been-described in the art which are characterized by having an enhanced cyan (CFP) or yellow fluorescent protein (YFP) directly fused to the cAMP-binding domain of Epac-proteins, which allowed to achieve a higher sensitivity and better temporal resolution of the cAMP measurements. Such system is, among others described in WO2005/052186. Such system can be used in connection with any diagnostic procedure using the cyclic peptides or other corresponding compounds according to the present invention. Also such system can be used for, however is not limited thereto, analyzing the prevalence of functionally active anti-$\beta_1$-AR antibodies. Preferably such diagnostic method is applied to a cohort of previously antibody-typed DCM patients or any individual to be assessed insofar or any individual suspected of suffering from any of the diseases described herein or being at risk to suffer therefrom. In a further step of the diagnostic method and screening method, the ability of $\beta$-blockers to inhibit anti-$\beta_1$-AR antibodies-induced receptor activation may be assessed and determined, respectively.

The afore described assay which is a FRET-based method as described in WO 2005/052186 making use of the peptides according to the present invention is advantageous insofar as it is simpler, less time consuming, and at the same time discloses or identifies all DCM patients previously considered anti-$\beta_1$-$EC_{II}$ antibody-positive. This embodiment of a FRET based method of diagnosing making use of one or several of the peptides according to the present invention is based on detecting antibody-induced increases in cAMP.

Taken together, screening by Epac-FRET appears to represent a very sensitive single step approach, allowing to detect activating antibodies directed against the human $\beta_1$-AR. Therefore, the present invention is also related to the use of one or several of the peptides according to the present invention for use in an Epac-FRET assay. More preferably such Epac-FRET assay is used for diagnosis, even more preferably for the diagnosis of patients suffering from or suspected of suffering from any of the disease described herein.

In view of the above, it is a particularly preferred use or apply the FRET technology, particularly a FRET-based detection system, in accordance with this invention.

In a further aspect, the present invention relates to a method for detecting of antibodies against a $\beta$-AR (for example in a sample as defined herein) comprising the step of contacting the cyclic peptide of the invention with said antibodies to be detected.

In a further aspect, the present invention relates to the cyclic peptide, composition or diagnostic agent as disclosed herein for detecting (for example in a sample as defined herein) antibodies against a $\beta$-AR.

The above method for detecting of antibodies or cyclic peptide, composition or diagnostic agent is particularly useful to be employed in context of the diagnostic applications as described and provided in context of this invention.

Throughout the present application, the following abbreviations shall have the following meanings: Ab or ab: antibody, Abs or abs: antibodies, AR: adrenergic receptor, EC extra cellular domain of a $\beta$-AR, $EC_{II}$ extra cellular domain II of a $\beta$-AR and AA amino acid.

The present invention is further described by reference to the following non-limiting figures and examples.

For the 3 Cys-containing $\beta_1$-$EC_{II}$-25AA Cys/Cys cyclopeptide, HPLC was carried out in a Waters Separation Modul 2690 together with a Waters Dual Lambda absorbance detector; absorbance was read at 220 nm. After peptide synthesis and cyclization, the samples were dissolved in $H_2O$/5% acetonitril (ACN) and loaded on a Nuclosil 100-5/C18 column (Macherey-Nagel Inc., Germany; column length 250 mm, lumen 4 mm) with a flow of 1 ml/min; then a separation-gradient from 5% to 60% ACN in the presence of 0.2% TFA was run. The remaining faint amount of linear $\beta$1-ECII-25AA peptide yielded a small peak, typically between 14 and 16 min, whereas the fractions containing the $\beta_1$-$EC_{II}$-25AA Cys/Cys cyclopeptide appeared in a range from 18 to 22 min.

HPLC of the mutant 25AA-cyclopeptides was performed with a Silica C18 column (15 µm, 120 A, length 250 mm, lumen 4 mm) with a flow of 1 ml/min followed by a separation-gradient from 5% to 60% ACN in the presence of 0.1%

TFA. The fractions containing the cyclic $\beta_1$-EC$_{II}$-25AA mutants were monitored by UV-absorption (210 nm) and showed a sharp single elution peak appearing at ~10.5 min (25AA Cys/Ser-mutant, left panel) or ~16.5 min (25AA Ser/Cys-mutant, right panel).

Figure 1:
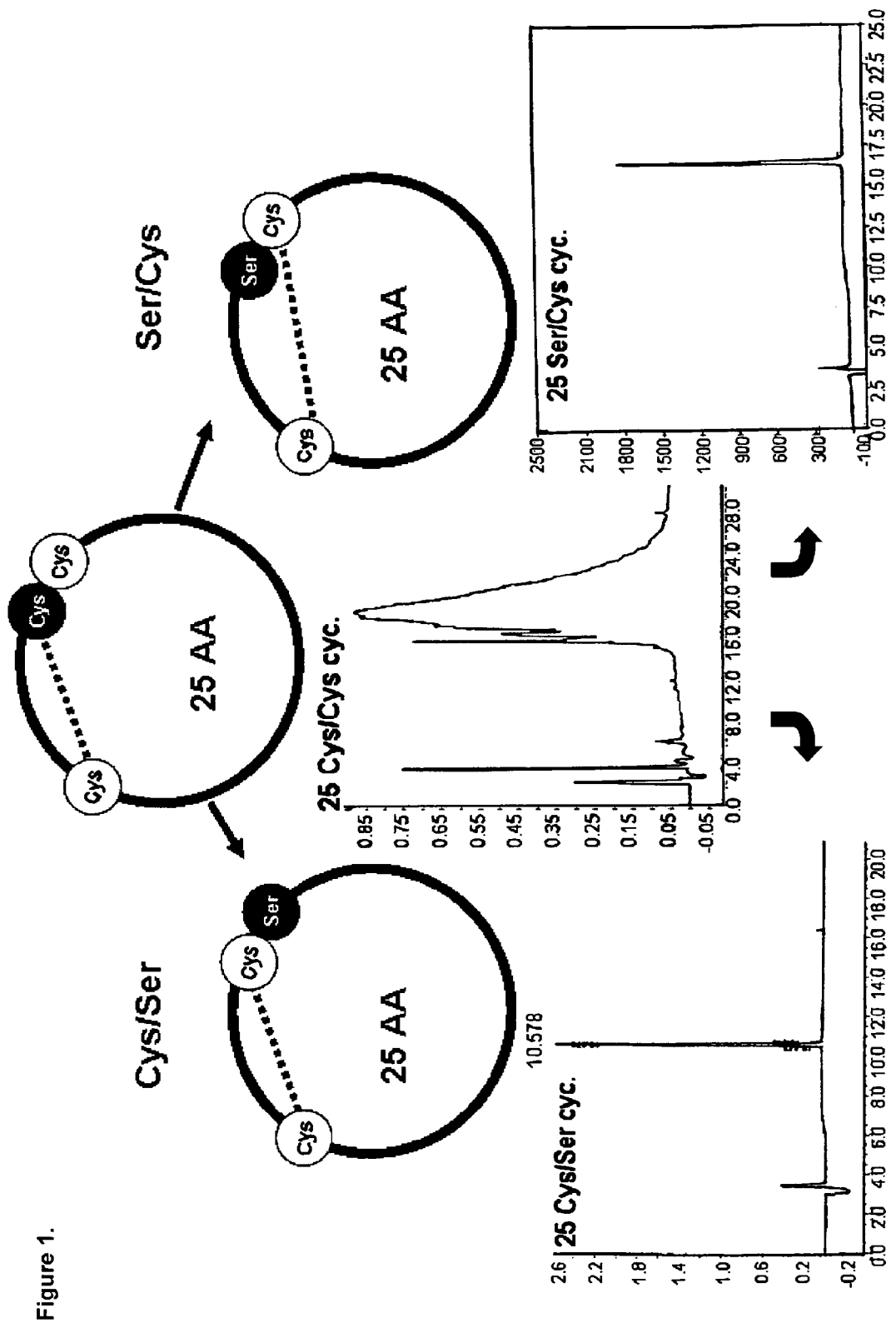
FIG. 1 is a diagram depicting the scheme of the $\beta_1$-$EC_{II}$-25 amino-acid (AA) cyclopeptide and the mutated $\beta_1$-$EC_{1-25}$AA cyclopeptides (black rings with the original Cys-residues (white balls) or the Ser mutated Cysteines (black balls; Cys/Ser or Ser/Cys, respectively), and the corresponding high liquid pressure liquid chromatographic elution profiles detected at a wave length of 210 nm or 220 nm, respectively.
Figure 2:
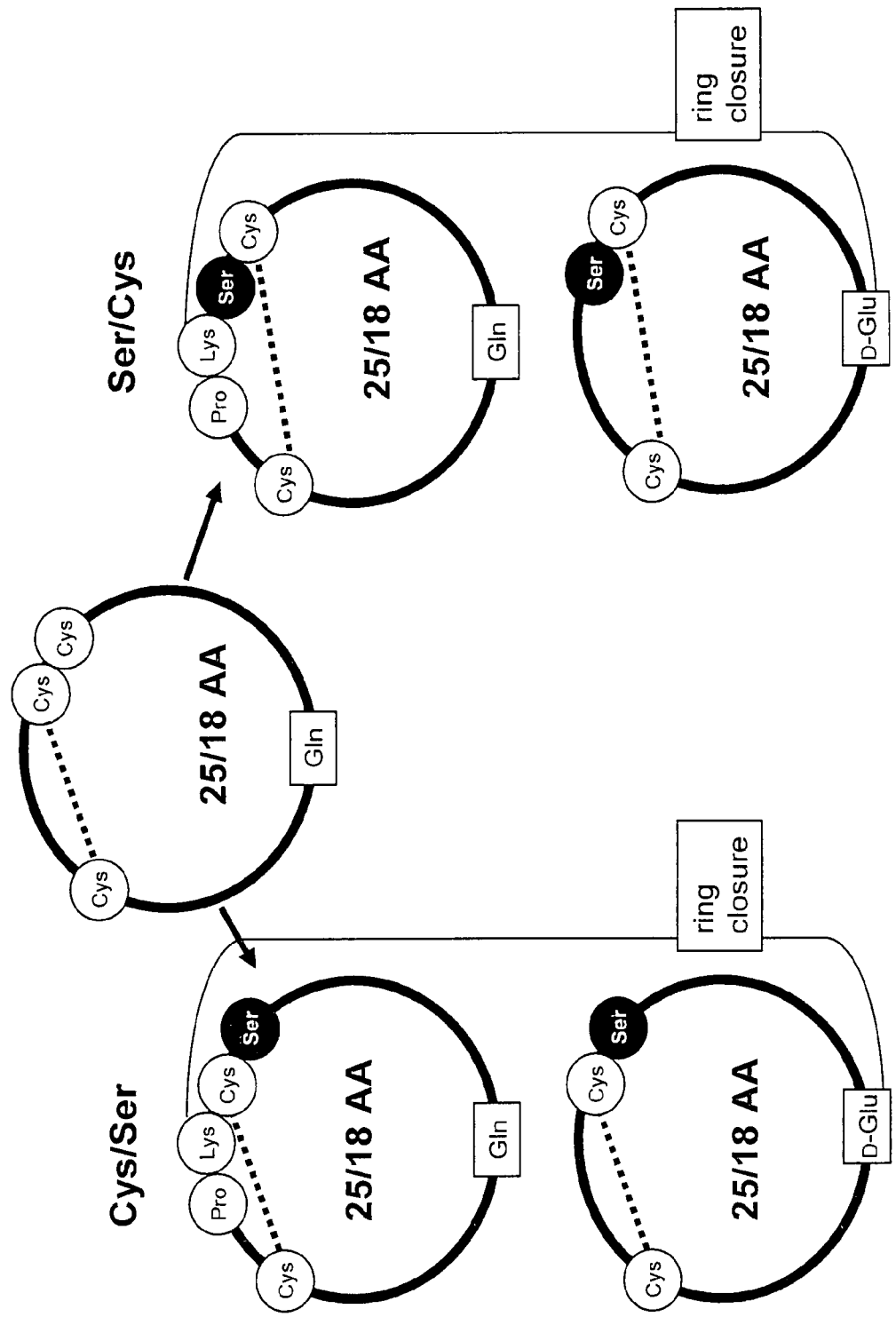

FIG. 2 is a diagram depicting the scheme of the mutated $\beta_1$-EC$_{II}$-25AA or 18AA-cyclo-peptides (black rings with the original Cys-residues (white balls) or the Ser mutated Cysteines (black balls; Cys/Ser or Ser/Cys, respectively), together with the amino-acids involved in forming the primary ring structure after head-to-tail closure (closure site either Ala-DGlu, or Pro-Lys).

For the synthesis of cyclic $\beta_1$-EC$_{II}$-18AA (or $\beta_1$-EC$_{II}$-25AA) peptides on the solid phase, Fmoc-Glu-ODmab or another Fmoc amino acid having a side chain protecting group which can be selectively cleaved off in an orthogonal manner, is incorporated at the C-terminal end of the linear peptide. The cleaving off of the cyclic peptide from the synthesis resin generates a peptide amide (in the case of D-Glu→Gln) and the removal of the protective groups of the side chain is done by treating the resin with trifluoro acetate acid/triisopropylsilane/ethandithiole/water for several hours.

Figure 3:
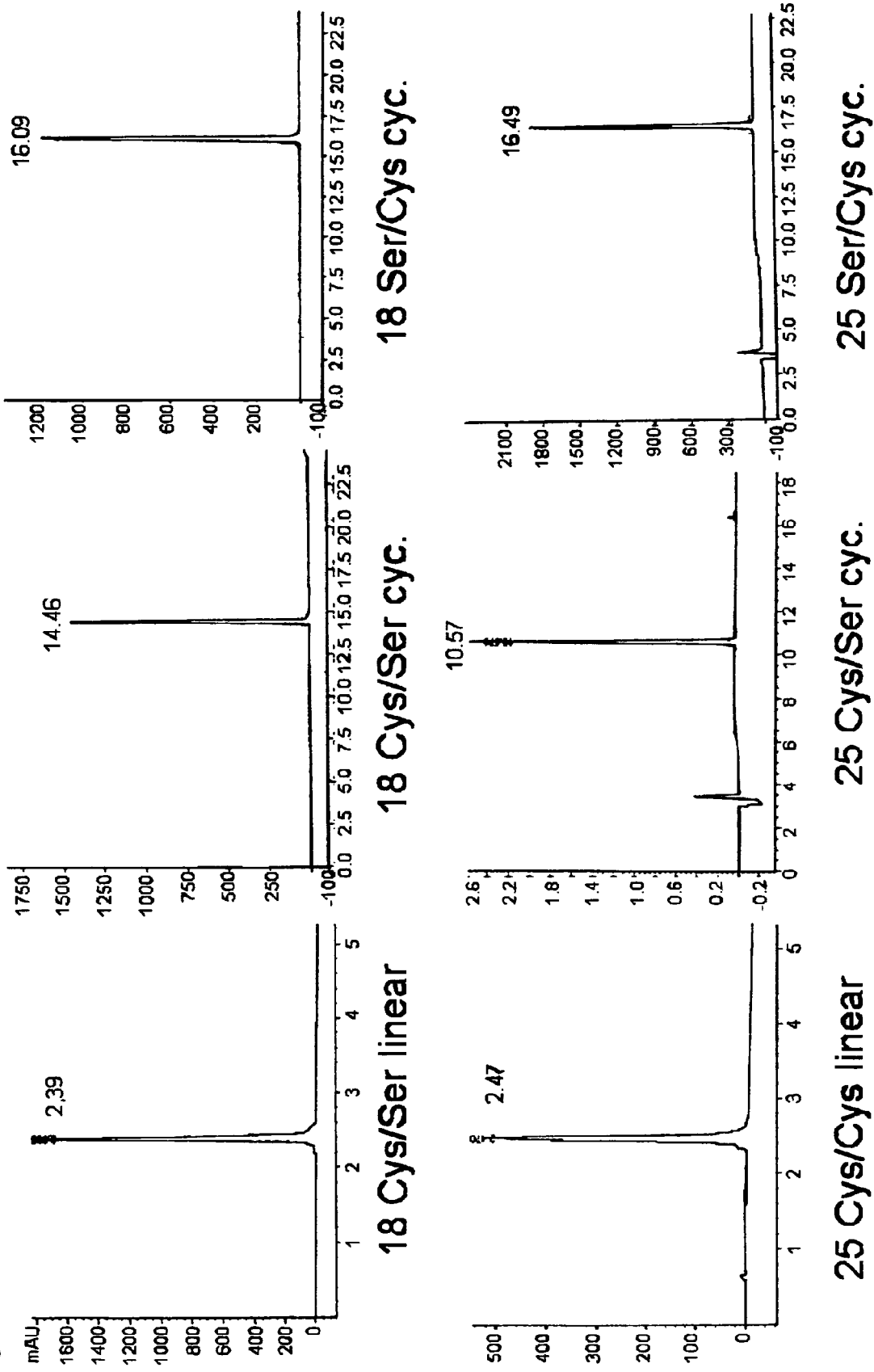

FIG. 3 shows six panels demonstrating the HPLC elution profiles of two linear (left panels, 18AA Cys/Ser and 25AA Cys/Cys, respectively) and four of the mutant cyclo-peptides of the present invention, all of them Gln-containing cyclopeptides with a Pro-Lys closure site. HPLC of the mutant 25AA- or 18AA-cyclopeptides was carried out in a Waters Separation Modul together with a UV absorbance detector; absorbance was read at 210 nm. After peptide-synthesis and cyclization, the samples were dissolved in H$_2$O/5% acetonitril (ACN) and loaded on a Silica C18 column (15 μm, 120 A, column length 250 mm, lumen 4 mm) with a flow of 1 ml/min; then a separation-gradient from 5% to 60% ACN in the presence of 0.1% TFA was run. As shown for their linear counterparts, the fractions containing the cyclic $\beta_1$-EC$_{II}$-18AA mutants (upper row, middle panel (Cys/Ser, ~14 min), right panel (Ser/Cys, ~16.5 min); or $\beta_1$-EC$_{II}$-25AA mutants (lower row, middle panel (Cys/Ser, ~10.6), right panel (Ser/Cys, ~16.5)) gave sharp single elution peaks appearing at the indicated time points.

Figure 4:
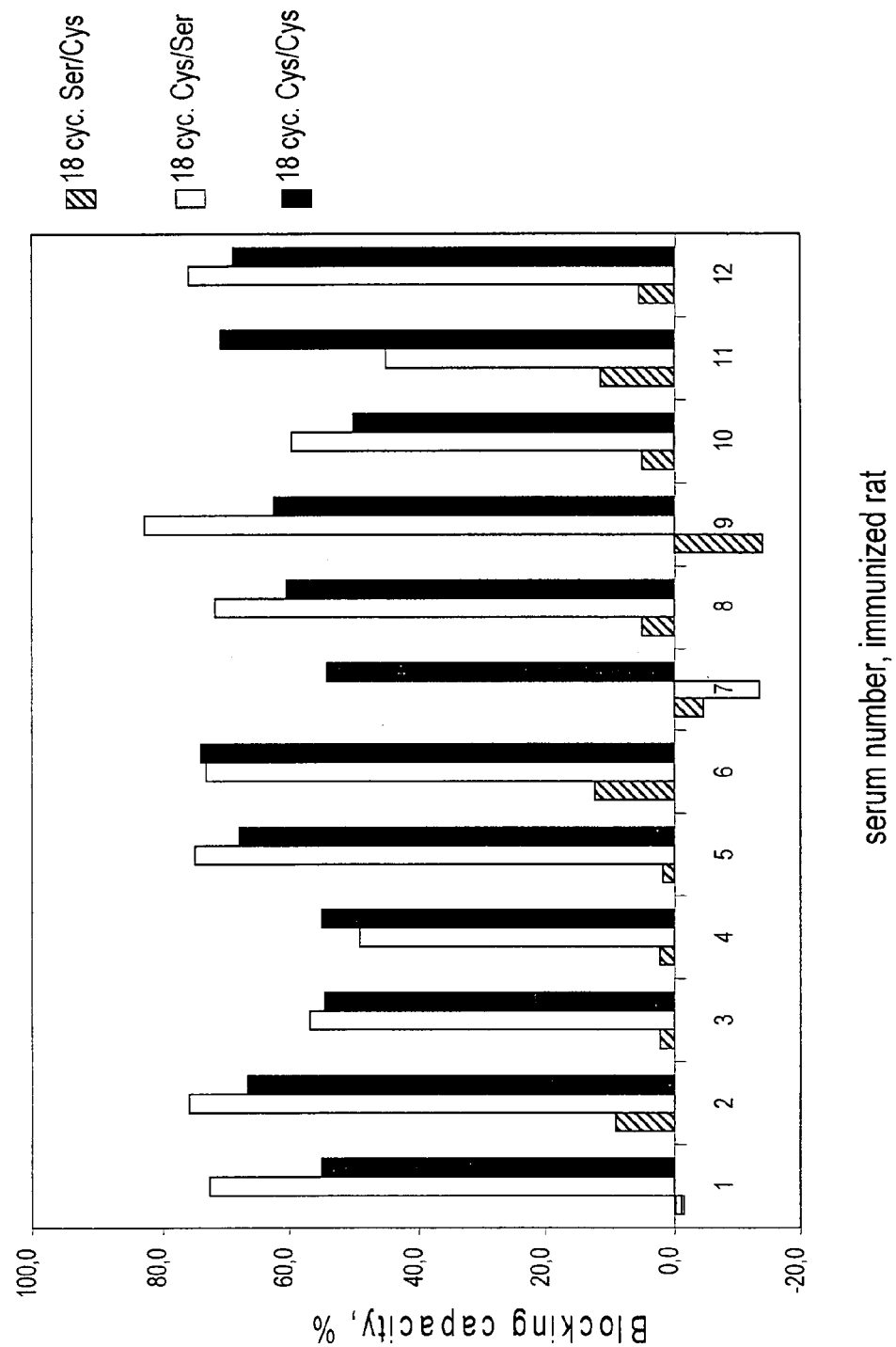

FIG. 4 is a diagram depicting the blocking capacity of $\beta_1$-EC$_{II}$-18AA cyclopeptide mutants having a D-Glu ring closure (Cys/Ser mutation, white columns; Ser/Cys mutation, diagonally right hatched columns) compared with the 3 Cys-containing 18AA cyclopeptide (black columns) in an ELISA-competition assay using the 3 Cys-containing linear 25AA Cys/Cys-peptide as an antigen. Representative results obtained with IgG-fractions isolated from the sera of 12 different immunized antibody-positive rats are depicted. The y-axis represents the blocking efficiency of the various peptides used given in % of blocked versus non-blocked ELISA-reactivity of the sera after preincubation (12 h over-night, 4° C., rotating incubator) with the indicated cyclopeptides.

Figure 5:
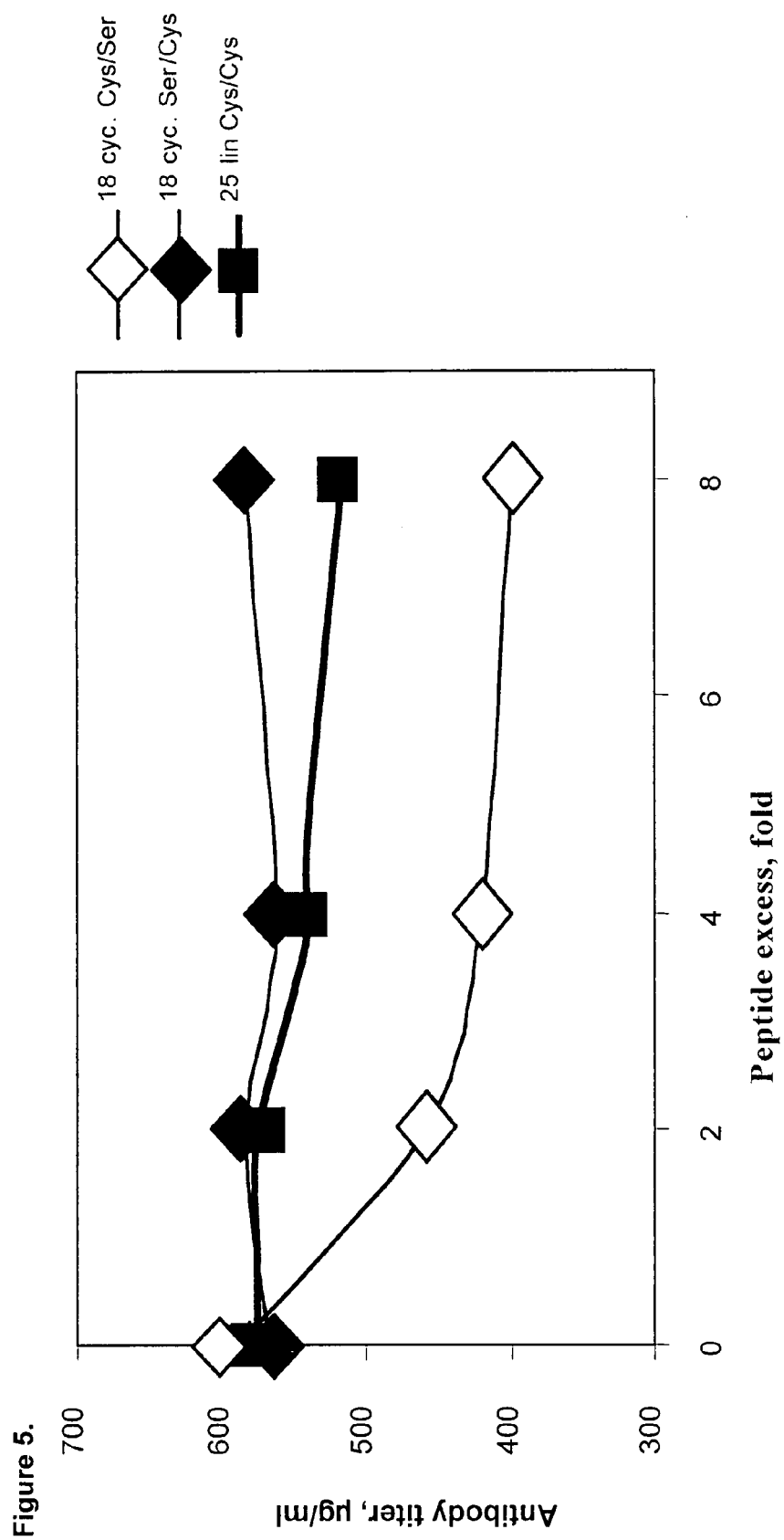

FIG. 5 is a diagram depicting the blocking capacity of $\beta_1$-EC$_{II}$-18AA cyclopeptide mutants having a D-Glu ring closure (Cys/Ser mutation, white diamonds; Ser/Cys mutation, black diamonds) compared with the 3 Cys-containing linear 25AA Cys/Cys-peptide (black squares) in an ELISA-competition assay using the 3 Cys-containing linear 25AA Cys/Cys-peptide as an antigen. A single representative serum from an antibody-positive cardiomyopathic rat was used (FIG. 4, rat number 4). The y-axis represents the concentration of specific anti-$\beta_1$-EC$_{II}$ IgG antibodies as determined by ELISA, the x-axis corresponds to the molar excess of linear or cyclic peptides used to preincubate the IgG-fractions (12 h, 4° C., rotating incubator) assuming a 1:1 stochiometry (one cyclic (2.1 kDa molecular mass (MM)) or linear peptide (3.0 kDa MM) was assumed to block one IgG-antibody (150 kDa MM)).

Figure 6:
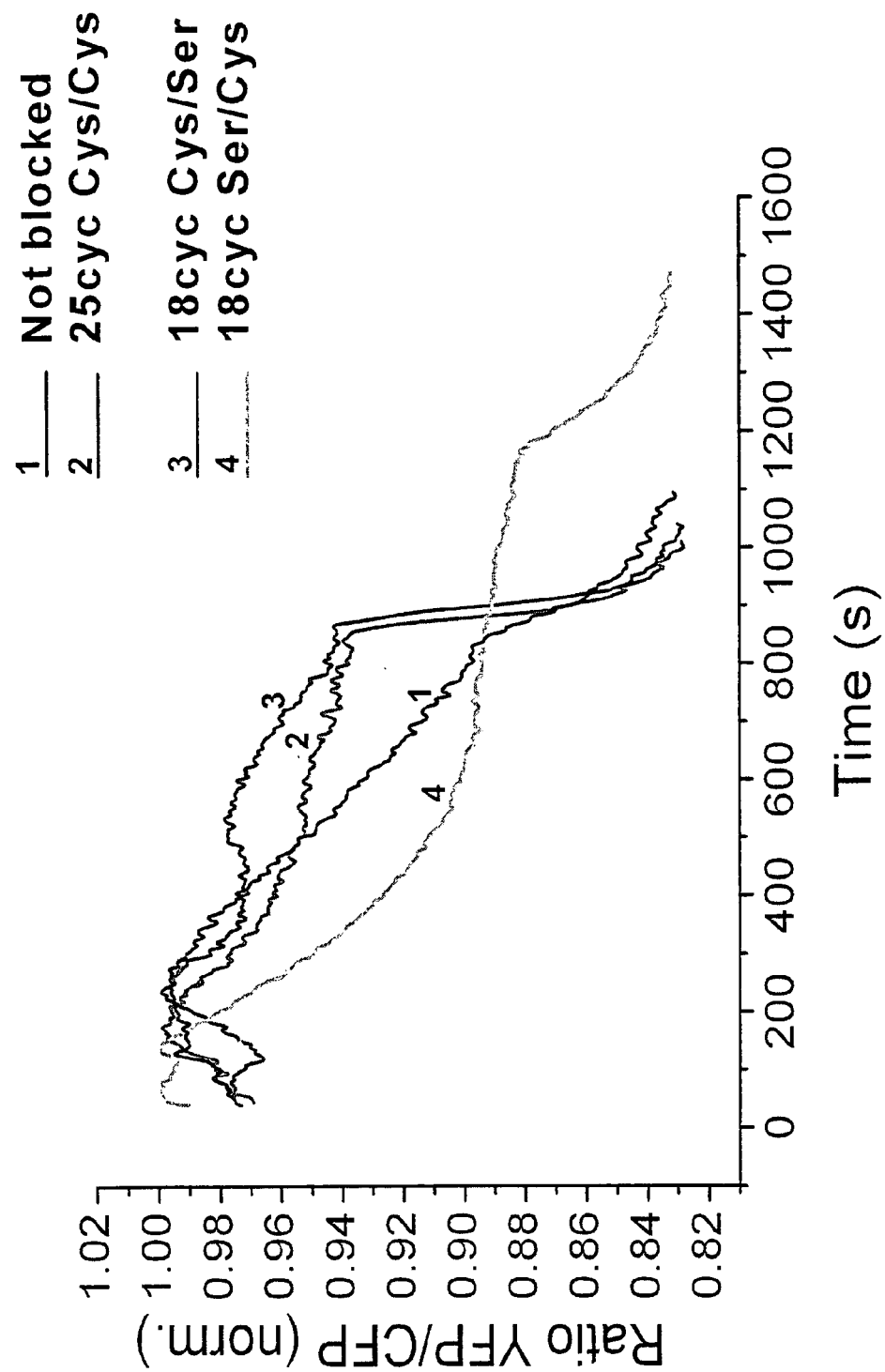

FIG. 6 is a diagram depicting the blocking capacity of $\beta_1$-EC$_{II}$-18AA cyclopeptide mutants having a D-Glu ring closure on $\beta_1$-receptor-mediated signalling (functional cAMP-assay) using an approach by fluorescence resonance energy transfer (FRET). The effect of the preincubation (12 h, 4° C., rotating incubator) of anti-$\beta$1-ECII IgG antibodies of a representative rat (serum) (FIG. 4, rat number 4) with $\beta_1$-EC$_{II}$-18AA-cyclopeptide mutants (Cys/Ser mutation, dark blue (3); Ser/Cys mutation, light blue (4)) was compared with the effect of a 3 Cys-containing 25AA Cys/Cys cyclopeptide (red (2)) or the result obtained with anti-$\beta_1$-EC$_{II}$ IgG antibodies in the absence of blocking peptides (black (1)). The y-axis represents the normalized YFP/CFP-ratio of the registered FRET emission signals, the x-axis corresponds to the registration time given in seconds (s).

Figure 7:
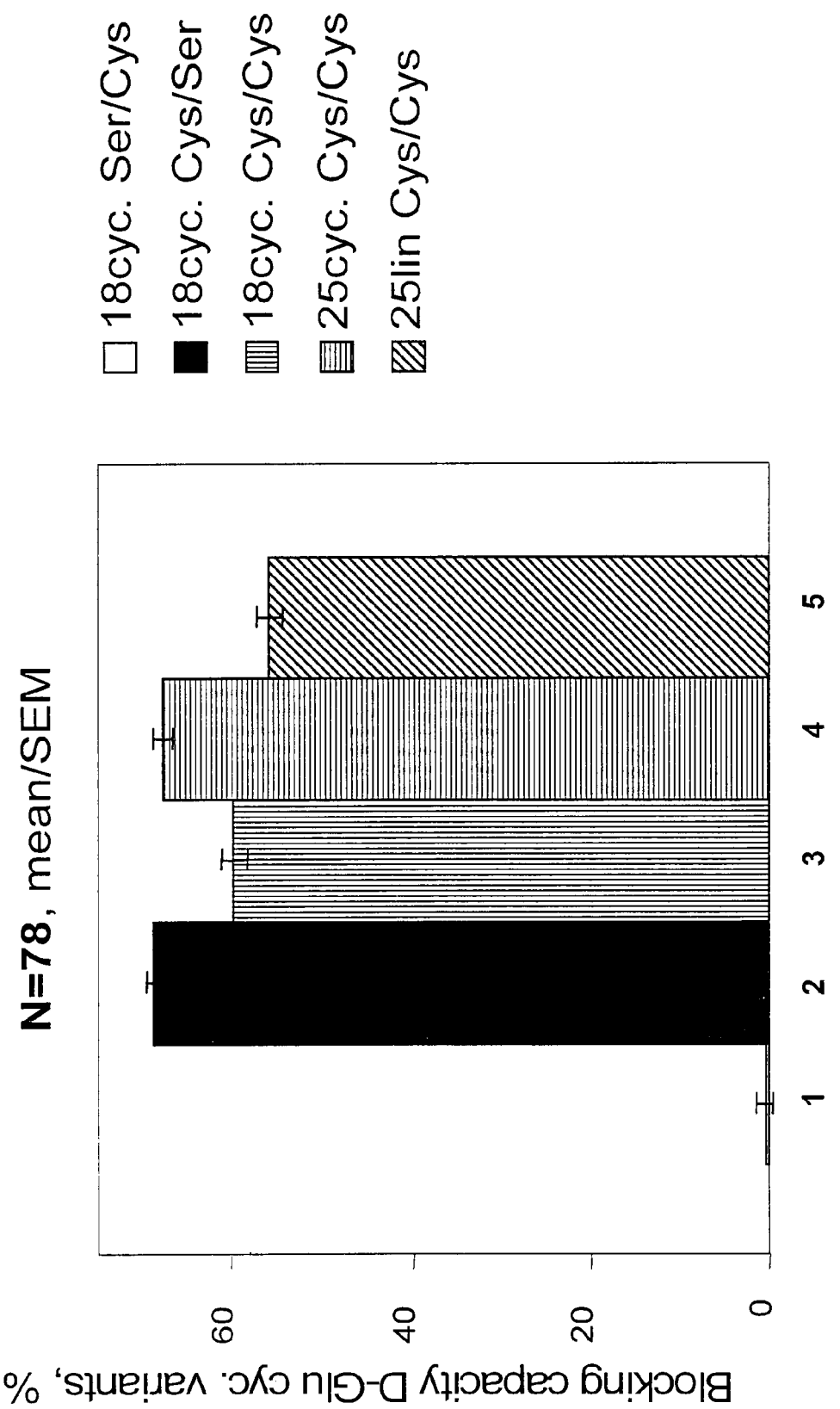

FIG. 7 is a diagram resuming the blocking effect of cyclopeptide mutants having a D-Glu ring closure after preincubation (12 h, 4° C., rotating incubator) with IgG isolated from 78 sera from immunized antibody-positive rats in an ELISA-competition assay using the linear 3 Cys-containing 25AA Cys/Cys-peptide as an antigen. Columns represent the results obtained with mutant $\beta_1$-EC$_{II}$-18AA cyclopeptides (Cys/Ser mutation black column; Ser/Cys mutation, white column) compared with the 3 Cys-containing 18AA cyclopeptide (vertically hatched column), the 3 Cys-containing 25AA cyclopeptide (horizontally hatched column), or the 3 Cys-containing linear 25AA peptide (diagonally right hatched column). Error bars indicate the standard error of the mean (±SEM). The y-axis represents the blocking efficiency of the various peptides used given in % of blocked versus non-blocked ELISA-reactivity of the sera.

Figure 8:
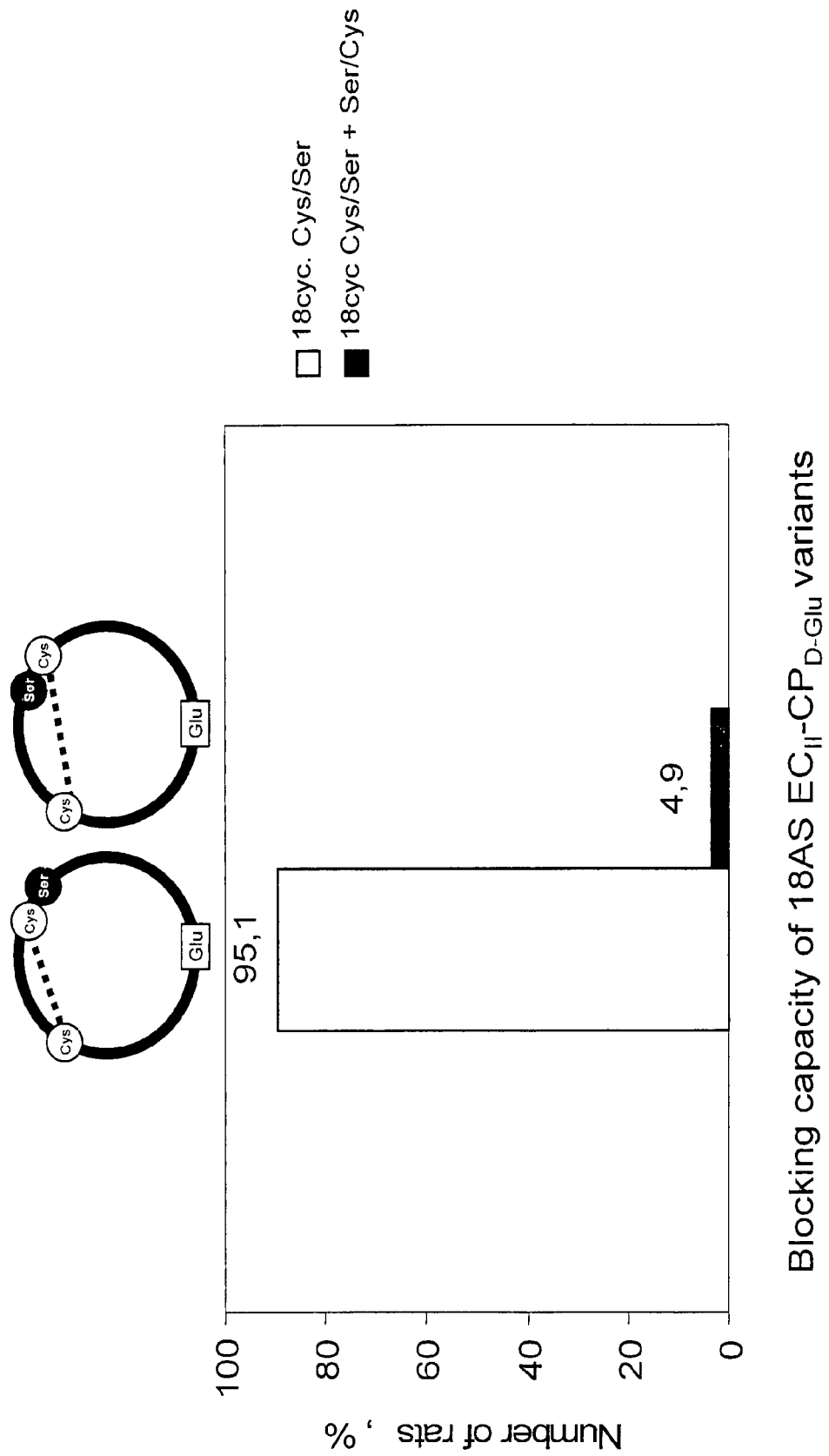

FIG. 8 is a diagram resuming the blocking capacity of $\beta_1$-EC$_{II}$-18AA cyclopeptide mutants (having a D-Glu ring closure) in an ELISA competition assay performed with sera from n=82 immunized antibody-positive rats. About 95% of the sera were efficiently blocked by the $\beta_1$-EC$_{II}$-18AA Cys/Ser mutated cyclopeptide alone (schematically depicted on the top of the left white column), whereas about 5% of the sera were blocked by both, the 18AA Cys/Ser- and the 18AA Ser/Cys-mutants (the latter schematically depicted on the top of the right black column).

Figure 9:
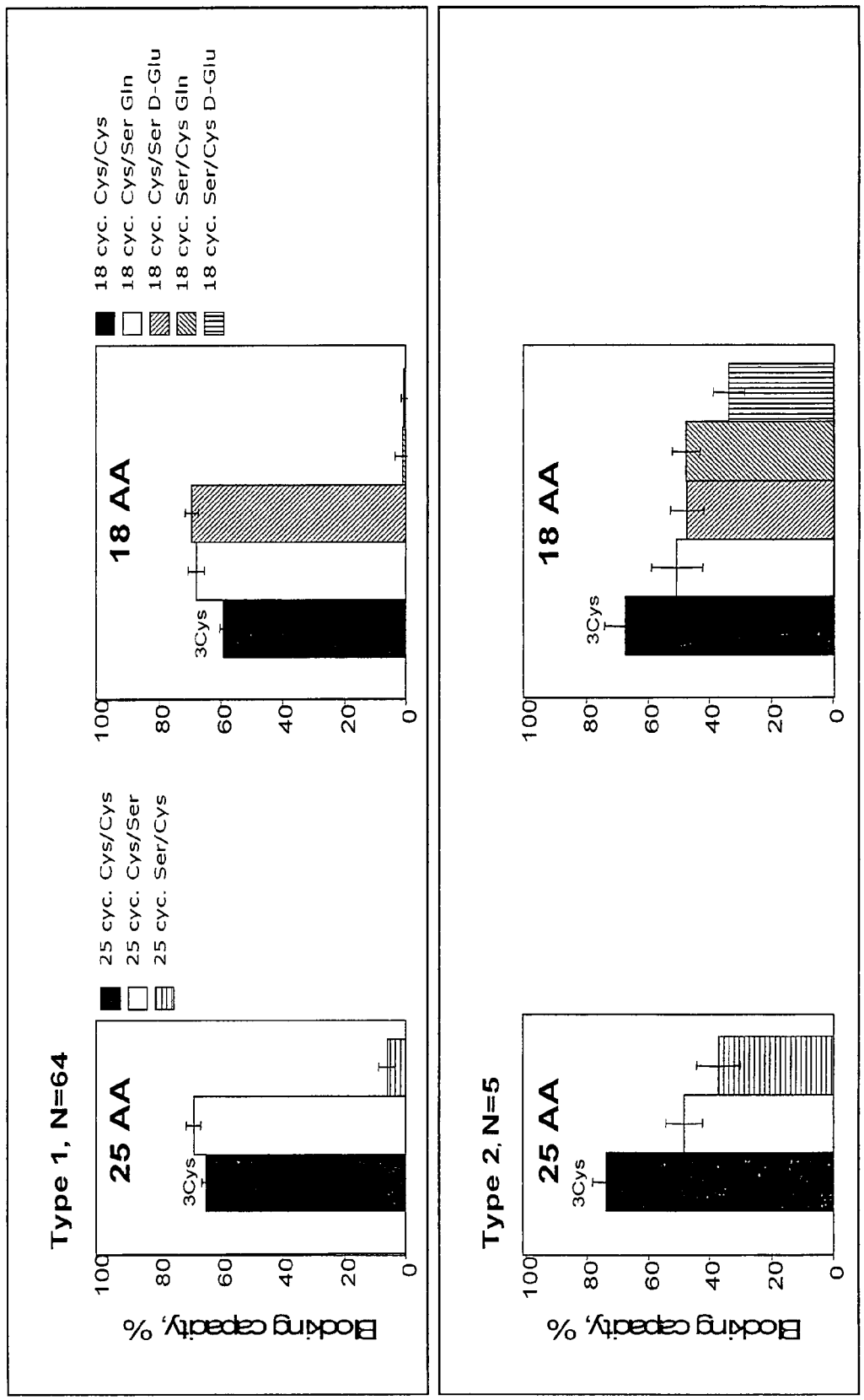

FIG. 9 is a diagram composed of two major-(upper and lower) panels resuming the blocking effect of both 25AA- and 18AA-cyclopeptide mutants having a Gln closure site, as well as 18AA cyclopeptide mutants having a D-Glu closure site after preincubation (12 h, 4° C., rotating incubation) with sera isolated from 69 different immunized antibody-positive rats in an ELISA-competition assay using the 3 Cys-containing linear 25AA Cys/Cys-peptide as an antigen. The upper panel depicts rat sera preferentially reacting with the Cys/Ser mutated cyclopeptides (type1 reaction, n=64), separated in cyc25AA(Gln)-peptides (left) and cyc18AA(Gln and D-Glu)-peptides (right). The lower panel depicts the rat sera reacting with both the Cys/Ser and the Ser/Cys mutated cyclopeptides (type2 reaction, n=5), again separated in the results obtained with cyc25AA(Gln)-peptides (left) and cyc18AA(Gln and D-Glu)-peptides (right).

The first three columns on the left side within the two panels represent the results obtained with the (non mutated) 3 Cys-containing 25AA (Gln-)cyclopeptide (black columns) and the mutant $\beta_1$-EC$_{II}$-25AA (Gln-)cyclopeptides (Cys/Ser mutation, white columns; Ser/Cys mutation, horizontally hatched columns).

The five columns on the right side within the two panels represent the results obtained with the (non-mutated) 3 Cys-containing 18AA (Gln-)cyclopeptide (black columns) compared with the different 2 Cys-containing mutant 18AA cyclopeptides (18AA Cys/Ser mutant with a Gln closure site, white columns; 18AA Cys/Ser mutant with a D-Glu closure site, diagonally left hatched columns; 18AA Ser/Cys mutant with a Gln closure site, diagonally right hatched columns; 18AA Ser/Cys mutant with a D-Glu closure site, vertically hatched columns).

The error bars represent the standard error of the mean (±SEM). The y-axis represents the blocking efficiency of the various peptides used given in % of blocked versus non-blocked ELISA reactivity of the sera.

Figure 10:
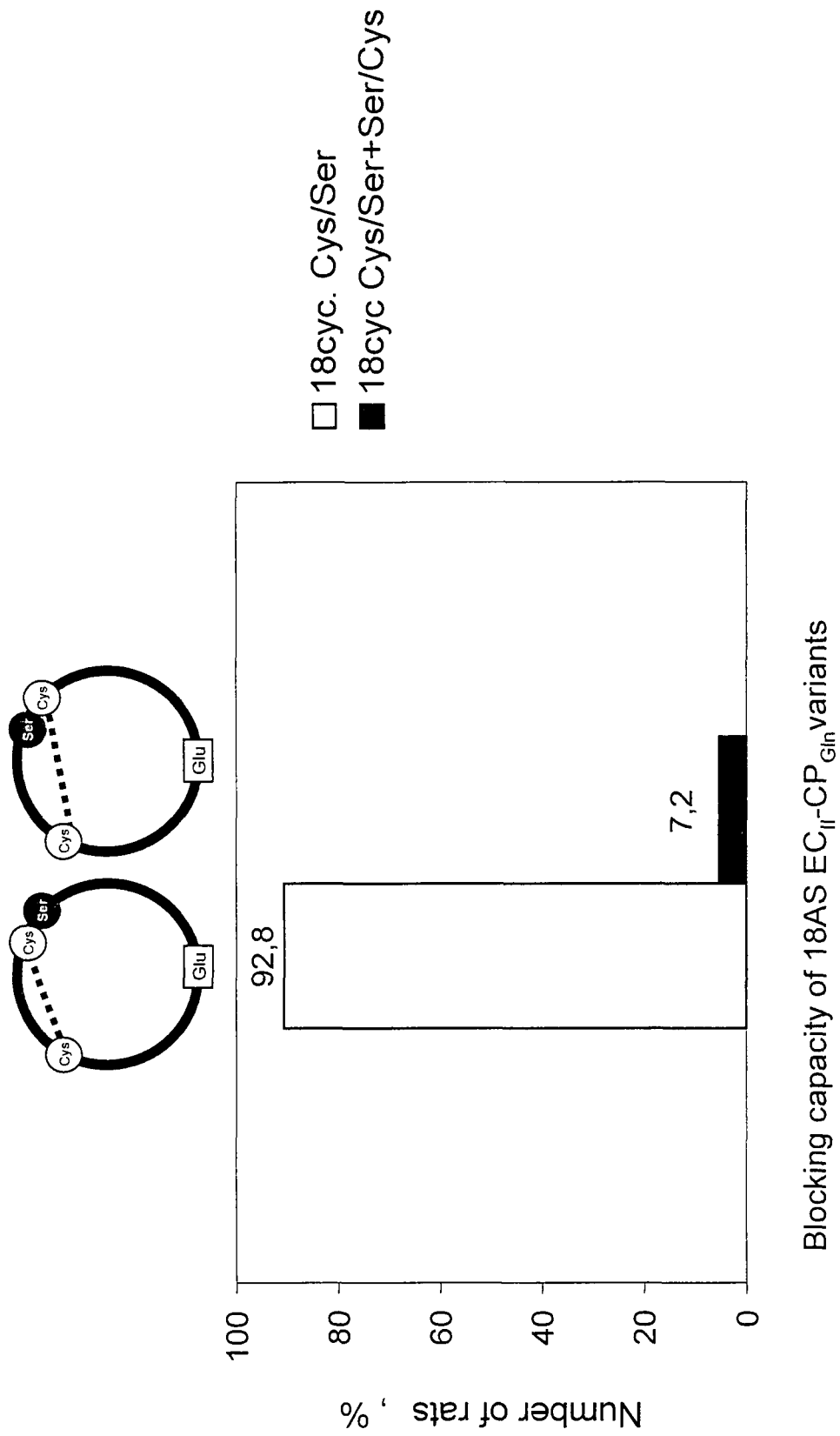

FIG. 10 is a diagram resuming the blocking capacity of $\beta_1$-$EC_{II}$-18AA (Gln-) cyclopeptide mutants in an ELISA competition assay performed with sera from n=69 immunized anti-body-positive rats. About 93% (n=64) of the sera were efficiently blocked by the $\beta_1$-$EC_{II}$-18AA Cys/Ser mutated cyclopeptide alone (schematically depicted on the top of the left white column), whereas about 7% (n=5) of the sera were blocked by both, the 18AA Cys/Ser- and the 18AA Ser/Cys-mutant (the latter schematically depicted on the top of the right black column).

Figure 11:
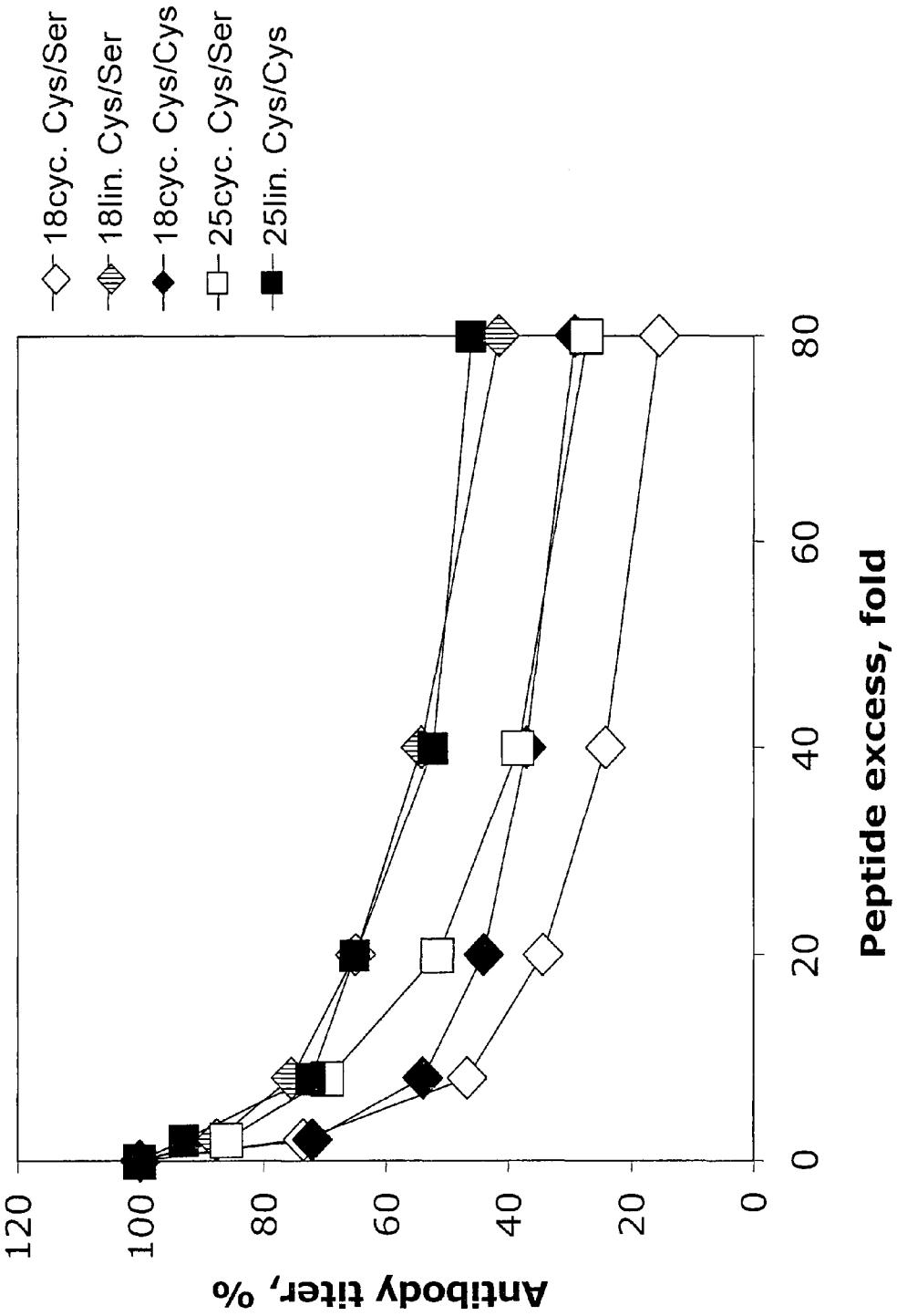

FIG. 11 is a diagram resuming the dose-dependent (x-axis, abscissa: fold molar excess of specific peptides) blocking capacity of various linear and cyclic beta1-ECII-peptides given in % of the unblocked antibody-titer (y-axis, ordinate), including 25AA Cys/Cys linear peptides (black squares), 25AA Cys/Ser cyclopeptide mutants (white squares), 18AA Cys/Cys cyclo-peptides (black diamonds), 18AA Cys/Ser cyclopeptide mutants (white diamonds), and 18AA Cys/Ser linear peptide mutants (vertically hatched diamonds) in an ELISA competition assay performed with sera from n=6 randomly chosen immunized antibody-positive rats. All sera were most efficiently blocked by the beta1-ECII-18AA Cys/Ser mutant cyclopeptide followed by the non-mutant 18AA Cys/Cys cylopeptide and the 25AA Cys/Ser mutant cyclopeptide. All cyclopeptides were largely superior to their linear counterparts (with or without mutation) in terms of their antibody blocking capacities ($P<0.005$).

Figure 12:
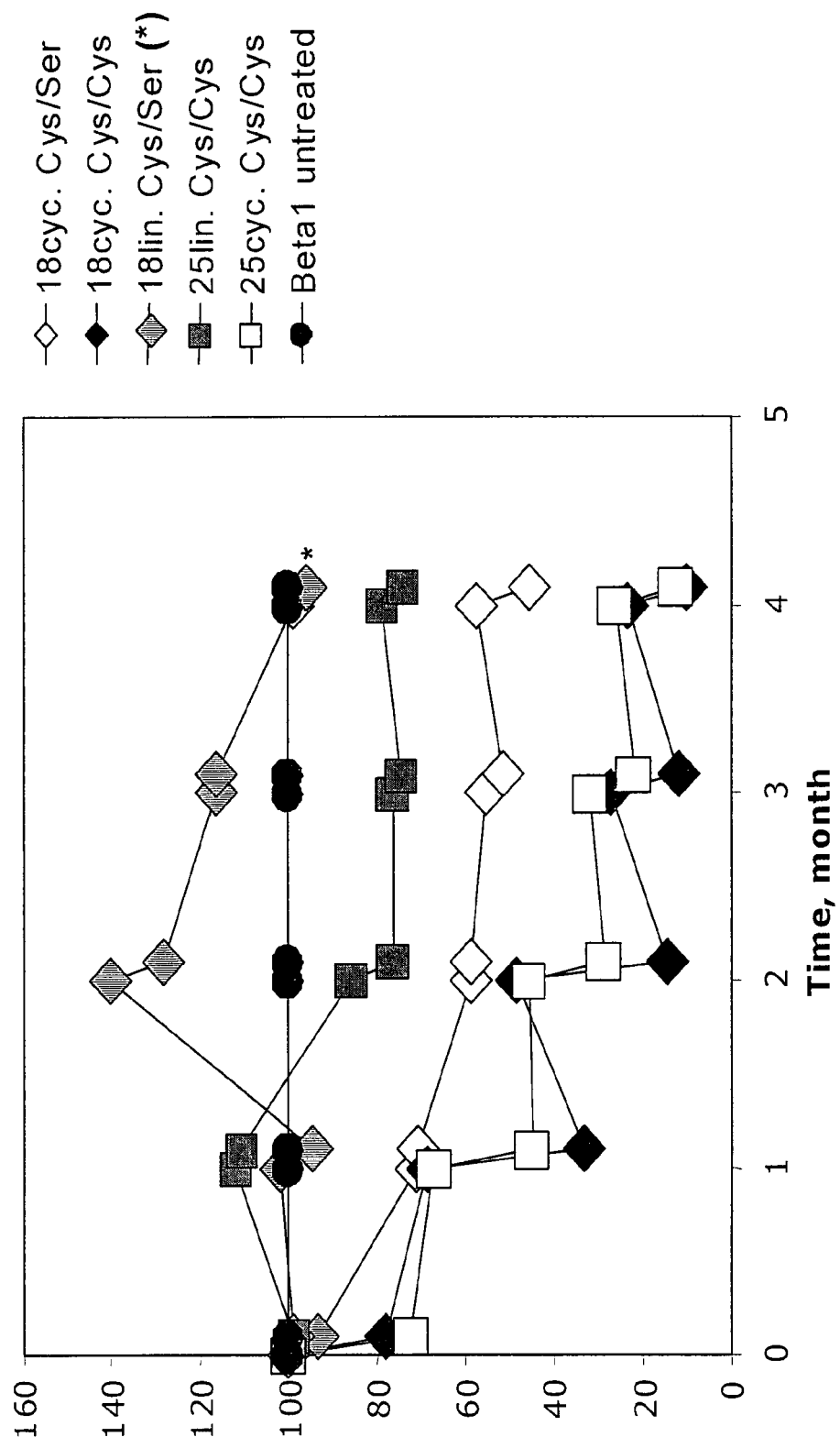

FIG. 12 is a diagram resuming the in vivo blocking capacity of in total five (prophylatic) applications of various linear and cyclic beta1-ECII-peptides, started 3 months after the first immunization (and two subsequent beta1-ECII/GST-antigen-boosts, corresponding to a prevention protocol). Serum-titers of the beta1-receptor antibodies were determined before and 18-20 h after each peptide injection (abscissa, time in months) and are given in % of the corresponding antibody-titers of immunized untreated rats (y-axis, ordinate). The injected peptides were: 25AA Cys/Cys linear peptide (black squares), 25AA Cys/Cys cyclopeptide (white squares), 18AA Cys/Cys cyclopeptide (black diamond), 18AA Cys/Ser cyclopeptide mutant (white diamonds), and the 18AA Cys/Ser linear peptide mutant (vertically hatched diamonds). Also in vivo, the efficiency of the cyclic peptides was largely superior to their linear counterparts. The highest efficiency in terms of antibody-neutralization was achieved with 1.0 mg/kg body weight (Bw) of non mutant 25AA Cys/Cys or 18AA Cys/Cys-cyclo-peptides (87.7±2% or 89.9±3% decrease after 5 cyclopeptide injections, compared with untreated immunized animals; both $P<0.005$), followed by the 18AA Cys/Ser mutant cyclopeptide (54.5±2% decrease after 5 cyclopeptide injections; $P<0.05$), whereas linear 25AA Cys/Cys peptides or linear 18AA Cys/Ser mutants at a same concentration had no significant blocking effects (25.8±3% or 4.5±11% decrease after 5 injections, $P=0.16$ or $P=0.8$, respectively). Black circles indicate antibody-titers of untreated regularly (every 4 weeks) immunized animals serving as reference, set at 100%.

Figure 13:
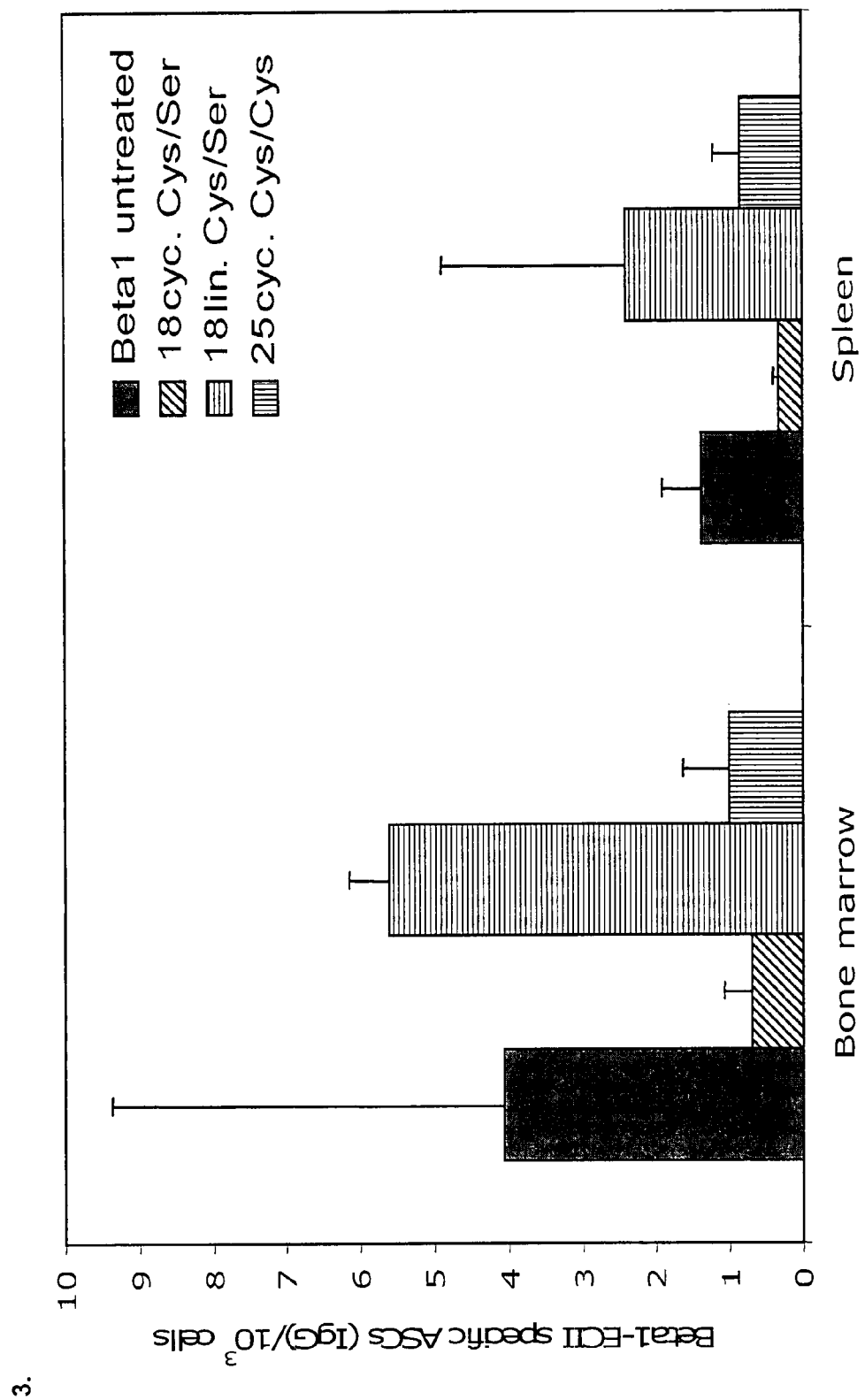

FIG. 13 shows the results of ELISPOT-assays carried out with B-cells prepared from either the bone marrow (left columns) or the spleen (right columns) of immunized anti-beta1-positive cardiomyopathic untreated animals (Beta1 untreated, black columns) compared with those isolated from immunized anti-beta1 antibody-positive cardiomyopathic animals prophy-lactically treated with the 25AA-ECII Cys/Cys cyclopeptides (25cyc. Cys/Cys, vertically hatched columns), the 18AA-ECII Cys/Ser cyclopeptide mutant (18cyc. Cys/Ser, diagonally right hatched columns), or the linear 18AA-ECII Cys/Ser peptide mutant (18 lin. Cys/Ser, horizontally hatched columns). For the assays, ELIspot plates were coated overnight with the specific antigen (GST/beta1-ECII-FP) in 0.05 mol/l Tris buffer, pH 9.4.; then the plates were washed 3 times and blocked with BSA for 3 hours at 37° C. Subsequently, the plates were incubated overnight at 37° C. with B-cells from either spleen or bone marrow (cultured in RPMI 1640/X-VIVO-15 medium supplemented with 10% fetal calf serum (FCS)) with $1\times10^6$ to $1\times10^3$ cells per well. After 12 hours the B-cells were discarded and the plates with the B-cell secreted IgG bound were washed several times (PBS/0.5° A) Tween) before the addition of alkaline phosphatase conjugated secondary anti-rat IgG (0.3 µg/ml) to detect bound rat IgG. Then the plates were incubated for another 3 hours at 37° C., washed several times with PBS/0.5% Tween, and developed using LMP/BICP 5:1 (1 ml per well; "LMP" means low melting agarose, and "BICP" means 5-bromo-4-chloro-3-indolyl phosphate p-toluidine salt, a blue-colored dye) allowing for a quantification of the blue spots obtained, with each spot representing an antigen-specific IgG secreting spleen or bone-marrow cell.

Figure 14:
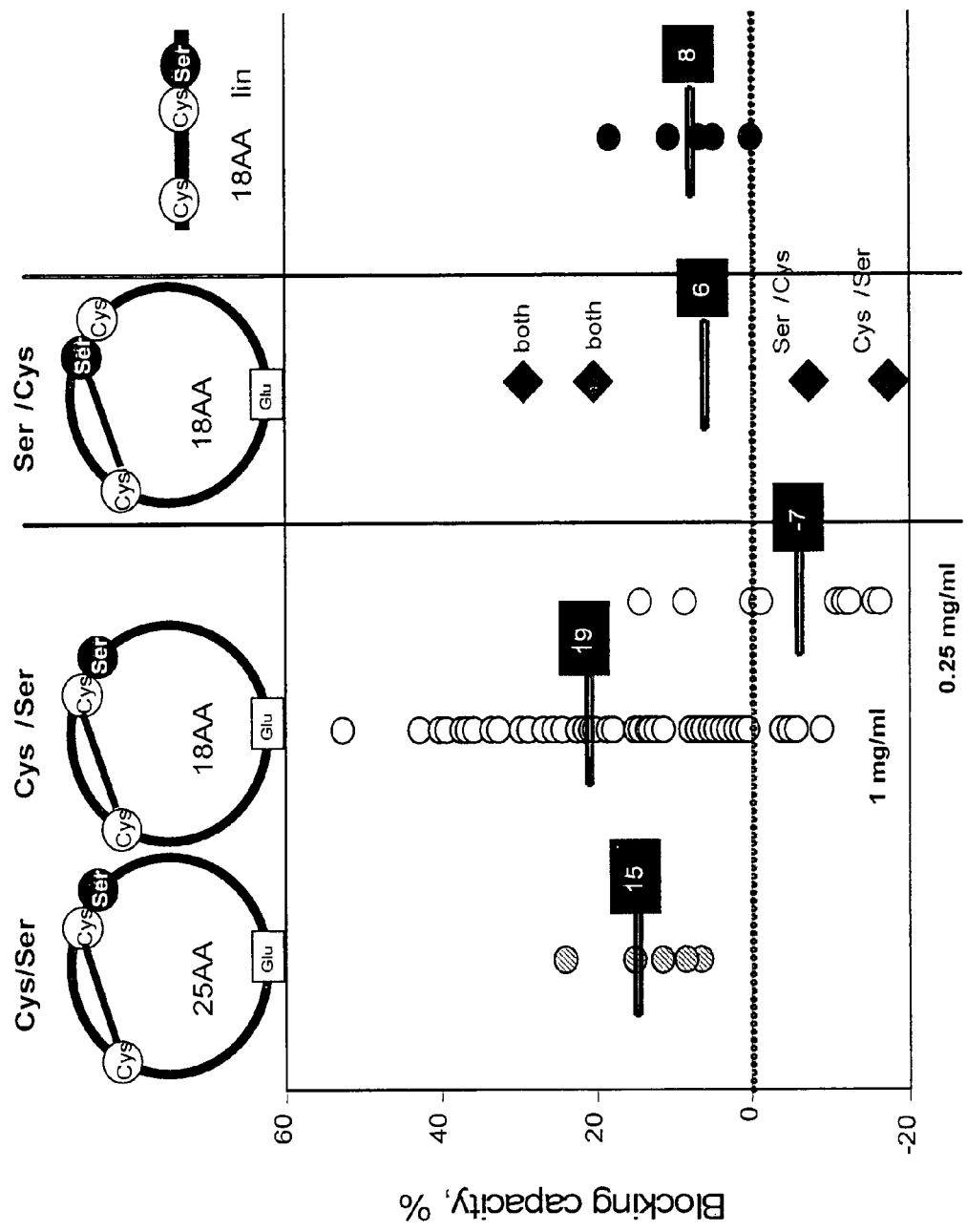

FIG. 14 is a diagram resuming the in-vivo blocking effect of both 25AA and 18AA cyclo-peptide mutants with a Gln closure site, determined after the first intravenous (i.v.) injection of 1.0 mg/kg body weight (Bw) into immunized antibody-positive rats. Sera were drawn 18-20 hours after i.v. injection of 1.0 or 0.25 mg/kg Bw of the indicated peptides and assayed for reactivity by ELISA using the 3 Cys-containing linear 25AA Cys/Cys-peptide as an antigen.

The first row within the panel represents the group of rats (n=5) treated with the mutant 2 Cys-containing 25AA Cys/Ser (Gln)-cyclopeptide (schematically depicted on the top of the first row, hatched circles), the second and third row represent groups of rats treated with the mutant 18AA Cys/Ser (Gln-)cyclopeptide at two different concentrations (n=40, 1 mg/kg Bw; n=9; 0.25 mg/kg Bw, scheme of the cyclic peptide depicted on the top of the second row, white circles), the fourth row represents n=4 animals treated with the mutant 18AA Ser/Cys (Gln-)cyclopeptide (1 mg/kg Bw, scheme of the cyclic peptide depicted on the top of the fourth row, black diamonds), and the fifth row represents the results obtained with i.v. injected (mutant) 2 Cys-containing linear 18AA Cys/Ser (Gln-)peptides (scheme of the linear peptide depicted on the top of the fifth row, black circles).

The bars and numbers (in boxes) of each row represent the mean values of the blocking capacity of the respectively indicated peptide given in % of the ELISA-immunoreactivity of the sera before and 18-20 hours after i.v. peptide injection (y-axis).

Figure 15:
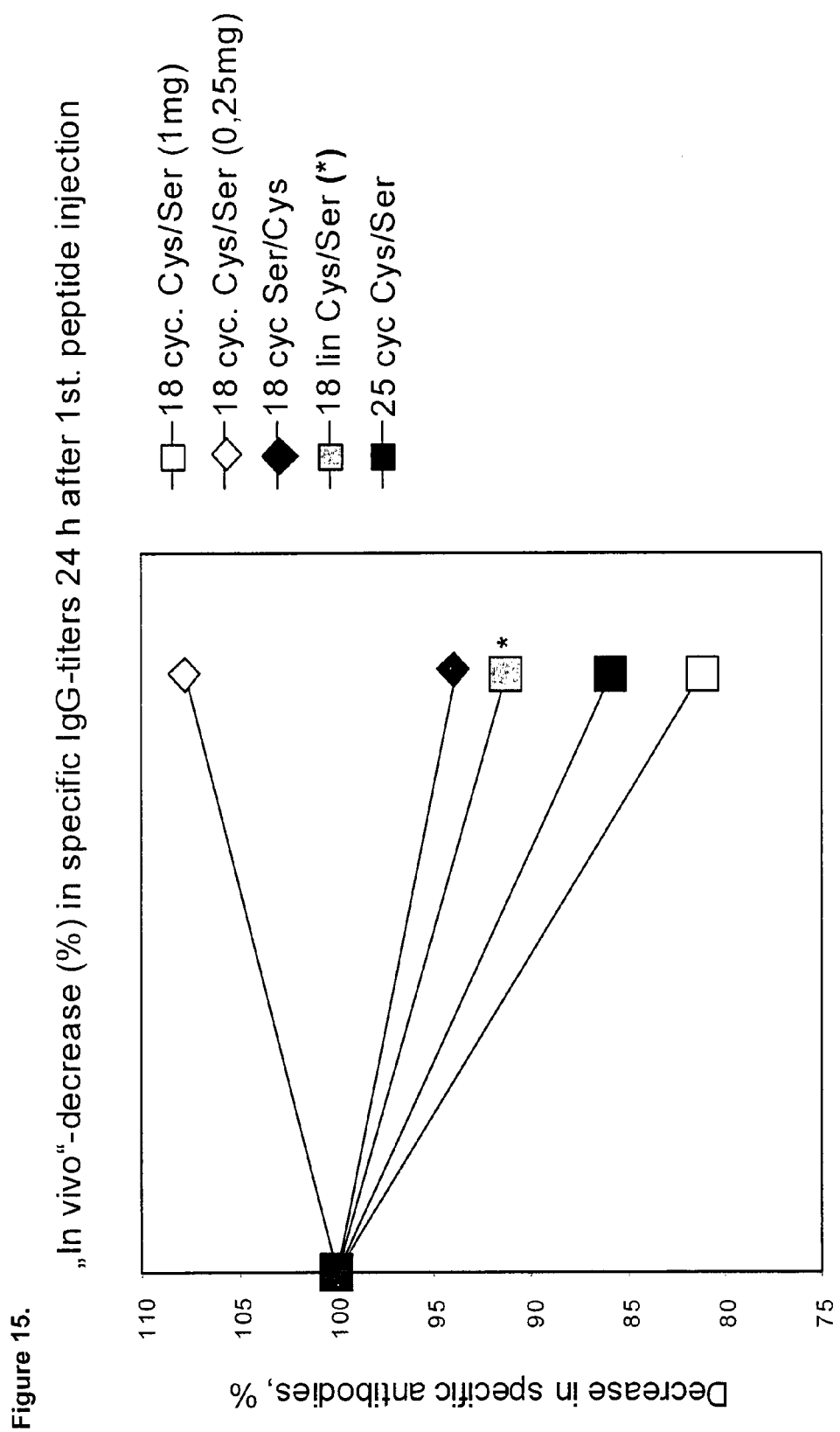

FIG. 15 is a diagram resuming the in-vivo blocking effect of both 25AA and 18AA cyclo-peptide mutants with a Gln closure site, determined after the first intravenous (i.v.) injection of 1 mg/kg Bw or 0.25 mg/kg/Bw into immunized antibody-positive rats. Sera were drawn 18-20 hours after i.v.

injection of the various peptides and assayed for reactivity by ELISA using the 3 Cys-containing linear 25AA Cys/Cys peptide as an antigen.

The graph depicts the relative decrease (or increase) in specific anti-$\beta_1$-receptor antibody-titers in sera from antibody-positive immunized rats after injection of the various peptides and shows the respective mean value of the blocking capacity of the indicated peptide given in % of the ELISA-immunoreactivity of the sera before and 18-20 hours after i.v. injection (y-axis). The symbols on the right side of the panel represent: white square, 18AA Cys/Ser mutant (Gln-)cyclopeptide (1 mg/kg Bw); white diamond, 18AA Cys/Ser mutant (Gln-)cyclopeptide (0.25 mg/kg Bw); black diamond, 18AA Ser/Cys mutant (Gln-)cyclopeptide (1 mg/kg Bw); horizontally hatched square, 18AA Cys/Ser mutant linear (Gln-) peptide (1 mg/kg Bw); black square, 25AA Cys/Ser mutant (Gln-)cyclopeptide (1 mg/kg Bw). For reasons of clarity error bars are not shown in the graph.

FIG. 16A is a diagram resuming the in vivo blocking effect of both 25AA and 18AA cyclopeptide mutants with a Gln closure site, determined after a total of nine intravenous (i.v.) in-jections of 1.0 mg/kg body weight (Bw) of the indicated peptides into immunized antibody-positive rats. Sera were drawn before and 18-20 hours after i.v. injection of the various peptides every 4 weeks (abscissa: time in months of treatment) and assayed for reactivity by ELISA using the 3 Cys-containing linear 25AA Cys/Cys-peptide as an antigen.

The graph depicts the relative decrease (or increase) in specific anti-beta1-receptor antibody-titers in sera from antibody-positive immunized rats after injection of the indicated peptides and shows the respective mean value of the blocking capacity of the peptide given in % of the initial ELISA-immunoreactivity before starting treatment (y-axis, ordinate).

The symbols indicate:
black circles, untreated regularly (every 4 weeks) immunized animals (n=9); white diamonds, 18AA Cys/Ser mutant (Gln-)cyclopeptide (1.0 mg/kg Bw, n=20); black squares, 25AA Cys/Ser mutant (Gln-)cyclopeptide (1.0 mg/kg Bw, n=5).

FIG. 16B is a diagram resuming the in vivo blocking effect of various concentrations of 18AA cyclopeptide mutants with a Gln closure site, determined after a total of nine intravenous (i.v.) injections of 0.25, 1.0, 2.0, and 4.0 mg/kg body weight (Bw) into immunized antibody-positive rats, irrespective of the cyclopeptide "responder-state" of individual animals. Sera were drawn before and 18-20 hours after i.v. injection of the various peptides every 4 weeks (abscissa: time in months), and assayed for reactivity by ELISA using the 3 Cys-containing linear 25AA Cys/Cys-peptide as an antigen.

The graph depicts the relative decrease (or increase) in specific anti-beta1-receptor antibody-titers in sera from antibody-positive immunized rats after injection of the indicated peptides and shows the respective mean values of the blocking capacity of the peptides given in % of the initial ELISA-immunoreactivity before starting treatment (y-axis, ordinate).

The symbols indicate:
black circles, untreated regularly (every 4 weeks) immunized animals (n=9); white circles, 18AA Cys/Ser mutant (Gln-)cyclopeptide (0.25 mg/kg Bw, n=4);
white diamonds, 18AA Cys/Ser mutant (Gln-)cyclopeptide (1.0 mg/kg Bw, n=20); vertically hatched diamonds, 18AA Cys/Ser mutant (Gln-)cyclopeptide (2.0 mg/kg Bw, n=5); black diamonds, 18AA Cys/Ser mutant (Gln-)cyclopeptide (4.0 mg/kg Bw, n=9).

FIG. 16C is a diagram resuming the in vivo blocking effect of various concentrations of 18AA cyclopeptide mutants with a Gln closure site, determined after a total of nine intravenous (i.v.) injections of 0.25, 1.0, 2.0, and 4.0 mg/kg body weight (Bw) into immunized antibody-positive rats, respecting only cyclopeptide-sensitive "responders", defined as animals having, after 7 cyclopeptide-injections, a maximum remaining receptor anti-body level equal or inferior to 80% of the respective titer at start of therapy (compare the curves between. 16c. and FIG. 16b., the latter representing the naturally occurring inhomogenous response of unselected animals). Sera were drawn as described above and assayed for reactivity by ELISA using the 3 Cys-containing linear 25AA Cys/Cys-peptide as an antigen.

The graph depicts the relative decrease in specific anti-beta1-receptor antibody-titers in sera from antibody-positive immunized responders after injection of the indicated peptides giving the blocking capacity in % of the initial ELISA-immunoreactivity (y-axis, ordinate).

The symbols indicate (number of responders in bold):
black circles, untreated regularly (every 4 weeks) immunized animals (n=9); white circles, 18AA Cys/Ser mutant (Gln-)cyclopeptide (0.25 mg/kg Bw, n=3/4); white diamonds, 18AA Cys/Ser mutant (Gln-)cyclopeptide (1.0 mg/kg Bw, n=16/20); vertically hatched diamonds, 18AA Cys/Ser mutant (Gln-)cyclopeptide (2.0 mg/kg Bw, n=2/5); black diamonds, 18AA Cys/Ser mutant (Gln-)cyclopeptide (4.0 mg/kg Bw, n=6/9).

FIG. 17.A is a diagram showing the time course (month 0 to 20) of the internal end-systolic and end-diastolic left ventricular diameters (LVES, LVED) of GST/$\beta_1$-EC$_{II}$-immunized un-treated (black circles) versus GST/$\beta_1$-ECII-immunized animals treated with the indicated various cyclopeptides (see legend) as determined by echocardiography (echocardiographic system: Visual Sonics, Vevo 770 (version V2.2.3), equipped with a 15-17.5 MHz transducer), whereby LVES/LVED is left ventricular end-systolic diameter/left ventricular end-diastolic diameter.

The symbols indicate:
white circles, untreated 0.9% NaCl-injected non immunized control animals (n=10); black circles, untreated regularly (every 4 weeks) immunized animals (n=9); white diamonds, 18AA Cys/Ser mutant (Gln-)cyclopeptide (1.0 mg/kg Bw, n=20); black squares, 25AA Cys/Ser mutant (Gln-)cyclopeptide (1.0 mg/kg Bw, n=5); white squares, 18AA Cys/Ser mutant linear (Gln-)peptide (1.0 mg/kg Bw, n=5).

FIG. 17.B is a similar diagram showing the time course (month 0 to 20) of the internal end-systolic and end-diastolic left ventricular diameters (LVES, LVED) of GST/$\beta_1$-ECII-immunized untreated (black circles) versus GST/$\beta_1$-ECII-immunized animals, treated with different concentrations of the 18AA Cys/Ser cyclopeptide mutant (see legend).

The symbols indicate:
white circles, untreated 0.9% NaCl-injected non immunized control animals (n=10); black circles, untreated regularly (every 4 weeks) immunized animals (n=9): white squares, 18AA Cys/Ser mutant (Gln-)cyclopeptide (0.25 mg/kg Bw, n=4); white diamonds, 18AA Cys/Ser mutant (Gln-)cyclopeptide (1.0 mg/kg Bw, n=20); vertically hatched diamonds, 18AA Cys/Ser mutant (Gln-)cyclopeptide (2.0 mg/kg Bw, n=5); black diamonds, 18AA Cys/Ser mutant (Gln-)cyclopeptide (4.0 mg/kg Bw, n=9).

Figure 18:
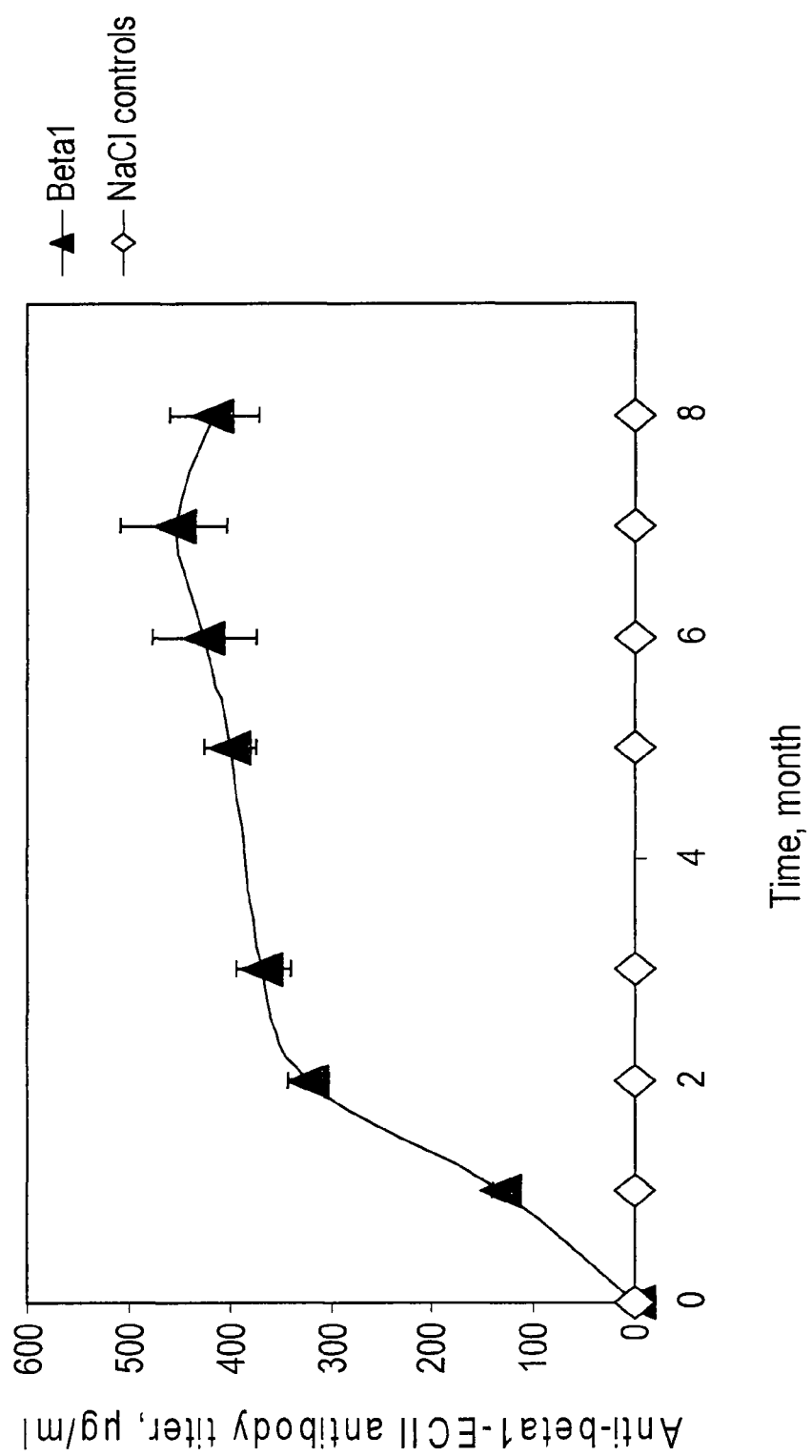

FIG. 18 is a diagram indicating the titer course (month 0 to 9) of specific anti-$\beta_1$-EC$_{II}$ antibodies in GST/$\beta_1$-EC$_{II}$-immunized versus 0.9% NaCl-injected rats, whereby "Beta1" means immunized animals (before starting treatment with peptides according to the present invention), and "NaCl controls" means corresponding NaCl-injected control animals.

Figure 19:
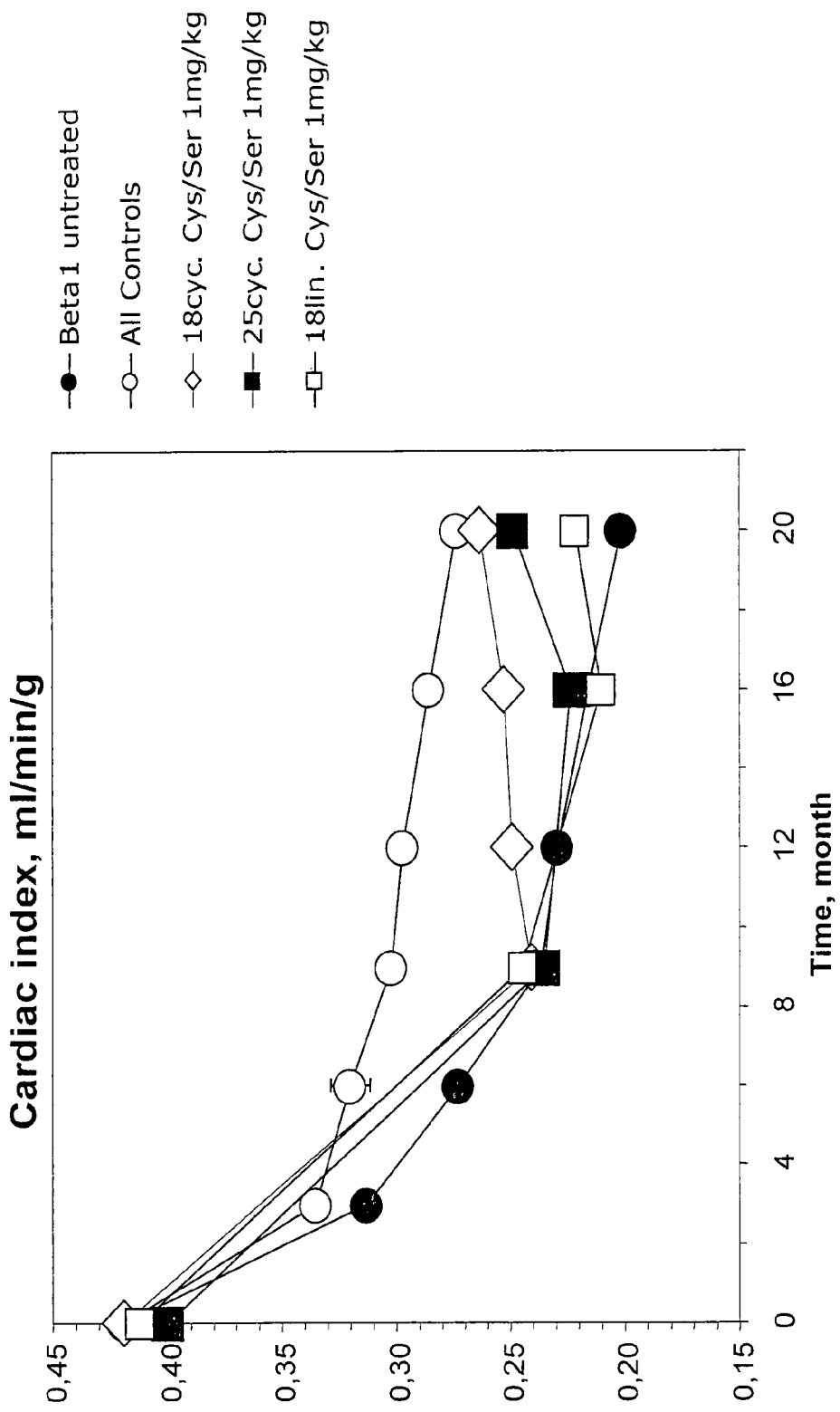

FIG. 19A is a diagram depicting the time course (month 0 to 20) of the "Cardiac index" (CI) in ml/min/g (body weight) as determined by echocardiography (echocardiographic system see legend to FIG. 17a.).

The symbols indicate:
white circles, untreated 0.9% NaCl-injected non immunized control animals (n=10); black circles, untreated regularly (every 4 weeks) immunized animals (n=9); white diamonds, 18AA Cys/Ser mutant (Gln-)cyclopeptide (1.0 mg/kg Bw, n=20); black squares, 25AA Cys/Ser mutant (Gln-)cyclopeptide (1.0 mg/kg Bw, n=5); white squares, 18AA Cys/Ser mutant linear (Gln-)peptide (1.0 mg/kg Bw, n=5).

FIG. 19B is a similar diagram showing the time course (month 0 to 20) of the "Cardiac index" (CI) in ml/min/g (body weight) as determined by echocardiography (echocardiographic system see legend to FIG. 17a.).

The symbols indicate:
white circles, untreated 0.9% NaCl-injected non immunized control animals (n=10); black circles, untreated regularly (every 4 weeks) immunized animals (n=9); white squares, 18AA Cys/Ser mutant (Gln-)cyclopeptide (0.25 mg/kg Bw, n=4); white diamonds, 18AA Cys/Ser mutant (Gln-)cyclopeptide (1.0 mg/kg Bw, n=20); vertically hatched diamonds, 18AA Cys/Ser mutant (Gln-)cyclopeptide (2.0 mg/kg Bw, n=5).

Figure 20:
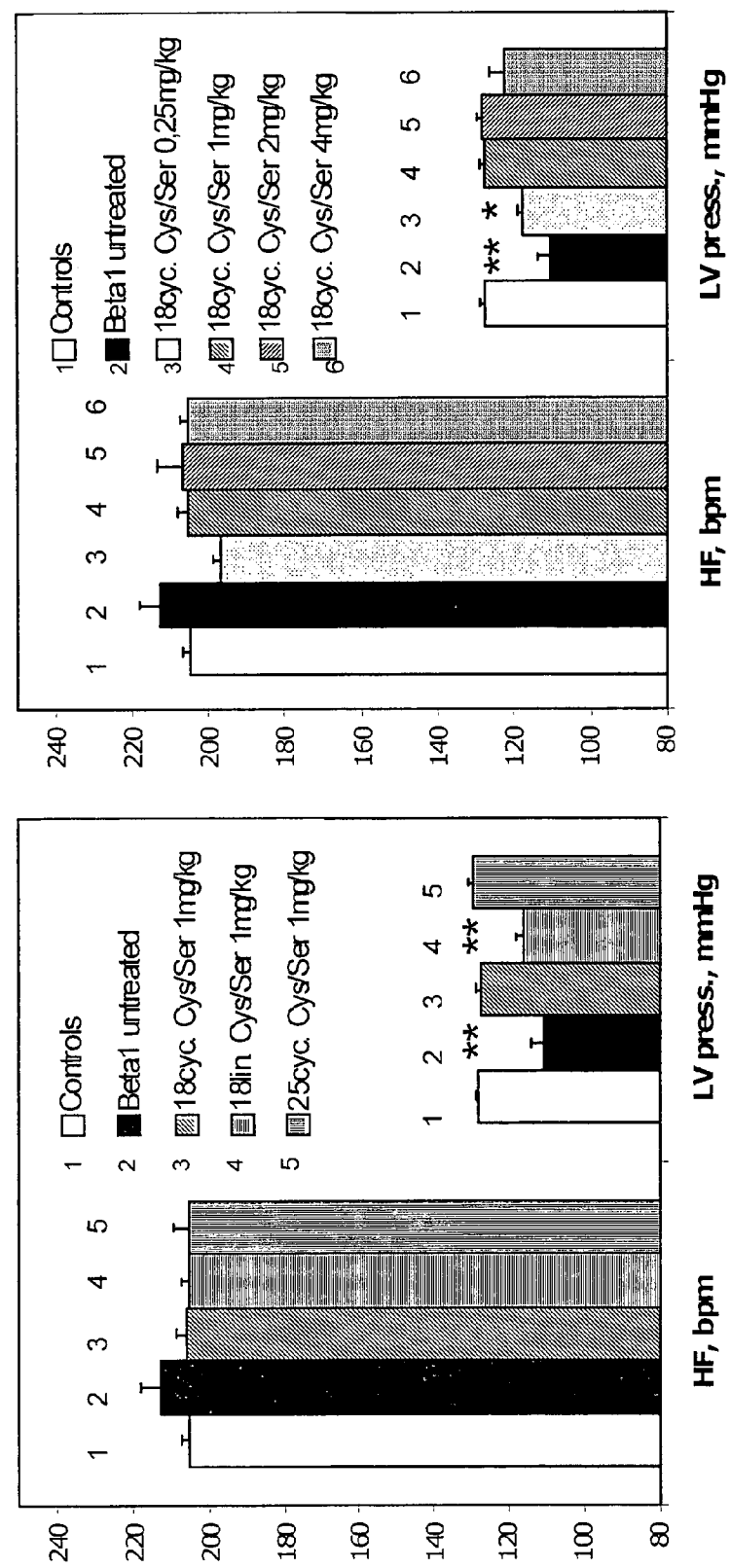
Figure 20B:
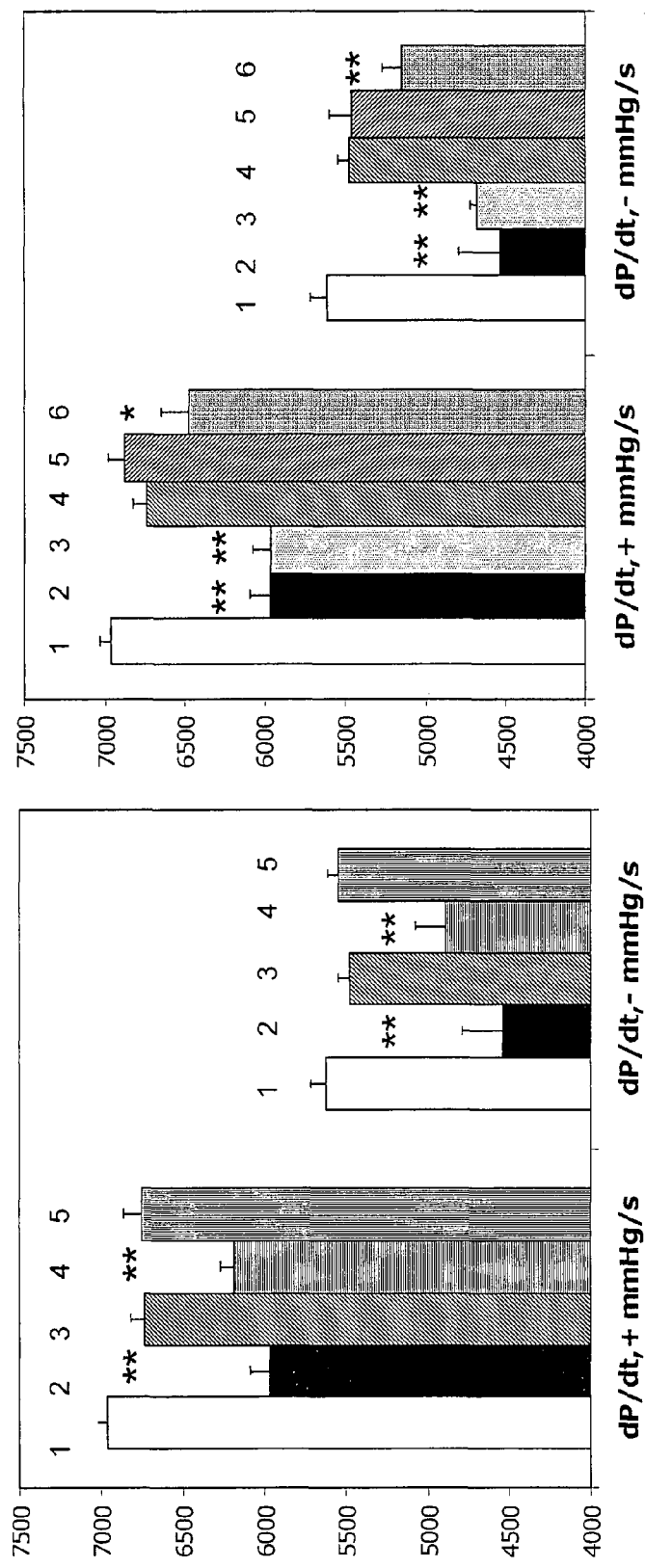

FIG. 20 shows three rows of panels (a, b, c) with hemodynamic parameters obtained in the therapy study after 10 months of treatment, in detail in the first row shows in each panel of the first row (a) on the left side the heart frequence (HF) given in beats per minute (=bpm), and on the right side the LV systolic blood pressure (LV press.) given in mmHg; in each panel of the second row (b) on the left side the contractility (+dP/dt) in mmHg/s, and on the right side the relaxation (−dP/dt) in −mmHg/s; the third row (c) shows the left ventricular end-diastolic pressure (LVEDP) as determined by cardiac catheterization in mmHg.

Left and right panels within each row separate data obtained with (left panels, constantly 1.0 mg/kg Bw of the different peptides) cyclic 18AA Cys/Ser (diagonally right hatched columns, n=20 animals), linear Cys/Ser mutants (horizontally hatched columns, n=5 animals), and cyclic 25AA Cys/Ser mutants (vertically hatched columns, n=5 animals). Columns in the right panels represent data obtained with various concentrations of the cyc18AA Cys/Ser mutant; with white filled, black dotted columns corresponding to 0.25 mg/kg Bw (n=4 animals), diagonally right hatched columns to 1.0 mg/kg Bw (n=10 animals), diagonally left hatched columns to 2.0 mg/kg Bw (n=5 animals), and black structured columns to 4.0 mg/kg/Bw (n=9 animals). Black and white columns in each panel serve as a reference and correspond to either untreated regularly (every 4 weeks) immunized animals (positive control, black, n=9), or to 0.9% NaCl-injected non immunized control animals (negative control, white, n=10).

In the legends "Beta1 untreated" means immunized anti-beta1 antibody positive cardiomyopathic not treated animals (n=9, black columns), "Controls" means the 0.9% NaCl-injected control group (n=10, white columns), "18cyc Cys/Ser." means immunized anti-beta1-positive cardiomyopathic animals therapeutically treated with the indicated linear 18 1 in Cys/Ser (n=5 [1.0 mg/kg Bw] or cyclic 18cyc Cys/Ser mutants (n=10 [1.0 mg/kg Bw], or cyclic 25AA Cys/Ser peptide mutants (n=4 [1.0 mg/kg Bw]) after 9 months of immunization. Panels on the right side depict the effects of different doses of intravenously injected beta1-ECII 18AA Cys/Ser cyclopeptide mutants (n=4 [0.25 mg/kg Bw]; n=20 [1.0 mg/kg Bw], n=5 [2.0 mg/kg Bw], and n=9 [4.0 mg/kg Bw], respectively). Differences between the groups were assessed by one way ANOVA; n.s.=not significant, *P<0.05, **P<0.005.

Figure 21A:
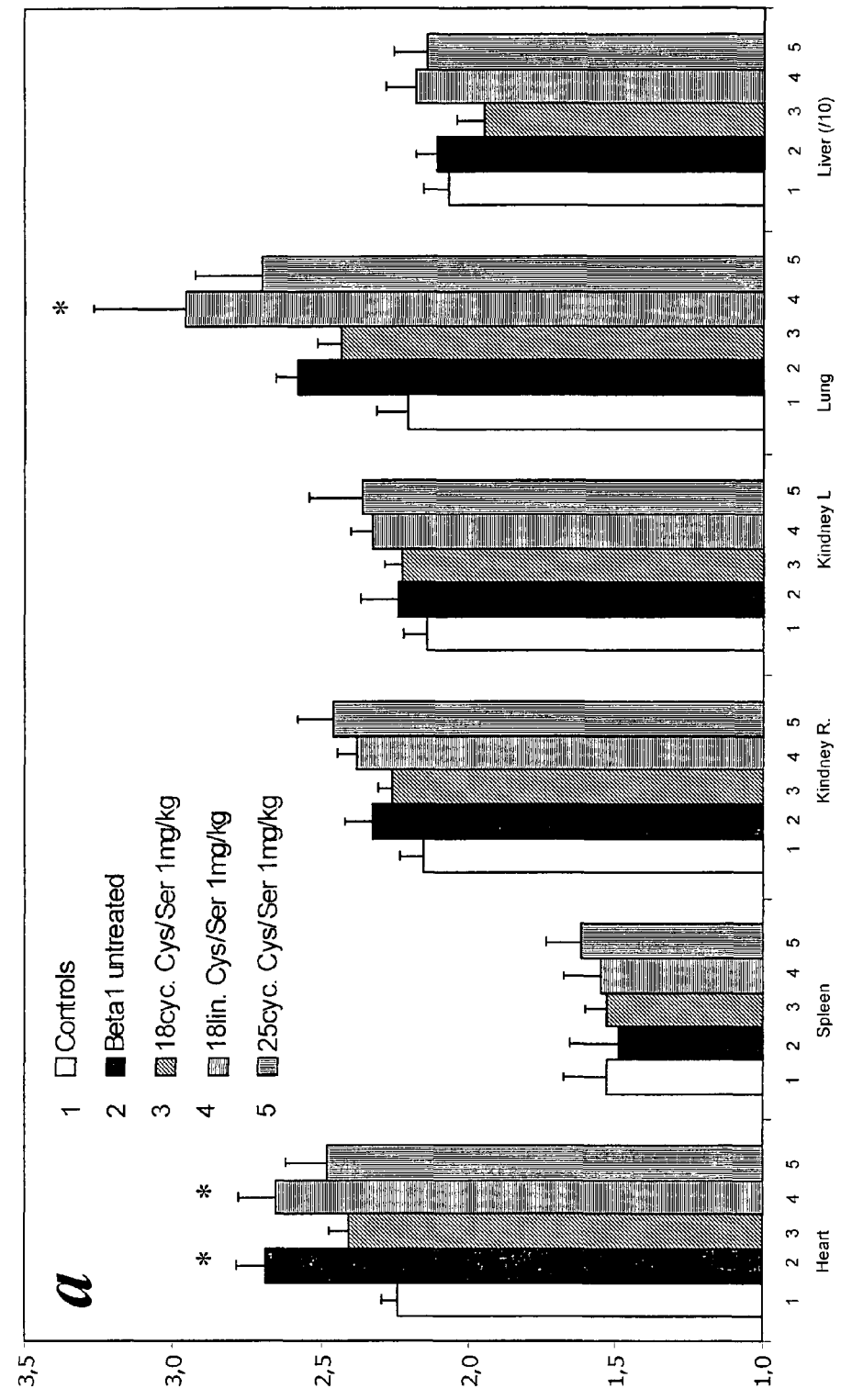
Figure 21B:
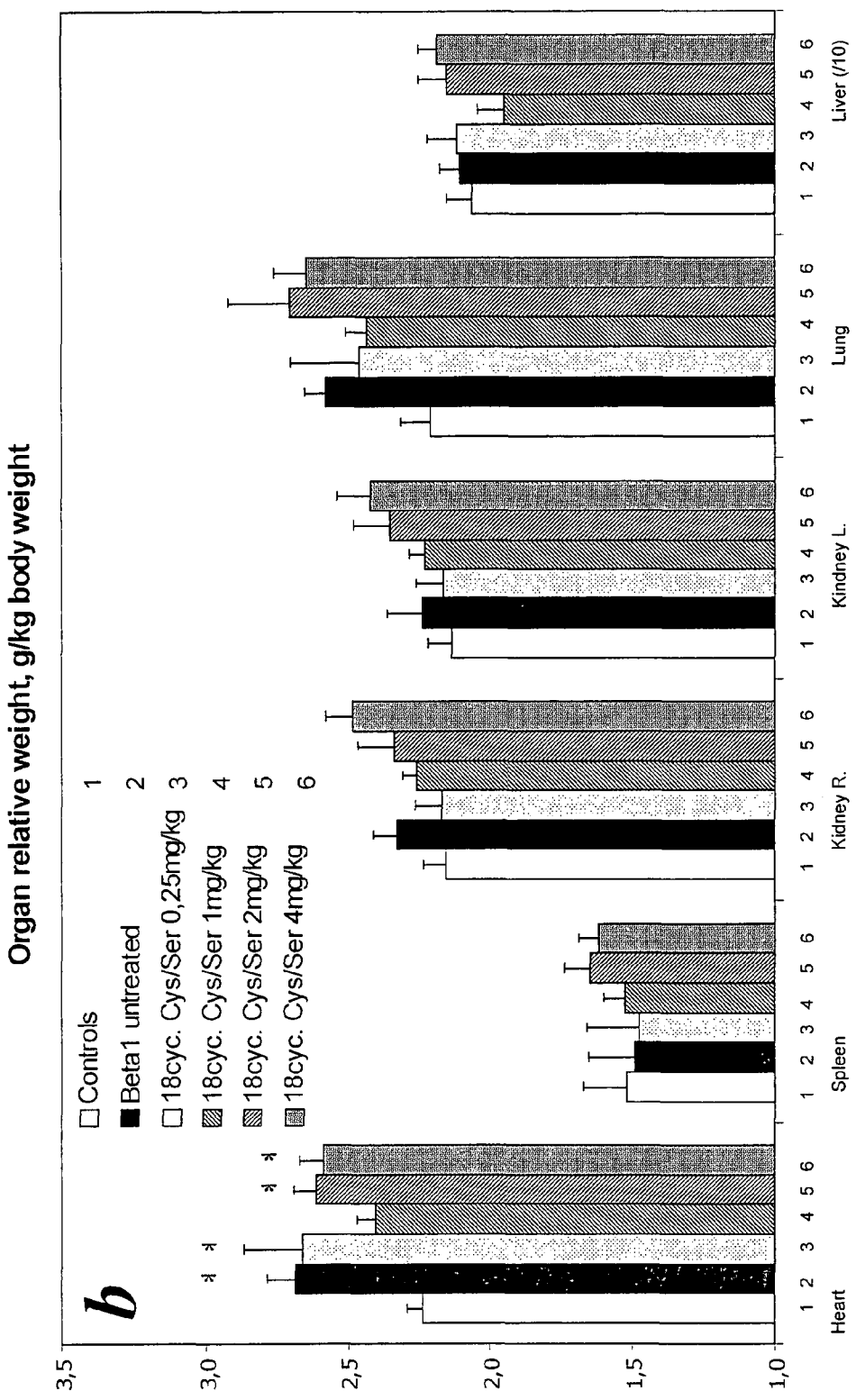

FIG. 21 shows two panels (a and b) with macro anatomic parameters of the animals from the therapy study as columns:

Upper panels (a.) show the relative wet weights of the indicated organs (from the left to the right: heart, spleen, right kidney, left kidney, lung, and liver) given in g/kg body weight, whereby "Beta1 untreated" means immunized anti-beta1 antibody positive cardiomyopathic not treated animals (n=9, black columns), "Controls" means the 0.9% NaCl-injected control group (n=10, white columns), "18cyc Cys/Ser" means immunized anti-beta1-positive cardiomyopathic animals therapeutically treated with the indicated linear 18 lin Cys/Ser (n=5 [1.0 mg/kg Bw], horizontally hatched columns), or cyclic 18cyc Cys/Ser mutants (n=20 [1.0 mg/kg Bw], diagonally right hatched columns), or cyclic 25AA Cys/Ser peptide mutants (n=4 [1.0 mg/kg Bw], vertically hatched columns) after 9 months of immunization.

Lower panels (b.) show the relative wet weights of the indicated organs (from the left to the right: heart, spleen, right kidney, left kidney, lung, and liver) given in g/kg body weight of immunized anti-beta1-positive cardiomyopathic animals therapeutically treated with the indicated doses of beta1-ECII 18AA Cys/Ser cyclopeptide mutants (n=4 [0.25 mg/kg Bw], white filled black dotted columns; n=20 [1.0 mg/kg Bw] diagonally right hatched columns, n=5 [2.0 mg/kg Bw], diagonally left hatched columns; n=9 [4.0 mg/kg Bw], black structured columns) after 9 months of immunization, whereby "Beta1 untreated" means immunized anti-beta1 antibody positive cardiomyopathic not treated animals (n=9, black columns), and "Controls" means the 0.9% NaCl-injected control group (n=10, white columns).

Kidney R means right and Kidney L means left. Differences between the groups were assessed by one way ANOVA; n.s.=not significant, *P<0.05, **P<0.005.

Figure 22A:
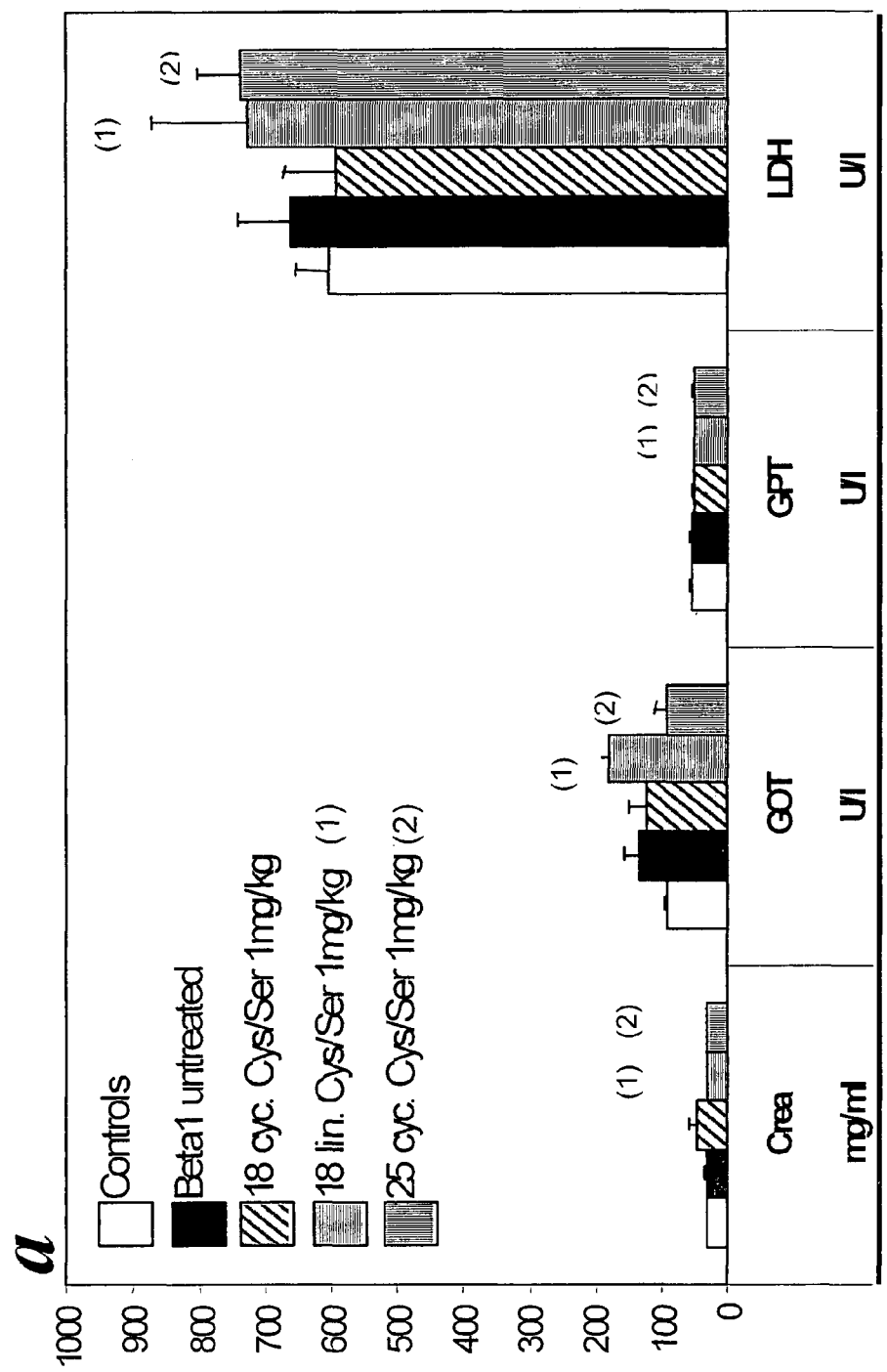
Figure 22B:
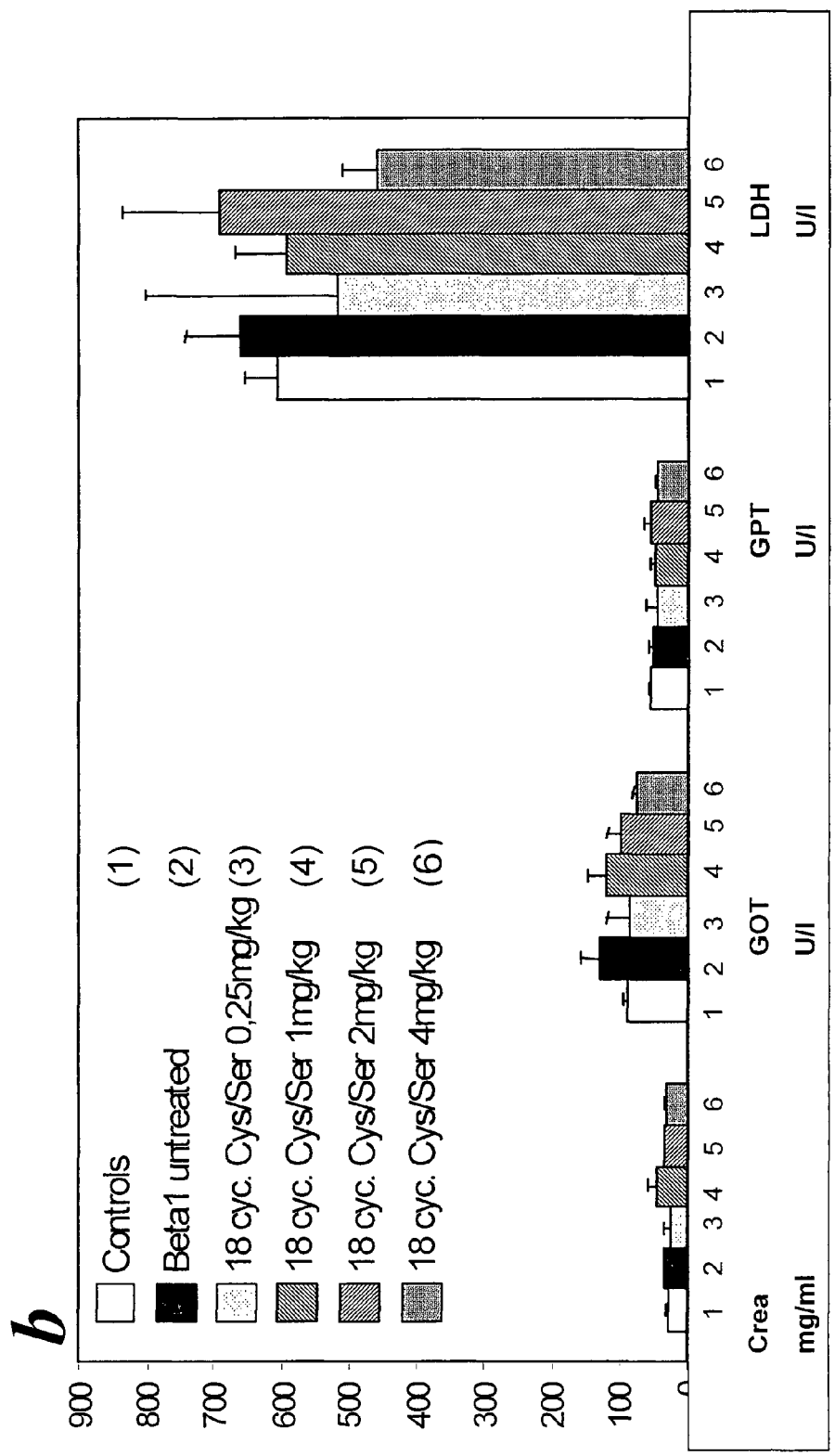

FIG. 22 shows two panels (a and b) with different laboratory parameters determined in the serum of animals after 10 months of treatment. "Beta1 untreated" and "Controls" in both panels means immunized anti-beta1 antibody positive cardiomyopathic not treated animals (n=5, black columns, positive control), and 0.9% NaCl-injected controls (n=6, white columns, negative control), respectively. Upper panels (a) show the parameters of immunized anti-beta1-positive cardiomyopathic animals therapeutically treated with the indicated linear 18 lin Cys/Ser (n=5 [1.0 mg/kg Bw], horizontally hatched columns), or cyclic 18cyc Cys/Ser mutants (n=20 [1.0 mg/kg Bw], diagonally right hatched columns), or cyclic 25AA Cys/Ser peptide mutants (n=4 [1.0 mg/kg Bw], vertically hatched columns) after 9 months of immunization.

Lower panels (b) show the parameters of immunized anti-beta1-positive cardiomyopathic animals therapeutically treated with the indicated doses of beta1-ECII 18AA Cys/Ser cyclo-peptide mutants (n=4 [0.25 mg/kg Bw], white filled black dotted columns; n=20 [1.0 mg/kg Bw] diagonally right hatched columns, n=5 [2.0 mg/kg Bw], diagonally left hatched columns; n=9 [4.0 mg/kg Bw], black structured columns) after 9 months of immunization; Crea means creatinine; GOT means glutamic oxaloacetic transaminase; GPT means glutamic pyruvate transaminase; LDH means lactate dehydrogenase.

Figure 23:
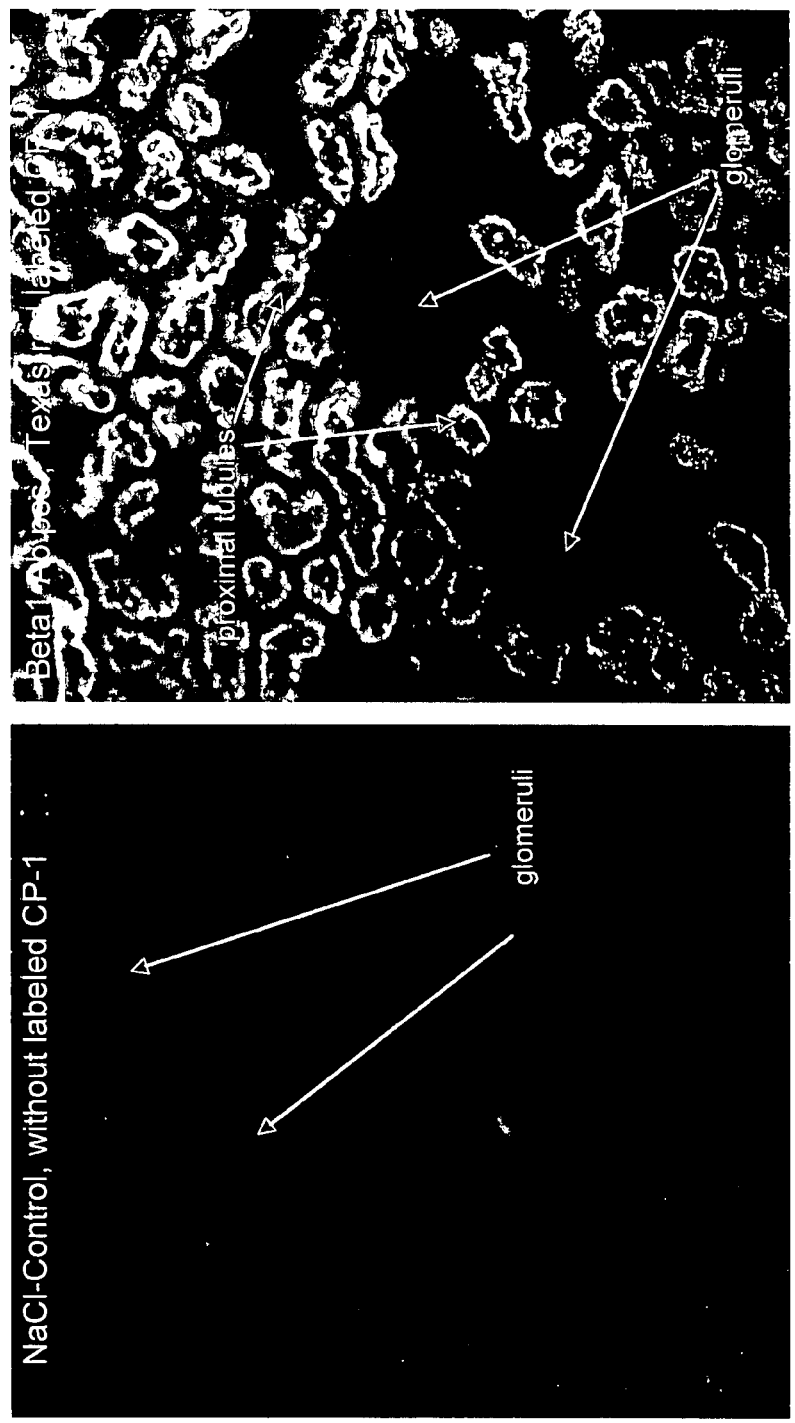

FIG. 23 shows the distribution pattern of texas red (fluorochrom-)labeled 18AA-ECII Cys/Ser cyclopeptide mutants ("CP-1") after i.v.-injection of 1.0 mg/kg body weight (Bw) of the labeled cyclopeptide into either non-immunized 0.9% NaCl treated control animals (left panel) or immunized antibody-positive cardiomyopathic Lewis-rats (550 g Bw). The photographs depict the subcellular distribution of texas red-labeled 18AA Cys/Ser cyclopeptide mutants in the kidney (2 μm sections of the cortical kidney region). The images show, that no toxicity on the kidney was exerted by the cyclic peptides of the invention and no mechanical obstruction of glomerular membranes was observed.

Figure 24:
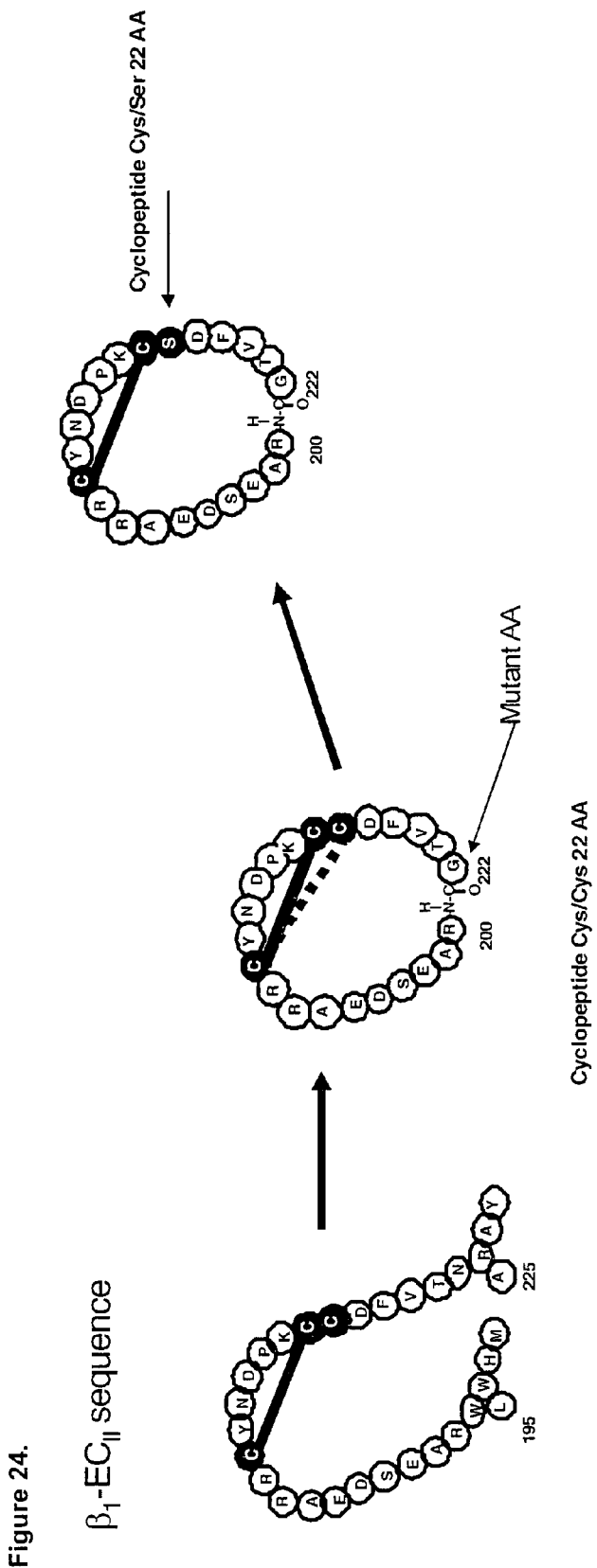

FIG. 24 is a diagram depicting the scheme of mutated cysteine-containing beta1-ECII-homologous cyclo-peptides (amino-acids (AA) are represented as white balls with the corresponding AA letter code written in each ball). Cysteine molecules and their substitutes are depicted as black balls. The assumed localization of the disulfide bridge is represented by a bold black line.

Left side: scheme depicting the original sequence of the ECU-loop of the human beta1 adrenergic receptor; middle: cyclic 22AA ECU-homologous peptide with the glycine mutation at the assumed ring closure site (Position 222).

The right panel depicts an example of a cyclic 22AA peptide-mutant containing only two cysteines (i.e., position 209 and 215). The Cys/Ser mutant of the cysteine at position 216 is shown (Cyclic 22AA beta1-ECII peptide $Cys_{216} \rightarrow Ser_{216}$).

Numbers given indicate the numbering of the amino-acids in the original primary sequence according to Frielle et al. 1987, PNAS 84, pages 7920-7924.

Figure 25A:
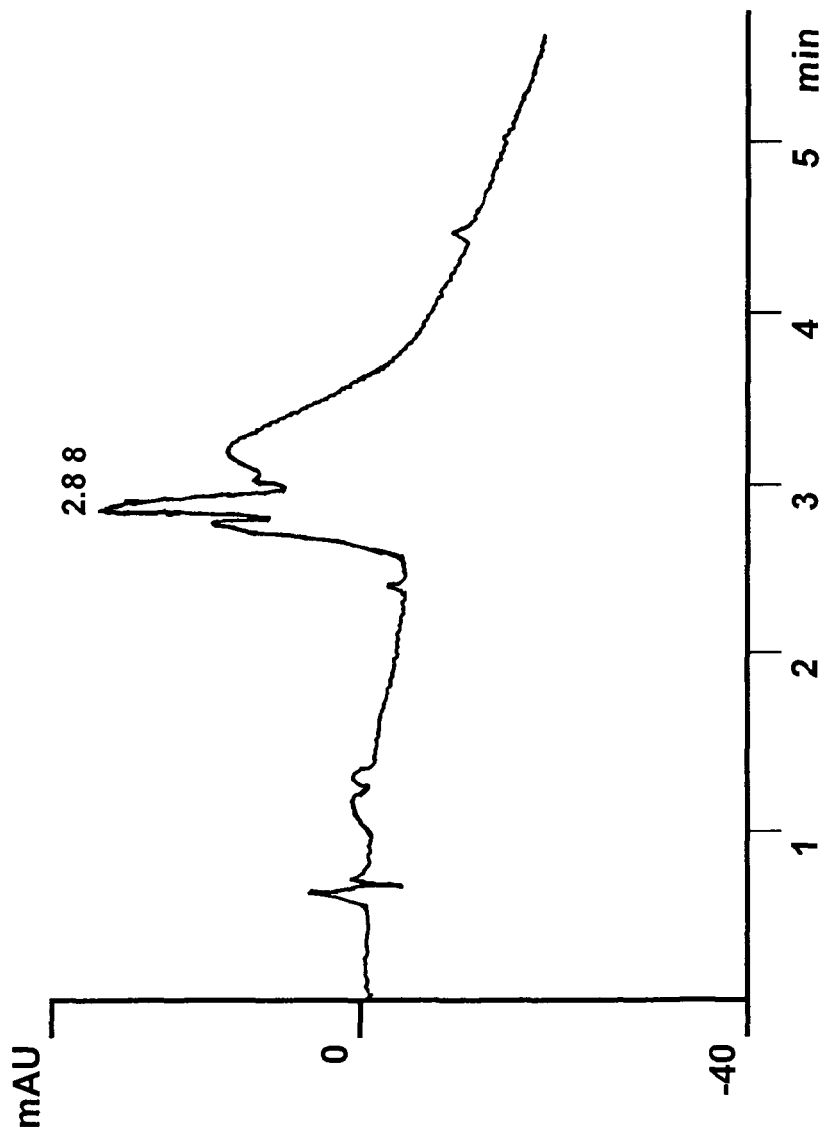
Figure 25B:
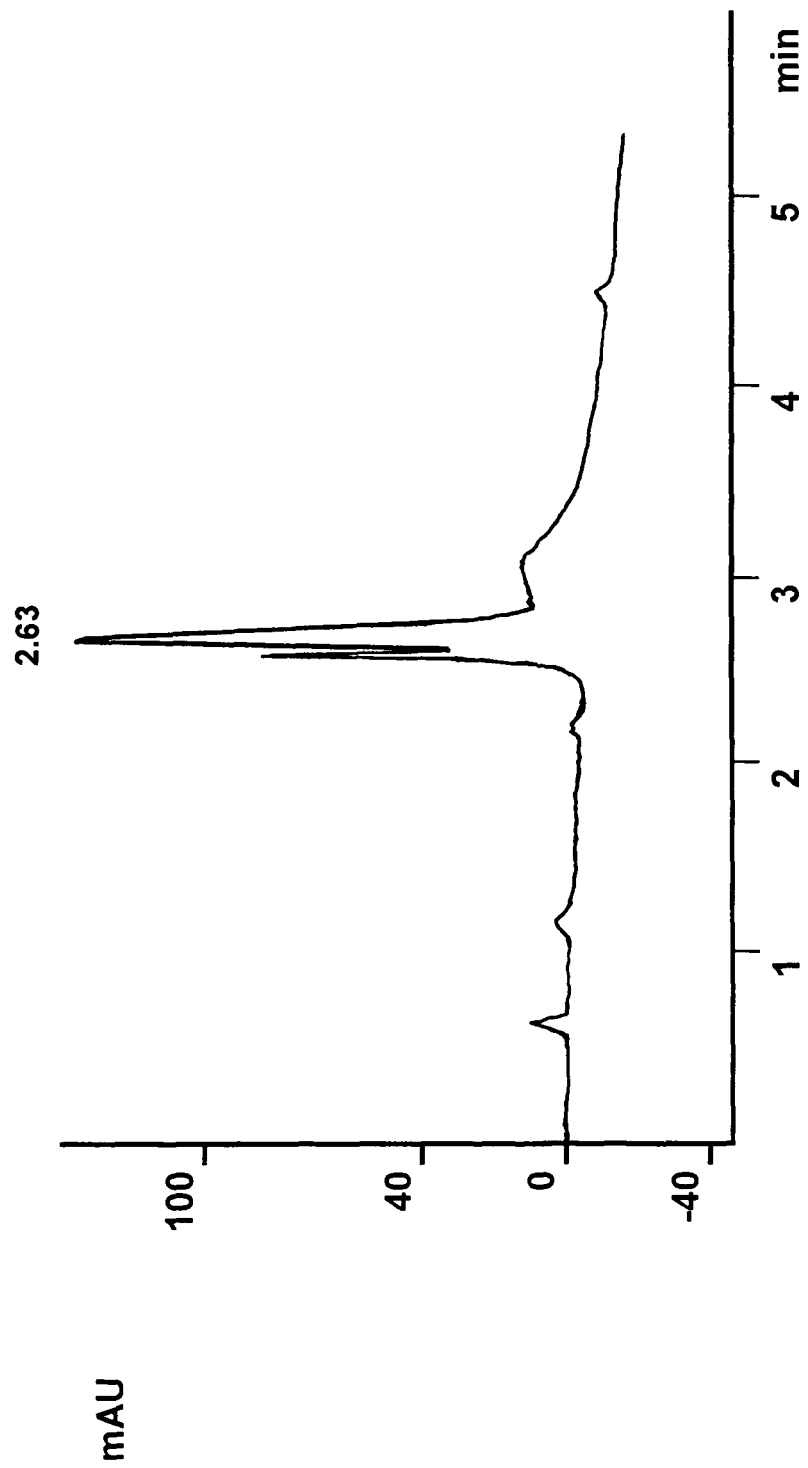

FIG. 25 shows two panels demonstrating the high pressure liquid chromatography (HPLC) elution profiles of two cyclic (22+1)=22 AA peptides; the first panel corresponds to the 3 cysteine-containing construct cyc22AA Cys/Cys (25A), and the second to the 2 cysteine-containing mutant cyc22AA Cys/Ser (25B) of the present invention, all of them cyclopeptides with a Gly closure site. HPLC was carried out in a Hewlett Packard Series 1050 analytical HPLC-system (Agilent Technologies Germany GmbH, Boblingen) equipped with a dual wavelength UV absorbance detector; absorbance was read at 216 nm. After peptide-synthesis and cyclization, the samples were dissolved in $H_2O/0.1\%$ tri-fluoro-acid (TFA) and loaded on a analytic HPLC-column (Waters GmbH, Eschborn) XBridge BEH130, C18, 3.5 μm (column length 50 mm, lumen 4.6 mm) with a flow of 2 ml/min; then a separation-gradient from 0% to 75% acetonitril (ACN) in the pre-sence of 0.1% TFA was run over 5 minutes.

The fractions containing the cyclic beta1-ECII-22AA Cys/Cys peptides with three freely accessible cysteine molecules exhibit the typical mountain-like elution pattern indicating the presence of cystein-racemates (25A, elution between 2.6 and 3.8 minutes). In contrast, the mutant cyclic 22AA peptide containing only two cysteines (connected by a second reinforced disulfide bridge) gave a sharp single elution peak appearing at 2.63 (cyc22AA Cys/Ser, 25B).

Figure 26A:
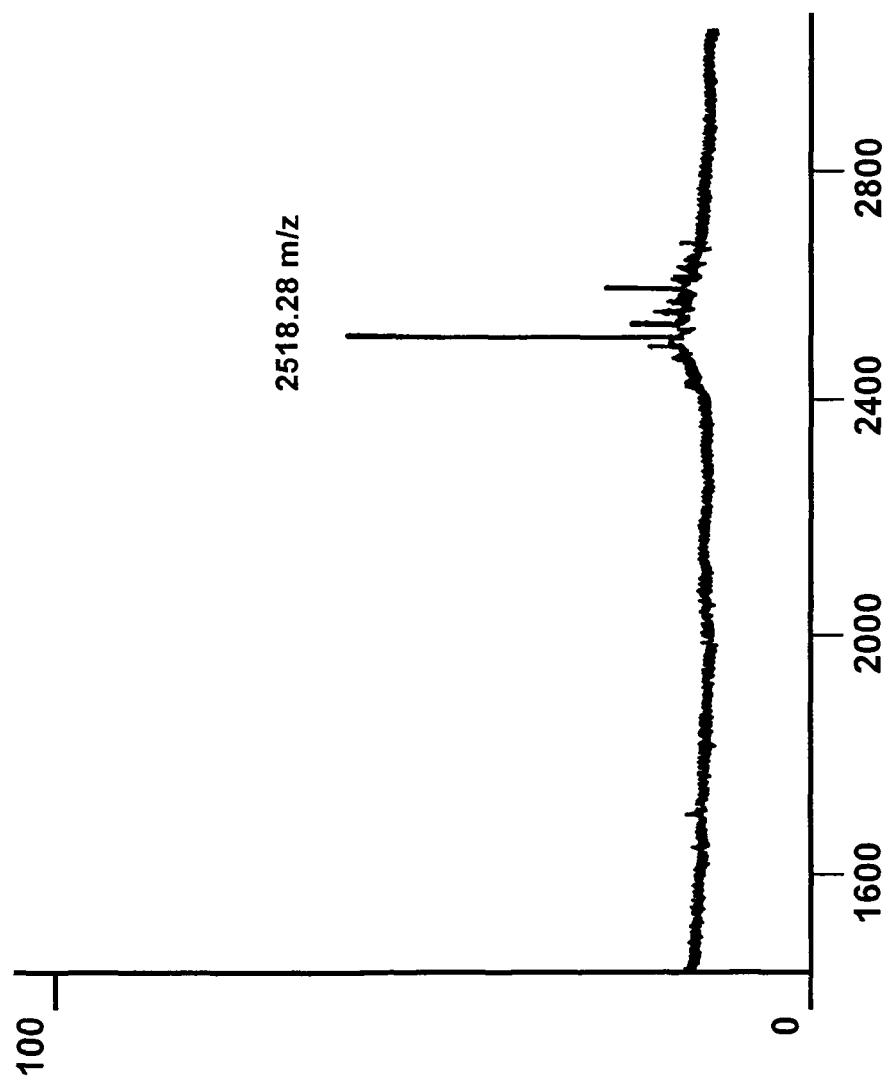
Figure 26B:
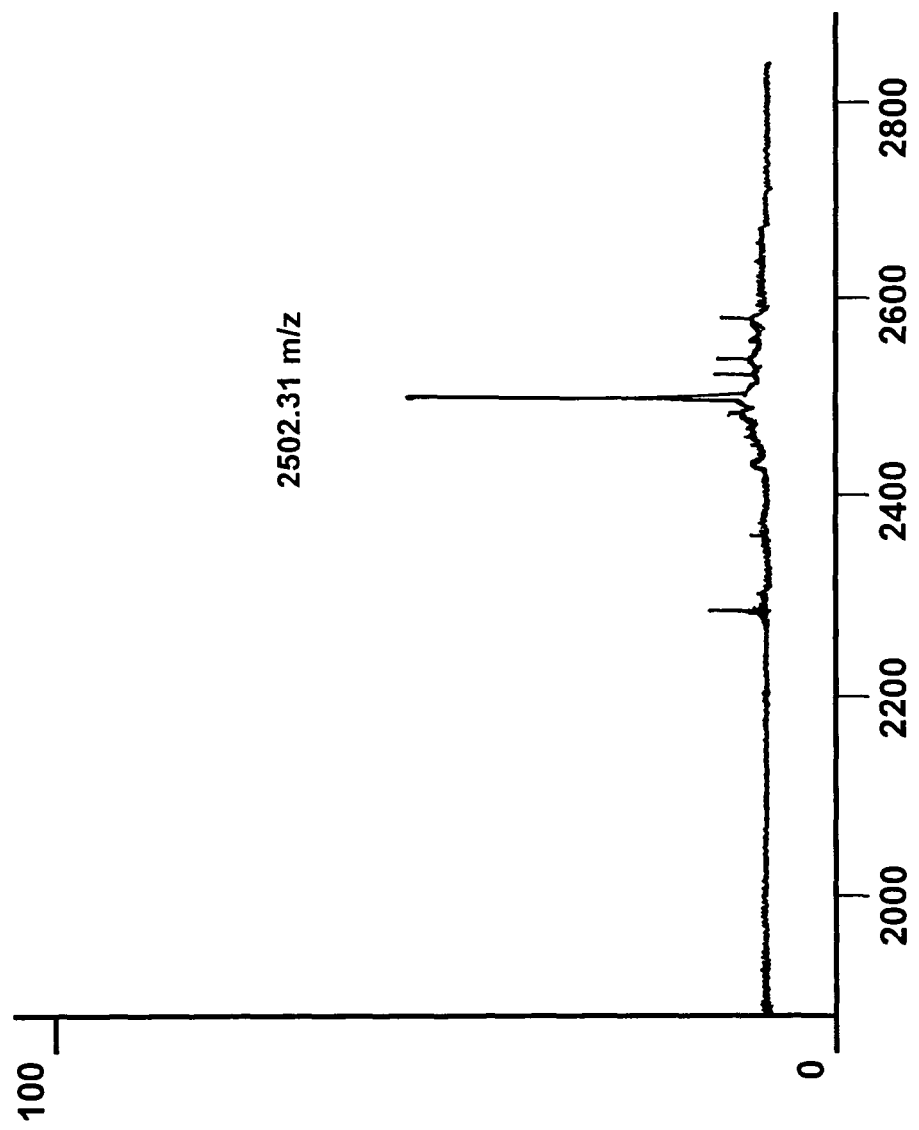

FIG. 26 shows two representative panels depicting the characterization of the 22AA-ECII cyclic peptides by mass spectroscopy (MALDI). The first panel corresponds to the 3 cysteine-containing construct cyc22AA Cys/Cys (26A), and the second to the 2 cysteine-containing mutant cyc22AA Cys/Ser (26B) of the present invention, all of them cyclopeptides with a Gly closure site. The panels show representative MALDI-tracings of the indicated cyclic beta1-ECII 22AA peptides.

The ordinate of each graph shows measured signal intensities ("a.u." means arbitrary units), the abscissa indicates the molecular mass (given in m/z). 26A corresponds to the cyc22AA Cys/Cys-peptide (2518.28 m/z) and 26B to the cyc22AA Cys/Ser-mutant (2502.31 m/z). The MALDI-analysis was carried out using a reflex II-mass spectroscope (Bruker Daltonic GmbH, Bremen), equipped with a Scout-26 sample carrier. In each case the simply protonated molecule was analyzed at 2200 m/z.

FIGS. 27A and B depict the in vitro blocking (=neutralization) capacity of various cysteine-containing cyclopeptide variants of the second extracellular loop (ECII) of the human beta1-adrenergic receptor, determined by testing n=6 individual sera (27A) of immunized beta1-ECII-antibody-positive rats after over-night incubation with the indicated cyclopeptides (12-14 h, 4° C.) by ELISA. Columns in 27A represent the receptor-antibody blocking efficiency of the indicated cyclopeptides in % of the antibody-(ELISA-)signals obtained with unblocked antibody-positive rat sera. Columns in 27B represent the mean blocking efficiency for each cyclopeptide, error bars indicate ±SEM.

white columns: cyc18AA Cys/Ser mutant (blocking-efficiency 60.0±8.3%, P=0.0014 when tested for significance against unblocked sera by two-sided t-test); vertically hatched columns: cyc 18AA Cys/Cys (blocking-efficiency 66.1±7.0%, P=0.00025);

black columns: cyc 22AA Cys/Cys (blocking-efficiency 82.0±5.0%, P=0.000046); diagonally (right) hatched columns: cyc 22AA Cys/Ser mutant (blocking-efficiency 74.9±5.0%, P=0.00026); horizontally hatched columns: cyc25AA Cys/Cys (blocking-efficiency 73.4±5.0%, P=0.00011).

FIGS. 28A and B depict the in vivo blocking (=neutralization) capacity of two cysteine-containing 18AA or 22AA cyclopeptide-mutants of the second extracellular loop (ECII) of the human beta1-adrenergic receptor upon therapeutic injection of the different constructs into rats regularly immunized since 8 months (first=basic immunization followed by 7 antigen-boosts every 4 weeks). The effects of four to five subsequent cyclopeptide-injections every 4 weeks are shown. FIG. 28A depicts the mean values±SEM of each of the treated groups of immunized beta1-ECII-antibody positive cardiomyopathic rats (animal number per group is given in the legend). 28A shows the mean effect of 4 subsequent cyclopeptide-injections, determined 20-22 hours after application of the indicated constructs. The remaining receptor antibody-titers after each injection in % of the antibody-titers at start therapy (month 8) are depicted (columns). Error bars indicate ±SEM. Numbers in columns indicate the number of (subsequent) monthly injection.

Black columns: untreated antibody-positive animals (reference-titer after in total 8+4 (=12) antigen-boosts (compared to the titer at start of therapy) 110.7±5.6%; n=5, positive control).

White columns: cyc18AA Cys/Ser mutant, n=5 animals (antibody-titer remaining after 4 injections in percent of the titer at start of therapy: 76.0±23.0%, P=0.44 when tested for significance against the antibody-titer of untreated antibody-positive animals by two-sided t-test).

Diagonally (right) hatched columns: cyc 22AA Cys/Ser mutant, n=8 animals (antibody-titer remaining after 4 injections in percent of the titer at start of therapy: 9.0±2.2%, $P=3.0 \times 10^{-7}$).

FIG. 28B depicts the time course of antibody-titers after 4 subsequent cyclopeptide-injections, determined before and 20-22 hours after application of the indicated constructs. Values are given in percent of increase or decrease in the respective antibody-titers after each cyclopeptide-injection compared with the antibody-titer determined at start of therapy (month 8).

black circles: untreated antibody-positive animals (n=5, positive control); white squares: cyc18AA Cys/Ser mutant, 4 injections, n=5 animals; black diamonds: cyc 22AA Cys/Ser mutant, 4 injections, n=8 animals.

Figure 29A:
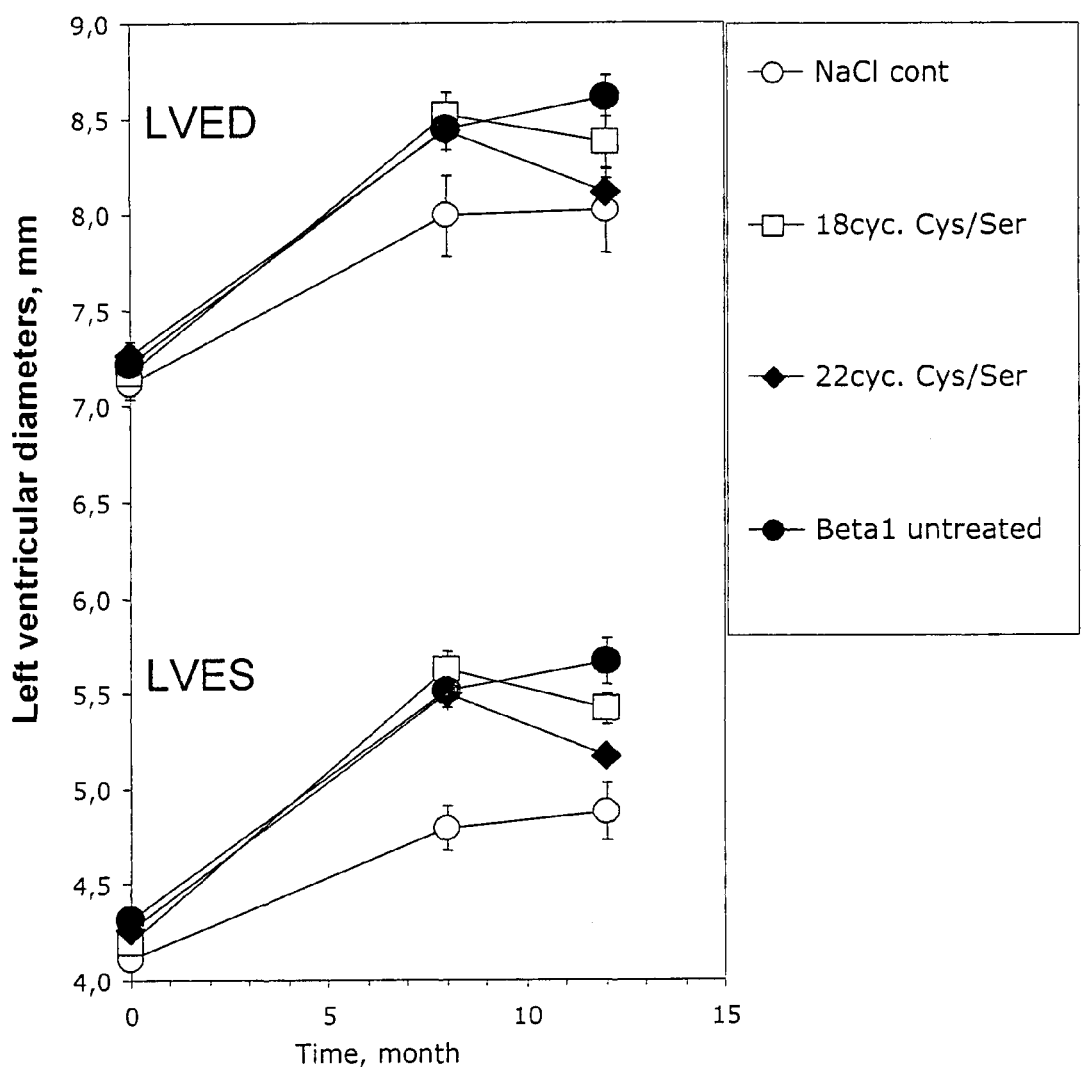

FIG. 29A is a diagram showing the time course (month 0 to 12) of the internal end-systolic and end-diastolic left ventricular diameters (LVES, LVED) of GST/beta1-ECII-immunized untreated (black circles) versus GST/beta1-ECII-immunized animals treated with the indicated various cyclopeptides (see legend) as determined by 2D- and M-mode echocardiography (echocardiographic system: Visual Sonics, Vevo 770 (version V2.2.3), equipped with a 15-17.5 MHz transducer), whereby LVES/LVED is left ventricular end-systolic diameter/left ventricular end-diastolic diameter.

white circles, untreated 0.9% NaCl-injected non immunized control animals (n=5); black circles, untreated regularly (every 4 weeks) immunized antibody-positive animals (n=6); white squares, cyc18AA Cys/Ser mutant (1.0 mg/kg Bw, n=5); black diamonds, cyc 22AA Cys/Ser mutant (Gly-)peptide (1.0 mg/kg Bw, n=8).

Figure 29B:
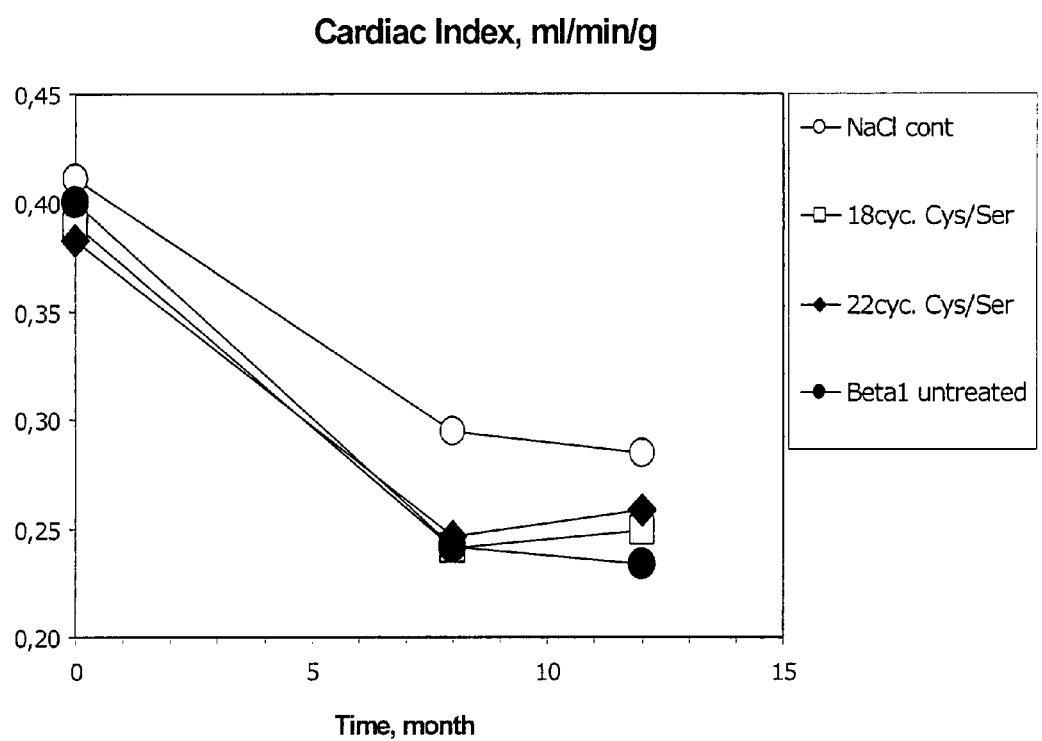

FIG. 29B is a diagram depicting the time course (month 0 to 12) of the "Cardiac index" (CI) in ml/min/g (body weight) as determined by 2D- and Doppler-echocardiography (echocardiographic system see above).

white circles, untreated 0.9% NaCl-injected non immunized control animals (n=5)
black circles, untreated regularly (every 4 weeks) immunized antibody-positive animals (n=6)
white squares, cyc18AA Cys/Ser mutant (1.0 mg/kg Bw, n=5);
black diamonds, cyc22AA Cys/Ser mutant (Gly-)peptide (1.0 mg/kg Bw, n=8)

Figures 30A, 30B:
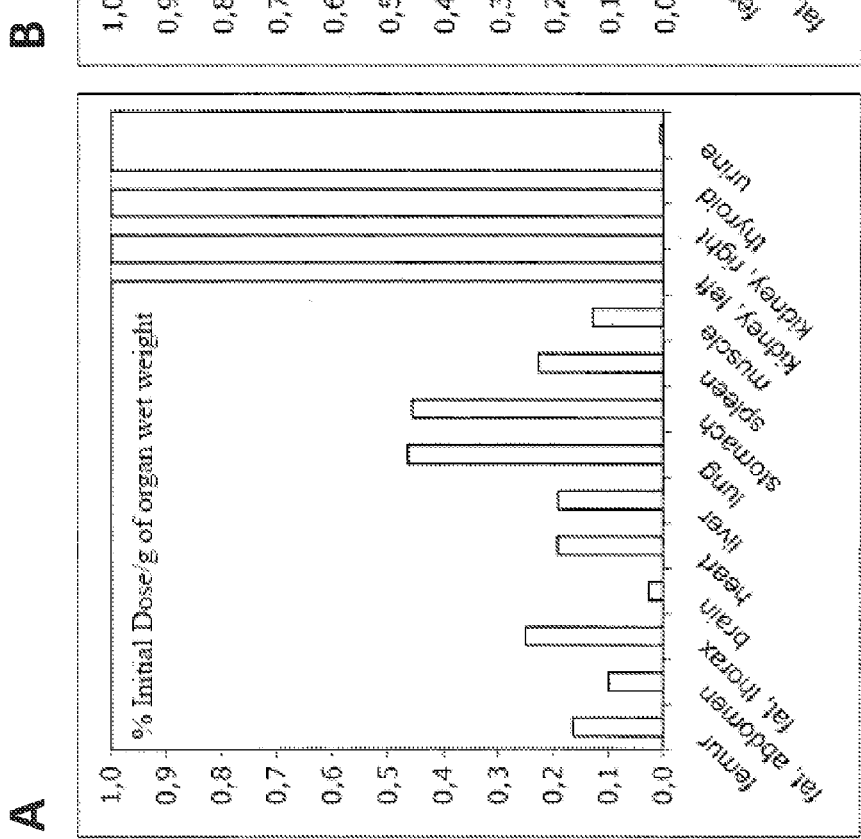

FIG. 30 shows the pattern of accumulated radioactivity in the indicated organs 20 min after i.v.-injection of either non-immunized 0.9% NaCl treated control animals (left panel) or immunized antibody-positive Lewis rats (350-400 g Bw) with 0.5-1.0 MBq of jodine 131-labeled 18AA-ECII Cys/Ser cyclopeptide mutants. Values are given in % activity of the initially injected radioactivity (ID) per g of organ wet weight.

The following, non-limiting examples illustrate the invention.

EXAMPLE 1

Synthesis of Mutant Cyclopeptides

Three particular examples of the herein disclosed cyclopeptides which can form only one single individual disulfide bond are composed of 18, 22 or 25 amino acids (AA): $EC_{II}$-18AA Cys/Ser mutant (Gln-)cyclopeptide, $EC_{II}$-22AA Cys/Ser mutant (Gly-) cyclopeptide and $EC_{11-25}$AA Cys/Ser mutant (Gln-)cyclopeptide, respectively. The primary sequence is partially homologous to the human sequence of the $\beta_1$-AR (amino acid positions 204 through 219, 200 through 220 and 200 through 222, respectively). By restricting conformational flexibility through head-to-tail cyclization of the linear peptide followed by a second (single) disulfide-bond stabilizing cyclization procedure, the 18AA, 22 or 25AA cyclopeptide mutant adopts a conformation which more closely mimics that of the epitope as presented on the surface of the native $\beta_1$-$EC_{II}$ protein loop. Furthermore, cyclization has often been employed as a tool to prolong the duration of action of peptide, since in general cyclic peptides are more stable to proteolysis than their linear counterparts.

In detail, the peptide sequence of the Cyclo(K-18-P) Cyclic S—S, Cys/Ser mutant is: Cyclo-Ala-Asp-Glu-Ala-Arg-Arg-Cys-Tyr-Asn-Asp-Pro-Lys-Cys-Ser-Asp-Phe-Val-Gln; Cyclization can occur between $Cys_7$ and $Cys_{13}$ (disulphide bond) and $Ala_1$ and $Gln_{18}$ (ring closure).

In detail, the peptide sequence of the Cyclo(K-22-P) Cyclic S—S, Cys/Ser mutant is: Cyclo-Arg-Ala-Glu-Ser-Asp-Glu-Ala-Arg-Arg-Cys-Tyr-Asn-Asp-Pro-Lys-Cys-Ser-Asp-Phe-Val-Thr-Gly; Cyclization can occur between $Cys_{10}$ and $Cys_{16}$ (disulphide bond) and $Arg_1$ and $Gly_{22}$ (ring closure).

In detail, the peptide sequence of the Cyclo(K-25-P) Cyclic S—S, Cys/Ser mutant is: Cyclo-Ala-Arg-Ala-Glu-Ser-Asp-Glu-Ala-Arg-Arg-Cys-Tyr-Asn-Asp-Pro-Lys-Cys-Ser-Asp-Phe-Val-Thr-Asn-Arg-Gln; Cyclization can occur between $Cys_{11}$ and $Cys_{17}$ (disulphide bond) and $Ala_1$ and $Gln_{25}$ (ring closure).

The cyclopeptide mutants of the present invention are first synthesized as linear peptides, and are then cyclized covalently on the backbone by condensation of the C-terminal carboxyl group with the amino group of the N-terminal amino acid. Subsequently, a disulphide bond between cysteine residues 7 and 13 (18mer cyclopeptide), cysteine residues 10 and 16 (22mer cyclopeptide) and cysteine residues 11 and 17 (25mer cyclopeptide) is established.

The linear peptide is assembled by stepwise solid phase peptide synthesis using an Fmoc/tert butyl strategy. Chlorotrityl is used as a starting resin. The first amino acid (Fmoc-Pro-OH) is coupling with DIEA in DMF, the second with PYBOP/HOBT/DIEA in DMF and the following amino acids with diisopropylcarboimide, HOBT in DMF. The peptide quality is monitored online by UV detection. Deprotection/coupling (two-fold excess) procedure is described below:

TABLE 1

Deprotection/coupling (two-fold excess) procedure

| Step | Solvents | | Cycle |
|---|---|---|---|
| 1 | Coupling/DMF | (*) min | Coupling |
| 2 | DMF | 3 × 1 min | Wash |
| 3 | Piperidine 25%/DMF | 1 min | Deprotection |
| 4 | Piperidine 25%/DMF | 2 × 15 min | Deprotections |
| 5 | DMF | 7 × 1 min | Wash |

(*) coupling time is determined by Kaiser test

For assembly, the following amino acids were used (exemplarily provided for the 18mer cyclic Cys/Ser peptide mutant):

TABLE 2 amino acids used for F-moc synthesis of the 18mer cyclic Cys/Ser peptide mutant

Amino acid

| | | |
|---|---|---|
| Fmoc-ASP (OtBu)-OH | Fmoc-Asn(Trt)-OH | Fmoc-Tyr(tBu)-OH |
| Fmoc-Cyc(Trt)-OH | Fmoc-Arg(Pbf)-OH | Fmoc-Ala-OH |
| Fmoc-Glu(OtBu)-OH | Fmoc-D-Glu(OtBu)-OH | Fmoc-Val-OH |
| Fmoc-Phe-OH | Fmoc-Ser(tBu)-OH | Fmoc-Lys(Boc)-OH |

The fully protected peptide with reactive N-terminal amino- and C-terminal carboxyl-groups is cleaved from the resin by treatment with hexafluoroisopropanol/dichloromethane.

Cyclization is carried out thereafter in solution according to the following protocol:

The "head to tail"-cyclization of the protected peptide is performed with PyBOP/NaHCO$_3$ in high DMF dilution (10 mmol of linear peptide/1 L of DMF). The cyclization is completed after 3 days. After DMF evaporation, the peptide is washed with 5% NaHCO$_3$, H$_2$O and pure H$_2$O. The reaction mixture is cooled down, and the peptide is deprotected excepting the cysteine groups. Afterwards, the partially protected peptide is isolated by precipitation with methyl t-butyl ether.

The crude peptide is pre-purified by liquid chromatography:
Stationary phase: silica C18, 15 μm, 120 A
Eluant: H$_2$O acetonitrile+0.1% TFA
Detection: UV (210 nm)

The disulfide cyclization is performed in H$_2$O (2 mg/mL) with the presence of dimethyl sulfoxyde (3%). The cyclization reaction is completed after 3 days.

The peptide is purified by HPLC, using the conditions described above.

The fractions with a purity greater than 95% are pooled. The peptide is exchanged on an ion exchange resin (Dowex 1×2) and the final solution lyophilized. The peptide content is determined by amino acid analysis (Edman sequencing).

The HPLC elution profiles in FIGS. 1, 3, 25 and 26 clearly demonstrate the sharp and well defined elution peaks obtained with mutant cyclopeptides all containing the same single disulfide bond in comparison to the relatively large (mountain-like) elution profile obtained with a 3 Cys-containing 18AA Cys$_{13}$-Cys$_{14}$, 22AA Cys$_{16}$-Cys$_{17}$ and 25AA Cys$_{17}$-Cys$_{18}$ cyclopeptide.

All following in vitro and in vivo studies were carried out with these cyclopeptide mutants.

EXAMPLE 2

In Vitro ELISA Competition Assay

The blocking capacity of $\beta_1$-EC$_{II}$-18AA cyclopeptide mutants (Cys$_{13}$-Ser$_{14}$ or Ser$_{13}$-Cys$_{14}$ mutation having an additional D-Glu-Gln exchange, e.g. at the ring closure site) was compared with the 3 Cys-containing 25AA or 18AA Cys/Cys cyclopeptides after preincubation (12 h, 4° C., rotating incubation over-night) of different numbers of sera from immunized antibody-positive rats in an ELISA-competition assay using the 3 Cys-containing linear 25AA Cys/Cys-peptide as an antigen. FIGS. 4, 5, and 7-10 show the results from measurements performed with sera of n=12 up to n=82 immunized antibody-positive rats using different cyclopeptides of the present invention.

The results obtained with IgG-fractions isolated from the sera of 12 different immunized antibody-positive rats revealed that, surprisingly, only the Cys/Ser but not the Ser/Cys cyclopeptide mutants were able to significantly block antibody-binding to the $\beta_1$-EC$_{II}$-antigen. The blocking effect of the 18AS Cys/Ser mutant cyclopeptide was comparable or (in more than half of the sera analyzed n=8/12) was even more effective than the blocking capacity of the 3 Cys-containing $\beta_1$-$EC_{II}$-18AA Cys/Cys cyclopeptide (FIG. 4). This finding was confirmed by dose-titration studies demonstrating a clear dose dependent blocking effect of the $\beta_1$-$EC_{II}$-18AA Cys/Ser cyclopeptide mutant, which at two to eight-fold molar excess (assuming a 1:1 stochiometry for both cyclic (2.1 kDa molecular mass (MM)) or linear peptides (3.0 kDa MM), considering a molecular weight of 150 kDa for an IgG-molecule) was consistently largely superior in blocking receptor antibodies than either its Ser/Cys mutated counterpart or a 3 Cys-containing linear 25AA Cys/Cys peptide (FIG. 5).

FIG. 7 resumes the blocking effect of different cyclopeptide mutants after preincubation with IgG isolated from n=78 immunized antibody-positive rats in an ELISA-competition assay with the linear 3 Cys-containing 25AA Cys/Cys-peptide as an antigen. The blocking capacity of 18AA Cys/Ser mutants was highest (69±2%), followed by 25AA Cys/Cys (67±2%), 18AA Cys/Cys cyclopeptides (60±4%), and 3 Cys-containing linear 25AA peptides (55±4%) compared with the totally inefficient cyclic 25AA or 18AA Ser/Cys mutants (6±2% or 1±2%, respectively; $P<5\times10^{-3o}$ or $P<3.7\times10^{-33}$). Only less than 5% of the tested rat sera (n=4) were also partially blocked by the cyclic ECII-18AA Ser/Cys mutants, whereas the large majority (>95%; n=78) was efficiently blocked by the $EC_{II}$-18AA Cys/Ser mutant (FIG. 8).

The in vitro blocking effect of cyclopeptide mutants having either a Gln-Ala closure site or an D-Glu-Ala closure site was analyzed by ELISA-competition assay (with the 3 Cys-containing linear 25AA Cys/Cys peptide as an antigen) after preincubation with sera isolated from 69 different immunized antibody positive rats. The results are shown in FIG. 9.

Again, there were two patterns of reaction of the rat sera tested (type1/type2). A major fraction of the sera (93%, FIG. 9, upper panel, type1 and FIG. 10) was very efficiently blocked by the 25AA or 18AA Cys/Ser mutant cyclopeptides (69±2% or 68±3% (Gln-closure)/69±2% (D-Glu-closure), respectively) which were even superior to the corresponding 3-Cys-containing 25AA or 18AA Cys/Cys cyclopeptides (65±2% or 59±2%, respectively), whereas the 25AA or 18AA Ser/Cys mutants had almost no inhibitory effect, irrespective of the amino-acid at the closure site (6±2%, 25AA Ser/Cys, $P<5\times10^{-30}$; 1±2%, 18AA Ser/Cys with Gln-($P<3.7\times10^{-33}$) or 1±2% with D-Glu-closure, ($P<6\times10^{-55}$).

A minor fraction of the sera (7%, FIG. 9, lower panel, type 2 and FIG. 10) was blocked similarly by Cys/Ser or Ser/Cys mutated peptides—although to a lesser extent in terms of inhibitory capacity; in addition, for both 25AA and 18AA cyclopeptides the mutants were less effective than their 3 Cys-containing 25AA or 18AA Cys/Cys counterparts. Blocking capacity of the 25AA or 18AA Cys/Ser mutant cyclopeptides was 48±6% or 50±8% (Gln-closure)/47±5% (D-Glu-closure), respectively, which was constantly inferior to that of the corresponding 3-Cys-containing 25AA or 18AA Cys/Cys cyclopeptides (72±5% or 67±6%, respectively); however, in these animals the 25AA or 18AA Ser/Cys mutants revealed blocking capacities which were almost comparable to those of Cys/Ser-mutants (37±7% 25AA Ser/Cys, P=0.22 n.s.; 47±3% 18AA Ser/Cys with Gln- or 33±5% with D-Glu-closure, P=0.7 n.s. or P=0.08 n.s., respectively).

Subsequently, the dose-dependent blocking capacity of various linear and cyclic beta1-ECII-peptides in vitro was analyzed by using the same ELISA competition assay (FIG. 11):

Experiments including linear 25AA Cys/Cys peptides, cyclic 25AA Cys/Ser peptide mutants, cyclic 18AA Cys/Cys peptides, cyclic 18AA Cys/Ser peptide mutants and a linear 18AA Cys/Ser peptide mutant revealed, that all sera from n=6 randomly chosen immunized antibody-positive rats were best blocked in a dose-dependent manner by beta1-ECII-18AA Cys/Ser mutant cyclopeptides, followed by non-mutant 18AA Cys/Cys cyclopeptides, and the 25AA Cys/Ser cyclopeptide mutant. All cyclopeptides were largely superior to their linear-counterparts (with or without mutation) in terms of antibody neutralizing capacity (P<0.005; FIG. 11), yielding a dose-dependent decrease in circulating free anti-beta1-ECII antibodies of 53% with an 8-fold excess, 66% with an 20-fold excess and about 85% with an 80-fold excess of 18AA Cys/Ser cyclopeptide mutants. The corresponding results for cyclic 18AA Cys/Cys- or cyclic 25AA Cys/Ser-peptides were: 46/30% [8-fold excess], 56/49% [20-fold excess], and 71/83% at a 80-fold excess. Linear peptides were clearly less efficient, yielding a dose-dependent decrease in receptor antibody-titers of only 24% [8-fold excess], 35% [20-fold excess], and about 50% at a 80-fold excess for both, linear 25AA Cys/Cys and linear 18AA Cys/Ser peptides.

Additionally, the in vitro blocking (=neutralization) capacity of various cyclopeptide variants of the second extracellular loop (ECII) of the human beta1-adrenergic receptor was tested with sera of immunized beta1-ECII antibody-positive rats after incubation for 12-14 h at 4° C. The in vitro blocking efficiency of the 22AA cyclopeptide cyc22AA Cys/Cys (blocking-efficiency 82.0±5.0% versus unblocked sera, P=0.000046) and of 22AA cyclopeptide mutants cyc22AA Cys/Ser (blocking-efficiency 74.9±5.0%, P=0.00026) was even higher than the blocking capacity of previously described 3 Cys-containing cyclopeptides, i.e., cyc25AA Cys/Cys (blocking-efficiency 73.4±5.0%, P=0.00011) or cyc18AA Cys/Cys (blocking-efficiency 66.1±7.0% versus unblocked sera, P=0.00025; see FIGS. 27A/B)

EXAMPLE 3

In Vitro Functional FRET-Assay

The blocking capacity of $\beta_1$-$EC_{II}$ 25AA or 18AA cyclopeptide mutants (having a D-Glu/Gln at the ring closure site or not) on $\beta_1$-receptor-mediated signalling (functional cAMP-assay) was assayed using an approach by fluorescence resonance energy transfer (FRET) (FIG. 6).

The effect of the pre-incubation (12 h, 4° C., rotating incubator) of anti-$\beta_1$-$EC_{II}$ IgG antibodies of a representative rat with $\beta_1$-$EC_{II}$-18AA cyclopeptide mutants (Cys/Ser or Ser/Cys mutations, respectively) was compared with the inhibitory effect of a 3 Cys-containing 25AA Cys/Cys cyclopeptide or with the effect of anti-$\beta_1$-$EC_{II}$ IgG antibodies not incubated with blocking peptides. The normalized YFP/CFP-ratio of the registered FRET emission signals served to quantify the effect of the cyclopeptide mutants of the present invention in terms of blockade (in percent) of antibody-induced cellular cAMP-production of transiently Epac1-transfected stably $\beta_1$-AR expressing human embryonic kidney cells (HEK 293-$\beta_1$ cells). The x-axis in FIG. 6 corresponds to the registration time given in seconds (s).

The inhibitory effect of $\beta_1$-$EC_{II}$-18AA cyclopeptide mutants on the antibody-induced stimulation of $\beta_1$-adrenergic transmembrane signalling was analyzed using an approach by fluorescence resonance energy transfer (FRET). Again, also in terms of inhibiting measurable functional antibody-effects (blocking intracellular cAMP-increases) the cyclic $\beta_1$-$EC_{II}$-18AA Cys/Ser mutant was largely superior to its Ser/Cys counterpart, and even slightly more effective than a 3 Cys-containing 25AA Cys/Cys cyclopeptide (FIG. 6).

Taken together, the results of the tests performed herein demonstrate that the antibody-blocking capacity of mutated cyclopeptides was not affected by the reduction of the number of amino-acids from a 25-meric to a 18-meric peptide. The results also demonstrate an excellent comparability of 25AA Cys/Cys and 18M Cys/Cys cyclopeptides with the cyclic 25AA or 18AA Cys/Ser mutants, but not with the cyclic 25AA or 18AA Ser/Cys mutants. Surprisingly, the exact nature of the exchange of one single cysteine residue with a serine residue markedly determines the neutralizing potency of the mutated peptides: the Cys→Ser exchange at position 18 (25-AA cyclopeptide) or at position 14 (18-AA cyclopeptide), respectively, yielded cyclic peptides with excellent antibody-neutralizing and pharmacological effects in vitro (FIGS. 6-10), whereas the $Cys_{17}$→$Ser_1$, or $Cys_{13}$→$Ser_{13}$ mutants (25-AA or 18-AA peptide, respectively) had almost no inhibitory effect, neither regarding their properties as antibody-scavengers nor in terms of their capability of inhibiting functional antibody-effects (neutralization of receptor-stimulation in vitro; FIGS. 6-10 and Example 3). The D-Glu/Gln exchange at position 25 (25AA cyclopeptide-mutants) or 18 (18AA cyclopeptide-mutants) did not significantly influence the blocking capacity of the cyclopeptides, regardless of their length (i.e., 25 versus 18 amino-acids; FIGS. 7-10).

EXAMPLE 4

Animal Model, "In Vivo" Blockade of Receptor Antibodies

The animal model used in this example and any other example described herein, if not indicated to the contrary, is the human analogue rat model. Prior to evaluating and testing, respectively, this human analogue rat model was treated as described herein-below using the various compounds of the present invention, more particularly compounds of formula VI, VII, VIII and IX, and, as controls, a linear $EC_{II}$-18AA Cys/Ser mutated ($Gln_{15}$-)peptide (with the following amino-acid sequence: Ala-Asp-Glu-Ala-Arg-Arg-Cys-Tyr-Asn-Asp-Pro-Lys-Cys-Ser-Asp-Phe-Val-Gln) and a linear non-mutated 3 Cys-containing $EC_{11-25}$AA Cys/Cys ($Gln_{25}$) peptide (with the following amino-acid sequence: Ala-Arg-Ala-Glu-Ser-Asp-Glu-Ala-Arg-Arg-Cys-Tyr-Asn-Asp-Pro-Lys-Cys-Cys-Asp-Phe-Val-Thr-Asn-Arg-Gln.

The in-vivo blocking effects of both 25AA and 18AA Cys/Ser mutant cyclopeptides (with a Gln closure site), the 18AA Ser/Cys mutant cyclopeptide, and a mutated linear 18AA Cys/Ser peptide were analyzed after intravenous (i.v.) injection of 1.0 mg/kg body weight (Bw) of each construct into freshly immunized antibody-positive rats (i.e., use of cyclo-peptides in a kind of "prevention" study), with a first cyclopeptide-application 3 months after the initial immunization (and two subsequent boost at months 2 and 3). In total, five prophylactic applications of the various constructs were given at 4-weekly intervals, always two weeks after the monthly continued antigen boost. Sera were drawn 18-20 hours after i.v. injection and assayed for reactivity by ELISA using the 3 Cys-containing linear 25AA Cys/Cys-peptide as an antigen (FIG. 12).

This first (prophylactic) in vivo cyclopeptide-applications demonstrated, that the highest efficiency in terms of antibody-neutralization was achieved with 1.0 mg/kg body weight (Bw) of non mutant 25AA Cys/Cys or 18AA Cys/Cys-cylopeptides (87.7±2% or 89.9±3% decrease after 5 cyclo-peptide injections, compared with untreated immunized animals; both P<0.005), followed by the 18AA Cys/Ser mutant cyclopeptide (54.5±2% decrease after 5 cyclopeptide injections; P<0.05), whereas linear 25AA Cys/Cys peptides or linear 18AA Cys/Ser mutants at a same concentration had no significant blocking effects (25.8±3% or 4.5±11% antibody-titer decrease after 5 injections, P=0.16 or P=0.8; FIG. 12).

This finding was confirmed by ELIspot analysis of bone marrow and spleen cell preparations of selected cyclopeptide-treated versus untreated immunized rats (n=3). FIG. 13 shows a significant decrease in the number of specific anti-beta1-ECII antibody-secreting cells (ASC), both in the spleen and—to a lesser extent—in the bone marrow only in rats treated with 25AA Cys/Cys cyclopeptide or with 18AA Cys/Ser cyclopeptide mutants (n=3 or 4, respectively), whereas the linear 18AA Cys/Ser peptide mutant (n=3) had no effect on ASC (neither spleen nor bone marrow).

Moreover, the in vivo blocking effects of therapeutically used 25AA and 18AA Cys/Ser cyclo-peptide mutants, the 18AA Ser/Cys mutant (Gln-)cyclopeptide, and a mutated linear 18AA Cys/Ser peptide were assessed after a first intravenous (i.v.) dose (i.e., 1.0 mg/kg body weight (Bw)) of each construct injected into long term immunized anti-beta1-ECII antibody-positive rats, yet presenting a cardiomyopathic phenotype (after nine months of 1× monthly immunization with the beta1-ECII/GST antigen; FIGS. 14-16 and 17). Sera were drawn 18-20 hours after the first i.v. injection of the various constructions and assayed for reactivity by ELISA using the 3 Cys-containing linear 25AA Cys/Cys-peptide as an antigen. "Therapeutic" application of various cyclopeptides in cardiomyopathic antibody-positive rats revealed a higher in vivo blocking capacity of 18AA Cys/Ser cyclopeptide mutants (1 mg/kg/Bw) compared with either 25AA Cys/Ser cyclopeptide mutants or the clearly less efficient 18AA Ser/Cys cyclopeptide mutants at a same concentration (FIGS. 14 and 15). Again, the in vivo efficiency of the 18AA Cys/Ser cyclopeptide mutant was largely superior to that of the linear 18AA Cys/Ser peptide mutant. However, when decreasing the applied dose of cyclic 18AA Cys/Ser mutants to 0.25 mg/kg body weight (Bw), no relevant decrease in receptor-antibodies was achieved, suggesting a dose-and-effect relation for cyclopeptide mutants.

Repeated therapeutic injections of mutant single S—S cyclopeptides every 4 weeks into long-term immunized rats with antibody-induced immune-cardiomyopathy confirmed a kind of "critical minimal dose"-and-effect relation for single S—S cyclopeptide mutants: a dose of 0.25 mg/kg Bw of the 18AA Cys/Ser cyclopeptide—albeit capable of scavenging receptor-anti-bodies to some extent—was clearly less efficient in terms of both, (1) the achieved decrease in circulating receptor-antibodies (even when respecting only cyclopeptide-sensitive-"responders", defined as animals having, after 7 cyclopeptide-injections, a maximum remaining antibody-level equal or inferior to 80% of the titer at start of therapy (FIGS. 16*b* and *c*), and (2) in the achieved cardioprotective effect (FIGS. 17*b*, 19*b*, 20, and 21*b*) compared with either a dose of 1.0 or 2.0 mg/kg body weight 18AA Cys/Ser cyclopeptide. The latter doses were almost equally efficient in terms of both, neutralization of circulating receptor antibodies (FIGS. 16*b* and *c*), and reversal of antibody-induced cardiomyopathic features (FIGS. 17*b*, 19*b*, 20, and 21*b*). A further increase in the applied dose to 4.0 mg/kg body weight, however, did not result in higher efficiency—neither regarding antibody scavenging capacity (FIGS. 16*b* and *c*), nor regarding cardioprotective effects (FIGS. 17*b*, 19*b*, 20, and 21*b*).

Upon injection of the peptides no serious local or systemic side effects were observed. In addition, after injection of the various mutant cyclopeptides, both the heart rate and the blood pressure of the animals were not affected (FIG. 20*a*). In addition, no obvious changes in routine laboratory parameters occurred associated with the application of the cyclopeptide-mutants (FIGS. 22*a* and *b*).

In order to generate anti-$\beta_1$-receptor antibodies the animals were immunized with a fusion protein containing bacterial glutathione-S-transferase and the sequence of the second extra-cellular loop of the human $\beta_1$-adrenergic receptor (GST/$\beta_1$-EC$_{II}$). Before treatment of the animals with mutated cyclopeptides according to the present invention, progressive dilated immune cardiomyopathy is observed after 6 to 8 months of regular immunization every four weeks (FIG. 17). All of the immunized animals developed high titers of stimulatory anti-$\beta_1$-EC$_{II}$ antibodies. The specific anti-$\beta_1$-EC$_{II}$ titer reached a maximum between 6 and 8 months of continuously boosting the animals every 4 weeks, whereas NaCl-injected control animals developed no specific receptor antibodies (FIG. 18).

Such immunized animals were used for the application of mutant cyclopeptides according to the present invention. The in-vivo blocking effect of both 25AA and 18AA Cys/Ser mutant cyclopeptides (with a Gln closure site) were determined after a first intravenous (i.v.) injection of 1.0 mg/kg body weight (Bw) (for 18AA Cys/Ser cyclopeptides also 0.25 mg/kg/Bw) into immunized antibody-positive rats. Sera were drawn 18-20 hours after i.v. injection of the different peptides and assayed for reactivity by ELISA using the 3 Cys-containing linear 25AA Cys/Cys-peptide as an antigen.

As mentioned, the in-vivo blocking effects of both 25AA and 18AA Cys/Ser mutated cyclopeptides (with a Gln closure site), the 18AA Ser/Cys mutant (Gln-)cyclopeptide, and a mutated linear 18AA Cys/Ser peptide were analyzed after a first intravenous (i.v.) injection of 1 mg/kg body weight (Bw) of each construct into immunized antibody-positive rats. Sera were drawn 18-20 hours after i.v. injection and assayed for reactivity by ELISA using the 3 Cys-containing linear 25AA Cys/Cys-peptide as an antigen.

The in vivo data confirmed a higher blocking capacity of the 18AA Cys/Ser mutated cyclo-peptides (1 mg/kg/Bw) compared with either 25AA Cys/Ser mutants or the clearly less effective 18AA Ser/Cys mutated cyclopeptides at a same concentration (FIGS. 14 and 15). The in vivo efficiency of the 18AA Cys/Ser cyclopeptide was also largely superior to that of the linear 18AA Cys/Ser peptide.

Upon injection of the peptides no serious local or systemic side effects were observed. In addition, after injection of the various mutant cyclopeptides, both the heart rate and the blood pressure of the animals were not affected.

However, the in vivo data also indicate, that the efficiency of the 18AA Cys/Ser mutated (Gln-)cyclopeptide seems to depend also on the applied dose; an injection of 0.25 mg/kg/Bw was less efficient in terms of antibody-neutralization than the same construct given at a concentration of 1 mg/kg/Bw (FIGS. 14 and 15).

The in vitro findings described in Examples 2 and 3 were generally confirmed in vivo (e.g. FIGS. 14-16). Interestingly, the difference in the blocking efficiency of the Cys/Ser mutated cyclopeptides compared with that of the linear peptides was even more pronounced in vivo (FIGS. 5, 7, and 14-16).

However, the in vivo data also indicate, that the efficiency of the 18AA Cys/Ser mutated cyclopeptide might equally depend on the applied dose (FIGS. 14-16). The obtained results are compatible with a (minimal) dose-and-effect relation for single S—S cyclopeptide mutants: a dose of 0.25 mg/kg of the 18AA Cys/Ser cyclopeptide mutant was largely less efficient in terms of both, the achieved decrease in circulating receptor-antibodies and in the achieved cardioprotective effect compared with either a dose of 1.0 or 2.0 mg/kg body weight (Bw) (FIGS. 14-16). These doses were almost equally efficient in terms of both, neutralization of circulating receptor antibodies and reversal of antibody-induced cardiomyopathic features (FIGS. 16-20). A further increase in the applied dose to 4.0 mg/kg Bw, however, did not result in higher efficiency—neither regarding antibody scavenging (FIG. 16) capacity nor regarding cardioprotective effects in vivo (FIGS. 17-21).

A high dose (=4.0 mg/kg Bw) of cyc18AA Cys/Ser mutants did not increase the efficiency; instead, it led to an transient increase in antibody-titers, allowing for significant reductions in receptor-antibody titers only after the third or fourth cyclo-peptide-injection. Most notably, the effect on the antibody-neutralizing capacity of the different injected concentrations of cyc18AA Cys/Ser mutant cyclopeptides was also confirmed in terms of reversal of antibody-induced cardiomyopathic features in the course of the study with the best cardioprotection achieved by 1.0 or 2.0 mg/kg Bw 18AA Cys/Ser cyclopeptide mutants (FIGS. 17B, 19B, 20, 21B).

As mentioned, both 1.0 mg/kg Bw of 25AA-meric Cys/Ser as well as high dose (=4.0 mg/kg Bw) of 18AA-meric Cys/Ser mutants led to an transient increase in antibody-titers, compatible with an initial immune reaction, allowing for significant reductions in receptor-antibody titers only after the third or fourth cyclopeptide-injection (third or fourth month of therapy; see FIGS. 16a and b). This phenomenon did not occur with either 1.0 or 2.0 mg/kg doses of 18AA Cys/Ser cyclopeptide mutants, resulting in higher absolute decreases in antibody-titers after 9 months of treatment (1.0 mg/kg: −59±14% or 2.0 mg/kg: −59±12%, respectively, P<0.0005 versus immunized untreated animals) corn-pared to only −37±13% (1.0 mg/kg 25AA Cys/Ser-CP; P=0.36 versus immunized untreated animals) or −39±14% (4.0 mg/kg 18AA Cys/Ser-CP, P=0.24 versus immunized untreated animals) of the respective antibody-titers at start of therapy. A dose of 1.0 or 2.0 mg/kg Bw cyc18AA Cys/Ser peptides were thus almost equally efficient in terms of neutralizing circulating receptor antibodies (FIGS. 16b and c), and in the course of the study also in terms of reversal of antibody-induced cardiomyopathic features (FIGS. 17b, 19b, 20, and 21b).

In addition, the in vivo experiments demonstrated that the antibody-blocking capacity of mutant cyclopeptides is seemingly not affected by a reduction in the number of amino acids from a 25-meric to a 18-meric cyclopeptide; both in vitro and in vivo data demonstrate an excellent comparability of the two 2 cysteine-containing single disulfide bond 25AA Cys/Ser or 18AA Cys/Ser cyclopeptide mutants (FIG. 17a). It should be noted, however, that both 1.0 mg/kg 25AA-meric Cys/Ser as well as high dose (i.e., 4.0 mg/kg Bw) 18AA-meric Cys/Ser mutants led to an initial transient increase in antibody-titers (FIGS. 16a and b), and thus postponed a significant reduction in receptor antibody titers to the third or fourth cyclo-peptide-application (third or fourth month of therapy). This phenomenon did not occur with either 1.0 or 2.0 mg/kg Bw doses of 18AA Cys/Ser cyclopeptide mutants.

The in vivo blocking (=neutralization) capacity of the cyc22AA Cys/Ser mutants of the second extracellular loop (ECII) of the human beta1-adrenergic receptor was also tested by "therapeutic" injection into rats which had been regularly immunized over 8 months (basic immunization and seven subsequent antigen-boosts every 4 weeks, see FIGS. 28A/B), and compared with the effects of the described cyc18AA Cys/Ser-mutant.

After four to five regular cyclopeptide injections every 4 weeks, the titers in untreated antibody-positive animals increased to 110.7±5.6% of the values at start of therapy (n=5, positive controls; reference-titer after in total 8+4 (=12) antigen-applications compared with the antibody-titers at month 8). In contrast, 4 injections of cyc22AA Cys/Ser mutants (n=8 animals) decreased the antibody titers to 9.0±2.2% of the antibody-titers at start of therapy (P=3.0×10⁻⁷, when tested for significance against the antibody-titers of untreated antibody-positive animals by two-sided t-test). The in vivo-efficiency of the cyc22AA-mutants is thus further enhanced compared to the described Cys/Ser cyclopeptide-mutant having a length of 18 amino-acids (cyc18AA Cys/Ser; n=5 animals), which after 4 injections decreased the antibody-titers to 76.0±23.0% of the titers at start of therapy (P=0.44 versus untreated antibody-positive animals, n.s.; see FIG. 28A).

In addition, echocardiographic follow-up data after 4 months of treatment also show a superiority of cyc22AA mutants compared with the cyc18AA Cys/Ser mutant regarding their cardioprotective effects in vivo, as assessed by the decrease in both left ventricular end-diastolic (LVED) and end-systolic (LVES) diameters (FIG. 29A), and an increase in "Cardiac Index" (CI, given in ml/min/g body weight; see FIG. 29B), as determined by 2 dimensional- and Doppler-echocardiography using a Visual Sonics echocardiographic system (Vevo 770, version V2.2.3), equipped with a 17.5 MHz transducer).

Taken together, because the cardioprotective and immunomodulating activity of the ECII-homologous cyclic peptides appears to depend largely on their conformation, an intramolecularly localized disulfide bridge is essential to stabilize and maintain the three-dimensional structure of the construction. In the cyclic 21+1 (=22) AA peptide, the remaining cysteines (i.e. in position 209 and 215, in case 216 has been mutated to Ser) maintain a defined intramolecular distance, further strengthened by introduction of the smallest naturally occurring amino-acid glycine at the (predicted) ring closure site, in order to allow for the formation of a structure-defining intramolecular disulfide bridge.

The present invention refers to the following nucleotide and amino acid sequences:

SEQ ID No. 1:
Amino acid sequence homologous to an $EC_{II}$ epitope of human $\beta_1$-AR (18AA; $Cys_{14} \rightarrow Ser_{14}$); Cyclization may occur between $Ala_1$ and $Gln_{18}$

```
Ala-Asp-Glu-Ala-Arg-Arg-Cys-Tyr-Asn-Asp-Pro-Lys-
Cys-Ser-Asp-Phe-Val-Gln
```

SEQ ID No. 2:
Amino acid sequence homologous to an $EC_{II}$ epitope of human $\beta_1$-AR (25AA; $Cys_{18} \rightarrow Ser_{18}$); Cyclization may occur between $Ala_1$ and $Gln_{25}$

```
Ala-Arg-Ala-Glu-Ser-Asp-Glu-Ala-Arg-Arg-Cys-Tyr-
Asn-Asp-Pro-Lys-Cys-Ser-Asp-Phe-Val-Thr-Asn-Arg-
Gln
```

SEQ ID No. 3:
Amino acid sequence homologous to an $EC_{II}$ epitope of human $\beta_1$-AR (18AA; $Cys_{14} \rightarrow Ser_{14}$; $Gln_{18} \rightarrow DGlu_{18}$); Cyclization may occur between $Ala_1$ and $DGlu_{18}$

```
Ala-Asp-Glu-Ala-Arg-Arg-Cys-Tyr-Asn-Asp-Pro-Lys-
Cys-Ser-Asp-Phe-Val-DGlu
```

SEQ ID No. 4:
Amino acid sequence homologous to an $EC_{II}$ epitope of human $\beta_1$-AR (25AA; $Cys_{18} \rightarrow Ser_{18}$; $Gln_{25} \rightarrow DGlu_{25}$); Cyclization may occur between $Ala_1$ and $DGlu_{25}$

```
Ala-Arg-Ala-Glu-Ser-Asp-Glu-Ala-Arg-Arg-Cys-Tyr-
Asn-Asp-Pro-Lys-Cys-Ser-Asp-Phe-Val-Thr-Asn-Arg-
DGlu
```

SEQ ID No. 5:
Amino acid sequence homologous to an $EC_{II}$ epitope of human $\beta_1$-AR (18AA; $Cys_{13} \rightarrow Ser_{13}$); Cyclization may occur between $Ala_1$ and $Gln_{18}$

```
Ala-Asp-Glu-Ala-Arg-Arg-Cys-Tyr-Asn-Asp-Pro-Lys-
Ser-Cys-Asp-Phe-Val-Gln
```

SEQ ID No. 6:
Amino acid sequence homologous to an $EC_{II}$ epitope of human $\beta_1$-AR (25AA; $Cys_{17} \rightarrow Ser_{17}$); Cyclization may occur between $Ala_1$ and $Gln_{25}$ Ala-Arg-Ala-Glu-Ser-Asp-Glu-Ala-Arg-Arg-Cys-Tyr- Asn-Asp-Pro-Lys-Ser-Cys-Asp-Phe-Val-Thr-Asn-Arg- Gln SEQ ID No. 7:
Amino acid sequence homologous to an $EC_{II}$ epitope of human $\beta_1$-AR (18AA; $Cys_{13} \rightarrow Ser_{13}$; Cyclization may occur between $Ala_1$ and $DGlu_{18}$ Ala-Asp-Glu-Ala-Arg-Arg-Cys-Tyr-Asn-Asp-Pro-Lys- Ser-Cys-Asp-Phe-Val-DGlu SEQ ID No. 8:
Amino acid sequence homologous to an $EC_{II}$ epitope of human $\beta_1$-AR (25AA; $Cys_{17} \rightarrow Ser_{17}$; $Gln_{25} \rightarrow DGlu_{25}$); Cyclization may occur between $Ala_1$ and $DGlu_{25}$ Ala-Arg-Ala-Glu-Ser-Asp-Glu-Ala-Arg-Arg-Cys-Tyr- Asn-Asp-Pro-Lys-Ser-Cys-Asp-Phe-Val-Thr-Asn-Arg- DGlu SEQ ID No. 9:
Nucleotide sequence encoding an amino acid sequence homologous to an $EC_{II}$ epitope of human $\beta_1$-AR (18AA; $Cys_{14} \rightarrow Ser_{14}$)

gcngacgaggcgcgccgctgctacaacgaccccaagtgcSERgacttcgt ccar

SEQ ID No. 10:
Nucleotide sequence encoding an amino acid sequence homologous to an $EC_{II}$ epitope of human $\beta_1$-AR (25AA; $Cys_{18} \rightarrow Ser_{18}$)

gcncgggcggagagcgacgaggcgcgccgctgctacaacgaccccaagtg cSERgacttcgtcaccaaccggcar

SEQ ID No. 11:
Nucleotide sequence encoding an amino acid sequence homologous to an $EC_{II}$ epitope of human $\beta_1$-AR (18AA; $Cys_{14} \rightarrow Ser_{14}$; $Gln_{18} \rightarrow DGlu_{18}$)

gcngacgaggcgcgccgctgctacaacgaccccaagtgcSERgacttcgt cgar

SEQ ID No. 12:
Nucleotide sequence encoding an amino acid sequence homologous to an $EC_{II}$ epitope of human $\beta_1$-AR (25AA; $Cys_{18} \rightarrow Ser_{18}$; $Gln_{25} \rightarrow DGlu_{25}$)

gcncgggcggagagcgacgaggcgcgccgctgctacaacgaccccaagtg cSERgacttcgtcaccaaccgggar

SEQ ID No. 13:
Nucleotide sequence encoding an amino acid sequence homologous to an $EC_{II}$ epitope of human $\beta_1$-AR (18AA; $Cys_{13} \rightarrow Ser_{13}$)

gcngacgaggcgcgccgctgctacaacgaccccaagSERtgcgacttcgt ccar

SEQ ID No. 14:
Nucleotide sequence encoding an amino acid sequence homologous to an $EC_{II}$ epitope of human $\beta_1$-AR (25AA; $Cys_{17} \rightarrow Ser_{17}$)

gcncgggcggagagcgacgaggcgcgccgctgctacaacgaccccaag

SERtgcgacttcgtcaccaaccggcar

SEQ ID No. 15:
Nucleotide sequence encoding an amino acid sequence homologous to an $EC_{II}$ epitope of human $\beta_1$-AR (18AA; $Cys_{13} \rightarrow Ser_{13}$; $Gln_{18} \rightarrow DGlu_{18}$)

gcngacgaggcgcgccgctgctacaacgaccccaagSERtgcgacttcgt cgar

SEQ ID No. 16:
Nucleotide sequence encoding an amino acid sequence homologous to an $EC_{II}$ epitope of human $\beta_1$-AR (25AA; $Cys_{17} \rightarrow Ser_{17}$; $Gln_{25} \rightarrow DGlu_{25}$)

gcncgggcggagagcgacgaggcgcgccgctgctacaacgaccccaag

SERtgcgacttcgtcaccaaccgggar

SEQ ID No. 17:
Amino acid sequence homologous to an $EC_{II}$ epitope of human $\beta_1$-AR (18AA; $Cys_3 \rightarrow Ser_3$); Cyclization may occur between $Lys_1$ and $Pro_{18}$ Lys-Cys-Ser-Asp-Phe-Val-Gln-Ala-Asp-Glu-Ala-Arg- Arg-Cys-Tyr-Asn-Asp-Pro SEQ ID No. 18:
Amino acid sequence homologous to an $EC_{II}$ epitope of human $\beta_1$-AR (25AA; $Cys_3 \rightarrow Ser_3$); Cyclization may occur between $Lys_1$ and $Pro_{25}$ Lys-Cys-Ser-Asp-Phe-Val-Thr-Asn-Arg-Gln-Ala-Arg- Ala-Glu-Ser-Asp-Glu-Ala-Arg-Arg-Cys-Tyr-Asn-Asp- Pro SEQ ID No. 19:
Amino acid sequence homologous to an $EC_{II}$ epitope of human $\beta_1$-AR (18AA; $Cys_3 \rightarrow Ser_3$; $Gln_7 \rightarrow DGlu_7$); Cyclization may occur between $Lys_1$ and $Pro_{18}$ Lys-Cys-Ser-Asp-Phe-Val-DGlu-Ala-Asp-Glu-Ala-Arg- Arg-Cys-Tyr-Asn-Asp-Pro SEQ ID No. 20:
Amino acid sequence homologous to an $EC_{II}$ epitope of human $\beta_1$-AR (25AA; $Cys_3 \to Ser_3$; $Gln_{10} \to DGlu_{10}$); Cyclization may occur between $Lys_1$ and $Pro_{25}$ Lys-Cys-Ser-Asp-Phe-Val-Thr-Asn-Arg-DGlu-Ala-Arg- Ala-Glu-Ser-Asp-Glu-Ala-Arg-Arg-Cys-Tyr-Asn-Asp- Pro SEQ ID No. 21:
Amino acid sequence homologous to an $EC_{II}$ epitope of human $\beta_1$-AR (18AA; $Cys_2 \to Ser_2$); Cyclization may occur between $Lys_1$ and $Pro_{18}$ Lys-Ser-Cys-Asp-Phe-Val-Gln-Ala-Asp-Glu-Ala-Arg- Arg-Cys-Tyr-Asn-Asp-Pro SEQ ID No. 22:
Amino acid sequence homologous to an $EC_{II}$ epitope of human $\beta_1$-AR (25AA; $Cys_2 \to Ser_2$); Cyclization may occur between $Lys_1$ and $Pro_{25}$ Lys-Ser-Cys-Asp-Phe-Val-Thr-Asn-Arg-Gln-Ala-Arg- Ala-Glu-Ser-Asp-Glu-Ala-Arg-Arg-Cys-Tyr-Asn-Asp- Pro SEQ ID No. 23:
Amino acid sequence homologous to an $EC_{II}$ epitope of human $\beta_1$-AR (18AA; $Cys_2 \to Ser_2$; $Gln_7 \to DGlu_7$); Cyclization may occur between $Lys_1$ and $Pro_{18}$ Lys-Ser-Cys-Asp-Phe-Val-DGlu-Ala-Asp-Glu-Ala-Arg- Arg-Cys-Tyr-Asn-Asp-Pro SEQ ID No. 24:
Amino acid sequence homologous to an $EC_{II}$ epitope of human $\beta_1$-AR (25AA; $Cys_2 \to Ser_2$; $Gln_{10} \to DGlu_{10}$); Cyclization may occur between $Lys_1$ and $Pro_{25}$ Lys-Ser-Cys-Asp-Phe-Val-Thr-Asn-Arg-DGlu-Ala-Arg- Ala-Glu-Ser-Asp-Glu-Ala-Arg-Arg-Cys-Tyr-Asn-Asp- Pro SEQ ID No. 25:
Nucleotide sequence encoding an amino acid sequence homologous to an $EC_{II}$ epitope of human $\beta_1$-AR (18AA; $Cys_3 \to Ser_3$)

aagtgcSERgacttcgtccargcngacgaggcgcgccgctgctacaacga cccc

SEQ ID No. 26:
Nucleotide sequence encoding an amino acid sequence homologous to an $EC_{II}$ epitope of human $\beta_1$-AR (25AA; $Cys_3 \to Ser_3$)

aagtgcSERgacttcgtcaccaaccggcargcngggcggagagcgacga ggcgcgccgctgctacaacgacccc

SEQ ID No. 27:
Nucleotide sequence encoding an amino acid sequence homologous to an $EC_{II}$ epitope of human $\beta_1$-AR (18AA; $Cys_3 \to Ser_3$; $Gln_7 \to DGlu_7$)

aagtgcSERgacttcgtcgargcngacgaggcgcgccgctgctacaacga cccc

SEQ ID No. 28:
Nucleotide sequence encoding an amino acid sequence homologous to an $EC_{II}$ epitope of human $\beta_1$-AR (25AA; $Cys_3 \to Ser_3$; $Gln_{10} \to DGlu_{10}$)

aagtgcSERgacttcgtcaccaaccgggargcngggcggagagcgacga ggcgcgccgctgctacaacgacccc

SEQ ID No. 29:
Nucleotide sequence encoding an amino acid sequence homologous to an $EC_{II}$ epitope of human $\beta_1$-AR (18AA; $Cys_2 \to Ser_2$)

aagSERtgcgacttcgtccargcngacgaggcgcgccgctgctacaacga cccc

SEQ ID No. 30:
Nucleotide sequence encoding an amino acid sequence homologous to an $EC_{II}$ epitope of human $\beta_1$-AR (25AA; $Cys_2 \to Ser_2$)

aagSERtgcgacttcgtcaccaaccggcargcngggcggagagcgacga ggcgcgccgctgctacaacgacccc

SEQ ID No. 31:
Nucleotide sequence encoding an amino acid sequence homologous to an $EC_{II}$ epitope of human $\beta_1$-AR (18AA; $Cys_2 \to Ser_2$; $Gln_7 \to DGlu_7$)

aagSERtgcgacttcgtcgargcngacgaggcgcgccgctgctacaacga cccc

SEQ ID No. 32:
Nucleotide sequence encoding an amino acid sequence homologous to an $EC_{II}$ epitope of human $\beta_1$-AR (25AA; $Cys_2 \to Ser_2$; $Gln_{10} \to DGlu_{10}$)

aagSERtgcgacttcgtcaccaacgggargcngggcggagagcgacga ggcgcgccgctgctacaacgacccc

SEQ ID No. 33:
Amino acid sequence of an $EC_{II}$ epitope bearing portion of human $\beta_1$-AR (16AA; AA positions 204 to 219)

DEARRCYNDPKCCDFV

SEQ ID No. 34:
Amino acid sequence of an $EC_{II}$ epitope bearing portion of human $\beta_1$-AR (23AA; AA positions 200 to 222)

```
RAESDEARRCYNDPKCCDFVTNR
```

SEQ ID No. 35:
Amino acid sequence of an $EC_H$ epitope of human $\beta_1$-AR

```
DEARR
```

SEQ ID No. 36:
Amino acid sequence of an $EC_H$ epitope (bearing portion) of human $\beta_1$-AR

```
RAESDEARR
```

SEQ ID No. 37:
Amino acid sequence of an $EC_{II}$ epitope of human $\beta_1$-AR

```
DFV
```

SEQ ID No. 38:
Amino acid sequence of an $EC_{II}$ epitope of human $\beta_1$-AR

```
DFVTNR
```

SEQ ID No. 39:
Amino acid sequence homologous to an $EC_{II}$ epitope of human $\beta_1$-AR (16AA; $Cys_{11} \rightarrow Ser_{11}$; N-terminal AA: $Gln_{16}$ or $DGlu_{16}$); Cyclization may occur between $Ala_1$ and $Gln_{16}$/$DGlu_{16}$

```
Ala-Arg-Arg-Cys-Tyr-Asn-Asp-Pro-Lys-Cys-Ser-Asp-
Phe-Val-Tyr-Gln/DGlu
```

SEQ ID No. 40:
Amino acid sequence of the human $\beta_1$-AR

```
  1 mgagvlvlga sepgnlssaa plpdgaataa rllvpasppa sllppasesp eplsqqwtag
 62 mgllmalivl livagnvlvi vaiaktprlq tltnlfimsl asadlvmgll vvpfgativv
121 wgrweygsff celwtsvdvl cvtasietlc vialdrylai tspfryqsll trararglvc
181 tvwaisalvs flpilmhwwr aesdearrcy ndpkccdfvt nrayaiassv vsfyvplcim
241 afvylrvfre aqkqvkkids cerrflggpa rppspspspv papapppgpp rpaaaaatap
301 langragkrr psrlvalreq kalktlgiim gvftlcwlpf flanvvkafh relvpdrlfv
361 ffnwlgyans afnpiiycrs pdfrkafqgl lccarraarr rhathgdrpr asgclarpgp
421 ppspgaasdd ddddvvgatp parllepwag cnggaaadsd ssldepcrpg faseskv
```

SEQ ID No. 41:
Amino acid sequence homologous to an $EC_{II}$ epitope of human $\beta_1$-AR (22AA; $Cys_{17} \rightarrow Ser_{17}$); Cyclization may occur between $Arg_1$ and $Gly_{22}$

```
Arg-Ala-Glu-Ser-Asp-Glu-Ala-Arg-Arg-Cys-Tyr-Asn-
Asp-Pro-Lys-Cys-Ser-Asp-Phe-Val-Thr-Gly
```

SEQ ID No. 42:
Nucleotide sequence encoding an amino acid sequence homologous to an $EC_{II}$ epitope of human $\beta_1$-AR (22AA; $Cys_{17} \rightarrow Ser_{17}$)

```
cgggcggagagcgacgaggcgcgccgctgctacaacgaccccaagtgc
SERgacttcgtcaccGLY
```

SEQ ID No. 43:
Amino acid sequence homologous to an $EC_{II}$ epitope of human $\beta_1$-AR (22AA; $Cys_3 \rightarrow Ser_3$); Cyclization may occur between Lys, and $Pro_{22}$

```
Lys-Cys-Ser-Asp-Phe-Val-Thr-Gly-Arg-Ala-Glu-Ser-
Asp-Glu-Ala-Arg-Arg-Cys-Tyr-Asn-Asp-Pro
```

SEQ ID No. 44:
Nucleotide sequence encoding an amino acid sequence homologous to an $EC_{II}$ epitope of human $\beta_1$-AR (22AA; $Cys_3 \rightarrow Ser_3$)

```
aagtgcSERgacttcgtcaccGLYcgggcggagagcgacgaggcgcgc
cgctgctacaacgacccc
```

SEQ ID No. 45:
Amino acid sequence of an $EC_{II}$ epitope (bearing portion) of human $\beta_1$-AR

```
DEARRCYNDPK
```

SEQ ID No. 46:
Amino acid sequence of an $EC_{II}$ epitope (bearing portion) of human $\beta_1$-AR

```
ESDEARRCYNDPK
```

SEQ ID No. 47:
Amino acid sequence of an $EC_{II}$ epitope of human $\beta_1$-AR

```
AESDEARR
```

SEQ ID No. 48:
Amino acid sequence of an $EC_{II}$ epitope of human $\beta_1$-AR

```
DFVT
```

SEQ ID No. 49:
Nucleotide sequence encoding an amino acid sequence homologous to an $EC_{II}$ epitope of human $\beta_1$-AR (19AA; $Cys_{15} \rightarrow Ser_{15}$ (18AA; $Cys_{14} \rightarrow Ser_{14}$))

gcnagcgacgaggcgcgccgctgctacaacgaccccaagtgcSERga cttcgtccar

SEQ ID No. 50:
Nucleotide sequence encoding an amino acid sequence homologous to an $EC_{II}$ epitope of human $\beta_1$-AR (19AA; $Cys_{15} \rightarrow Ser_{15}$ (18AA; $Cys_{14} \rightarrow Ser_{14}$);

gcnagcgacgaggcgcgccgctgctacaacgaccccaagtgcSERga cttcgtcgar

SEQ ID No. 51:
Nucleotide sequence encoding an amino acid sequence homologous to an $EC_{II}$ epitope of human $\beta_1$-AR (19AA; $Cys_{14} \rightarrow Ser_{14}$ (18AA; $Cys_{13} \rightarrow Ser_{13}$))

gcnagcgacgaggcgcgccgctgctacaacgaccccaagSERtgcgactt cgtccar

SEQ ID No. 52:
Nucleotide sequence encoding an amino acid sequence homologous to an $EC_{II}$ epitope of human 31-AR (19AA; $Cys_{14} \rightarrow Ser_{14}$ (18AA; $Cys_{13} \rightarrow Ser_{13}$); $Gln_{18} \rightarrow DGlu_{18}$)

gcnagcgacgaggcgcgccgctgctacaacgaccccaagSERtgcgactt cgtcgar

SEQ ID No. 53:
Nucleotide sequence encoding an amino acid sequence homologous to an $EC_{II}$ epitope of human $\beta_1$-AR (19AA; $Cys_3 \rightarrow Ser_3$ (18AA; $Cys_3 \rightarrow Ser_3$))

aagtgcSERgacttcgtccargcnagcgacgaggcgcgccgctgctacaac gacccc

SEQ ID No. 54:
Nucleotide sequence encoding an amino acid sequence homologous to an $EC_{II}$ epitope of human $\beta_1$-AR (19AA; $Cys_3 \rightarrow Ser_3$ (18AA; $Cys_3 \rightarrow Ser_3$); $Gln_7 \rightarrow DGlu_7$)

aagtgcSERgacttcgtcgargcnagcgacgaggcgcgccgctgctacaac gacccc

SEQ ID No. 55:
Nucleotide sequence encoding an amino acid sequence homologous to an $EC_{II}$ epitope of human $\beta_1$-AR (19AA; $Cys_2 \rightarrow Ser_2$; (18AA; $Cys_2 \rightarrow Ser_2$))

aagSERtgcgacttcgtccargcnagcgacgaggcgcgccgctgctacaa cgacccc

SEQ ID No. 56:
Nucleotide sequence encoding an amino acid sequence homologous to an $EC_{II}$ epitope of human $\beta_1$-AR (19AA; $Cys_2 \rightarrow Ser_2$; (18AA; $Cys_2 \rightarrow Ser_2$); $Gln_7 \rightarrow DGlu_7$)

aagSERtgcgacttcgtcgargcnagcgacgaggcgcgccgctgctacaa cgacccc

In the nucleotide sequences; "SER" stands for any nucleotide triplet coding for Ser (serine), i.e. for tcn or agy; and "GLY" stands for any nucleotide triplet coding for Gly (Glycine), i.e. for ggn.

n stands for any nucleotide, particularly a, c, g or t, y stands for t or c and r stands for a or g.

As used herein, the sequences of the various peptides are indicated from the N-terminus to the C-terminus, whereby the N-terminus is at the left side and the C-terminus is at the right side of the respective depicted amino acid sequence.

The following additional abbreviations are used herein:

| amino acid: | 3-letter code: | 1-letter code: |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Asparagine or arpartic acids | Asx | B |
| Glutamine or glutamic acid | Glx | Z |
| Leucine or Isoleucine | Xle | J |
| Unspecified or unknown amino acid | Xaa | X |

ADDITIONAL REFERENCES CITED

American, Heart, Association: 2007. Dallas; Heart disease and stroke statistics—2007 update. Circulation 115: e69-e171
Anderton 2001 Immunology 104: 367-376
Baba 2004 Eur. Heart J. 25: 1108-1115
Boivin 2005 Eur. J. Heart Fail. 4, suppl. 1: 24 (104)
Caforio 2002 Eur. J. Heart Fail. 4: 411-417
Chiale 2001 Circulation 103: 1765-1771
Chien 2000 Oncol. 27: 9-17
Christ 2001 J. Mol. Cell. Cardiol. 33: 1515-1525
Christ 2006 J. Mol. Cell. Cardiol. 41: 716-723
Elies 1996 J. Immunol. 157: 4203-4211
Engelhardt 1999 Proc. Natl. Acad. Sci. USA 96: 7059-7064
Eriksson 2003 Nat. Med. 9: 1484-1490
Fabrizio 1994 Drugs Ther. 8: 89-94
Felix 2000 J. Am. Coll. Cardiol. 35: 1590-1598
Ferrari 1995 J. Exp. Med. 182: 59-65
Freedman 2004 J. Clin. Invest. 113: 1379-1382
Fu 1993 J. Clin. Invest. 91: 1964-1968
Göser 2006 Circulation 114: 1693-1702
Hershko 2005 Ann. N.Y. Acad. Sci. 1051: 635-646
Hoebeke 1996 Int. J. Cardiol. 54: 103-111
Iwata 2001a J. Am. Coll. Cardiol. 37: 418-424
Iwata 2001b Circ. Res. 88: 578-586
Jahns 1996 Eur. J. Pharmacol. 316: 111-121
Jahns 1999a J. Am. Coll. Cardiol. 34: 1545-1551
Jahns 1999b Circulation 99: 649-654
Jahns 2000 J. Am. Coll. Cardiol. 36: 1280-1287
Jahns 2004 J. Clin. Invest. 113: 1419-1429
Jahns 2006 Trends Cardiovasc Med 16: 20-24
Khoynezhad 2007 Eur. J. Heart Fail. 9: 120-123
Kühl 2005 Circulation 112: 1965-1970
Li 2006 177: 8234-8240
Limas 1992 Am. Heart J. 123: 967-970
Limas 1996 Int. J. Cardiol. 54: 113-116
Limas 1997 Circulation 95: 1979-1980
Limas 2004 Am. J. Cardiol. 93: 1189-1191
Lohse 2003 Circ. Res. 93: 896-906
Luppi 1998 Circulation 98: 777-785
MacLellan 2003 Nat. Med. 9: 1455-1456
Maekawa 2007 Circulation 115: 5-8
Magnusson 1994 Circulation 89: 2760-2767
Magnusson 1996 Int. J. Cardiol. 54: 137-141
Mahrholdt 2006 Circulation 114: 1581-1590
Matsui 1995 Autoimmunity 21: 85-88
Matsui 2001 Autoimmunity 43: 217-220
Mobini 2004 Autoimmunity Rev. 3: 277-284
Morita 2005 J. Clin. Invest. 115: 518-526
Neumann 1990 J. Am. Coll. Cardiol. 16: 839-846
Nikolaev 2007 J. Am. Coll. Cardiol. 50: 423-431
Okazaki 2003 Nat. Med. 9: 1477-1483
Okazaki 2005 Trends Mol Med 11: 322-326
Pohlner 1997 Am. J. Cardiol. 80: 1040-1045
Rose 1993 Immunol. Today 14: 426-430
Rose 2001 J. Clin. Invest. 107: 943-944
Schultheiss 1985 J. Mol. Cell. Cardiol. 17: 603-617
Schultheiss 1988 J. Exp. Med. 168: 2102-2109
Schulze 1999 Cardiovasc. Res. 44: 91-100
Sewald 2002 Peptides: Chemistry and Biology, Willey-VCH.
Smulski 2006 FASEB J. 20: 1396-1406
Störk 2006 Am. Heart J. 152: 697-704
Wallukat 1995 J. Mol. Cell. Cardiol. 27: 397-406
Wallukat 2002 N. Engl. J. Med. 347: 1806
Wang 1996 Blood Pressure 3: 25-27
Witebsky 1957 J. Am. Med. Assoc. 164: 1439-1447
Woodiwiss 2001 Circulation 103: 155-160

---

What is claimed is:

1. A cyclic peptide of formula I:

```
cyclo {x-(x)_h-Cys-x-x-x-Pro-x-Cys-y-(x)_i-x},     (I)
SEQ ID NO: 58
``` wherein x is an amino acid other than Cys;
h is any integer from 1 to 15;
i is any integer from 0 to 14; and
y is an amino acid other than Cys, and
wherein said cyclic peptide consists of at least 16 and at most 25 amino acids and comprises one of amino acid sequences:

```
Asp-x-x-Arg-Arg-Cys-x-Asn-Asp-Pro-Lys;
SEQ ID NO: 59
or

Glu-Ser-Asp-x-x-Arg-Arg-Cys-x-Asn-Asp-Pro-Lys,
SEQ ID NO: 60
and
``` wherein said peptide
i) is capable of reducing an antibody-mediated activation of $\beta_1$-adrenergic receptor ($\beta_1$-AR);
ii) is capable of binding (auto-)antibodies against $EC_{II}$ loop of $\beta_1$-AR;
iii) is capable of inhibiting interaction(s) between $\beta_1$-AR and (auto-)antibodies against the $EC_{II}$ loop of $\beta_1$-AR; and
iv) mimics epitope(s) presented in the native conformation of the $EC_{II}$ loop of $\beta_1$-AR.

2. The cyclic peptide of claim 1, wherein y is any polar amino-acid except Cys.

3. The cyclic peptide according to claim 1, wherein y is Ser or a Ser analogue but not Cys.

4. The cyclic peptide according to claim 1, wherein h is 5, 8 or 9.

5. The cyclic peptide according to claim 1, wherein i is 3, 4 or 6.

6. The cyclic peptide according to claim 1, wherein the cyclic peptide is formula I' or I":

```
cyclo{x_I-(x)_h-Cys-x-x-x-Pro-x-Cys-y-(x)_i-x};    (I')
SEQ ID NO: 61 cyclo{x_III-(x)_h-Cys-x-x-x-Pro-x-Cys-y-(x)_i-x},  (I")
SEQ ID NO: 62
``` wherein $x_I$ is Ala, Gly, Val, Thr or Ser and $x_{III}$ is Arg.

7. The cyclic peptide according to claim 1, wherein the cyclic peptide is formula I''' or I'''':

```
cyclo{x_I-(x)_h-Cys-x-x-x-Pro-x-Cys-y-(x)_i-x_II};    (I''')
SEQ ID NO: 63 cyclo{x_III-(x)_h-Cys-x-x-x-Pro-x-Cys-y-(x)_i-x_IV},  (I'''')
SEQ ID NO: 64
``` wherein $x_I$ is Ala, Gly, Val, Thr or Ser, $x_{II}$ is Gln, Glu, Asp or Asn and $x_{IV}$ is Gly or a Gly analogue.

8. The cyclic peptide of claim 6, wherein $x_I$ is Ala.

9. The cyclic peptide according to claim 6, wherein $x_{II}$ is Gln or Glu.

10. The cyclic peptide according to claim 6, wherein $x_{II}$ is DGlu.

11. The cyclic peptide according to claim 1, wherein at least one of y is not Pro or x is not Pro.

12. The cyclic peptide according to claim 1, wherein the cyclic peptide is formula II, III or III':

```
cyclo{x_I-x-x_1-x-x-x-Cys-x-x-x-Pro-x-Cys-         (II)
y-(x)_i-x_II}; SEQ ID NO: 65 cyclo{x_I-x_2-x-x_1-x-x-x_1-Cys-x-x-x-Pro-x-Cys-   (III)
y-(x)_i-x_II}; SEQ ID NO: 66 cyclo{x_III-x-x_1-x-x-x_1-x-x-x-Cys-x-x-x-Pro-x-Cys-  (III')
y-(x)_i-x_IV}, SEQ ID NO: 67
``` wherein $x_1$ is an acidic amino acid; and
$x_2$ is a basic amino acid; and
wherein $x_I$ is Ala, Gly, Val, Thr or Ser; $x_{II}$ is Gln, Glu, Asp or Asn; $x_{III}$ is Arg; and $x_{IV}$ is Gly or a Gly analogue.

13. The cyclic peptide according to claim 1, wherein the cyclic peptide is formula IV, V or V':

```
cyclo{x_I-x-x_1-x_4-x-x-Cys-x_3-x-x-Pro-x-Cys-y-   (IV)
x_1-x_3-x_3-x_II}; SEQ ID NO: 68 cyclo{x_I-x_2-x_4-x_1-x_4-x-x_1-x_4-x-x-Cys-x_3-x-x-  (V)
Pro-x-Cys-y-x_1-x_3-x_3-x_4-x_5-x_2-x_II}; SEQ ID NO: 69 cyclo{x_III-x_4-x_1-x_4-x-x_1-x_4-x-x-Cys-x_3-x-x-   (V')
Pro-x-Cys-y-x_1-x_3-x_3-x_4-x_IV}, SEQ ID NO: 70
``` wherein $x_1$ is an acidic amino acid;
$x_2$ is a basic amino acid;

x₃ is selected from the group consisting of Leu, Ile, Val, Met, Trp, Tyr and Phe; and x₄ is selected from the group consisting of Ser, Thr, Ala and Gly; and wherein $x_I$ is Ala, Gly, Val, Thr or Ser, $x_{II}$ is Gln, Glu, Asp or Asn, $x_{III}$ is Arg and $x_{IV}$ is Gly or a Gly analogue.

14. The cyclic peptide according to claim 1, comprising the amino acid sequence:

```
                                      SEQ ID NO: 45
Asp-Glu-Ala-Arg-Arg-Cys-Tyr-Asn-Asp-Pro-Lys;
or
                                      SEQ ID NO: 46
Glu-Ser-Asp-Glu-Ala-Arg-Arg-Cys-Tyr-Asn-Asp-
Pro-Lys.
```

15. The cyclic peptide according to claim 1, wherein the cyclic peptide is selected from the group consisting of:
 a cyclic peptide formable or formed by the amino acid sequence as depicted in any one of SEQ ID NO: 41, 43, 1 to 4 and 17 to 20;
 a cyclic peptide formable or formed by an amino acid sequence as encoded by a nucleotide sequence as depicted in any one of SEQ ID NO: 42, 44, 9 to 12 and 25 to 28:
 c) a cyclic peptide formable or formed by an amino acid sequence as encoded by a nucleotide sequence which differs from the nucleotide sequence as depicted in any one of SEQ ID NO: 42, 44, 9 to 12 and 25 to 28 due to the degeneracy of the genetic code; and
 d) a cyclic peptide of any one of formula VI to IX':

```
                                              (IX')
cyclo{Arg-Ala-Glu-Ser-Asp-Glu-Ala-Arg-Arg-
Cys-Tyr-Asn-Asp-Pro-Lys-Cys-Ser-Asp-Phe-Val-
Thr-Gly}; SEQ ID NO: 41

(VI)
cyclo{Ala-Asp-Glu-Ala-Arg-Arg-Cys-Tyr-Asn-
Asp-Pro-Lys-Cys-Ser-Asp-Phe-Val-Gln}; SEQ ID NO: 1

(VII)
cyclo{Ala-Arg-Ala-Glu-Ser-Asp-Glu-Ala-Arg-
Arg-Cys-Tyr-Asn-Asp-Pro-Lys-Cys-Ser-Asp-Phe-
Val-Thr-Asn-Arg-Gln}; SEQ ID NO: 2

(VIII)
cyclo{Ala-Asp-Glu-Ala-Arg-Arg-Cys-Tyr-Asn-
Asp-Pro-Lys-Cys-Ser-Asp-Phe-Val-DGlu}; SEQ ID NO: 3

(IX)
cyclo{Ala-Arg-Ala-Glu-Ser-Asp-Glu-Ala-Arg-
Arg-Cys-Tyr-Asn-Asp-Pro-Lys-Cys-Ser-Asp-Phe-
Val-Thr-Asn-Arg-DGlu} SEQ ID NO: 4.
```

16. The cyclic peptide of claim 1, wherein the peptide is selected from the group consisting of: cyclo{Arg-Ala-$x_1$-Ser-$x_1$-$x_1$-Ala-Arg-Arg-Cys-Tyr-$x_1$-$x_1$-Pro-Lys-Cys-Ser-$x_1$-Phe-Val-Thr-Gly} SEQ ID NO: 71;
 cyclo{Ala-$x_1$-$x_1$-Ala-Arg-Arg-Cys-Tyr-$x_1$-$x_1$-Pro-Lys-Cys-Ser-$x_1$-Phe-Val-$x_1$} SEQ ID NO: 72;
 cyclo{Ala-Arg-Ala-Glu-Ser-$x_1$-$x_1$-Ala-Arg-Arg-Cys-Tyr-$x_1$-$x_1$-Pro-Lys-Cys-Ser-$x_1$-Phe-Val-Thr-$x_1$-Arg-$x_1$} SEQ ID NO: 73;
 cyclo{Ala-$x_1$-$x_1$-Ala-Arg-Arg-Cys-Tyr-$x_1$-$x_1$-Pro-Lys-Cys-Ser-$x_1$-Phe-Val-DGlu} SEQ ID NO: 74; and
 cyclo{Ala-Arg-Ala-$x_1$-Ser-$x_1$-$x_1$-Ala-Arg-Arg-Cys-Tyr-$x_1$-$x_1$-Pro-Lys-Cys-Ser-$x_1$-Phe-Val-Thr-Asn-Arg-DGlu} SEQ ID NO: 75, wherein $x_1$ is an acidic amino acid.

17. The cyclic peptide of claim 1, wherein the peptide is selected from the group consisting of: cyclo{$x_2$-Ala-Glu-Ser-Asp-Glu-Ala-$x_2$-$x_2$-Cys-$x_2$-Asn-Asp-Pro-$x_2$-Cys-Ser-Asp-Phe-Val-Thr-Gly} SEQ ID NO: 76;
 cyclo{Ala-Asp-Glu-Ala-$x_2$-$x_2$-Cys-$x_2$-Asn-Asp-Pro-$x_2$-Cys-Ser-Asp-Phe-Val-Gln} SEQ ID NO: 77 (VI);
 cyclo{Ala-$x_2$-Ala-Glu-Ser-Asp-Glu-Ala-$x_2$-$x_2$-Cys-Tyr-Asn-Asp-Pro-Lys-Cys-Ser-Asp-Phe-Val-Thr-Asn-$x_2$-Gln} SEQ ID NO: 78;
 cyclo{Ala-Asp-Glu-Ala-$x_2$-Arg-Cys-$x_2$-Asn-Asp-Pro-$x_2$-Cys-Ser-Asp-Phe-Val-DGlu} SEQ ID NO: 79; and
 cyclo{Ala-$x_2$-Ala-Glu-Ser-Asp-Glu-Ala-$x_2$-$x_2$-Cys-Tyr-Asn-Asp-Pro-$x_2$-Cys-Ser-Asp-Phe-Val-Thr-Asn-$x_2$-DGlu} SEQ ID NO: 80,
 wherein $x_2$ is a basic amino acid.

18. The cyclic peptide according to claim 15, wherein at least one of the aliphatic amino acid residues except Cys is replaced by a different aliphatic amino acid except Cys.

19. The cyclic peptide according to claim 1, wherein cyclization occurs by at least one linkage which is a covalent bond selected from the group consisting of S—S linkages, peptide bonds, carbon-carbon bonds such as C—C or C=C, ester bonds, ether bonds, azo bonds, C—S—C linkages, C—N—C linkages and C=N—C linkages.

20. The cyclic peptide according to claim 1, wherein cyclization occurs by at least two linkages, one is an S—S linkage and one is a peptide bond.

21. The cyclic peptide of claim 19, wherein said S—S linkage is formed by two Cys residues of the peptide.

22. The cyclic peptide according to claim 19, wherein said peptide bond is formed by the NH₂ group of the N-terminal amino acid and the COOH group of the C-terminal amino acid.

23. The cyclic peptide according to claim 19, wherein at least one additional bond is formed by a side chain-amino group and a side chain-COOH group of the constituent amino acids.

24. A method for producing a cyclic peptide of claim 1, comprising the steps of
 a) (i) culturing a recombinant host cell comprising a nucleic acid molecule encoding the amino acid backbone of the cyclic peptide according to claim 1 or a vector comprising said nucleic acid molecule under conditions such that the amino acid backbone of the polypeptide of claim 1 is expressed, and recovering said amino acid backbone; or
 (ii) chemically synthesizing the amino acid backbone of the polypeptide of claim 1; and
 b) cyclization of said amino acid backbone to form the cyclic peptide of claim 1.

25. The method of claim 24, wherein said cyclization occurs by at least one linkage which is a covalent bond selected from the group consisting of S—S linkages, peptide bonds, carbon-carbon bonds such as C—C or C=C, ester bonds, ether bonds, azo bonds, C—S—C linkages, C—N—C linkages and C=N—C linkages.

26. The method of claim 25, wherein said N-terminal amino acid is Ala or Arg and said C-terminal amino acid is Gln or Glu or Gly, respectively, or said N-terminal amino acid is Lys and said C-terminal amino acid is Pro.

27. The method of claim 26, wherein Glu is DGlu.

28. A composition comprising a cyclic peptide of claim 1 and a carrier.

29. The composition of claim 28, wherein said composition is a pharmaceutical composition and said carrier is a pharmaceutically acceptable carrier.

30. A method for a) treating, ameliorating or reducing the risk of heart disease where the activity of a β-adrenergic receptor (β-AR) is enhanced by reducing the activity of the antibodies against β-AR;

b) treating a patient having antibodies against a β-AR by binding said antibodies; or c) inducing immune tolerance by suppressing the production of antibodies against a β-AR in a patient, comprising the step of administering to the patient in need of such medical intervention a pharmaceutically effective amount of a cyclic peptide of claim 1.

31. The pharmaceutical composition according to claim 29, wherein said pharmaceutical composition comprises at least one further pharmaceutically active agent.

32. The pharmaceutical composition of claim 31, wherein said at least one further pharmaceutically active agent is a β-receptor blocker.

33. The pharmaceutical composition of claim 32, wherein said β-receptor blocker is a selective β-AR blocker.

34. The pharmaceutical composition of claim 33, wherein said selective β-AR blocker is selected from the group consisting of atenolol, metoprolol, nebivolol, and bisoprolol.

35. The method according to claim 30, wherein said heart disease is selected from the group consisting of infectious and non-infectious heart disease, ischemic and non-ischemic heart disease, inflammatory heart disease and myocarditis, cardiac dilatation, idiopathic cardio-myopathy, (idiopathic) dilated cardiomyopathy (DCM), immune-cardiomyopathy, heart failure, and any cardiac arrhythmia including ventricular and/or supraventricular premature capture beats as well as any atrial arrhythmia including atrial fibrillation and/or atrial flutter.

36. The method according to claim 30, wherein said heart disease is (idiopathic) DCM.

37. The method according to claim 30, wherein said disease is induced by antibodies against a β-AR.

38. The method according to claim 30, wherein said induction of immune tolerance is obtained by suppression of the production of antibodies against a β-AR.

39. The method according to claim 38, wherein said induction of immune tolerance is obtained by suppression of the production of antibodies against a β-AR through blockade of the antigen-recognition sites of the antibody-producing early B-cells and memory B-cells.

40. A method for detecting antibodies against a β-AR in a sample comprising the step of contacting the sample with the cyclic peptide of claim 1 and detecting the presence or level of anti-β-AR antibodies in the sample based on binding to the cyclic peptide.

41. The method according to claim 30, wherein said β-AR is $\beta_1$-AR.

42. The cyclic peptide according to claim 15, wherein the cyclic peptide is formula VI:

```
                                                    (VI)
cyclo{Ala-Asp-Glu-Ala-Arg-Arg-Cys-Tyr-Asn-
Asp-Pro-Lys-Cys-Ser-Asp-Phe-Val-Gln}. SEQ ID NO: 1
```

43. The cyclic peptide according to claim 42, wherein cyclization occurs by at least one linkage which is a covalent bond selected from the group consisting of S—S linkages, peptide bonds, carbon-carbon bonds such as C—C or C═C, ester bonds, ether bonds, azo bonds, C—S—C linkages, C—N—C linkages and C═N—C linkages.

44. The cyclic peptide according to claim 42, wherein cyclization occurs by at least two linkages, one of which is an S—S linkage and one of which is a peptide bond.

45. The cyclic peptide of claim 43, wherein said S—S linkage is formed by two Cys residues of the peptide.

46. The cyclic peptide according to claim 43, wherein said peptide bond is formed by the $NH_2$ group of the N-terminal amino acid and the COOH group of the C-terminal amino acid.

47. The cyclic peptide of claim 1, wherein the formula I peptide is cyclo{Ala-$x_1$-$x_1$-Ala-Arg-Arg-Cys-Tyr-Asn-$x_1$-Pro-Lys-Cys-Ser-$x_1$-Phe-Val-Gln}, and $x_1$ is an acidic amino acid.

48. The method according to claim 24, wherein the cyclic peptide is cyclo{Ala-Asp-Glu-Ala-Arg-Arg-Cys-Tyr-Asn-Asp-Pro-Lys-Cys-Ser-Asp-Phe-Val-Gln} (VI) SEQ ID NO: 1.

49. The composition according to claim 29, wherein the cyclic peptide is cyclo{Ala-Asp-Glu-Ala-Arg-Arg-Cys-Tyr-Asn-Asp-Pro-Lys-Cys-Ser-Asp-Phe-Val-Gln} (VI) SEQ ID NO: 1.

50. The composition according to claim 49, wherein said composition is a pharmaceutical composition and said carrier is a pharmaceutically acceptable carrier.

51. The method according to claim 30, wherein the cyclic peptide is cyclo{Ala-Asp-Glu-Ala-Arg-Arg-Cys-Tyr-Asn-Asp-Pro-Lys-Cys-Ser-Asp-Phe-Val-Gln} (VI) SEQ ID NO: 1.

52. The method according to claim 51, wherein said cyclic peptide is administered until at least 0.05 mg of said cyclic peptide per kg body weight is reached.

53. The method according to claim 40, wherein the cyclic peptide is cyclo{Ala-Asp-Glu-Ala-Arg-Arg-Cys-Tyr-Asn-Asp-Pro-Lys-Cys-Ser-Asp-Phe-Val-Gln} (VI) SEQ ID NO: 1.

54. The method according to claim 30 wherein said cyclic peptide is administered until a level of at least 0.05 mg of the cyclic peptide per kg body weight is achieved.

* * * * *

SEQUENCE LISTING

```
<160> NUMBER OF SEQ ID NOS: 80

<210> SEQ ID NO 1
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 1

Ala Asp Glu Ala Arg Arg Cys Tyr Asn Asp Pro Lys Cys Ser Asp Phe
1               5                   10                  15

Val Gln

<210> SEQ ID NO 2
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 2

Ala Arg Ala Glu Ser Asp Glu Ala Arg Arg Cys Tyr Asn Asp Pro Lys
1               5                   10                  15

Cys Ser Asp Phe Val Thr Asn Arg Gln
                20                  25
```

```
<210> SEQ ID NO 3
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 3

Ala Asp Glu Ala Arg Arg Cys Tyr Asn Asp Pro Lys Cys Ser Asp Phe
1               5                   10                  15

Val Glu

<210> SEQ ID NO 4
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 4

Ala Arg Ala Glu Ser Asp Glu Ala Arg Arg Cys Tyr Asn Asp Pro Lys
1               5                   10                  15

Cys Ser Asp Phe Val Thr Asn Arg Glu
            20                  25

<210> SEQ ID NO 5
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 5

Ala Asp Glu Ala Arg Arg Cys Tyr Asn Asp Pro Lys Ser Cys Asp Phe
1               5                   10                  15

Val Gln

<210> SEQ ID NO 6
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 6

Ala Arg Ala Glu Ser Asp Glu Ala Arg Arg Cys Tyr Asn Asp Pro Lys
1               5                   10                  15

Ser Cys Asp Phe Val Thr Asn Arg Gln
            20                  25

<210> SEQ ID NO 7
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 7

Ala Asp Glu Ala Arg Arg Cys Tyr Asn Asp Pro Lys Ser Cys Asp Phe
1               5                   10                  15
```

Val Glu

<210> SEQ ID NO 8
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 8

Ala Arg Ala Glu Ser Asp Glu Ala Arg Arg Cys Tyr Asn Asp Pro Lys
1               5                   10                  15

Ser Cys Asp Phe Val Thr Asn Arg Glu
            20                  25

<210> SEQ ID NO 9
<211> LENGTH: 54
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (40)..(42)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (54)..(54)
<223> OTHER INFORMATION: r is a or g

<400> SEQUENCE: 9
gcngacgagg cgcgccgctg ctacaacgac cccaagtgct ctgacttcgt ccar         54

<210> SEQ ID NO 10
<211> LENGTH: 75
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (52)..(54)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (75)..(75)
<223> OTHER INFORMATION: r is a or g

<400> SEQUENCE: 10
gcncgggcgg agagcgacga ggcgcgccgc tgctacaacg accccaagtg ctctgacttc   60
gtcaccaacc ggcar                                                    75

<210> SEQ ID NO 11
<211> LENGTH: 54
<212> TYPE: DNA
<213> ORGANISM: Artificial
<220> FEATURE:

```
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (40)..(42)
<223> OTHER INFORMATION: /replace ="tcc" /replace ="agc" /replace ="tca"
      /replace ="tcg" /replace ="agt"
<220> FEATURE:
<221> NAME/KEY: misc_feature
<222> LOCATION: (54)..(54)
<223> OTHER INFORMATION: r is a or g

<400> SEQUENCE: 11
gcngacgagg cgcgccgctg ctacaacgac cccaagtgct ctgacttcgt cgar        54

<210> SEQ ID NO 12
<211> LENGTH: 75
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (52)..(54)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (75)..(75)
<223> OTHER INFORMATION: r is a or g

<400> SEQUENCE: 12
gcncgggcgg agagcgacga ggcgcgccgc tgctacaacg accccaagtg ctctgacttc   60
gtcaccaacc gggar                                                    75

<210> SEQ ID NO 13
<211> LENGTH: 54
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (37)..(39)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (54)..(54)
<223> OTHER INFORMATION: r is a or g

<400> SEQUENCE: 13
gcngacgagg cgcgccgctg ctacaacgac cccaagtctt gcgacttcgt ccar         54

<210> SEQ ID NO 14
<211> LENGTH: 75
<212> TYPE: DNA
<213> ORGANISM: Artificial
```

-continued

```
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (49)..(51)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (75)..(75)
<223> OTHER INFORMATION: r is a or g

<400> SEQUENCE: 14
gcncgggcgg agagcgacga ggcgcgccgc tgctacaacg accccaagtc ttgcgacttc    60
gtcaccaacc ggcar                                                    75

<210> SEQ ID NO 15
<211> LENGTH: 54
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (37)..(39)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (54)..(54)
<223> OTHER INFORMATION: r is a or g

<400> SEQUENCE: 15
gcngacgagg cgcgccgctg ctacaacgac cccaagtctt gcgacttcgt cgar          54

<210> SEQ ID NO 16
<211> LENGTH: 75
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (49)..(51)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (75)..(75)
<223> OTHER INFORMATION: r is a or g

<400> SEQUENCE: 16
gcncgggcgg agagcgacga ggcgcgccgc tgctacaacg accccaagtc ttgcgacttc    60
gtcaccaacc gggar                                                    75

<210> SEQ ID NO 17
```

```
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 17

Lys Cys Ser Asp Phe Val Gln Ala Asp Glu Ala Arg Arg Cys Tyr Asn
1               5                   10                  15

Asp Pro

<210> SEQ ID NO 18
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 18

Lys Cys Ser Asp Phe Val Thr Asn Arg Gln Ala Arg Ala Glu Ser Asp
1               5                   10                  15

Glu Ala Arg Arg Cys Tyr Asn Asp Pro
            20                  25

<210> SEQ ID NO 19
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 19

Lys Cys Ser Asp Phe Val Glu Ala Asp Glu Ala Arg Arg Cys Tyr Asn
1               5                   10                  15

Asp Pro

<210> SEQ ID NO 20
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 20

Lys Cys Ser Asp Phe Val Thr Asn Arg Glu Ala Arg Ala Glu Ser Asp
1               5                   10                  15

Glu Ala Arg Arg Cys Tyr Asn Asp Pro
            20                  25

<210> SEQ ID NO 21
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 21

Lys Ser Cys Asp Phe Val Gln Ala Asp Glu Ala Arg Arg Cys Tyr Asn
1               5                   10                  15

Asp Pro
```

<210> SEQ ID NO 22
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 22

Lys Ser Cys Asp Phe Val Thr Asn Arg Gln Ala Arg Ala Glu Ser Asp
1               5                   10                  15

Glu Ala Arg Arg Cys Tyr Asn Asp Pro
            20                  25

<210> SEQ ID NO 23
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 23

Lys Ser Cys Asp Phe Val Glu Ala Asp Glu Ala Arg Arg Cys Tyr Asn
1               5                   10                  15

Asp Pro

<210> SEQ ID NO 24
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 24

Lys Ser Cys Asp Phe Val Thr Asn Arg Glu Ala Arg Ala Glu Ser Asp
1               5                   10                  15

Glu Ala Arg Arg Cys Tyr Asn Asp Pro
            20                  25

<210> SEQ ID NO 25
<211> LENGTH: 54
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (7)..(9)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 25
aagtgctctg acttcgtcca rgcngacgag gcgcgccgct gctacaacga cccc       54

<210> SEQ ID NO 26

```
<211> LENGTH: 75
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (7)..(9)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (30)..(30)
<223> OTHER INFORMATION: r is a or g
<220> FEATURE:
<221> NAME/KEY: misc_feature
<222> LOCATION: (33)..(33)
<223> OTHER INFORMATION: n is a, c, g, t or u

<400> SEQUENCE: 26
aagtgctctg acttcgtcac caaccggcar gncgggcgg agagcgacga ggcgcgccgc    60
tgctacaacg acccc                                                   75

<210> SEQ ID NO 27
<211> LENGTH: 54
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (7)..(9)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 27
aagtgctctg acttcgtcga rgcngacgag gcgcgccgct gctacaacga cccc         54

<210> SEQ ID NO 28
<211> LENGTH: 75
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (7)..(9)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (30)..(30)
<223> OTHER INFORMATION: r is a or g
<220> FEATURE:
<221> NAME/KEY: misc_feature
<222> LOCATION: (33)..(33)
<223> OTHER INFORMATION: n is a, c, g, t or u

<400> SEQUENCE: 28
aagtgctctg acttcgtcac caaccgggar gncgggcgg agagcgacga ggcgcgccgc    60
tgctacaacg acccc                                                   75
```

<210> SEQ ID NO 29
<211> LENGTH: 54
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (4)..(6)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 29
aagtcttgcg acttcgtcca rgcngacgag gcgcgccgct gctacaacga cccc            54

<210> SEQ ID NO 30
<211> LENGTH: 75
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (4)..(6)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (30)..(30)
<223> OTHER INFORMATION: r is a or g
<220> FEATURE:
<221> NAME/KEY: misc_feature
<222> LOCATION: (33)..(33)
<223> OTHER INFORMATION: n is a, c, g, t or u

<400> SEQUENCE: 30
aagtcttgcg acttcgtcac caaccggcar gcncgggcgg agagcgacga ggcgcgccgc      60
tgctacaacg acccc                                                      75

<210> SEQ ID NO 31
<211> LENGTH: 54
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (4)..(6)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 31

-continued

```
aagtcttgcg acttcgtcga rgcngacgag gcgcgccgct gctacaacga cccc      54
```

<210> SEQ ID NO 32
<211> LENGTH: 75
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (4)..(6)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (30)..(30)
<223> OTHER INFORMATION: r is a or g
<220> FEATURE:
<221> NAME/KEY: misc_feature
<222> LOCATION: (33)..(33)
<223> OTHER INFORMATION: n is a, c, g, t or u

<400> SEQUENCE: 32

```
aagtcttgcg acttcgtcac caaccgggar gcncgggcgg agagcgacga ggcgcgccgc   60
tgctacaacg acccc                                                    75
```

<210> SEQ ID NO 33
<211> LENGTH: 16
<212> TYPE: PRT
<213> ORGANISM: Artificial
<220> FEATURE:
<223> OTHER INFORMATION: Amino acid sequence of an ECII epitope of human
      beta1-AR

<400> SEQUENCE: 33

```
Asp Glu Ala Arg Arg Cys Tyr Asn Asp Pro Lys Cys Cys Asp Phe Val
1               5                   10                  15
```

<210> SEQ ID NO 34
<211> LENGTH: 23
<212> TYPE: PRT
<213> ORGANISM: Artificial
<220> FEATURE:
<223> OTHER INFORMATION: Amino acid sequence of an ECII epitope of human
      beta1-AR

<400> SEQUENCE: 34

```
Arg Ala Glu Ser Asp Glu Ala Arg Arg Cys Tyr Asn Asp Pro Lys Cys
1               5                   10                  15

Cys Asp Phe Val Thr Asn Arg
            20
```

<210> SEQ ID NO 35
<211> LENGTH: 5
<212> TYPE: PRT
<213> ORGANISM: Artificial
<220> FEATURE:
<223> OTHER INFORMATION: Amino acid sequence of an ECII epitope of human
      beta1-AR

<400> SEQUENCE: 35

```
Asp Glu Ala Arg Arg
1               5
```

<210> SEQ ID NO 36
<211> LENGTH: 9
<212> TYPE: PRT

```
<213> ORGANISM: Artificial
<220> FEATURE:
<223> OTHER INFORMATION: Amino acid sequence of an ECII epitope of human
      beta1-AR

<400> SEQUENCE: 36

Arg Ala Glu Ser Asp Glu Ala Arg Arg
1               5

<210> SEQ ID NO 37
<211> LENGTH: 4
<212> TYPE: PRT
<213> ORGANISM: Artificial
<220> FEATURE:
<223> OTHER INFORMATION: Amino acid sequence of an ECII epitope of human
      beta1-AR

<400> SEQUENCE: 37

Asp Phe Val Phe
1

<210> SEQ ID NO 38
<211> LENGTH: 6
<212> TYPE: PRT
<213> ORGANISM: Artificial
<220> FEATURE:
<223> OTHER INFORMATION: Amino acid sequence of an ECII epitope of human
      beta1-AR

<400> SEQUENCE: 38

Asp Phe Val Thr Asn Arg
1               5

<210> SEQ ID NO 39
<211> LENGTH: 16
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: VARIANT
<222> LOCATION: (16)..(16)
<223> OTHER INFORMATION: /replace ="DGlu" /replace ="Glu"

<400> SEQUENCE: 39

Ala Arg Arg Cys Tyr Asn Asp Pro Lys Cys Ser Asp Phe Val Tyr Glu
1               5                   10                  15

<210> SEQ ID NO 40
<211> LENGTH: 477
<212> TYPE: PRT
<213> ORGANISM: Homo sapiens

<400> SEQUENCE: 40

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
                20                  25                  30

Leu Val Pro Ala Ser Pro Pro Ala Ser Leu Leu Pro Pro Ala Ser Glu
            35                  40                  45

Ser Pro Glu Pro Leu Ser Gln Gln Trp Thr Ala Gly Met Gly Leu Leu
        50                  55                  60

Met Ala Leu Ile Val Leu Leu Ile Val Ala Gly Asn Val Leu Val Ile
65                  70                  75                  80
```

```
Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
    370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475

<210> SEQ ID NO 41
<211> LENGTH: 22
<212> TYPE: PRT
```

```
<213> ORGANISM: Artificial
<220> FEATURE:
<223> OTHER INFORMATION: Amino acid sequence homologous to an ECII
      epitope of human beta1-AR

<400> SEQUENCE: 41

Arg Ala Glu Ser Asp Glu Ala Arg Arg Cys Tyr Asn Asp Pro Lys Cys
1               5                   10                  15

Ser Asp Phe Val Thr Gly
            20

<210> SEQ ID NO 42
<211> LENGTH: 66
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (49)..(51)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (66)..(66)
<223> OTHER INFORMATION: n is a, c, g, t or u

<400> SEQUENCE: 42
cgggcggaga gcgacgaggc gcgccgctgc tacaacgacc ccaagtgctc tgacttcgtc     60 accggn                                                               66

<210> SEQ ID NO 43
<211> LENGTH: 22
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 43

Lys Cys Ser Asp Phe Val Thr Gly Arg Ala Glu Ser Asp Glu Ala Arg
1               5                   10                  15

Arg Cys Tyr Asn Asp Pro
            20

<210> SEQ ID NO 44
<211> LENGTH: 66
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (7)..(9)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (24)..(24)
<223> OTHER INFORMATION: n is a, c, g, t or u

<400> SEQUENCE: 44
aagtgctctg acttcgtcac cggncgggcg gagagcgacg aggcgcgccg ctgctacaac     60
gacccc                                                               66
```

-continued

```
<210> SEQ ID NO 45
<211> LENGTH: 11
<212> TYPE: PRT
<213> ORGANISM: Artificial
<220> FEATURE:
<223> OTHER INFORMATION: Amino acid sequence of an ECII epitope (bearing
      portion) of human beta1-AR
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 45

Asp Xaa Xaa Arg Arg Cys Xaa Asn Asp Pro Lys
1               5                   10

<210> SEQ ID NO 46
<211> LENGTH: 13
<212> TYPE: PRT
<213> ORGANISM: Artificial
<220> FEATURE:
<223> OTHER INFORMATION: Amino acid sequence of an ECII epitope (bearing
      portion) of human beta1-AR

<400> SEQUENCE: 46

Glu Ser Asp Ala Ala Arg Arg Cys Ala Asn Asp Pro Lys
1               5                   10

<210> SEQ ID NO 47
<211> LENGTH: 8
<212> TYPE: PRT
<213> ORGANISM: Artificial
<220> FEATURE:
<223> OTHER INFORMATION: Amino acid sequence of an ECII epitope of human
      beta1-AR

<400> SEQUENCE: 47

Ala Glu Ser Asp Glu Ala Arg Arg
1               5

<210> SEQ ID NO 48
<211> LENGTH: 4
<212> TYPE: PRT
<213> ORGANISM: Artificial
<220> FEATURE:
<223> OTHER INFORMATION: Amino acid sequence of an ECII epitope of human
      beta1-AR

<400> SEQUENCE: 48

Asp Phe Val Thr
1

<210> SEQ ID NO 49
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (45)..(45)
<223> OTHER INFORMATION: /replace ="tcc" /replace ="agc" /replace ="tca"
```

```
        /replace ="tcg"
<220> FEATURE:
<221> NAME/KEY: misc_feature
<222> LOCATION: (57)..(57)
<223> OTHER INFORMATION: r is a or g

<400> SEQUENCE: 49
gcnagcgacg aggcgcgccg ctgctacaac gaccccaagt gctctgactt cgtccar      57

<210> SEQ ID NO 50
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (43)..(45)
<223> OTHER INFORMATION: /replace ="tcc" /replace ="agc" /replace ="tca"
        /replace ="tcg"
<220> FEATURE:
<221> NAME/KEY: misc_feature
<222> LOCATION: (45)..(45)
<223> OTHER INFORMATION: /replace ="tcc" /replace ="agc" /replace ="tca"
        /replace ="tcg"
<220> FEATURE:
<221> NAME/KEY: misc_feature
<222> LOCATION: (57)..(57)
<223> OTHER INFORMATION: r is a or g

<400> SEQUENCE: 50
gcnagcgacg aggcgcgccg ctgctacaac gaccccaagt gctctgactt cgtcgar      57

<210> SEQ ID NO 51
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (40)..(42)
<223> OTHER INFORMATION: /replace ="tcc" /replace ="agc" /replace ="tca"
        /replace ="tcg"
<220> FEATURE:
<221> NAME/KEY: misc_feature
<222> LOCATION: (57)..(57)
<223> OTHER INFORMATION: r is a or g

<400> SEQUENCE: 51
gcnagcgacg aggcgcgccg ctgctacaac gaccccaagt cttgcgactt cgtccar      57

<210> SEQ ID NO 52
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (3)..(3)
<223> OTHER INFORMATION: n is a, c, g, t or u
```

```
<220> FEATURE:
<221> NAME/KEY: misc_feature
<222> LOCATION: (40)..(42)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (57)..(57)
<223> OTHER INFORMATION: r is a or g

<400> SEQUENCE: 52
gcnagcgacg aggcgcgccg ctgctacaac gaccccaagt cttgcgactt cgtcgar      57

<210> SEQ ID NO 53
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (7)..(9)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 53
aagtgctctg acttcgtcca rgcnagcgac gaggcgcgcc gctgctacaa cgacccc      57

<210> SEQ ID NO 54
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (7)..(9)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 54
aagtgctctg acttcgtcga rgcnagcgac gaggcgcgcc gctgctacaa cgacccc      57

<210> SEQ ID NO 55
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (4)..(6)
<223> OTHER INFORMATION: /replace ="tcc" /replace ="agc" /replace ="tca"
      /replace ="tcg"
```

```
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 55
aagtcttgcg acttcgtcca rgcnagcgac gaggcgcgcc gctgctacaa cgacccc        57

<210> SEQ ID NO 56
<211> LENGTH: 57
<212> TYPE: DNA
<213> ORGANISM: Artificial
<220> FEATURE:
<223> OTHER INFORMATION: Nucleotide sequence encoding an amino acid
      sequence homologous to an ECII epitope of human  beta1-AR
<220> FEATURE:
<221> NAME/KEY: misc_feature
<222> LOCATION: (4)..(6)
<223> OTHER INFORMATION: /replace ="tcc" /replace ="agc" /replace ="tca"
      /replace ="tcg"
<220> FEATURE:
<221> NAME/KEY: misc_feature
<222> LOCATION: (21)..(21)
<223> OTHER INFORMATION: r is a or g
<220> FEATURE:
<221> NAME/KEY: misc_feature
<222> LOCATION: (24)..(24)
<223> OTHER INFORMATION: n is a, c, g, t or u

<400> SEQUENCE: 56
aagtcttgcg acttcgtcga rgcnagcgac gaggcgcgcc gctgctacaa cgacccc        57

<210> SEQ ID NO 57
<211> LENGTH: 24
<212> TYPE: PRT
<213> ORGANISM: Artificial
<220> FEATURE:
<223> OTHER INFORMATION: Amino acid sequence homologous to an ECII
      epitope of human beta1-AR

<400> SEQUENCE: 57

Ala Arg Ala Glu Ser Asp Glu Ala Arg Arg Cys Tyr Asn Asp Pro Lys
1               5                   10                  15

Cys Cys Asp Phe Val Thr Asn Arg
            20

<210> SEQ ID NO 58
<211> LENGTH: 39
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(2)
<223> OTHER INFORMATION: Xaa is any amino acid other than Cys
<220> FEATURE:
<221> NAME/KEY: misc_feature
<222> LOCATION: (3)..(16)
<223> OTHER INFORMATION: Xaa is either present or absent at positions 3
      to 16, and if present, is any amino acid other than Cys
<220> FEATURE:
<221> NAME/KEY: misc_feature
<222> LOCATION: (18)..(20)
<223> OTHER INFORMATION: Xaa is any amino acid other than Cys
<220> FEATURE:
<221> NAME/KEY: misc_feature
```

```
<222> LOCATION: (22)..(22)
<223> OTHER INFORMATION: Xaa is any amino acid other than Cys
<220> FEATURE:
<221> NAME/KEY: misc_feature
<222> LOCATION: (24)..(24)
<223> OTHER INFORMATION: Xaa is any amino acid other than Cys
<220> FEATURE:
<221> NAME/KEY: misc_feature
<222> LOCATION: (25)..(38)
<223> OTHER INFORMATION: Xaa is either present or absent at positions 25
      to 38, and if present, is any amino acid other than Cys
<220> FEATURE:
<221> NAME/KEY: misc_feature
<222> LOCATION: (39)..(39)
<223> OTHER INFORMATION: Xaa is any amino acid other than Cys

<400> SEQUENCE: 58

Xaa Xaa Xaa Xaa Xaa Xaa Xaa Xaa Xaa Xaa Xaa Xaa Xaa Xaa Xaa Xaa
1               5                   10                  15

Cys Xaa Xaa Xaa Pro Xaa Cys Xaa Xaa Xaa Xaa Xaa Xaa Xaa Xaa
            20                  25                  30

Xaa Xaa Xaa Xaa Xaa Xaa Xaa
            35

<210> SEQ ID NO 59
<211> LENGTH: 11
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (2)..(3)
<223> OTHER INFORMATION: Xaa is any amino acid other than Cys
<220> FEATURE:
<221> NAME/KEY: misc_feature
<222> LOCATION: (7)..(7)
<223> OTHER INFORMATION: Xaa is any amino acid other than Cys

<400> SEQUENCE: 59

Asp Xaa Xaa Arg Arg Cys Xaa Asn Asp Pro Lys
1               5                   10

<210> SEQ ID NO 60
<211> LENGTH: 13
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (4)..(5)
<223> OTHER INFORMATION: Xaa is any amino acid other than Cys
<220> FEATURE:
<221> NAME/KEY: misc_feature
<222> LOCATION: (9)..(9)
<223> OTHER INFORMATION: Xaa is any amino acid other than Cys

<400> SEQUENCE: 60

Glu Ser Asp Xaa Xaa Arg Arg Cys Xaa Asn Asp Pro Lys
1               5                   10

<210> SEQ ID NO 61
<211> LENGTH: 39
<212> TYPE: PRT
<213> ORGANISM: Artificial
<220> FEATURE:
<223> OTHER INFORMATION: Amino acid sequence homologous to an ECII
      epitope of human beta1-AR
```

```
<220> FEATURE:
<221> NAME/KEY: misc_feature
<222> LOCATION: (1)..(1)
<223> OTHER INFORMATION: Xaa is Ala, Gly, Val, Thr, or Ser
<220> FEATURE:
<221> NAME/KEY: misc_feature
<222> LOCATION: (2)..(2)
<223> OTHER INFORMATION: Xaa is any amino acid other than Cys
<220> FEATURE:
<221> NAME/KEY: misc_feature
<222> LOCATION: (3)..(16)
<223> OTHER INFORMATION: Xaa is either absent or present at positions
      3 to 16, and if present, is any amino acid other than Cys
<220> FEATURE:
<221> NAME/KEY: misc_feature
<222> LOCATION: (18)..(20)
<223> OTHER INFORMATION: Xaa is any amino acid other than Cys
<220> FEATURE:
<221> NAME/KEY: misc_feature
<222> LOCATION: (22)..(22)
<223> OTHER INFORMATION: Xaa is any amino acid other than Cys
<220> FEATURE:
<221> NAME/KEY: misc_feature
<222> LOCATION: (24)..(24)
<223> OTHER INFORMATION: Xaa is any amino acid other than Cys
<220> FEATURE:
<221> NAME/KEY: misc_feature
<222> LOCATION: (25)..(38)
<223> OTHER INFORMATION: Xaa is either absent or present at positions
      24 to 38, and if present, is any amino acid other than Cys
<220> FEATURE:
<221> NAME/KEY: misc_feature
<222> LOCATION: (39)..(39)
<223> OTHER INFORMATION: Xaa is any amino acid other than Cys

<400> SEQUENCE: 61

Xaa Xaa Xaa Xaa Xaa Xaa Xaa Xaa Xaa Xaa Xaa Xaa Xaa Xaa Xaa Xaa
1               5                   10                  15

Cys Xaa Xaa Xaa Pro Xaa Cys Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 62
<211> LENGTH: 39
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Arg
<220> FEATURE:
<221> NAME/KEY: misc_feature
<222> LOCATION: (2)..(2)
<223> OTHER INFORMATION: Xaa is any amino acid other than Cys
<220> FEATURE:
<221> NAME/KEY: misc_feature
<222> LOCATION: (3)..(16)
<223> OTHER INFORMATION: Xaa is either present or absent at positions
      3 to 16, and if present, is any amino acid other than Cys
<220> FEATURE:
<221> NAME/KEY: misc_feature
<222> LOCATION: (18)..(20)
<223> OTHER INFORMATION: Xaa is any amino acid other than Cys
<220> FEATURE:
<221> NAME/KEY: misc_feature
<222> LOCATION: (22)..(22)
<223> OTHER INFORMATION: Xaa is any amino acid other than Cys
<220> FEATURE:
<221> NAME/KEY: misc_feature
<222> LOCATION: (24)..(24)
<223> OTHER INFORMATION: Xaa is any amino acid other than Cys
```

```
<220> FEATURE:
<221> NAME/KEY: misc_feature
<222> LOCATION: (25)..(38)
<223> OTHER INFORMATION: Xaa is either present or absent at positions
      25 to 38, and if present, is any amino acid other than Cys
<220> FEATURE:
<221> NAME/KEY: misc_feature
<222> LOCATION: (39)..(39)
<223> OTHER INFORMATION: Xaa is any amino acid other than Cys

<400> SEQUENCE: 62

Xaa Xaa Xaa Xaa Xaa Xaa Xaa Xaa Xaa Xaa Xaa Xaa Xaa Xaa Xaa
1               5                   10                  15

Cys Xaa Xaa Xaa Pro Xaa Cys Xaa Xaa Xaa Xaa Xaa Xaa Xaa Xaa
            20                  25                  30

Xaa Xaa Xaa Xaa Xaa Xaa Xaa
        35

<210> SEQ ID NO 63
<211> LENGTH: 39
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Ala, Gly, Val, Thr or Ser
<220> FEATURE:
<221> NAME/KEY: misc_feature
<222> LOCATION: (2)..(2)
<223> OTHER INFORMATION: Xaa is any amino acid other than Cys
<220> FEATURE:
<221> NAME/KEY: misc_feature
<222> LOCATION: (3)..(16)
<223> OTHER INFORMATION: Xaa is either absent or present at positions
      3 to 16, and if present, is any amino acid other than Cys
<220> FEATURE:
<221> NAME/KEY: misc_feature
<222> LOCATION: (18)..(20)
<223> OTHER INFORMATION: Xaa is any amino acid other than Cys
<220> FEATURE:
<221> NAME/KEY: misc_feature
<222> LOCATION: (22)..(22)
<223> OTHER INFORMATION: Xaa is any amino acid other than Cys
<220> FEATURE:
<221> NAME/KEY: misc_feature
<222> LOCATION: (24)..(24)
<223> OTHER INFORMATION: Xaa is any amino acid other than Cys
<220> FEATURE:
<221> NAME/KEY: misc_feature
<222> LOCATION: (25)..(38)
<223> OTHER INFORMATION: Xaa is either absent or present at positions
      25 to 38, and if present, is any amino acid other than Cys
<220> FEATURE:
<221> NAME/KEY: misc_feature
<222> LOCATION: (39)..(39)
<223> OTHER INFORMATION: Xaa is Gln, Glu, Asp or Asn

<400> SEQUENCE: 63

Xaa Xaa Xaa Xaa Xaa Xaa Xaa Xaa Xaa Xaa Xaa Xaa Xaa Xaa Xaa
1               5                   10                  15

Cys Xaa Xaa Xaa Pro Xaa Cys Xaa Xaa Xaa Xaa Xaa Xaa Xaa Xaa
            20                  25                  30

Xaa Xaa Xaa Xaa Xaa Xaa Xaa
        35

<210> SEQ ID NO 64
<211> LENGTH: 39
<212> TYPE: PRT
```

```
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Gln, Glu, Asp or Asn
<220> FEATURE:
<221> NAME/KEY: misc_feature
<222> LOCATION: (2)..(2)
<223> OTHER INFORMATION: Xaa is any amino acid other than Cys
<220> FEATURE:
<221> NAME/KEY: misc_feature
<222> LOCATION: (3)..(16)
<223> OTHER INFORMATION: Xaa is either absent or present at positions
      3 to 16, and if present, is any amino acid other than Cys
<220> FEATURE:
<221> NAME/KEY: misc_feature
<222> LOCATION: (18)..(20)
<223> OTHER INFORMATION: Xaa is any amino acid other than Cys
<220> FEATURE:
<221> NAME/KEY: misc_feature
<222> LOCATION: (22)..(22)
<223> OTHER INFORMATION: Xaa is any amino acid other than Cys
<220> FEATURE:
<221> NAME/KEY: misc_feature
<222> LOCATION: (24)..(24)
<223> OTHER INFORMATION: Xaa is any amino acid other than Cys
<220> FEATURE:
<221> NAME/KEY: misc_feature
<222> LOCATION: (25)..(38)
<223> OTHER INFORMATION: Xaa is either absent or present at positions
      25 to 38, and if present, is any amino acid other than Cys
<220> FEATURE:
<221> NAME/KEY: misc_feature
<222> LOCATION: (39)..(39)
<223> OTHER INFORMATION: Xaa is Gly or a Gly analogue

<400> SEQUENCE: 64

Xaa Xaa Xaa Xaa Xaa Xaa Xaa Xaa Xaa Xaa Xaa Xaa Xaa Xaa Xaa Xaa
1               5                   10                  15

Cys Xaa Xaa Xaa Pro Xaa Cys Xaa Xaa Xaa Xaa Xaa Xaa Xaa Xaa
            20                  25                  30

Xaa Xaa Xaa Xaa Xaa Xaa Xaa
        35

<210> SEQ ID NO 65
<211> LENGTH: 29
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Ala, Gly, Val, Thr or Ser
<220> FEATURE:
<221> NAME/KEY: misc_feature
<222> LOCATION: (2)..(2)
<223> OTHER INFORMATION: Xaa is any amino acid other than Cys
<220> FEATURE:
<221> NAME/KEY: misc_feature
<222> LOCATION: (3)..(3)
<223> OTHER INFORMATION: Xaa is an acidic amino acid
<220> FEATURE:
<221> NAME/KEY: misc_feature
<222> LOCATION: (4)..(6)
<223> OTHER INFORMATION: Xaa is any amino acid other than Cys
<220> FEATURE:
<221> NAME/KEY: misc_feature
<222> LOCATION: (8)..(10)
<223> OTHER INFORMATION: Xaa is any amino acid other than Cys
<220> FEATURE:
```

```
<221> NAME/KEY: misc_feature
<222> LOCATION: (12)..(12)
<223> OTHER INFORMATION: Xaa is any amino acid other than Cys
<220> FEATURE:
<221> NAME/KEY: misc_feature
<222> LOCATION: (14)..(14)
<223> OTHER INFORMATION: Xaa is any amino acid other than Cys
<220> FEATURE:
<221> NAME/KEY: misc_feature
<222> LOCATION: (15)..(28)
<223> OTHER INFORMATION: Xaa is absent or present at positions 15 to 28,
      and if present, is any amino acid other than Cys
<220> FEATURE:
<221> NAME/KEY: misc_feature
<222> LOCATION: (29)..(29)
<223> OTHER INFORMATION: Xaa is Gln, Glu, Asp or Asn

<400> SEQUENCE: 65

Xaa Xaa Xaa Xaa Xaa Xaa Cys Xaa Xaa Xaa Pro Xaa Cys Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 66
<211> LENGTH: 33
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Ala, Gly, Val, Thr or Ser
<220> FEATURE:
<221> NAME/KEY: misc_feature
<222> LOCATION: (2)..(2)
<223> OTHER INFORMATION: Xaa is a basic amino acid
<220> FEATURE:
<221> NAME/KEY: misc_feature
<222> LOCATION: (3)..(3)
<223> OTHER INFORMATION: Xaa is any amino acid other than Cys
<220> FEATURE:
<221> NAME/KEY: misc_feature
<222> LOCATION: (4)..(4)
<223> OTHER INFORMATION: Xaa is an acidic amino acid
<220> FEATURE:
<221> NAME/KEY: misc_feature
<222> LOCATION: (5)..(6)
<223> OTHER INFORMATION: Xaa is any amino acid other than Cys
<220> FEATURE:
<221> NAME/KEY: misc_feature
<222> LOCATION: (7)..(7)
<223> OTHER INFORMATION: Xaa is an acidic amino acid
<220> FEATURE:
<221> NAME/KEY: misc_feature
<222> LOCATION: (8)..(10)
<223> OTHER INFORMATION: Xaa is any amino acid other than Cys
<220> FEATURE:
<221> NAME/KEY: misc_feature
<222> LOCATION: (12)..(14)
<223> OTHER INFORMATION: Xaa is any amino acid other than Cys
<220> FEATURE:
<221> NAME/KEY: misc_feature
<222> LOCATION: (16)..(16)
<223> OTHER INFORMATION: Xaa is any amino acid other than Cys
<220> FEATURE:
<221> NAME/KEY: misc_feature
<222> LOCATION: (18)..(18)
<223> OTHER INFORMATION: Xaa is any amino acid other than Cys
<220> FEATURE:
<221> NAME/KEY: misc_feature
<222> LOCATION: (19)..(32)
<223> OTHER INFORMATION: Xaa is either present or absent at positions
      19 to 32, and if present, is any amino acid other than Cys
<220> FEATURE:
```

<221> NAME/KEY: misc_feature
<222> LOCATION: (33)..(33)
<223> OTHER INFORMATION: Xaa is Gln, Glu, Asp or Asn

<400> SEQUENCE: 66

Xaa Xaa Xaa Xaa Xaa Xaa Xaa Xaa Xaa Cys Xaa Xaa Xaa Pro Xaa
1               5                   10                  15

Cys Xaa Xaa Xaa Xaa Xaa Xaa Xaa Xaa Xaa Xaa Xaa Xaa Xaa Xaa
                20                  25                  30

Xaa

<210> SEQ ID NO 67
<211> LENGTH: 32
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Arg
<220> FEATURE:
<221> NAME/KEY: misc_feature
<222> LOCATION: (2)..(2)
<223> OTHER INFORMATION: Xaa is any amino acid other than Cys
<220> FEATURE:
<221> NAME/KEY: misc_feature
<222> LOCATION: (3)..(3)
<223> OTHER INFORMATION: Xaa is an acidic amino acid
<220> FEATURE:
<221> NAME/KEY: misc_feature
<222> LOCATION: (4)..(5)
<223> OTHER INFORMATION: Xaa is any amino acid other than Cys
<220> FEATURE:
<221> NAME/KEY: misc_feature
<222> LOCATION: (6)..(6)
<223> OTHER INFORMATION: Xaa is an acidic amino acid
<220> FEATURE:
<221> NAME/KEY: misc_feature
<222> LOCATION: (7)..(9)
<223> OTHER INFORMATION: Xaa is any amino acid other than Cys
<220> FEATURE:
<221> NAME/KEY: misc_feature
<222> LOCATION: (11)..(13)
<223> OTHER INFORMATION: Xaa is any amino acid other than Cys
<220> FEATURE:
<221> NAME/KEY: misc_feature
<222> LOCATION: (15)..(15)
<223> OTHER INFORMATION: Xaa is any amino acid other than Cys
<220> FEATURE:
<221> NAME/KEY: misc_feature
<222> LOCATION: (17)..(17)
<223> OTHER INFORMATION: Xaa is any amino acid other than Cys
<220> FEATURE:
<221> NAME/KEY: misc_feature
<222> LOCATION: (18)..(31)
<223> OTHER INFORMATION: Xaa is either present or absent at positions
      18 to 31, and if present, is any amino acid other than Cys
<220> FEATURE:
<221> NAME/KEY: misc_feature
<222> LOCATION: (32)..(32)
<223> OTHER INFORMATION: Xaa is Gly or a Gly analogue

<400> SEQUENCE: 67

Xaa Xaa Xaa Xaa Xaa Xaa Xaa Xaa Xaa Cys Xaa Xaa Xaa Pro Xaa Cys
1               5                   10                  15

Xaa Xaa Xaa Xaa Xaa Xaa Xaa Xaa Xaa Xaa Xaa Xaa Xaa Xaa
                20                  25                  30

<210> SEQ ID NO 68
<211> LENGTH: 18

```
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Ala, Gly, Val, Thr or Ser
<220> FEATURE:
<221> NAME/KEY: misc_feature
<222> LOCATION: (2)..(2)
<223> OTHER INFORMATION: Xaa is any amino acid other than Cys
<220> FEATURE:
<221> NAME/KEY: misc_feature
<222> LOCATION: (3)..(3)
<223> OTHER INFORMATION: Xaa is an acidic amino acid
<220> FEATURE:
<221> NAME/KEY: misc_feature
<222> LOCATION: (4)..(4)
<223> OTHER INFORMATION: Xaa is Ser, Thr, Ala or Gly
<220> FEATURE:
<221> NAME/KEY: misc_feature
<222> LOCATION: (5)..(6)
<223> OTHER INFORMATION: Xaa is any amino acid other than Cys
<220> FEATURE:
<221> NAME/KEY: misc_feature
<222> LOCATION: (8)..(8)
<223> OTHER INFORMATION: Xaa is Leu, Ile, Val, Met, Trp, Tyr or Phe
<220> FEATURE:
<221> NAME/KEY: misc_feature
<222> LOCATION: (9)..(10)
<223> OTHER INFORMATION: Xaa is any amino acid other than Cys
<220> FEATURE:
<221> NAME/KEY: misc_feature
<222> LOCATION: (12)..(12)
<223> OTHER INFORMATION: Xaa is any amino acid other than Cys
<220> FEATURE:
<221> NAME/KEY: misc_feature
<222> LOCATION: (14)..(14)
<223> OTHER INFORMATION: Xaa is any amino acid other than Cys
<220> FEATURE:
<221> NAME/KEY: misc_feature
<222> LOCATION: (15)..(15)
<223> OTHER INFORMATION: Xaa is an acidic amino acid
<220> FEATURE:
<221> NAME/KEY: misc_feature
<222> LOCATION: (16)..(17)
<223> OTHER INFORMATION: Xaa is Leu, Ile, Val, Met, Trp, Tyr or Phe
<220> FEATURE:
<221> NAME/KEY: misc_feature
<222> LOCATION: (18)..(18)
<223> OTHER INFORMATION: Xaa is Gln, Glu, Asp or Asn

<400> SEQUENCE: 68

Xaa Xaa Xaa Xaa Xaa Xaa Cys Xaa Xaa Xaa Pro Xaa Cys Xaa Xaa Xaa
1               5                   10                  15

Xaa Xaa

<210> SEQ ID NO 69
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Ala, Gly, Val, Thr or Ser
<220> FEATURE:
<221> NAME/KEY: misc_feature
<222> LOCATION: (2)..(2)
<223> OTHER INFORMATION: Xaa is a basic amino acid
<220> FEATURE:
<221> NAME/KEY: misc_feature
```

```
<222> LOCATION: (3)..(3)
<223> OTHER INFORMATION: Xaa is Ser, Thr, Ala or Gly
<220> FEATURE:
<221> NAME/KEY: misc_feature
<222> LOCATION: (4)..(4)
<223> OTHER INFORMATION: Xaa is an acidic amino acid
<220> FEATURE:
<221> NAME/KEY: misc_feature
<222> LOCATION: (5)..(5)
<223> OTHER INFORMATION: Xaa is Ser, Thr, Ala or Gly
<220> FEATURE:
<221> NAME/KEY: misc_feature
<222> LOCATION: (6)..(6)
<223> OTHER INFORMATION: Xaa is any amino acid other than Cys
<220> FEATURE:
<221> NAME/KEY: misc_feature
<222> LOCATION: (7)..(7)
<223> OTHER INFORMATION: Xaa is an acidic amino acid
<220> FEATURE:
<221> NAME/KEY: misc_feature
<222> LOCATION: (8)..(8)
<223> OTHER INFORMATION: Xaa is Ser, Thr, Ala or Gly
<220> FEATURE:
<221> NAME/KEY: misc_feature
<222> LOCATION: (9)..(10)
<223> OTHER INFORMATION: Xaa is any amino acid other than Cys
<220> FEATURE:
<221> NAME/KEY: misc_feature
<222> LOCATION: (12)..(12)
<223> OTHER INFORMATION: Xaa is Leu, Ile, Val, Met, Trp, Tyr or Phe
<220> FEATURE:
<221> NAME/KEY: misc_feature
<222> LOCATION: (13)..(14)
<223> OTHER INFORMATION: Xaa is any amino acid other than Cys
<220> FEATURE:
<221> NAME/KEY: misc_feature
<222> LOCATION: (16)..(16)
<223> OTHER INFORMATION: Xaa is any amino acid other than Cys
<220> FEATURE:
<221> NAME/KEY: misc_feature
<222> LOCATION: (18)..(18)
<223> OTHER INFORMATION: Xaa is any amino acid other than Cys
<220> FEATURE:
<221> NAME/KEY: misc_feature
<222> LOCATION: (19)..(19)
<223> OTHER INFORMATION: Xaa is an acidic amino acid
<220> FEATURE:
<221> NAME/KEY: misc_feature
<222> LOCATION: (20)..(21)
<223> OTHER INFORMATION: Xaa is Leu, Ile, Val, Met, Trp, Tyr or Phe
<220> FEATURE:
<221> NAME/KEY: misc_feature
<222> LOCATION: (22)..(22)
<223> OTHER INFORMATION: Xaa is Ser, Thr, Ala or Gly
<220> FEATURE:
<221> NAME/KEY: misc_feature
<222> LOCATION: (23)..(23)
<223> OTHER INFORMATION: Xaa is Gln or Asn
<220> FEATURE:
<221> NAME/KEY: misc_feature
<222> LOCATION: (24)..(24)
<223> OTHER INFORMATION: Xaa is a basic amino acid
<220> FEATURE:
<221> NAME/KEY: misc_feature
<222> LOCATION: (25)..(25)
<223> OTHER INFORMATION: Xaa is Gln, Glu, Asp or Asn

<400> SEQUENCE: 69

Xaa Xaa Xaa Xaa Xaa Xaa Xaa Xaa Xaa Xaa Cys Xaa Xaa Xaa Pro Xaa
1               5                   10                  15

Cys Xaa Xaa Xaa Xaa Xaa Xaa Xaa Xaa
            20                  25

<210> SEQ ID NO 70
<211> LENGTH: 22
<212> TYPE: PRT
```

```
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is Arg
<220> FEATURE:
<221> NAME/KEY: misc_feature
<222> LOCATION: (2)..(2)
<223> OTHER INFORMATION: Xaa is Ser, Thr, Ala or Gly
<220> FEATURE:
<221> NAME/KEY: misc_feature
<222> LOCATION: (3)..(3)
<223> OTHER INFORMATION: Xaa is an acidic amino acid
<220> FEATURE:
<221> NAME/KEY: misc_feature
<222> LOCATION: (4)..(4)
<223> OTHER INFORMATION: Xaa Ser, Thr, Ala or Gly
<220> FEATURE:
<221> NAME/KEY: misc_feature
<222> LOCATION: (5)..(5)
<223> OTHER INFORMATION: Xaa is any amino acid other than Cys
<220> FEATURE:
<221> NAME/KEY: misc_feature
<222> LOCATION: (6)..(6)
<223> OTHER INFORMATION: Xaa is an acidic amino acid
<220> FEATURE:
<221> NAME/KEY: misc_feature
<222> LOCATION: (7)..(7)
<223> OTHER INFORMATION: Xaa is Ser, Thr, Ala or Gly
<220> FEATURE:
<221> NAME/KEY: misc_feature
<222> LOCATION: (8)..(9)
<223> OTHER INFORMATION: Xaa is any amino acid other than Cys
<220> FEATURE:
<221> NAME/KEY: misc_feature
<222> LOCATION: (11)..(11)
<223> OTHER INFORMATION: Xaa is Leu, Ile, Val, Met, Trp, Tyr or Phe
<220> FEATURE:
<221> NAME/KEY: misc_feature
<222> LOCATION: (12)..(13)
<223> OTHER INFORMATION: Xaa is any amino acid other than Cys
<220> FEATURE:
<221> NAME/KEY: misc_feature
<222> LOCATION: (15)..(15)
<223> OTHER INFORMATION: Xaa is any amino acid other than Cys
<220> FEATURE:
<221> NAME/KEY: misc_feature
<222> LOCATION: (17)..(17)
<223> OTHER INFORMATION: Xaa is any amino acid other than Cys
<220> FEATURE:
<221> NAME/KEY: misc_feature
<222> LOCATION: (18)..(18)
<223> OTHER INFORMATION: Xaa is an acidic amino acid
<220> FEATURE:
<221> NAME/KEY: misc_feature
<222> LOCATION: (19)..(20)
<223> OTHER INFORMATION: Xaa is Leu, Ile, Val, Met, Trp, Tyr or Phe
<220> FEATURE:
<221> NAME/KEY: misc_feature
<222> LOCATION: (21)..(21)
<223> OTHER INFORMATION: Xaa is Ser, Thr, Ala or Gly
<220> FEATURE:
<221> NAME/KEY: misc_feature
<222> LOCATION: (22)..(22)
<223> OTHER INFORMATION: Xaa is Gly or a Gly analogue

<400> SEQUENCE: 70

Xaa Xaa Xaa Xaa Xaa Xaa Xaa Xaa Xaa Cys Xaa Xaa Xaa Pro Xaa Cys
1               5                   10                  15

Xaa Xaa Xaa Xaa Xaa Xaa
            20

<210> SEQ ID NO 71
```

```
<211> LENGTH: 22
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (3)..(3)
<223> OTHER INFORMATION: Xaa is an acidic amino acid
<220> FEATURE:
<221> NAME/KEY: misc_feature
<222> LOCATION: (5)..(6)
<223> OTHER INFORMATION: Xaa is an acidic amino acid
<220> FEATURE:
<221> NAME/KEY: misc_feature
<222> LOCATION: (12)..(13)
<223> OTHER INFORMATION: Xaa is an acidic amino acid
<220> FEATURE:
<221> NAME/KEY: misc_feature
<222> LOCATION: (18)..(18)
<223> OTHER INFORMATION: Xaa is an acidic amino acid

<400> SEQUENCE: 71

Arg Ala Xaa Ser Xaa Xaa Ala Arg Arg Cys Tyr Xaa Xaa Pro Lys Cys
1               5                   10                  15

Ser Ala Phe Val Thr Gly
            20

<210> SEQ ID NO 72
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (2)..(3)
<223> OTHER INFORMATION: Xaa is an acidic amino acid
<220> FEATURE:
<221> NAME/KEY: misc_feature
<222> LOCATION: (9)..(10)
<223> OTHER INFORMATION: Xaa is an acidic amino acid
<220> FEATURE:
<221> NAME/KEY: misc_feature
<222> LOCATION: (15)..(15)
<223> OTHER INFORMATION: Xaa is an acidic amino acid
<220> FEATURE:
<221> NAME/KEY: misc_feature
<222> LOCATION: (18)..(18)
<223> OTHER INFORMATION: Xaa is an acidic amino acid

<400> SEQUENCE: 72

Ala Xaa Xaa Ala Arg Arg Cys Tyr Xaa Xaa Pro Lys Cys Ser Xaa Phe
1               5                   10                  15

Val Xaa

<210> SEQ ID NO 73
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (6)..(7)
<223> OTHER INFORMATION: Xaa is an acidic amino acid
<220> FEATURE:
<221> NAME/KEY: misc_feature
<222> LOCATION: (13)..(14)
<223> OTHER INFORMATION: Xaa is an acidic amino acid
```

```
<220> FEATURE:
<221> NAME/KEY: misc_feature
<222> LOCATION: (19)..(19)
<223> OTHER INFORMATION: Xaa is an acidic amino acid
<220> FEATURE:
<221> NAME/KEY: misc_feature
<222> LOCATION: (23)..(23)
<223> OTHER INFORMATION: Xaa is an acidic amino acid
<220> FEATURE:
<221> NAME/KEY: misc_feature
<222> LOCATION: (25)..(25)
<223> OTHER INFORMATION: Xaa is an acidic amino acid

<400> SEQUENCE: 73

Ala Arg Ala Glu Ser Xaa Xaa Ala Arg Arg Cys Tyr Xaa Xaa Pro Lys
1               5                   10                  15

Cys Ser Xaa Phe Val Thr Xaa Arg Xaa
            20                  25

<210> SEQ ID NO 74
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (2)..(3)
<223> OTHER INFORMATION: Xaa is an acidic amino acid
<220> FEATURE:
<221> NAME/KEY: misc_feature
<222> LOCATION: (9)..(10)
<223> OTHER INFORMATION: Xaa is an acidic amino acid
<220> FEATURE:
<221> NAME/KEY: misc_feature
<222> LOCATION: (15)..(15)
<223> OTHER INFORMATION: Xaa is an acidic amino acid
<220> FEATURE:
<221> NAME/KEY: misc_feature
<222> LOCATION: (18)..(18)
<223> OTHER INFORMATION: Xaa is DGlu

<400> SEQUENCE: 74

Ala Xaa Xaa Ala Arg Arg Cys Tyr Xaa Xaa Pro Lys Cys Ser Xaa Phe
1               5                   10                  15

Val Xaa

<210> SEQ ID NO 75
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (4)..(4)
<223> OTHER INFORMATION: Xaa is an acidic amino acid
<220> FEATURE:
<221> NAME/KEY: misc_feature
<222> LOCATION: (6)..(7)
<223> OTHER INFORMATION: Xaa is an acidic amino acid
<220> FEATURE:
<221> NAME/KEY: misc_feature
<222> LOCATION: (13)..(14)
<223> OTHER INFORMATION: Xaa is an acidic amino acid
<220> FEATURE:
<221> NAME/KEY: misc_feature
<222> LOCATION: (19)..(19)
<223> OTHER INFORMATION: Xaa is an acidic amino acid
<220> FEATURE:
<221> NAME/KEY: misc_feature
```

<222> LOCATION: (25)..(25)
<223> OTHER INFORMATION: Xaa is DGlu

<400> SEQUENCE: 75

Ala Arg Ala Xaa Ser Xaa Xaa Ala Arg Arg Cys Tyr Xaa Xaa Pro Lys
1               5                   10                  15

Cys Ser Xaa Phe Val Thr Asn Arg Xaa
            20                  25

<210> SEQ ID NO 76
<211> LENGTH: 22
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (1)..(1)
<223> OTHER INFORMATION: Xaa is a basic amino acid
<220> FEATURE:
<221> NAME/KEY: misc_feature
<222> LOCATION: (8)..(9)
<223> OTHER INFORMATION: Xaa is a basic amino acid
<220> FEATURE:
<221> NAME/KEY: misc_feature
<222> LOCATION: (11)..(11)
<223> OTHER INFORMATION: Xaa is a basic amino acid
<220> FEATURE:
<221> NAME/KEY: misc_feature
<222> LOCATION: (15)..(15)
<223> OTHER INFORMATION: Xaa is a basic amino acid

<400> SEQUENCE: 76

Xaa Ala Glu Ser Asp Glu Ala Xaa Xaa Cys Xaa Asn Asp Pro Xaa Cys
1               5                   10                  15

Ser Asp Phe Val Thr Gly
            20

<210> SEQ ID NO 77
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (5)..(6)
<223> OTHER INFORMATION: Xaa is a basic amino acid
<220> FEATURE:
<221> NAME/KEY: misc_feature
<222> LOCATION: (8)..(8)
<223> OTHER INFORMATION: Xaa is a basic amino acid
<220> FEATURE:
<221> NAME/KEY: misc_feature
<222> LOCATION: (12)..(12)
<223> OTHER INFORMATION: Xaa is a basic amino acid

<400> SEQUENCE: 77

Ala Asp Glu Ala Xaa Xaa Cys Xaa Asn Asp Pro Xaa Cys Ser Asp Phe
1               5                   10                  15

Val Gln

<210> SEQ ID NO 78
<211> LENGTH: 25
<212> TYPE: PRT
<213> ORGANISM: Artificial
<220> FEATURE:
<223> OTHER INFORMATION: Amino acid sequence homologous to an ECII epitope of human beta1-AR
<220> FEATURE:
<221> NAME/KEY: misc_feature
<222> LOCATION: (2)..(2)
<223> OTHER INFORMATION: Xaa is a basic amino acid
<220> FEATURE:
<221> NAME/KEY: misc_feature
<222> LOCATION: (9)..(10)
<223> OTHER INFORMATION: Xaa is a basic amino acid
<220> FEATURE:
<221> NAME/KEY: misc_feature
<222> LOCATION: (24)..(24)
<223> OTHER INFORMATION: Xaa is a basic amino acid

<400> SEQUENCE: 78

Ala Xaa Ala Glu Ser Asp Glu Ala Xaa Xaa Cys Tyr Asn Asp Pro Lys
1               5                   10                  15

Cys Ser Asp Phe Val Thr Asn Xaa Gln
            20                  25

<210> SEQ ID NO 79
<211> LENGTH: 18
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (5)..(5)
<223> OTHER INFORMATION: Xaa is a basic amino acid
<220> FEATURE:
<221> NAME/KEY: misc_feature
<222> LOCATION: (8)..(8)
<223> OTHER INFORMATION: Xaa is a basic amino acid
<220> FEATURE:
<221> NAME/KEY: misc_feature
<222> LOCATION: (12)..(12)
<223> OTHER INFORMATION: Xaa is a basic amino acid
<220> FEATURE:
<221> NAME/KEY: misc_feature
<222> LOCATION: (18)..(18)
<223> OTHER INFORMATION: Xaa is DGlu

<400> SEQUENCE: 79

Ala Asp Glu Ala Xaa Arg Cys Xaa Asn Asp Pro Xaa Cys Ser Asp Phe
1               5                   10                  15

Val Xaa

<210> SEQ ID NO 80
<211> LENGTH: 25
<212> TYPE: PRT
<213> ORGANISM: Artificial
<220> FEATURE:
<223> OTHER INFORMATION: Amino acid sequence homologous to an ECII
      epitope of human beta1-AR
<220> FEATURE:
<221> NAME/KEY: misc_feature
<222> LOCATION: (2)..(2)
<223> OTHER INFORMATION: Xaa is a basic amino acid
<220> FEATURE:
<221> NAME/KEY: misc_feature
<222> LOCATION: (9)..(10)
<223> OTHER INFORMATION: Xaa is a basic amino acid
<220> FEATURE:
<221> NAME/KEY: misc_feature
<222> LOCATION: (16)..(16)
<223> OTHER INFORMATION: Xaa is a basic amino acid
<220> FEATURE:
<221> NAME/KEY: misc_feature
<222> LOCATION: (24)..(24)
<223> OTHER INFORMATION: Xaa is a basic amino acid
<220> FEATURE:

```
<221> NAME/KEY: misc_feature
<222> LOCATION: (25)..(25)
<223> OTHER INFORMATION: Xaa is DGlu

<400> SEQUENCE: 80

Ala Xaa Ala Glu Ser Asp Glu Ala Xaa Xaa Cys Tyr Asn Asp Pro Xaa
1               5                  10                 15

Cys Ser Asp Phe Val Thr Asn Xaa Xaa
            20                  25
```